United States Patent
Cha et al.

(10) Patent No.: US 11,877,509 B2
(45) Date of Patent: Jan. 16, 2024

(54) ORGANIC LIGHT-EMITTING ELEMENT

(71) Applicant: LG Chem, Ltd., Seoul (KR)

(72) Inventors: Yongbum Cha, Daejeon (KR); Seong So Kim, Daejeon (KR); Sung Jae Lee, Daejeon (KR); Sung Kil Hong, Daejeon (KR)

(73) Assignee: LG Chem, Ltd.

( * ) Notice: Subject to any disclaimer, the term of this patent is extended or adjusted under 35 U.S.C. 154(b) by 534 days.

(21) Appl. No.: 16/301,574

(22) PCT Filed: Jun. 1, 2017

(86) PCT No.: PCT/KR2017/005737
§ 371 (c)(1),
(2) Date: Nov. 14, 2018

(87) PCT Pub. No.: WO2017/209538
PCT Pub. Date: Dec. 7, 2017

(65) Prior Publication Data
US 2019/0296238 A1  Sep. 26, 2019

(30) Foreign Application Priority Data
Jun. 2, 2016 (KR) .................. 10-2016-0069085

(51) Int. Cl.
*H10K 85/60* (2023.01)
*C07C 211/61* (2006.01)
(Continued)

(52) U.S. Cl.
CPC ........... *H10K 85/633* (2023.02); *C07C 15/27* (2013.01); *C07C 211/61* (2013.01); *C07D 235/08* (2013.01); *C07D 401/10* (2013.01); *C07D 405/10* (2013.01); *C09K 11/06* (2013.01); *H10K 50/00* (2023.02); *H10K 85/615* (2023.02); *H10K 85/622* (2023.02); *H10K 85/626* (2023.02); *H10K 85/654* (2023.02);
(Continued)

(58) Field of Classification Search
CPC ............ H01L 51/5056; H01L 51/5072; H01L 51/0072; H01L 51/006; H01L 51/0052; C07C 2603/18; H10K 50/16; H10K 50/15; H10K 85/6572; H10K 85/633
See application file for complete search history.

(56) References Cited

U.S. PATENT DOCUMENTS

2006/0147747 A1 * 7/2006 Yamamoto .......... H01L 51/0052
428/917
2007/0104977 A1 5/2007 Arakane et al.
(Continued)

FOREIGN PATENT DOCUMENTS

JP 2002038141 A 2/2002
JP 3838766 B2 10/2006
(Continued)

OTHER PUBLICATIONS

Chinese Search Report for Application No. 201780033292.0 dated Mar. 16, 2020, 3 pages.
(Continued)

*Primary Examiner* — Sean M DeGuire
(74) *Attorney, Agent, or Firm* — Lerner David LLP

(57) ABSTRACT

The present specification relates to an organic light emitting device.

20 Claims, 1 Drawing Sheet

(51) Int. Cl.
    *C07D 235/08*    (2006.01)
    *C07D 401/10*    (2006.01)
    *C07D 405/10*    (2006.01)
    *C09K 11/06*     (2006.01)
    *C07C 15/27*     (2006.01)
    *H10K 50/00*     (2023.01)
    *H10K 99/00*     (2023.01)
    *H10K 50/11*     (2023.01)
    *H10K 50/15*     (2023.01)
    *H10K 50/17*     (2023.01)
    *H10K 50/18*     (2023.01)
    *H10K 101/10*    (2023.01)

(52) U.S. Cl.
    CPC ..... *H10K 85/6572* (2023.02); *H10K 85/6574* (2023.02); *H10K 99/00* (2023.02); *C07C 2603/18* (2017.05); *C07C 2603/42* (2017.05); *C07C 2603/97* (2017.05); *C09K 2211/1007* (2013.01); *C09K 2211/1011* (2013.01); *C09K 2211/1014* (2013.01); *C09K 2211/1018* (2013.01); *H10K 50/11* (2023.02); *H10K 50/15* (2023.02); *H10K 50/17* (2023.02); *H10K 50/18* (2023.02); *H10K 85/624* (2023.02); *H10K 2101/10* (2023.02)

(56) References Cited

U.S. PATENT DOCUMENTS

| | | | |
|---|---|---|---|
| 2007/0131929 A1* | 6/2007 | Bae | C07D 519/00 428/917 |
| 2007/0200490 A1 | 8/2007 | Kawamura et al. | |
| 2010/0301312 A1 | 12/2010 | Jinde et al. | |
| 2010/0301318 A1* | 12/2010 | Kuma | C09B 57/001 257/E51.026 |
| 2011/0042660 A1* | 2/2011 | Kawamura | H05B 33/14 257/40 |
| 2011/0315965 A1 | 12/2011 | Takashima et al. | |
| 2012/0112173 A1 | 5/2012 | Matsumoto et al. | |
| 2013/0256649 A1 | 10/2013 | Huh et al. | |
| 2015/0053933 A1 | 2/2015 | Lee et al. | |
| 2015/0171356 A1 | 6/2015 | Nakamura et al. | |
| 2015/0179953 A1 | 6/2015 | Mujica-Fernaud et al. | |
| 2016/0181526 A1 | 6/2016 | Kato et al. | |

FOREIGN PATENT DOCUMENTS

| | | | | |
|---|---|---|---|---|
| JP | 2011003793 A | * | 1/2011 | |
| JP | 5280687 B2 | | 9/2013 | |
| KR | 20070023676 A | | 2/2007 | |
| KR | 2010004727 A | * | 1/2010 | ........... C07D 403/08 |
| KR | 20100106415 A | | 10/2010 | |
| KR | 20110114545 A | | 10/2011 | |
| KR | 20120048472 A | | 5/2012 | |
| KR | 20120076314 A | | 7/2012 | |
| KR | 101350581 B1 | | 1/2014 | |
| KR | 20150030659 A | | 3/2015 | |
| KR | 20150036721 A | | 4/2015 | |
| KR | 20150044592 A | | 4/2015 | |
| WO | 2003012890 A2 | | 2/2003 | |
| WO | 2015053403 A1 | | 4/2015 | |
| WO | 2015162912 A1 | | 10/2015 | |
| WO | WO-2015162912 A1 | * | 10/2015 | ............. H01L 51/50 |

OTHER PUBLICATIONS

Search report from International Application No. PCT/KR2017/005737, dated Sep. 11, 2017.

\* cited by examiner

[FIG. 1]
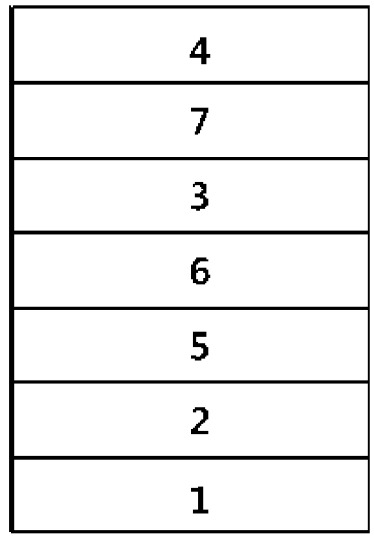
[FIG. 2]
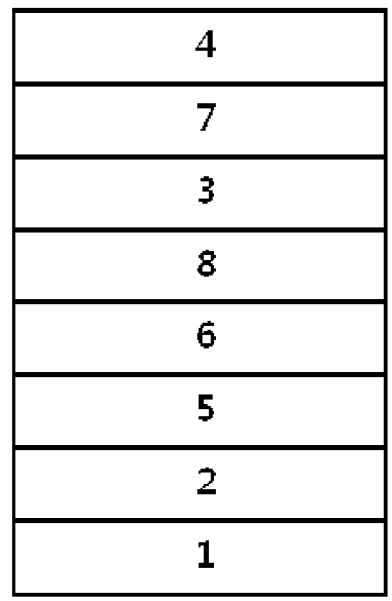

ORGANIC LIGHT-EMITTING ELEMENT

CROSS-REFERENCE TO RELATED APPLICATIONS

The present application is a national phase entry under 35 U.S.C. § 371 of International Application No. PCT/KR2017/005737 filed Jun. 1, 2017, which claims priority from Korean Patent Application No. 10-2016-0069085 filed Jun. 2, 2016, all of which are incorporated herein by reference.

TECHNICAL FIELD

The present specification relates to an organic light emitting device.

BACKGROUND ART

An organic light emitting device has a structure in which an organic thin film is disposed between two electrodes. When a voltage is applied to an organic light emitting device having the structure, electrons and holes injected from the two electrodes combine with each other in the organic thin film to make a pair, and then, emit light while being extinguished. The organic thin film may be composed of a single layer or multi layers, if necessary.

A material for the organic thin film may have a light emitting function, if necessary. For example, as the material for the organic thin film, it is also possible to use a compound, which may itself constitute a light emitting layer alone, or it is also possible to use a compound, which may serve as a host or a dopant of a host-dopant-based light emitting layer. In addition, as a material for the organic thin film, it is also possible to use a compound, which may perform a function such as hole injection, hole transport, electron blocking, hole blocking, electron transport or electron injection.

In order to improve the performance, service life, or efficiency of the organic light emitting device, there is a continuous need for developing a material for an organic thin film.

REFERENCES OF THE RELATED ART

Patent Documents

International Publication No. 2003-012890

DISCLOSURE

Technical Problem

The present specification provides an organic light emitting device.

Technical Solution

Provided is an organic light emitting device including: a first electrode; a second electrode disposed to face the first electrode; and a light emitting layer disposed between the first electrode and the second electrode, in which the light emitting device includes an organic material layer including a compound represented by the following Chemical Formula 1 between the first electrode and the light emitting layer and an organic material layer including a compound represented by the following Chemical Formula 2 between the second electrode and the light emitting layer.

[Chemical Formula 1]

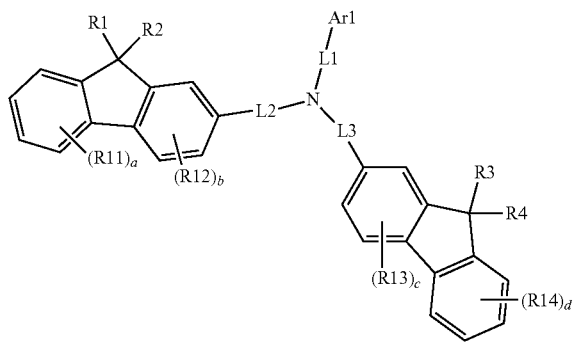

[Chemical Formula 2]

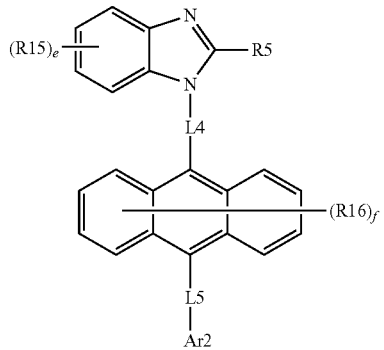

In Chemical Formulae 1 and 2,

Ar1 and Ar2 are the same as or different from each other, and are each independently a substituted or unsubstituted aryl group having 6 to 30 carbon atoms; or a substituted or unsubstituted heterocyclic group having 2 to 30 carbon atoms, L1 to L5 are the same as or different from each other, and are each independently a direct bond; or a substituted or unsubstituted arylene group having 6 to 30 carbon atoms, R1 to R5 are the same as or different from each other, and are each independently hydrogen; deuterium; a substituted or unsubstituted alkyl group having 1 to 20 carbon atoms; a substituted or unsubstituted cycloalkyl group having 3 to 30 carbon atoms; or a substituted or unsubstituted aryl group having 6 to 30 carbon atoms, or R1 and R2 or R3 and R4 may be bonded to each other to form a ring, R11 to R16 are the same as or different from each other, and are each independently hydrogen; deuterium; a substituted or unsubstituted alkyl group having 1 to 20 carbon atoms; a substituted or unsubstituted cycloalkyl group having 3 to 30 carbon atoms; a substituted or unsubstituted aryl group having 6 to 30 carbon atoms; or a substituted or unsubstituted heterocyclic group having 2 to 30 carbon atoms, and a, d, and e are each an integer from 0 to 4, b and c are each an integer from 0 to 3, f is an integer from 0 to 8, and when a to f are 2 or more, the substituents in the parenthesis are the same as or different from each other.

Advantageous Effects

An organic light emitting device according to an exemplary embodiment of the present application has a low driving voltage, and the service life characteristics of the device may be improved by the thermal stability of a compound.

Since Chemical Formula 1 in the form of a monoamine having two fluorene-type substituents has high hole mobility and a highest occupied molecular orbital (HOMO) value of 5.3 eV to 5.4 eV, the organic light emitting device has a characteristic in that the driving voltage is decreased when Chemical Formula 1 is used in not only a hole injection layer but also a hole transporting layer, still, the service life is reduced. Chemical Formula 2 having a benzimidazole-type substituent at the ninth position of anthracene has excellent thermal stability, and when Chemical Formula 2 is used as an electron transporting layer, the organic light emitting device has long service life characteristics, but the driving voltage is increased.

Accordingly, when a charge balance is established by using a compound of Chemical Formula 1 as a hole injection layer or a hole transporting layer and simultaneously using a compound of Chemical Formula 2 in an electron transporting layer, the organic light emitting device has low driving voltage and long service life characteristics, and the efficiency characteristics may be improved.

DESCRIPTION OF DRAWINGS

FIG. 1 illustrates an example of an organic light emitting device in which a substrate 1, a positive electrode 2, a hole injection layer 5, a hole transporting layer 6, a light emitting layer 3, an electron transporting layer 7, and a negative electrode 4 are sequentially stacked.

FIG. 2 illustrates an example of an organic light emitting device in which the substrate 1, the positive electrode 2, the hole injection layer 5, the hole transporting layer 6, an electron blocking layer 8, the light emitting layer 3, the electron transporting layer 7, and the negative electrode 4 are sequentially stacked.

MODE FOR INVENTION

Hereinafter, the present specification will be described in more detail.

Examples of the substituents in the present specification will be described below, but are not limited thereto.

The term "substitution" means that a hydrogen atom bonded to a carbon atom of a compound is changed into another substituent, and a position to be substituted is not limited as long as the position is a position at which the hydrogen atom is substituted, that is, a position at which the substituent may be substituted, and when two or more are substituted, the two or more substituents may be the same as or different from each other.

In the present specification, the term "substituted or unsubstituted" means being substituted with one or two or more substituents selected from the group consisting of deuterium; a halogen group; a cyano group; an alkyl group; a cycloalkyl group; an aryl group; and a heterocyclic group, being substituted with a substituent to which two or more substituents among the exemplified substituents are linked, or having no substituent. For example, "the substituent to which two or more substituents are linked" may be a biphenyl group. That is, the biphenyl group may also be an aryl group, and may be interpreted as a substituent to which two phenyl groups are linked.

In the present specification, examples of a halogen group include fluorine, chlorine, bromine or iodine.

In the present specification, the alkyl group may be straight or branched, and the number of carbon atoms thereof is not particularly limited, but is preferably 1 to 50. Specific examples thereof include methyl, ethyl, propyl, n-propyl, isopropyl, butyl, n-butyl, isobutyl, tert-butyl, sec-butyl, 1-methylbutyl, 1-ethylbutyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethylpropyl, 1,1-dimethylpropyl, isohexyl, 2-methylpentyl, 4-methylhexyl, 5-methylhexyl, and the like, but are not limited thereto.

In the present specification, a cycloalkyl group is not particularly limited, but the number of carbon atoms thereof is preferably 3 to 60, and specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, when the aryl group is a monocyclic aryl group, the number of carbon atoms thereof is not particularly limited, but is preferably 6 to 25. Specific examples of the monocyclic aryl group include a phenyl group, a biphenyl group, a terphenyl group, and the like, but are not limited thereto.

When the aryl group is a polycyclic aryl group, the number of carbon atoms thereof is not particularly limited, but is preferably 10 to 24. Specific examples of the polycyclic aryl group include a naphthyl group, an anthracene group, a phenanthrene group, a pyrene group, a perylenyl group, a chrysenyl group, a fluorene group, and the like, but are not limited thereto.

In the present specification, the fluorene group may be substituted, and adjacent substituents may be bonded to each other to form a ring.

When the fluorene group is substituted, the group may be

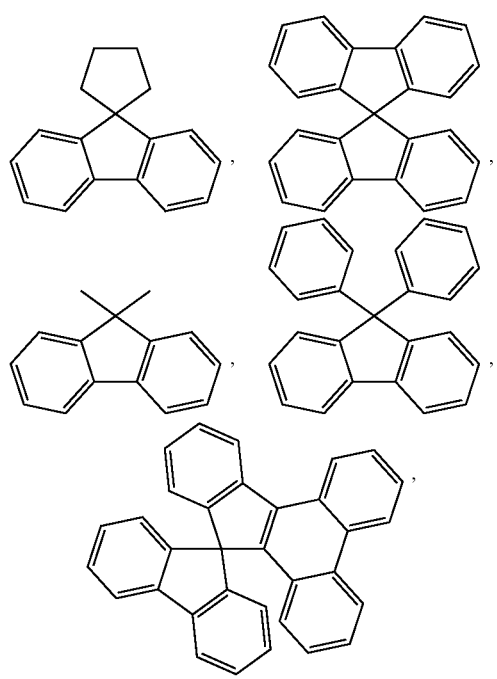

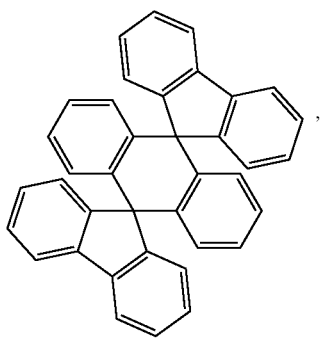

and the like, but is not limited thereto.

In the present specification, a heterocyclic group includes one or more of an atom other than carbon, that is, a heteroatom, and specifically, the heteroatom may include one or more atoms selected from the group consisting of O, N, Se, and S, and the like. The number of carbon atoms of the heterocyclic group is not particularly limited, but is preferably 2 to 60. Examples of the heterocyclic group include a thiophenyl group, a furanyl group, a pyrrole group, an imidazolyl group, a thiazolyl group, an oxazolyl group, an oxadiazolyl group, a triazolyl group, a pyridyl group, a bipyridyl group, a pyrimidyl group, a triazinyl group, an acridyl group, a hydroacridyl group (for example,

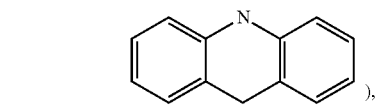 [SMILES: c1ccc2c(c1)Cc1ccccc1N2]

), a pyridazinyl group, a pyrazinyl group, a qinolinyl group, a quinazolinyl group, a quinoxalinyl group, a phthalazinyl group, a pyridopyrimidinyl group, a pyridopyrazinyl group, a pyrazinopyrazinyl group, an isoquinolinyl group, an indole group, a carbazolyl group, a benzoxazolyl group, a benzimidazolyl group, a benzothiazolyl group, a benzocarbazolyl group, a dibenzocarbazolyl group, a benzothiophenyl group, a dibenzothiophenyl group, a benzofuranyl group, a dibenzofuranyl group; a benzosilole group; a dibenzosilole group; a phenanthrolinyl group, a thiazolyl group, an isoxazolyl group, an oxadiazolyl group, a thiadiazolyl group, a benzothiazolyl group, a phenothiazinyl group, a phenoxazinyl group, and fused structures thereof, and the like, but are not limited thereto. In addition, examples of the heterocyclic group include a heterocyclic structure including a sulfonyl group, for example,

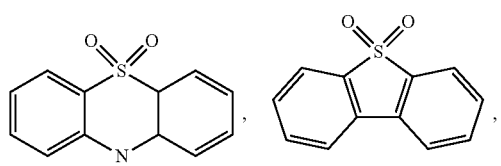

and the like.

In an exemplary embodiment of the present specification, Chemical Formula 1 is represented by any one of the following Chemical Formulae 1-1 to 1-6.

[Chemical Formula 1-1]

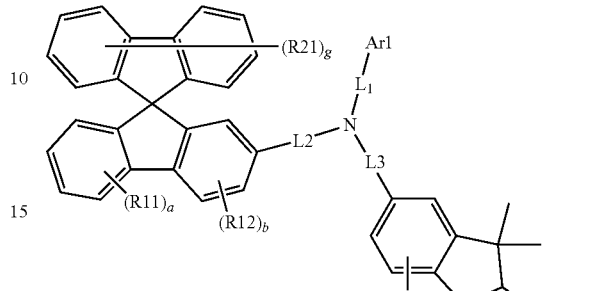

[Chemical Formula 1-2]

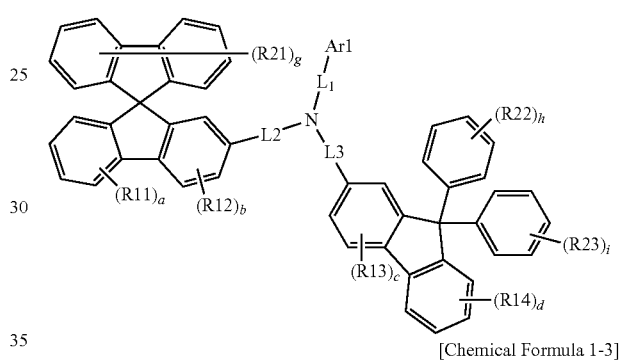

[Chemical Formula 1-3]

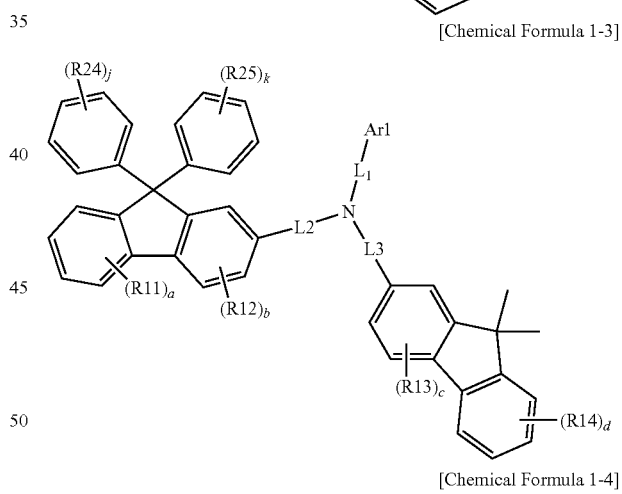

[Chemical Formula 1-4]

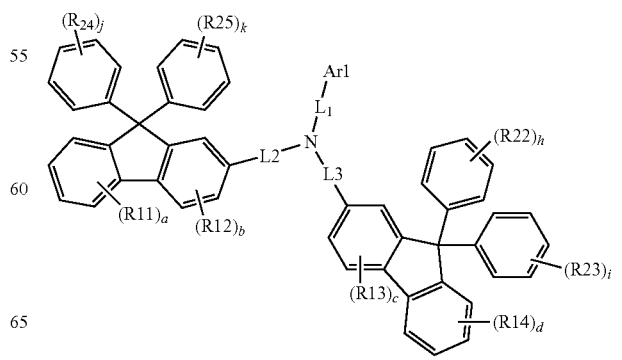

-continued

[Chemical Formula 1-5]

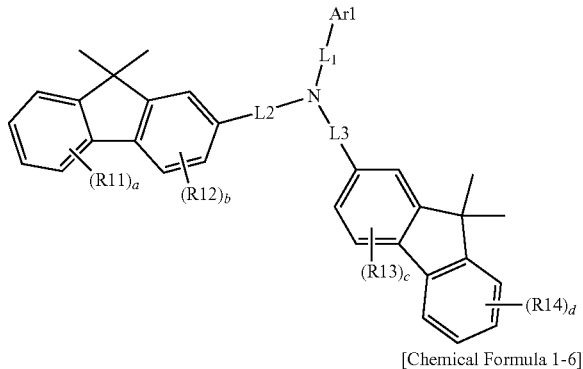

[Chemical Formula 1-6]

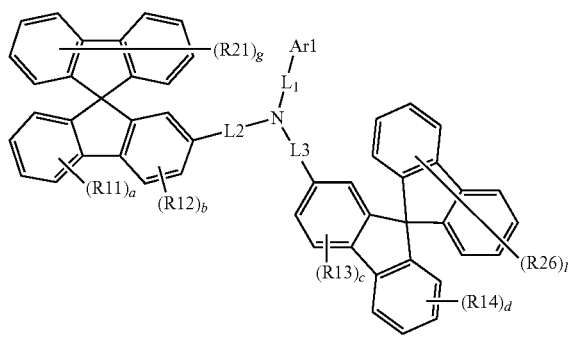

In Chemical Formulae 1-1 to 1-6, the definitions of Ar1, L1 to L3, R11 to R14, and a to d are the same as those in Chemical Formula 1, R21 to R26 are the same as or different from each other, and are each independently hydrogen; deuterium; a substituted or unsubstituted alkyl group having 1 to 20 carbon atoms; a substituted or unsubstituted cycloalkyl group having 3 to 30 carbon atoms; a substituted or unsubstituted aryl group having 6 to 30 carbon atoms; or a substituted or unsubstituted heterocyclic group having 2 to 30 carbon atoms, and g and l are an integer from 0 to 8, h to k are each an integer from 0 to 5, and when g to l are 2 or more, the substituents in the parenthesis are the same as or different from each other.

In an exemplary embodiment of the present specification, Ar1 and Ar2 are the same as or different from each other, and are each independently a substituted or unsubstituted phenyl group; a substituted or unsubstituted naphthyl group; a substituted or unsubstituted biphenyl group; a substituted or unsubstituted terphenyl group; a substituted or unsubstituted quarterphenyl group; a substituted or unsubstituted fluorene group; a substituted or unsubstituted phenanthrene group; a substituted or unsubstituted triphenylene group; a substituted or unsubstituted anthracene group; a substituted or unsubstituted fluoranthene group; a substituted or unsubstituted pyrene group; a substituted or unsubstituted carbazole group; a substituted or unsubstituted benzocarbazole group; a substituted or unsubstituted benzonaphthofuran group; a substituted or unsubstituted dibenzofuran group; a substituted or unsubstituted dibenzothiophene group; a substituted or unsubstituted pyridine group; or a substituted or unsubstituted quinoline group.

In an exemplary embodiment of the present specification, Ar1 is a substituted or unsubstituted phenyl group; a substituted or unsubstituted naphthyl group; a substituted or unsubstituted biphenyl group; a substituted or unsubstituted terphenyl group; a substituted or unsubstituted quarterphenyl group; a substituted or unsubstituted fluorene group; a substituted or unsubstituted phenanthrene group; a substituted or unsubstituted triphenylene group; a substituted or unsubstituted anthracene group; a substituted or unsubstituted fluoranthene group; a substituted or unsubstituted pyrene group; a substituted or unsubstituted carbazole group; a substituted or unsubstituted benzocarbazole group; a substituted or unsubstituted dibenzofuran group; or a substituted or unsubstituted dibenzothiophene group.

In an exemplary embodiment of the present specification, Ar1 is a phenyl group; a naphthyl group; a biphenyl group; a terphenyl group; a quarterphenyl group; a fluorene group unsubstituted or substituted with an alkyl group or an aryl group; a phenanthrene group; a triphenylene group; an anthracene group; a fluoranthene group; a pyrene group; a carbazole group unsubstituted or substituted with an aryl group; a benzocarbazole group unsubstituted or substituted with an aryl group; a dibenzofuran group; a dibenzothiophene group; a pyridine group; or a quinoline group.

In an exemplary embodiment of the present specification, Ar1 is a phenyl group; a naphthyl group; a biphenyl group; a terphenyl group; a quarterphenyl group; a dimethylfluorene group; a diphenylfluorene group; a phenanthrene group; a triphenylene group; an anthracene group; a fluoranthene group; a pyrene group; a carbazole group unsubstituted or substituted with a phenyl group, a biphenyl group, or a naphthyl group; a benzocarbazole group unsubstituted or substituted with a phenyl group, a biphenyl group, or a naphthyl group; a dibenzofuran group; a dibenzothiophene group; a pyridine group; or a quinoline group.

In an exemplary embodiment of the present specification, Ar1 is a phenyl group; a naphthyl group; a biphenyl group; a terphenyl group; a dimethylfluorene group; a diphenylfluorene group; a phenanthrene group; a triphenylene group; a fluoranthene group; a pyrene group; a dibenzofuran group; a dibenzothiophene group; a pyridine group; or a quinoline group.

In an exemplary embodiment of the present specification, Ar2 is a substituted or unsubstituted phenyl group; a substituted or unsubstituted naphthyl group; a substituted or unsubstituted biphenyl group; a substituted or unsubstituted terphenyl group; a substituted or unsubstituted quarterphenyl group; a substituted or unsubstituted fluorene group; a substituted or unsubstituted phenanthrene group; a substituted or unsubstituted triphenylene group; a substituted or unsubstituted anthracene group; a substituted or unsubstituted fluoranthene group; a substituted or unsubstituted pyrene group; a substituted or unsubstituted pyridine group; a substituted or unsubstituted benzonaphthofuran group; a substituted or unsubstituted dibenzofuran group; or a substituted or unsubstituted dibenzothiophene group.

In an exemplary embodiment of the present specification, Ar2 is a phenyl group; a naphthyl group; a biphenyl group; a terphenyl group; a quarterphenyl group; a fluorene group unsubstituted or substituted with an alkyl group; a phenanthrene group; a triphenylene group; an anthracene group; a fluoranthene group; a pyrene group; a carbazole group unsubstituted or substituted with an aryl group; a benzocarbazole group unsubstituted or substituted with an aryl group; a benzonapthofuran group; a dibenzofuran group; a dibenzothiophene group; a pyridine group; or a quinoline group.

In an exemplary embodiment of the present specification, Ar2 is a phenyl group; a naphthyl group; a biphenyl group; a terphenyl group; a quarterphenyl group; a fluorene group unsubstituted or substituted with an alkyl group or an aryl group; a phenanthrene group; a triphenylene group; an anthracene group; a fluoranthene group; a pyrene group; a pyridine group; a benzonaphthofuran group; a dibenzofuran group; or a dibenzothiophene group.

In an exemplary embodiment of the present specification, Ar2 is a phenyl group; a naphthyl group; a biphenyl group; a terphenyl group; a quarterphenyl group; a dimethylfluorene group; a diphenylfluorene group; a phenanthrene group; a triphenylene group; an anthracene group; a fluoranthene group; a pyrene group; a pyridine group; a benzonaphthofuran group; a dibenzofuran group; or a dibenzothiophene group.

In an exemplary embodiment of the present specification, L1 to L5 are the same as or different from each other, and are each independently a direct bond; a substituted or unsubstituted phenylene group; a substituted or unsubstituted naphthylene group; a substituted or unsubstituted biphenylylene group; a substituted or unsubstituted terphenylylene group; or a substituted or unsubstituted divalent phenanthrene group.

In an exemplary embodiment of the present specification, L1 to L5 are the same as or different from each other, and are each independently a direct bond; or a substituted or unsubstituted phenylene group.

In an exemplary embodiment of the present specification, L1 is a direct bond; or a phenylene group.

In an exemplary embodiment of the present specification, L2 to L5 are the same as or different from each other, and are each independently a direct bond; or a substituted or unsubstituted phenylene group.

In an exemplary embodiment of the present specification, L2 is a direct bond; or a phenylene group.

In an exemplary embodiment of the present specification, L3 is a direct bond; or a phenylene group.

In an exemplary embodiment of the present specification, L4 is a direct bond; or a phenylene group.

In an exemplary embodiment of the present specification, L4 is a phenylene group.

In an exemplary embodiment of the present specification, L5 is a direct bond; or a phenylene group.

In an exemplary embodiment of the present specification, R5 is a substituted or unsubstituted alkyl group having 1 to 20 carbon atoms; or a substituted or unsubstituted aryl group having 6 to 30 carbon atoms.

In an exemplary embodiment of the present specification, R5 is a methyl group; an ethyl group; a phenyl group; a biphenyl group; or a naphthyl group.

In an exemplary embodiment of the present specification, R5 is a methyl group; an ethyl group; or a phenyl group.

In an exemplary embodiment of the present specification, R11 to R16 are the same as or different from each other, and are each independently hydrogen; deuterium; a substituted or unsubstituted alkyl group having 1 to 20 carbon atoms; or a substituted or unsubstituted aryl group having 6 to 30 carbon atoms.

In an exemplary embodiment of the present specification, R11 to R16 are the same as or different from each other, and are each independently hydrogen; deuterium; or a substituted or unsubstituted aryl group having 6 to 30 carbon atoms.

In an exemplary embodiment of the present specification, R11 to R16 are the same as or different from each other, and are each independently hydrogen; deuterium; a substituted or unsubstituted phenyl group; a substituted or unsubstituted biphenyl group; a substituted or unsubstituted naphthyl group; or a substituted or unsubstituted fluorene group.

In an exemplary embodiment of the present specification, R11 to R16 are the same as or different from each other, and are each independently hydrogen; deuterium; a phenyl group; a biphenyl group; a naphthyl group; or a dimethylfluorene group.

In an exemplary embodiment of the present specification, R11 to R16 are the same as or different from each other, and are each independently hydrogen or deuterium.

In an exemplary embodiment of the present specification, R11 to R16 are hydrogen.

In an exemplary embodiment of the present specification, R11 and R13 to R16 are hydrogen, and R12 is a substituted or unsubstituted aryl group.

In an exemplary embodiment of the present specification, R11 and R13 to R16 are hydrogen, and R12 is an aryl group.

In an exemplary embodiment of the present specification, R11 and R13 to R16 are hydrogen, and R12 is a phenyl group.

In an exemplary embodiment of the present specification, R21 to R26 are the same as or different from each other, and are each independently hydrogen or deuterium.

In an exemplary embodiment of the present specification, R21 to R26 are hydrogen.

In an exemplary embodiment of the present specification, the compound represented by Chemical Formula 1 is selected from the following structural formulae.

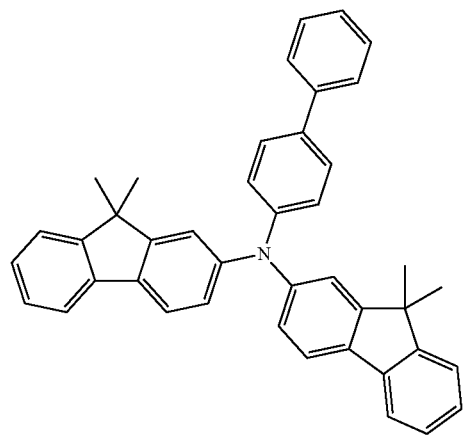

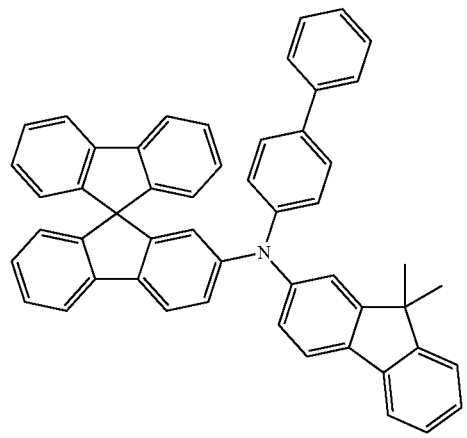

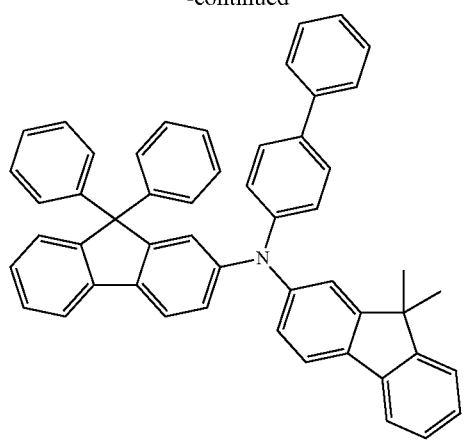
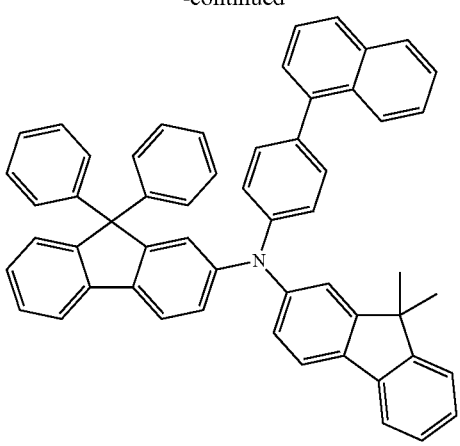
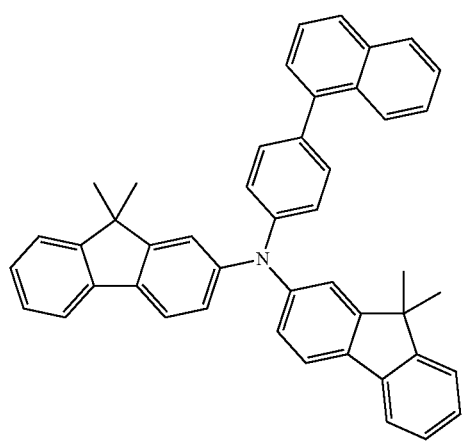
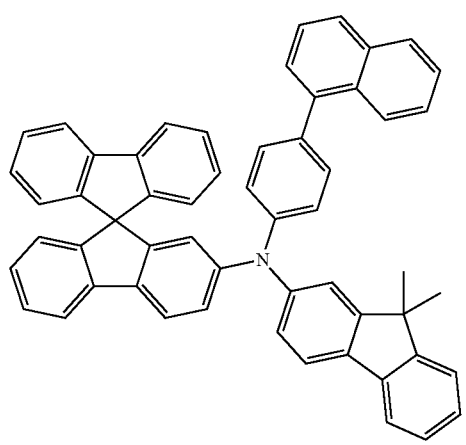
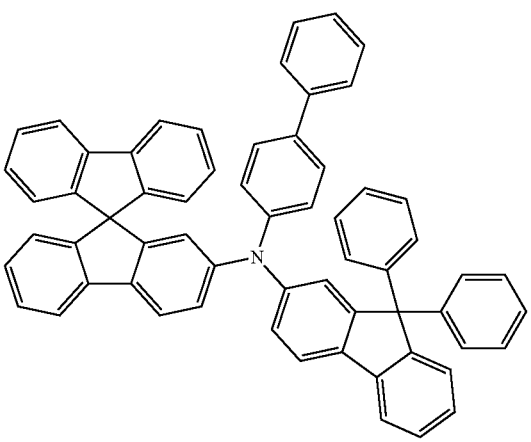

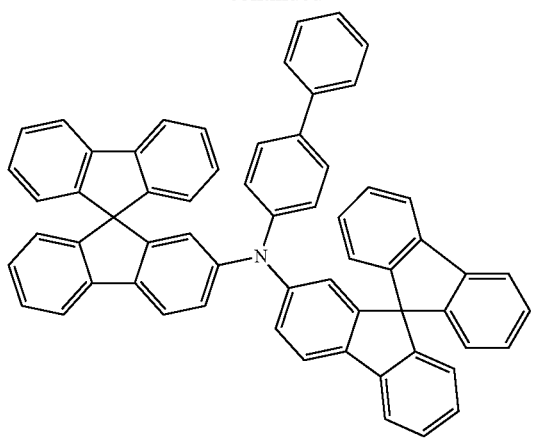
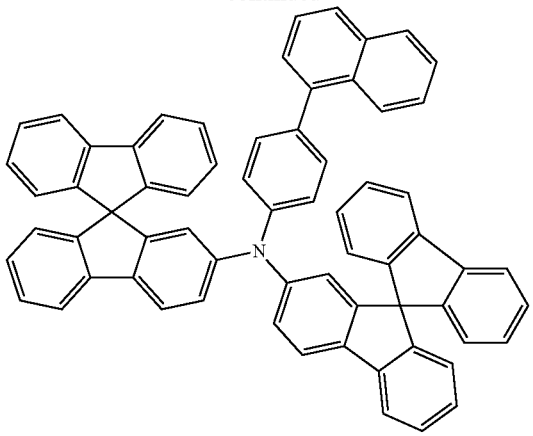
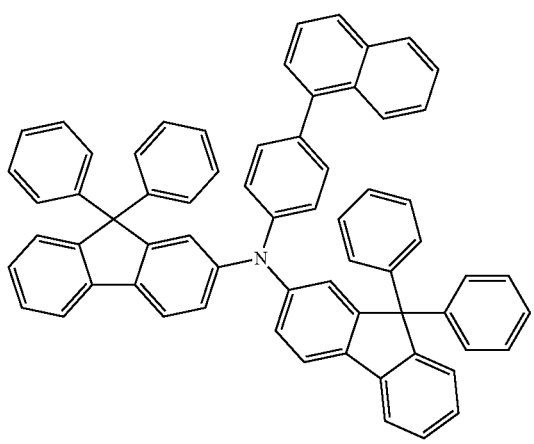
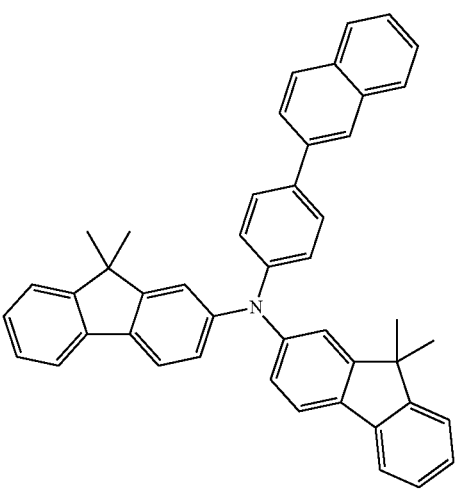
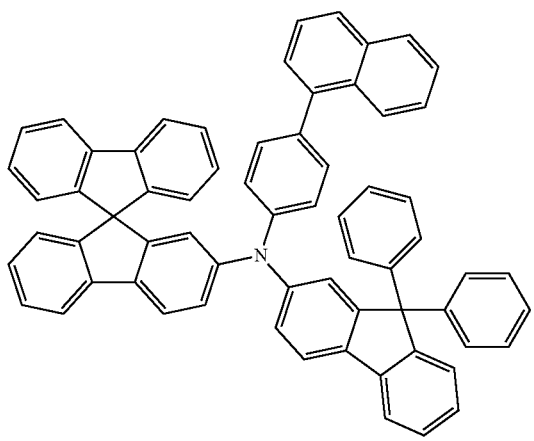
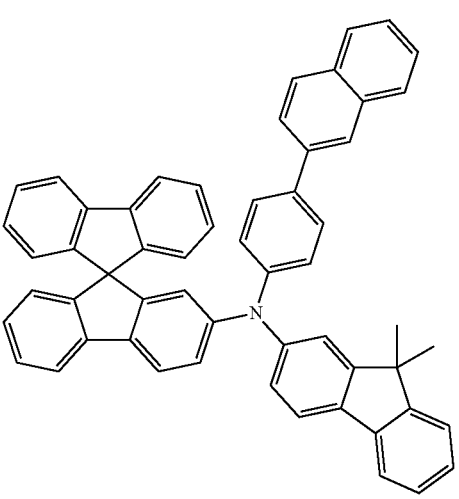

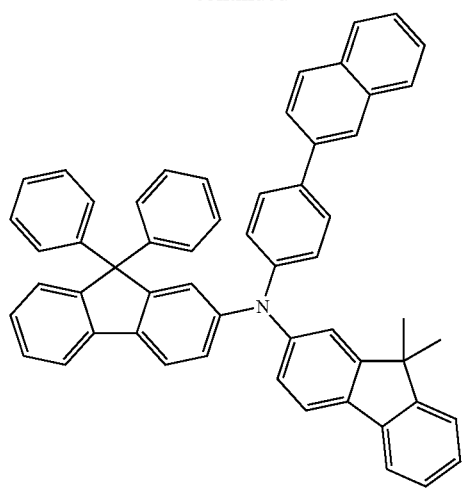
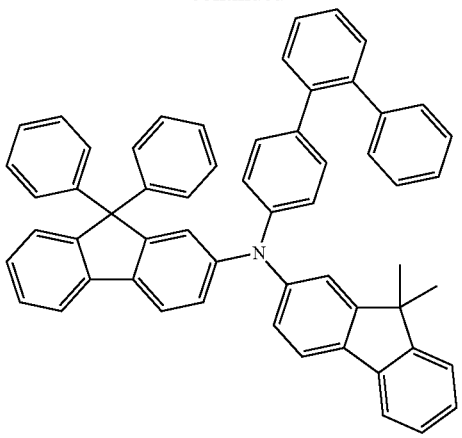
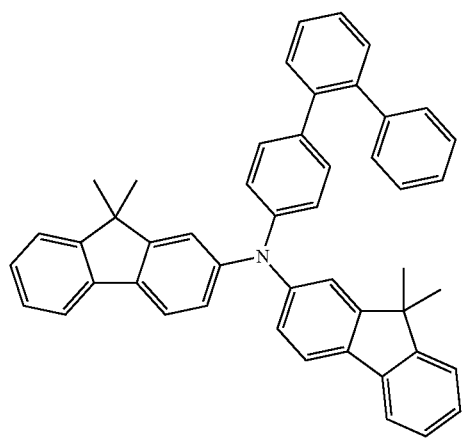
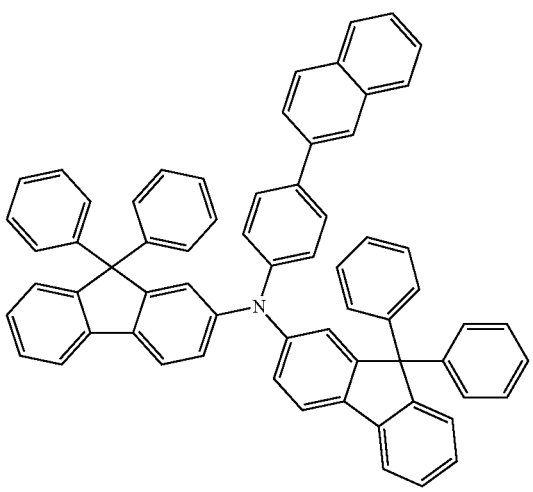
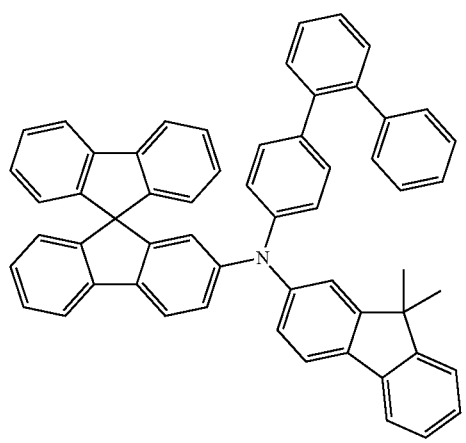
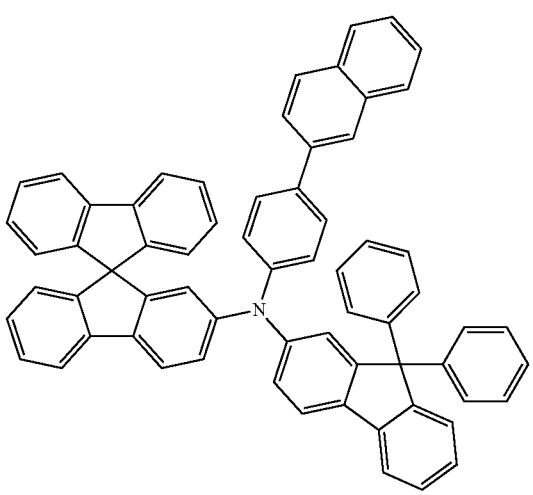

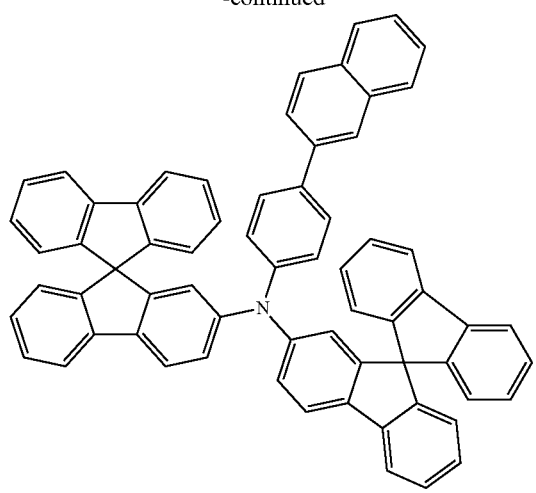
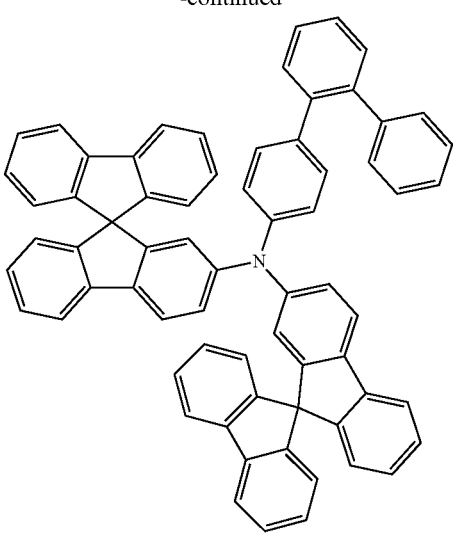
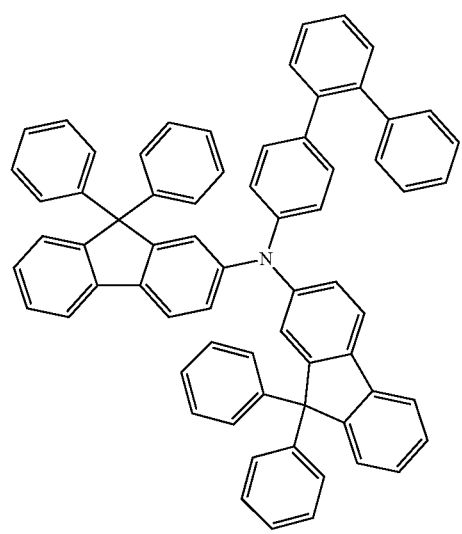
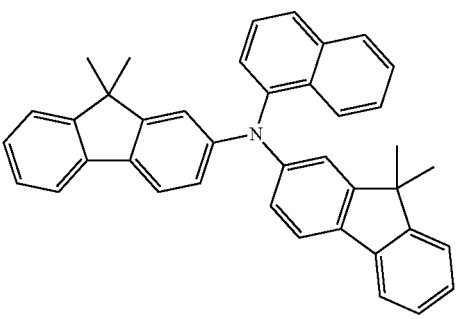
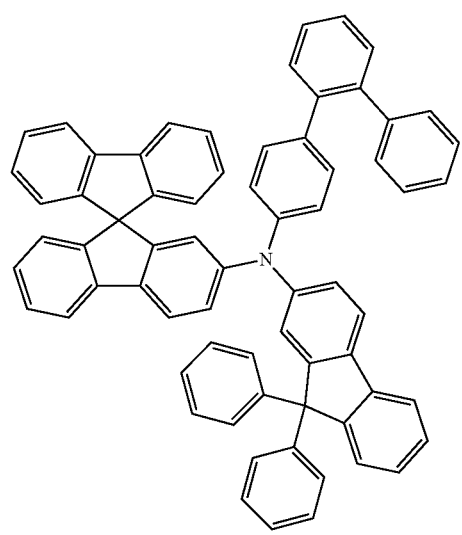
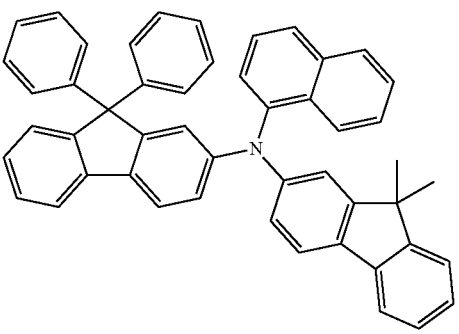

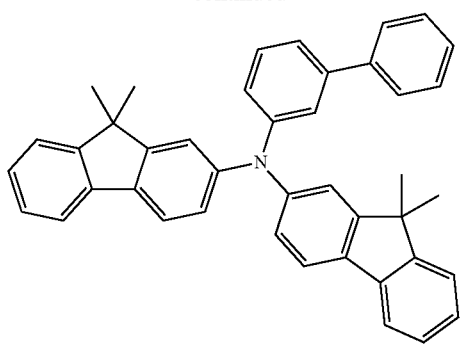
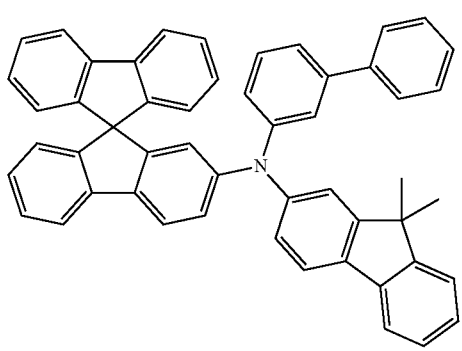
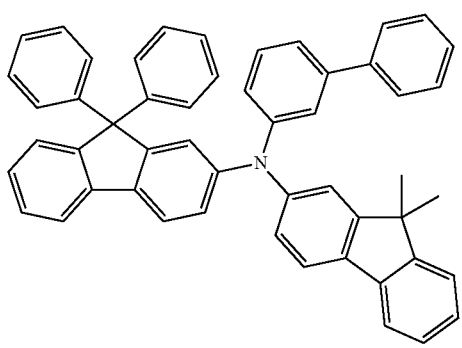
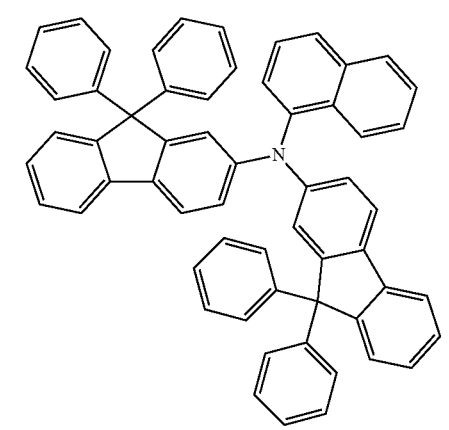
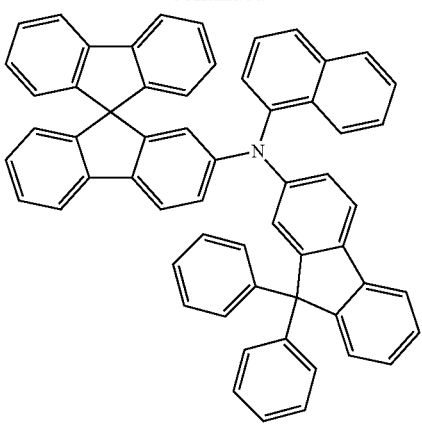
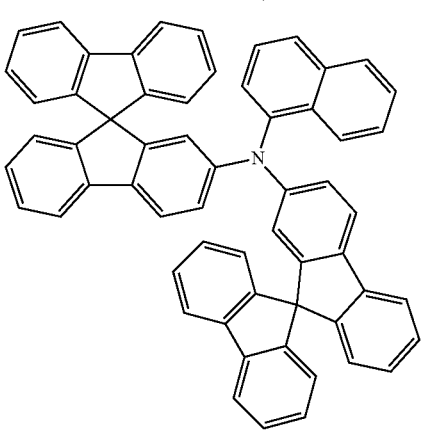
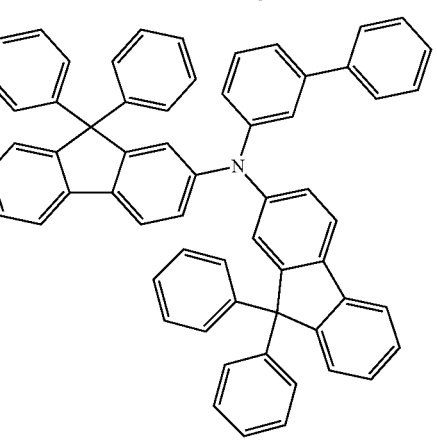
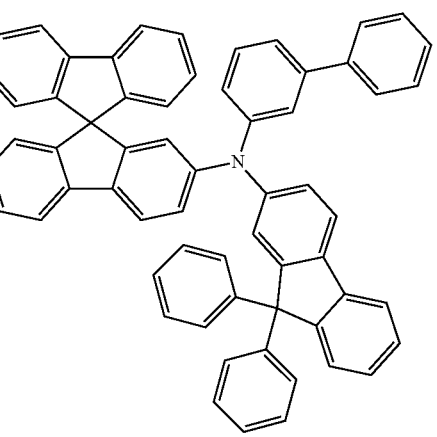

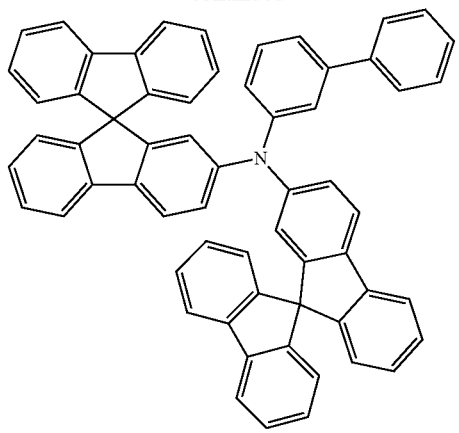
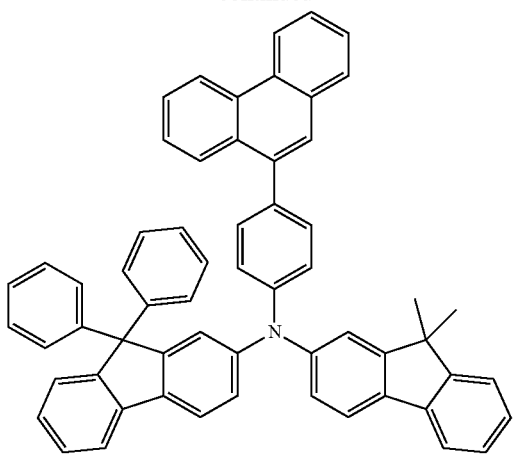
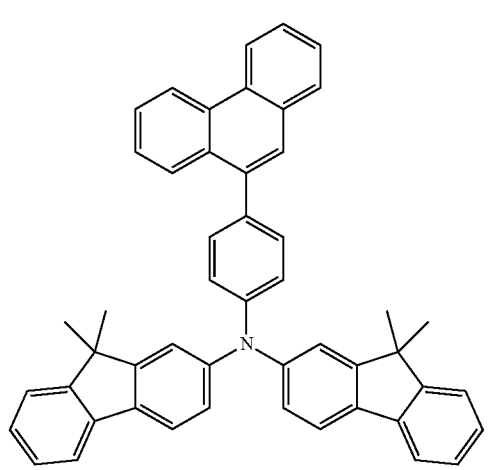
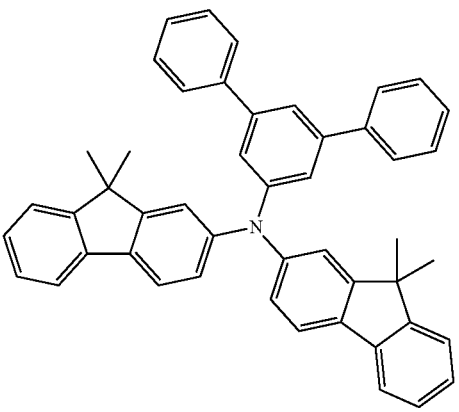
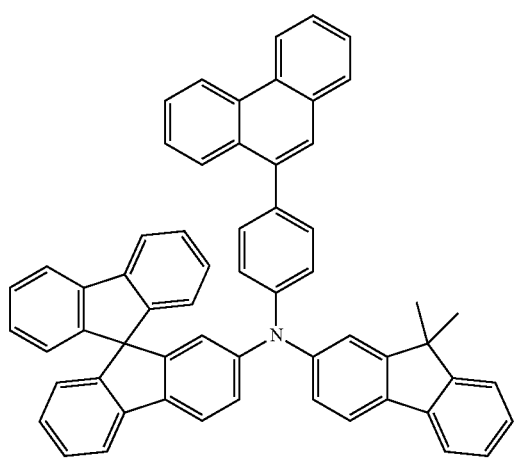
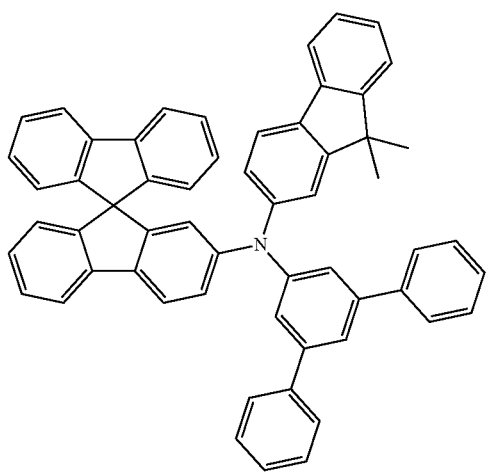

23
-continued
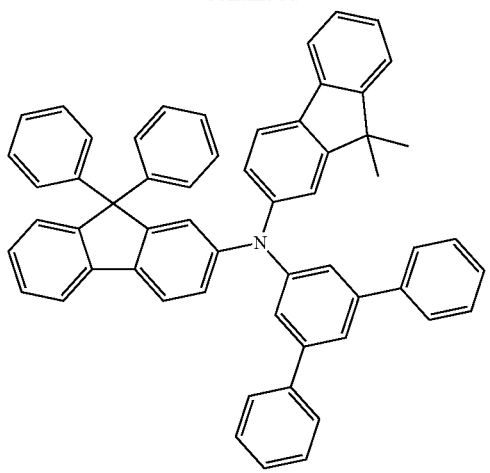
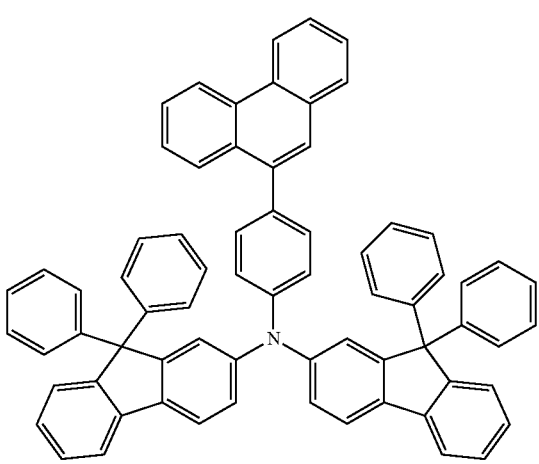
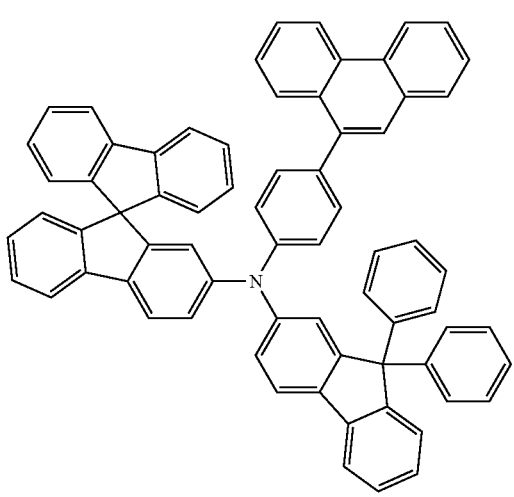
24
-continued
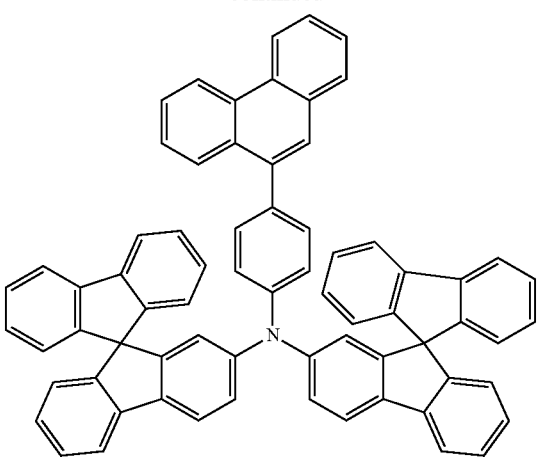
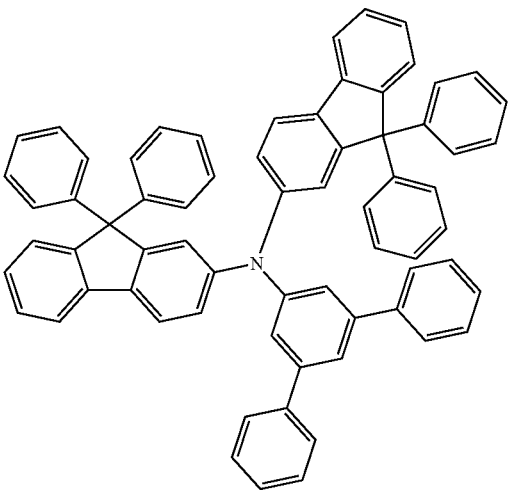
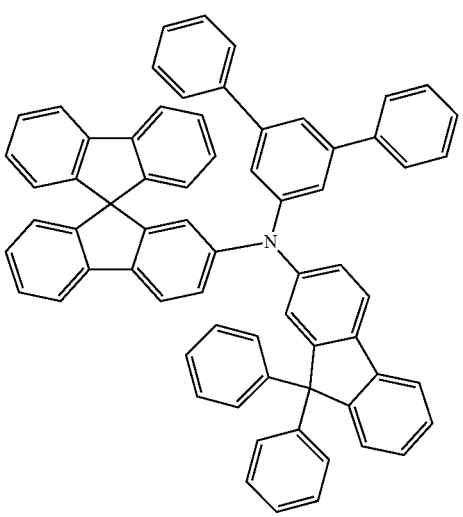

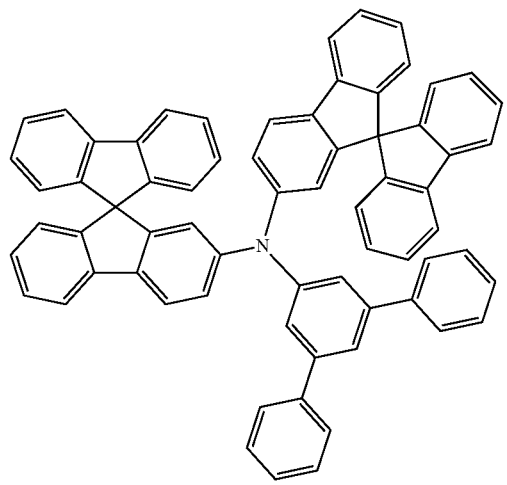
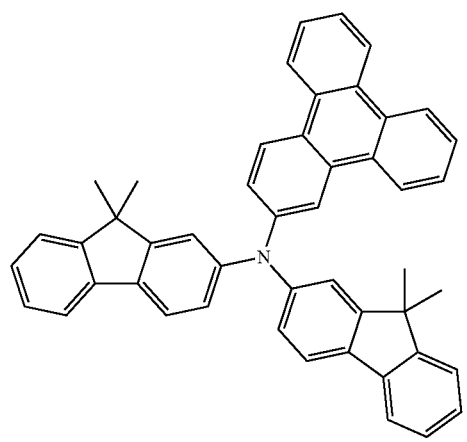
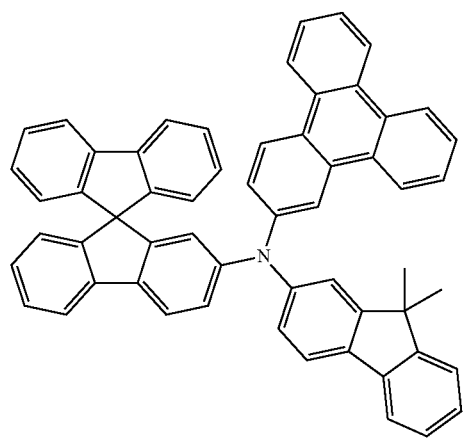
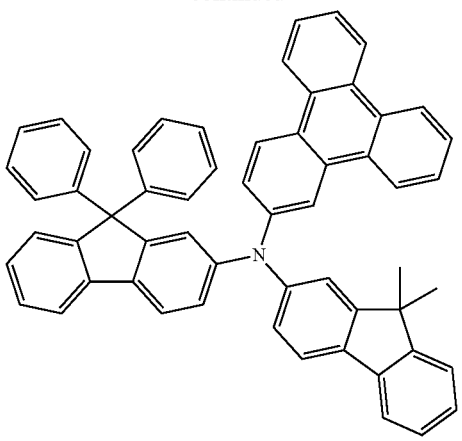
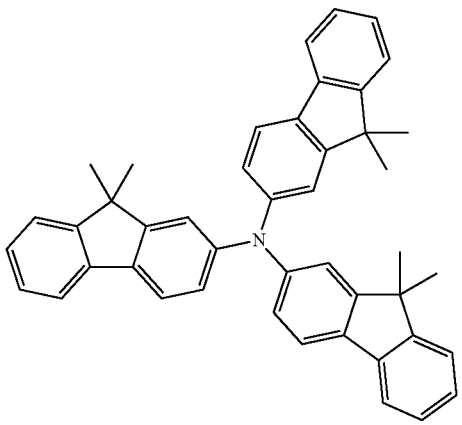
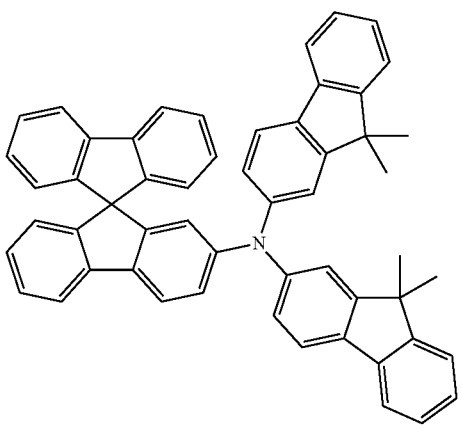
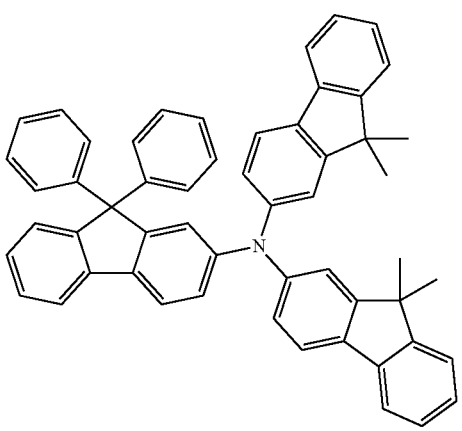

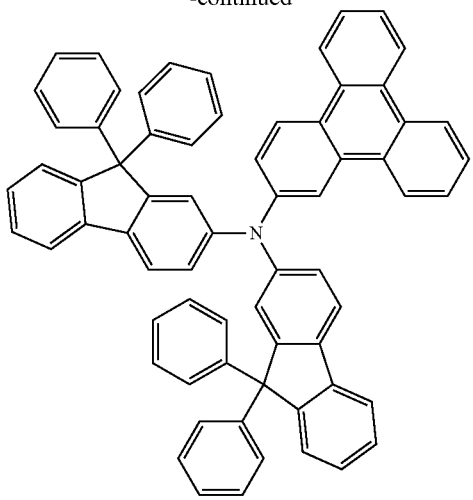
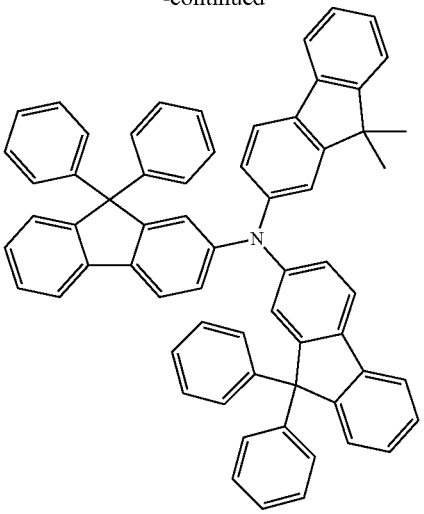
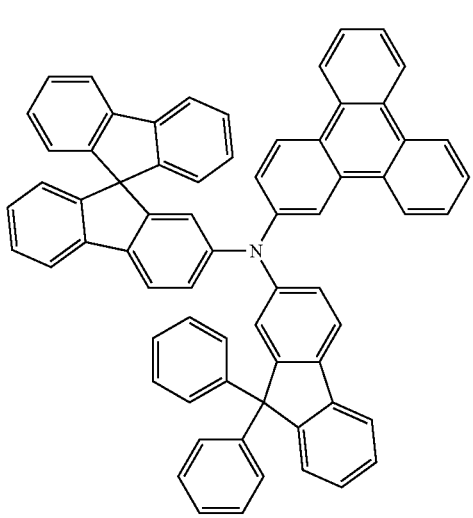
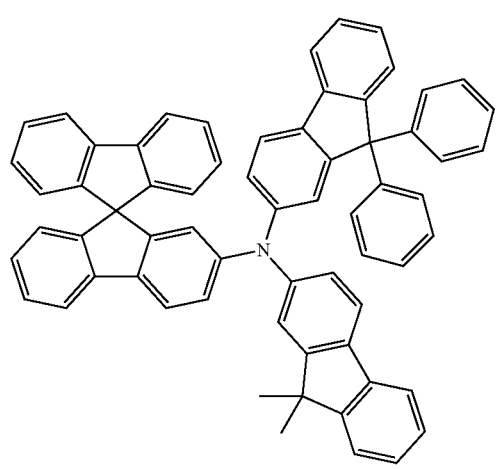
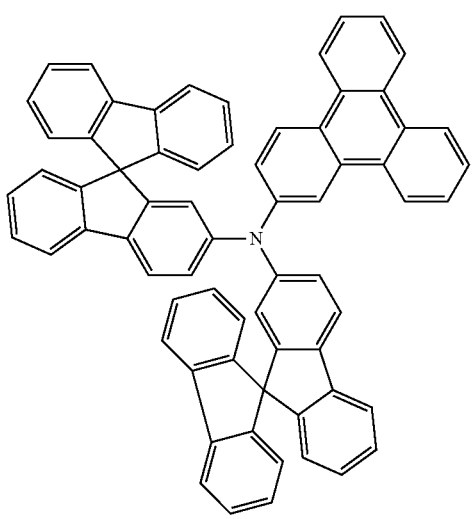
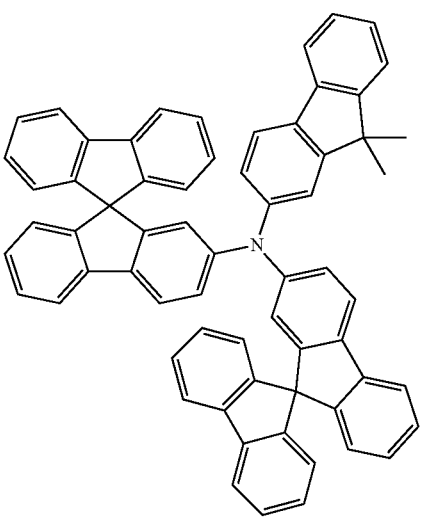

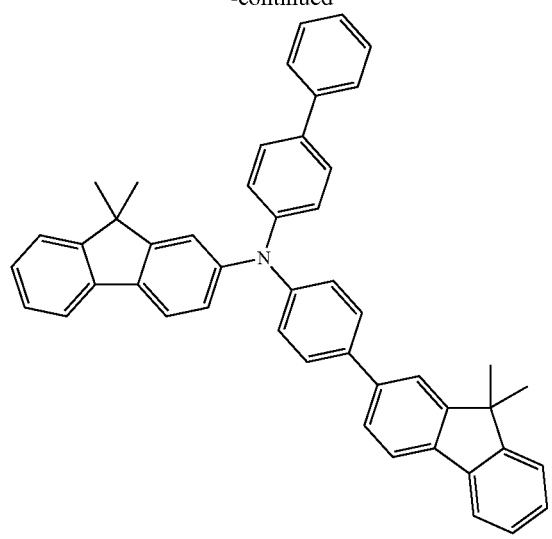
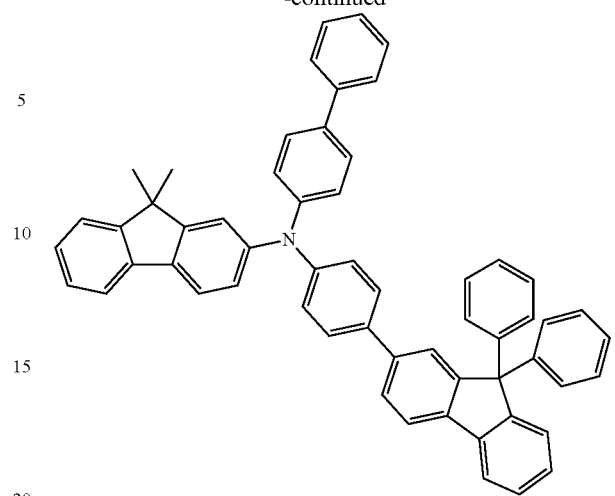
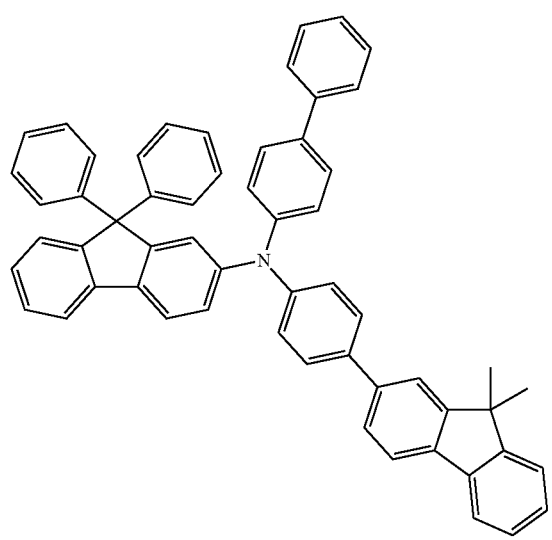
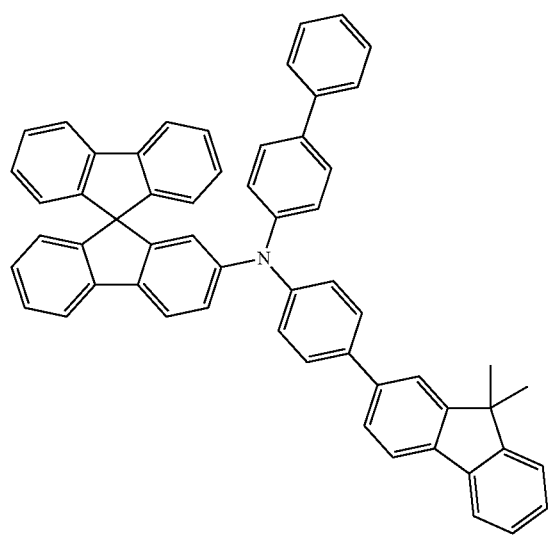
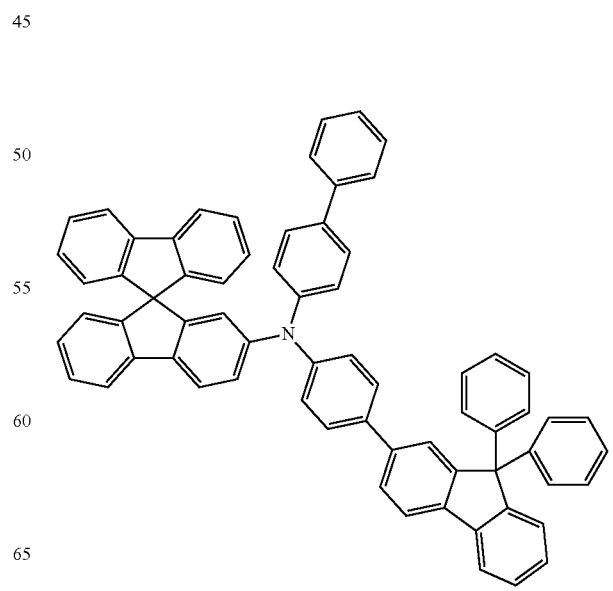

31
-continued
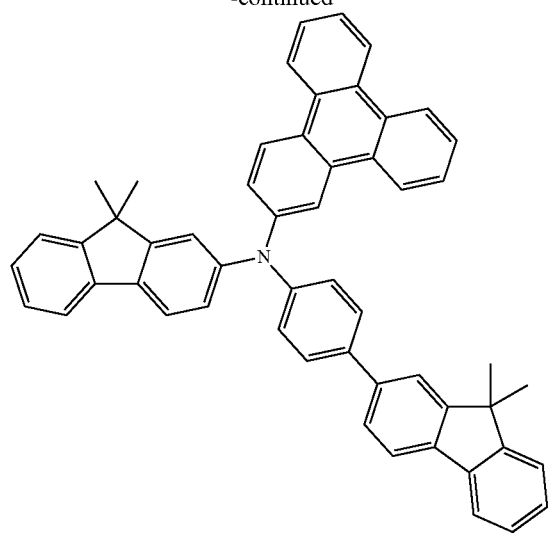
32
-continued
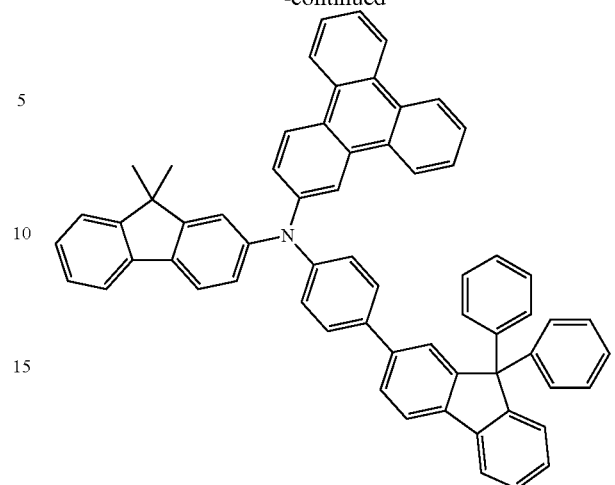
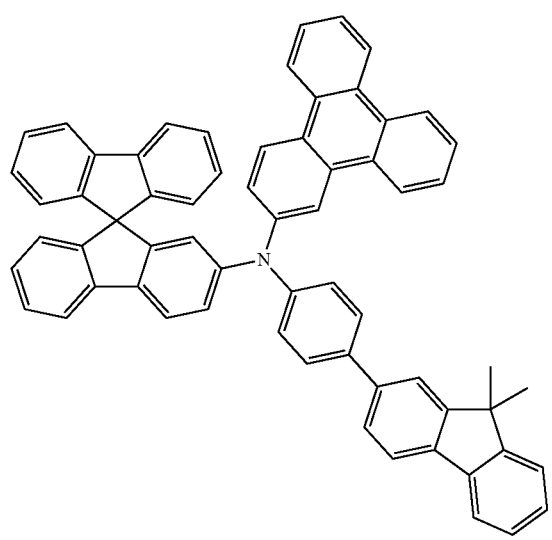
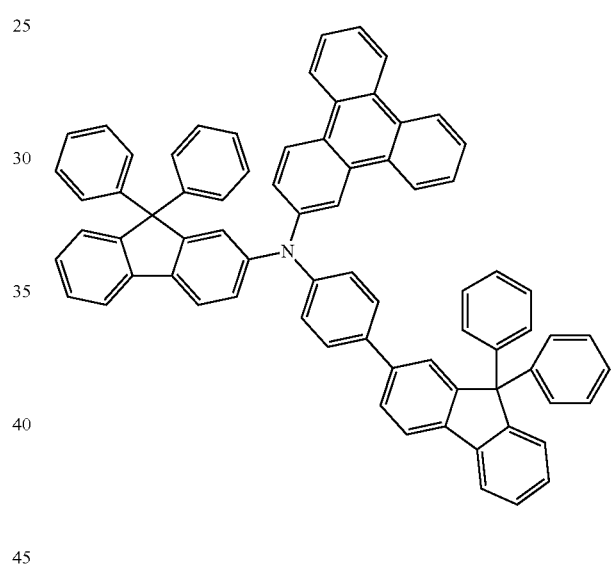

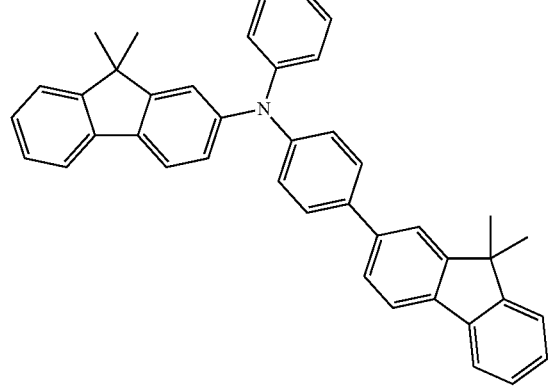
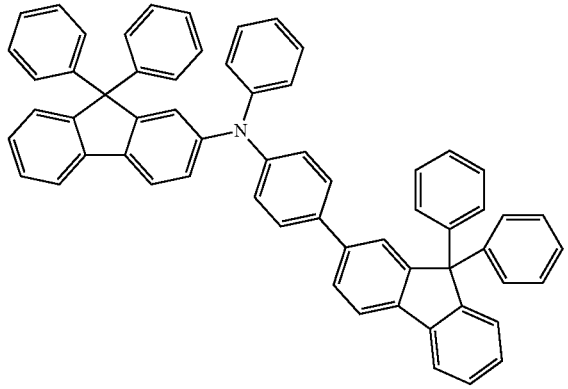
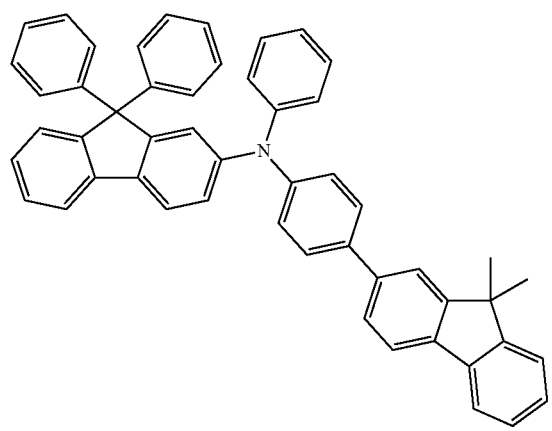
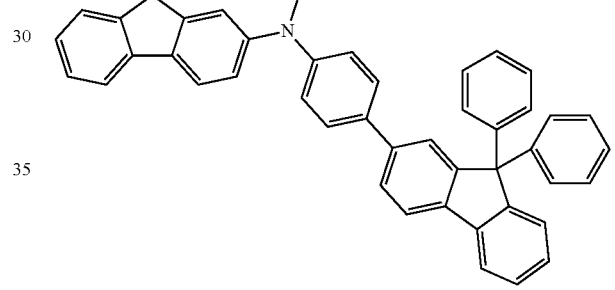
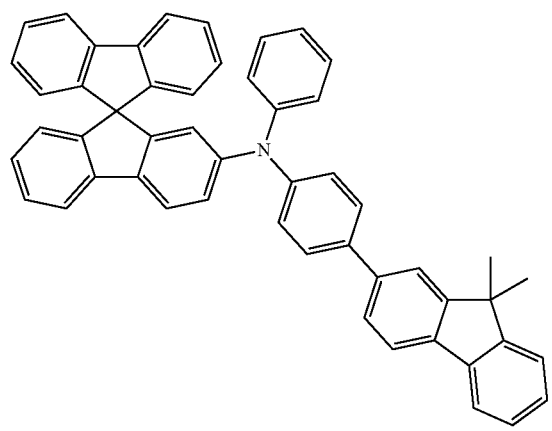
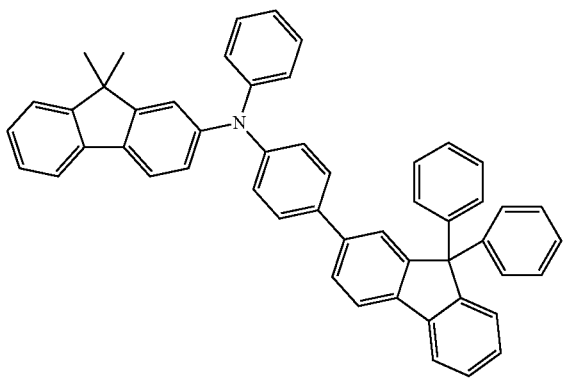
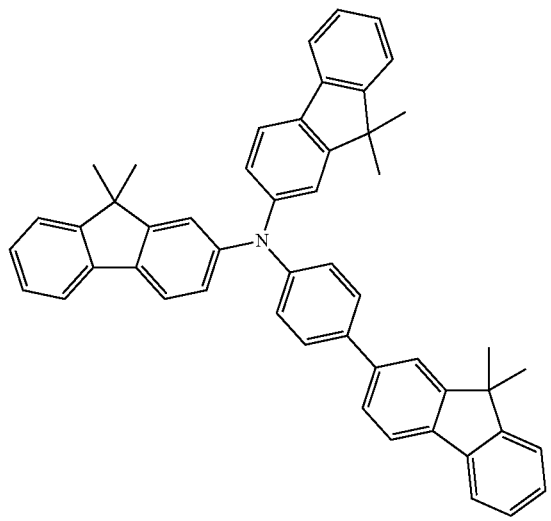

35
-continued
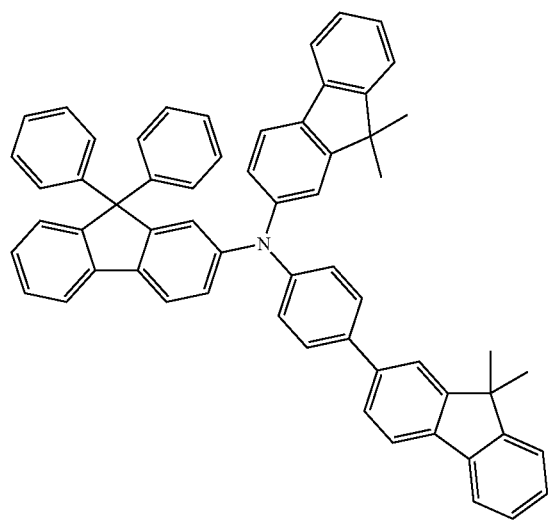
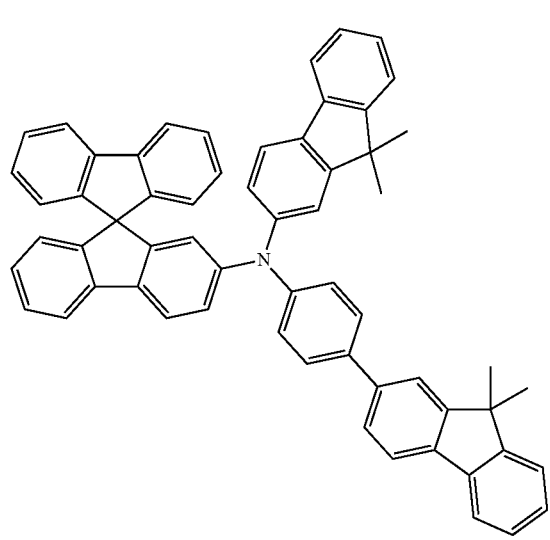
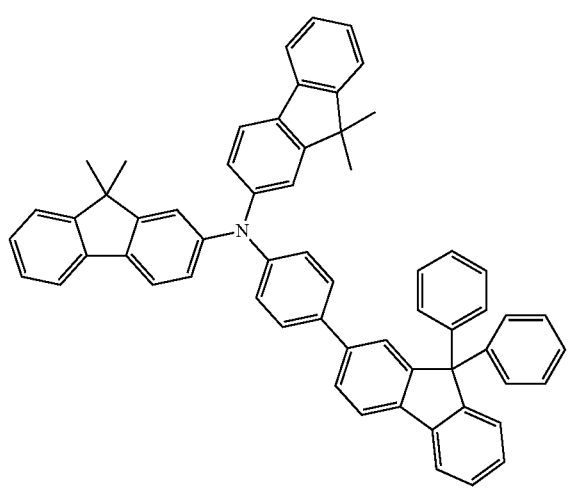
36
-continued
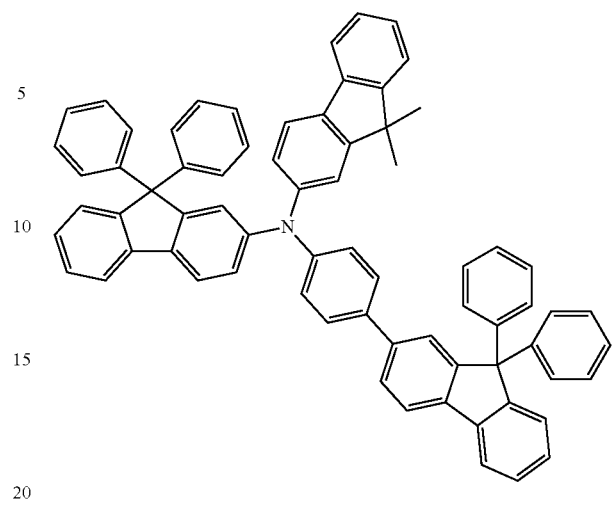
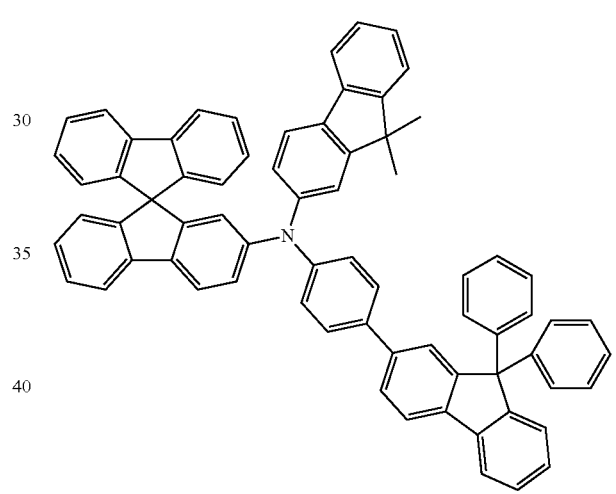
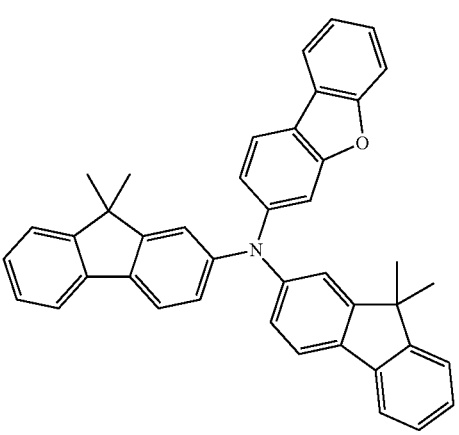

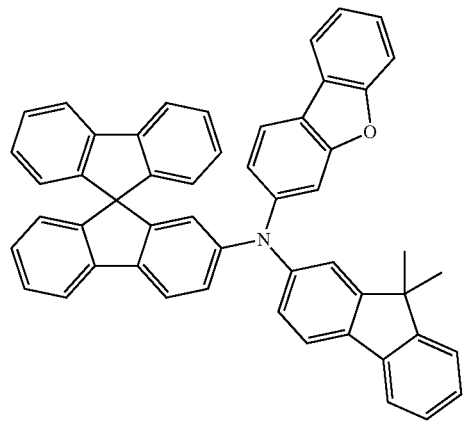
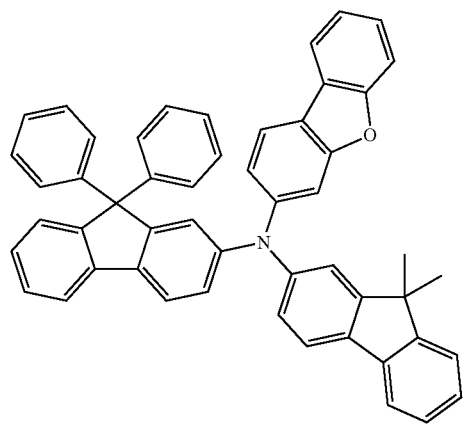
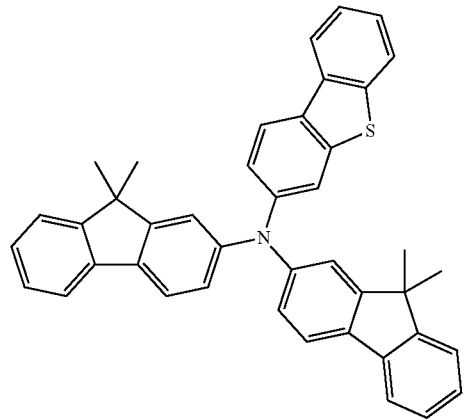
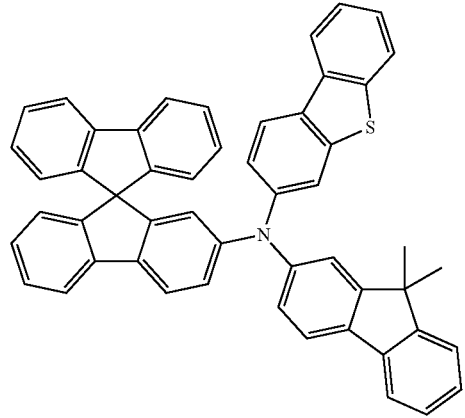
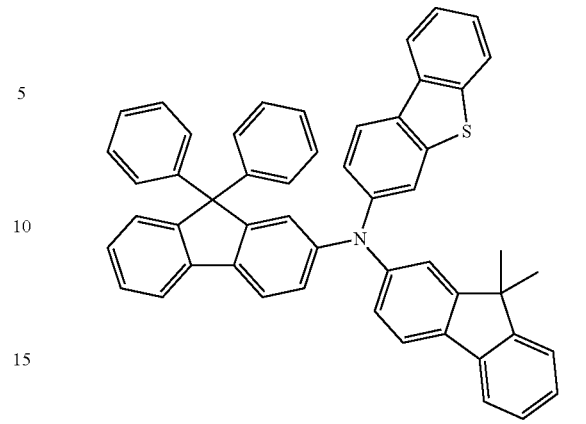
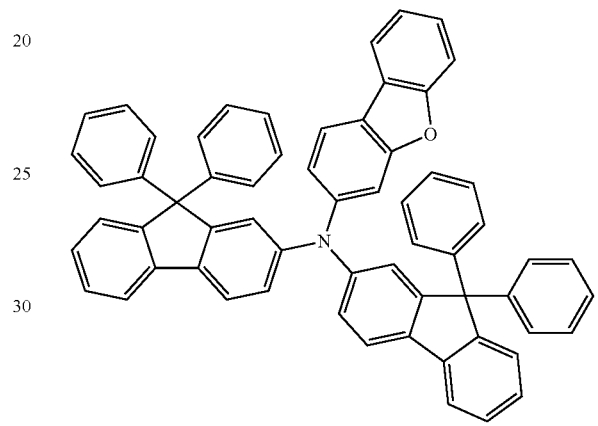
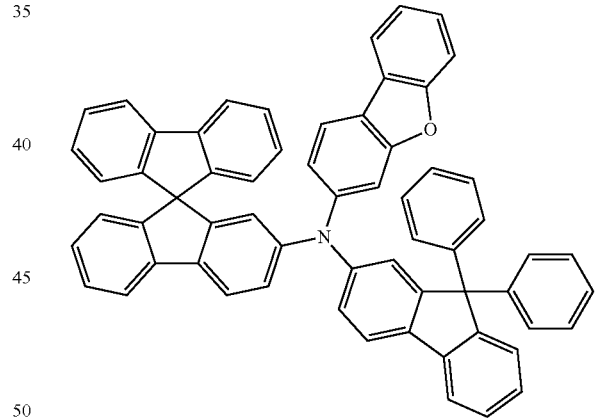
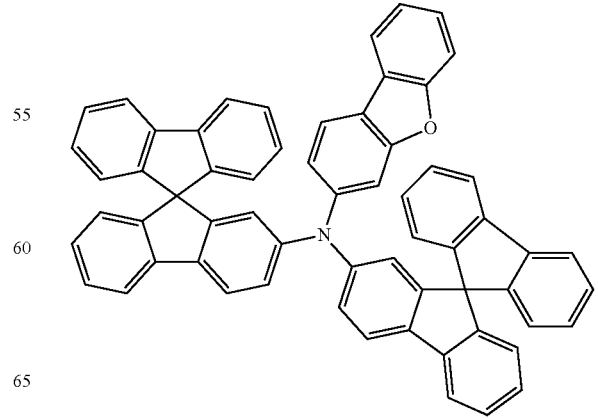

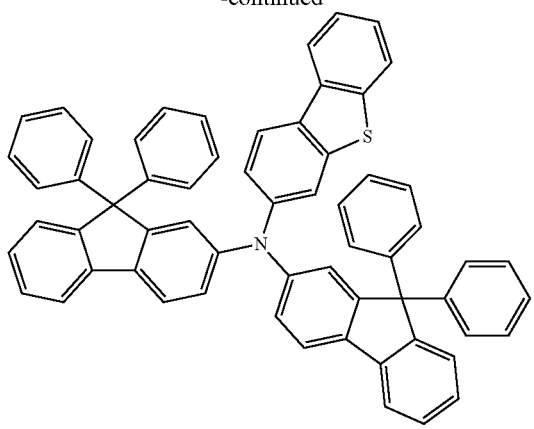
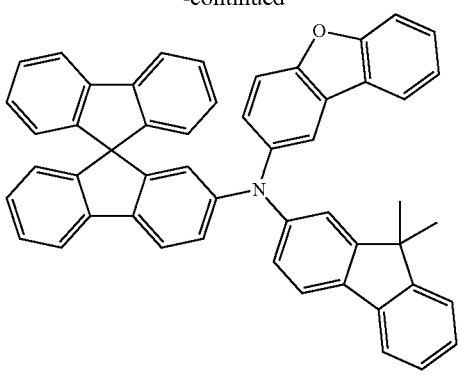
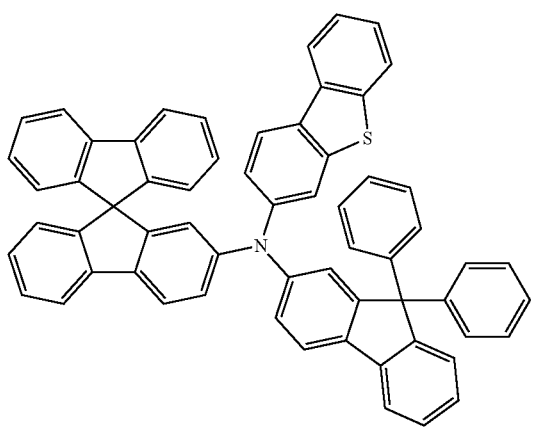
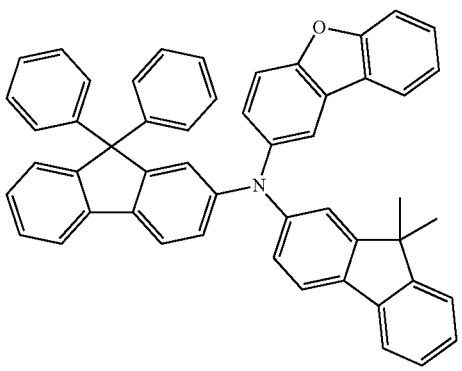
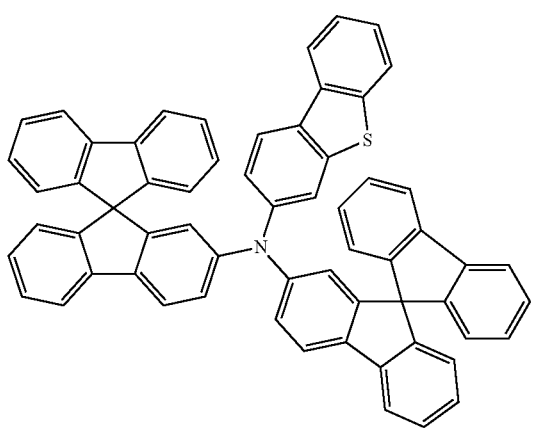
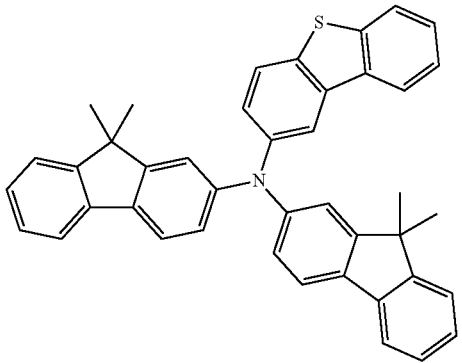
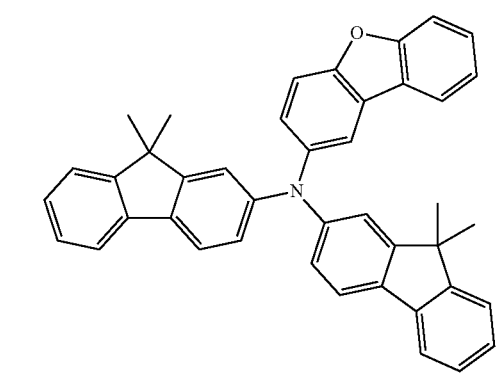
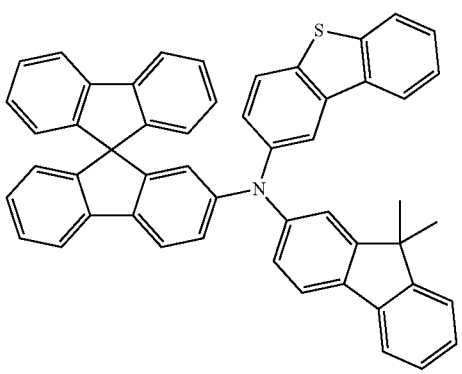

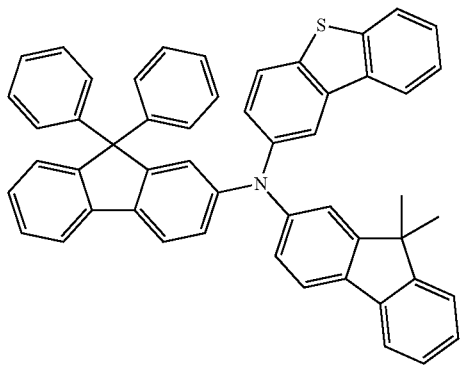
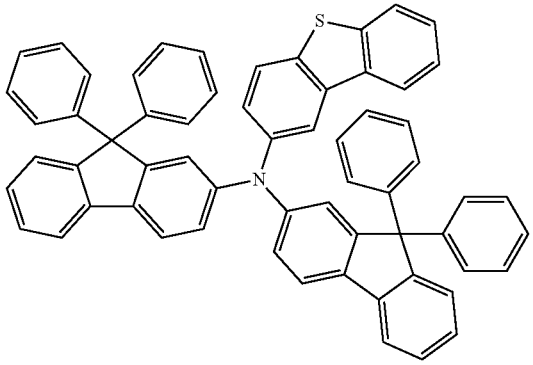
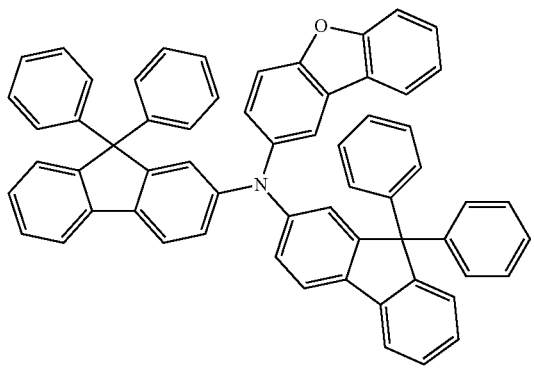

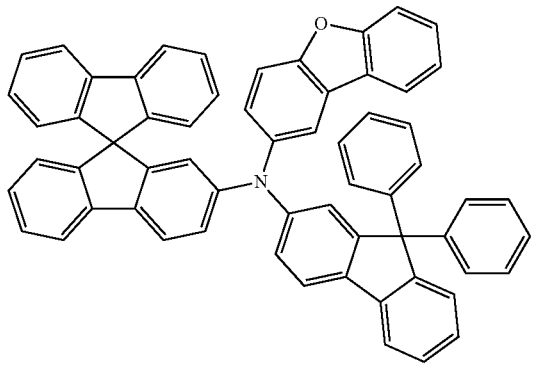
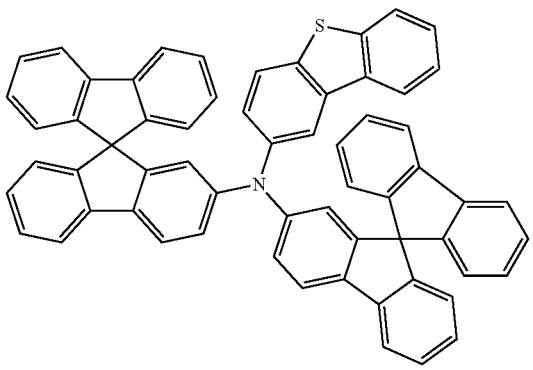
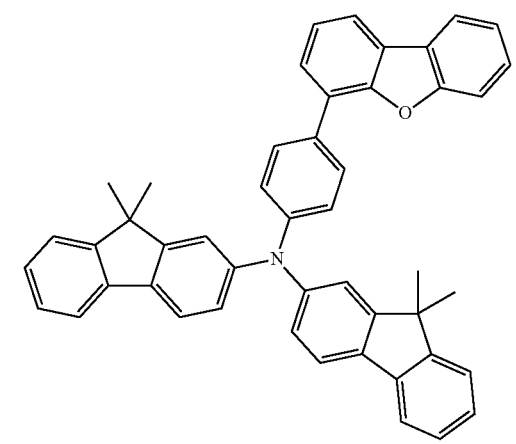

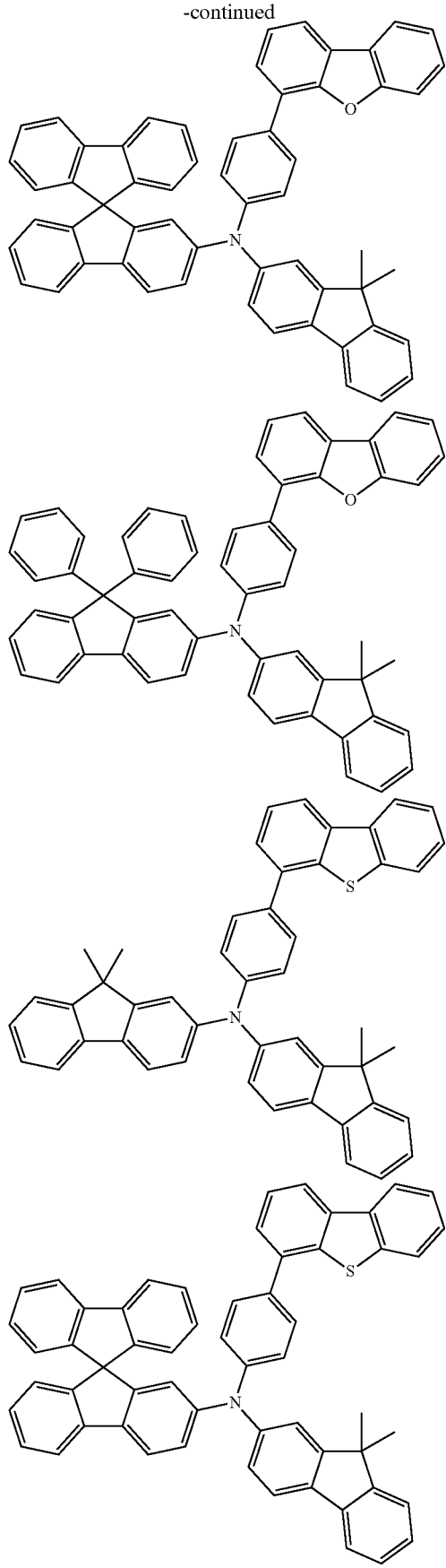
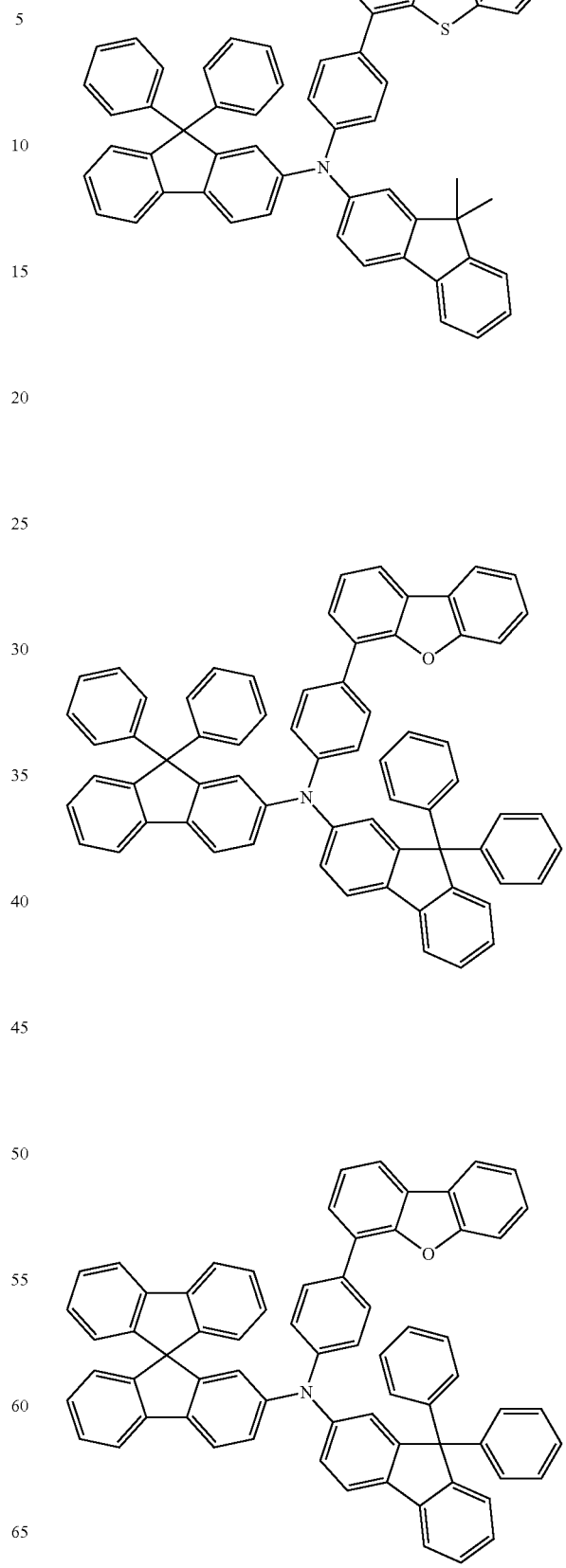

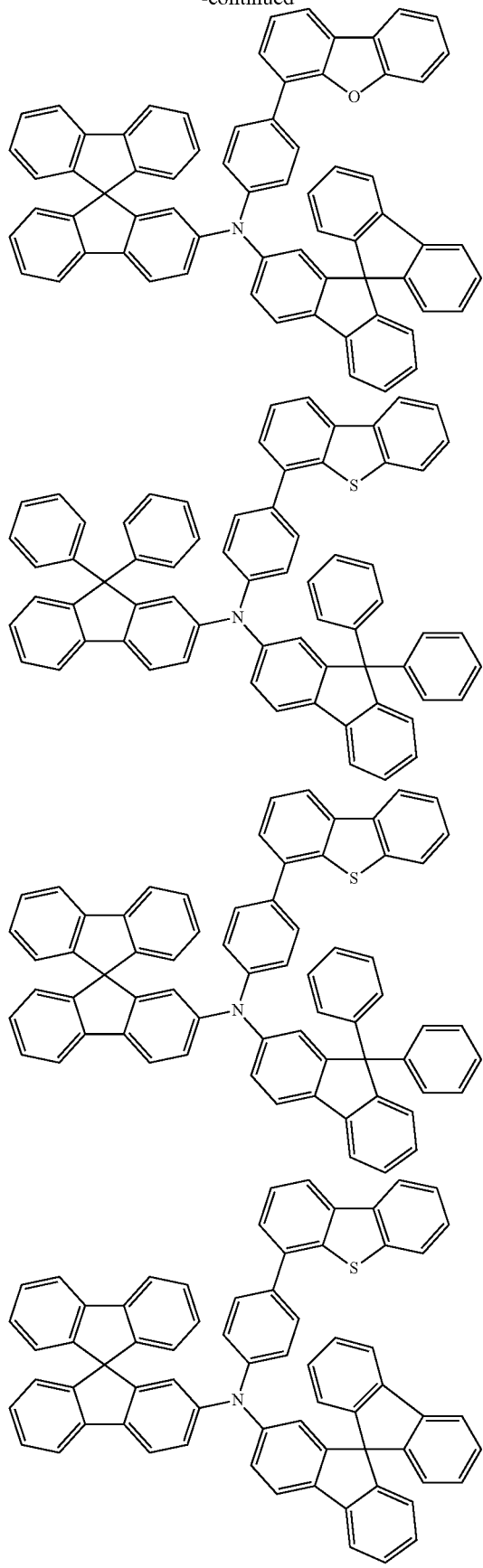
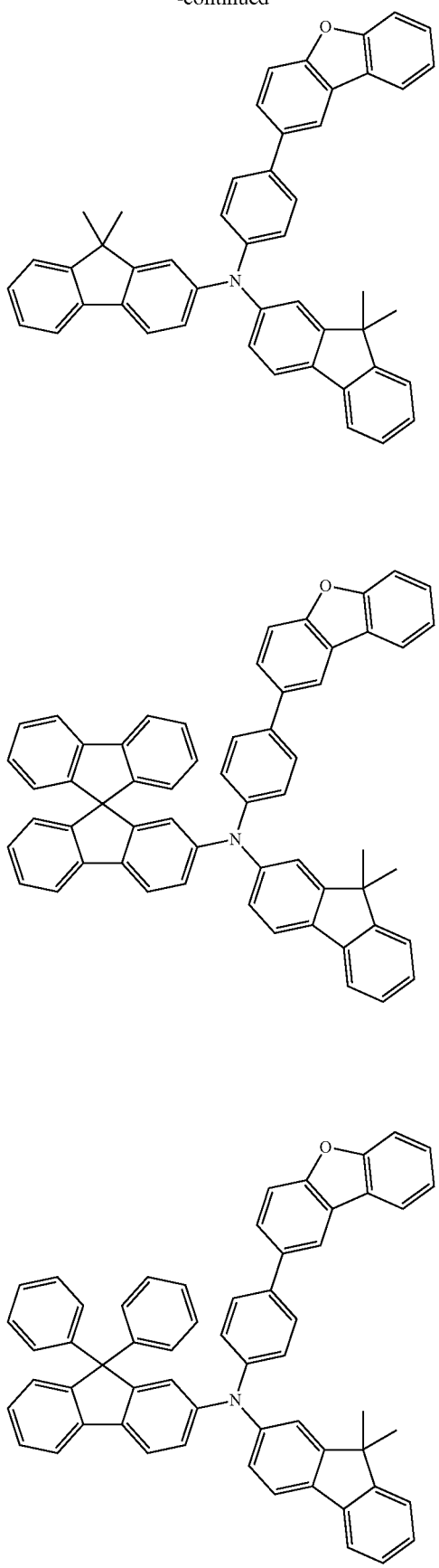

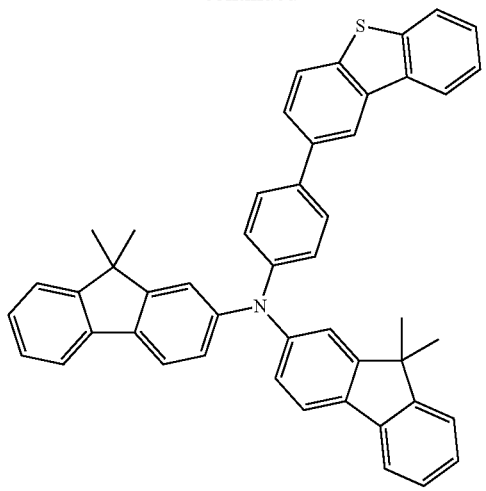
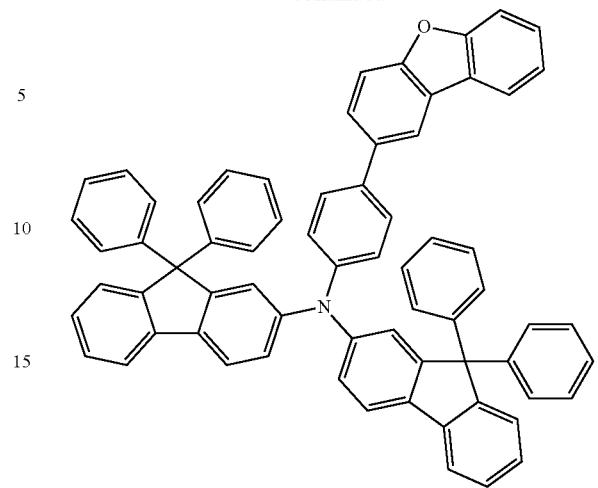
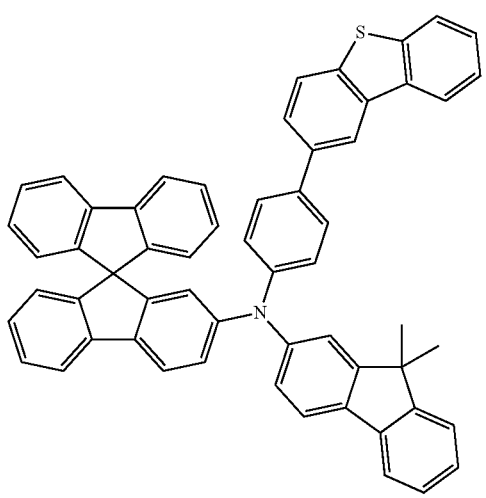
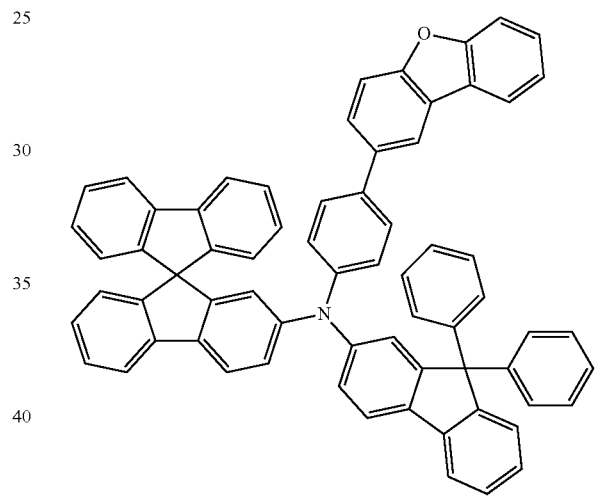
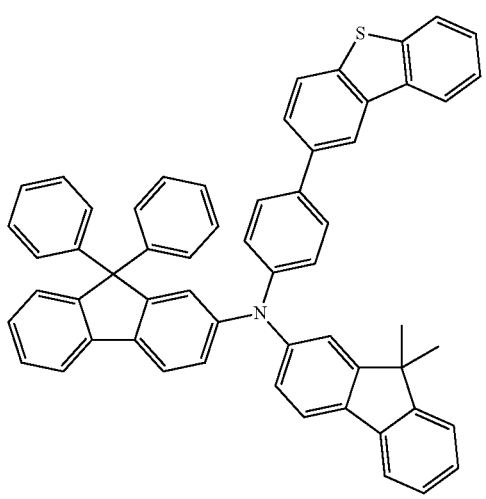
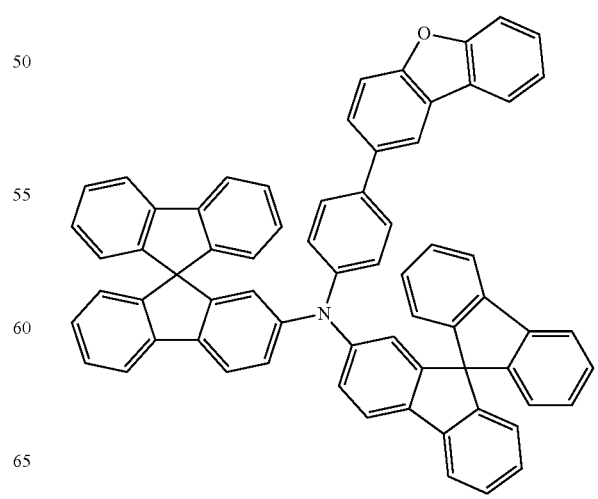

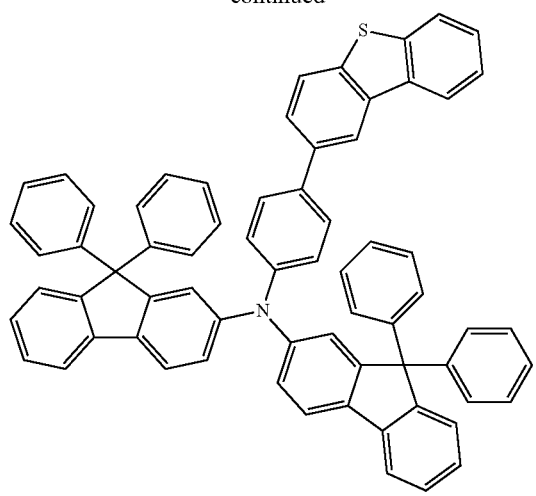
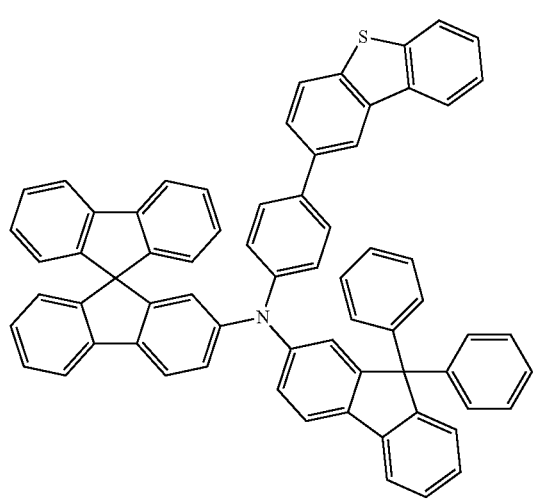
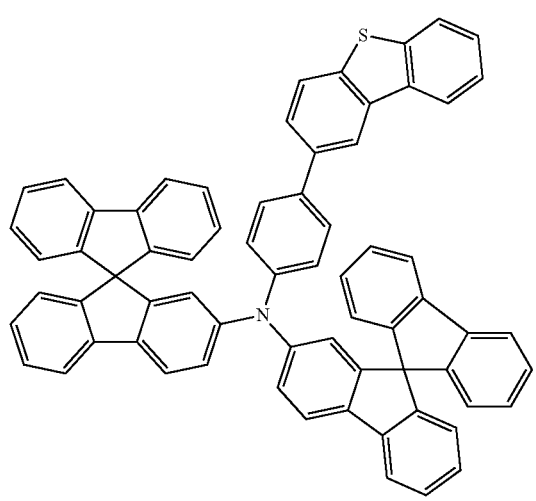
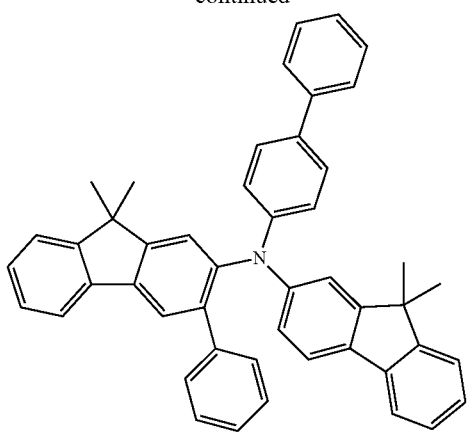
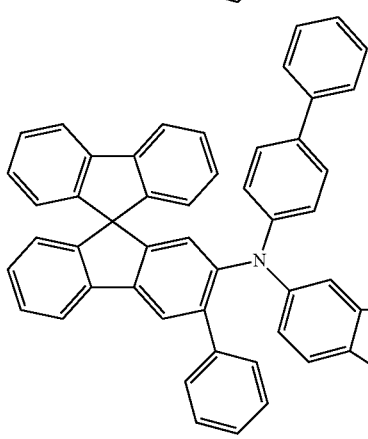
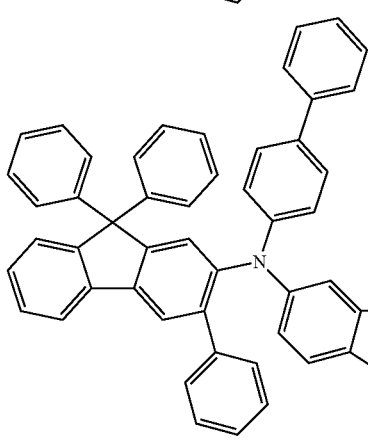
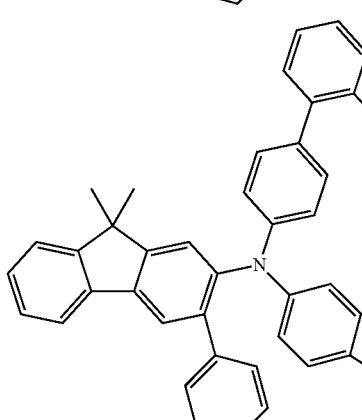

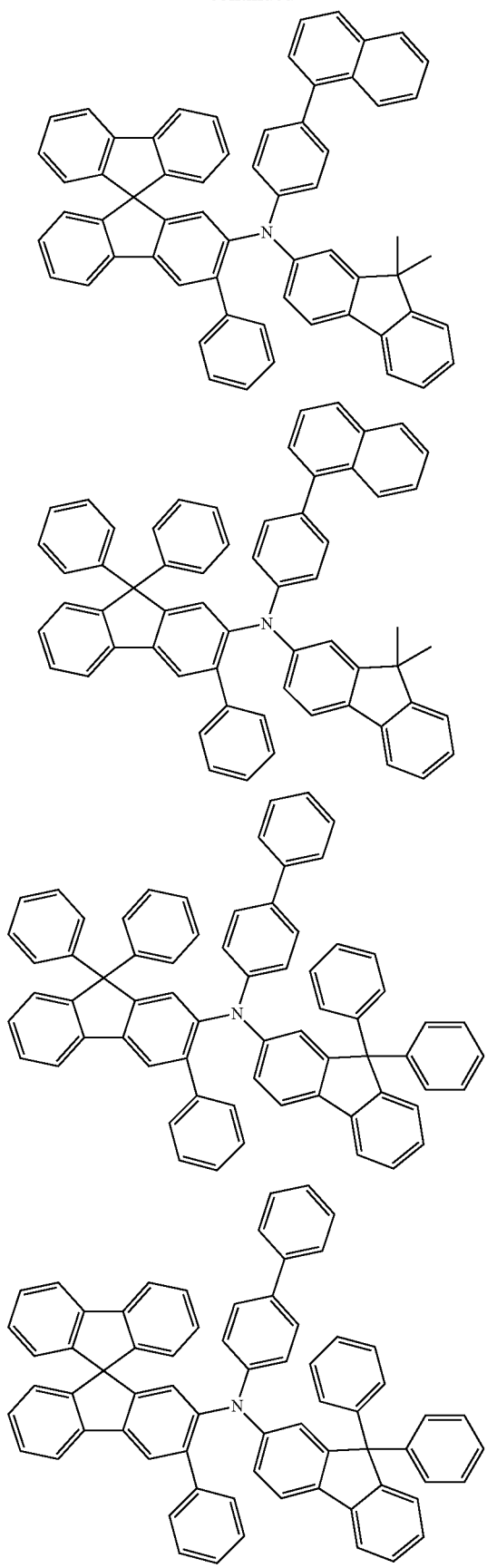
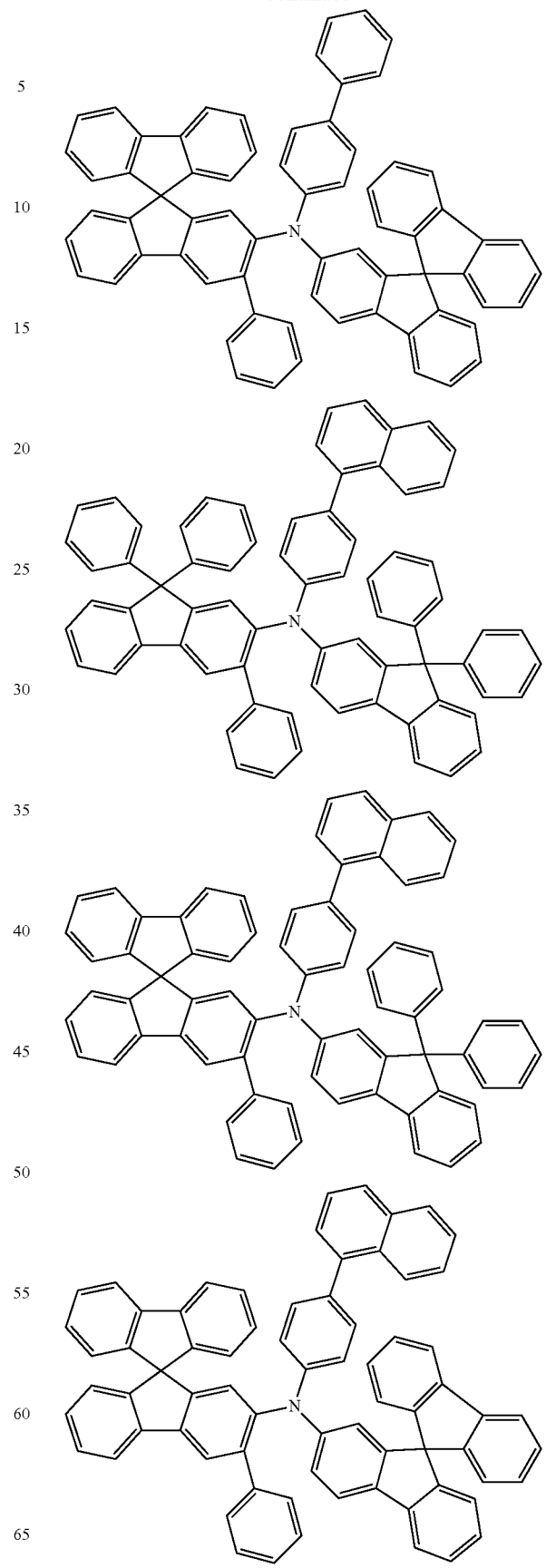

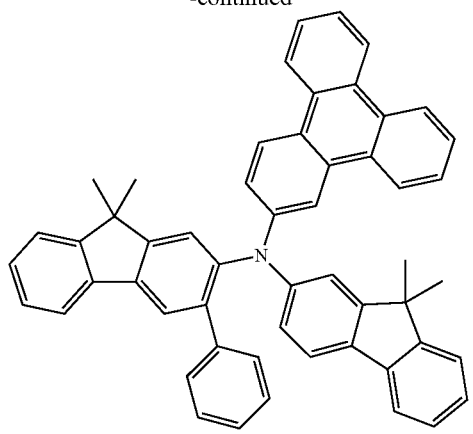
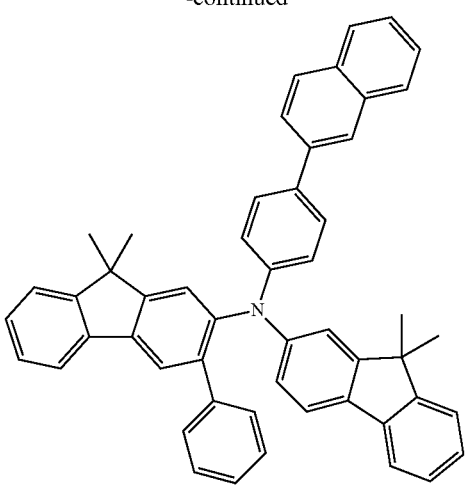
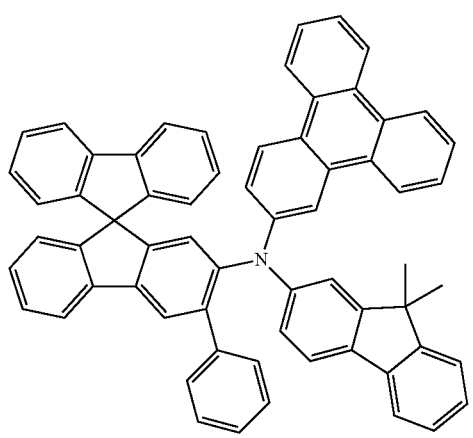
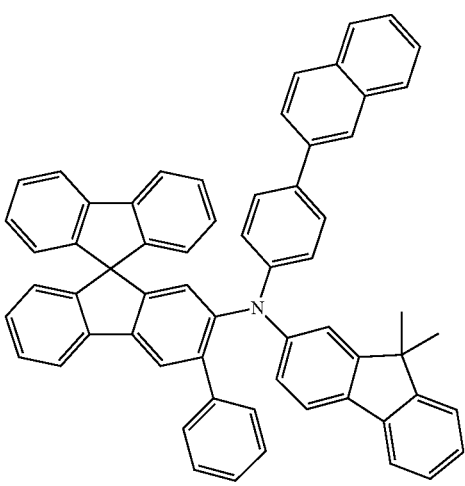
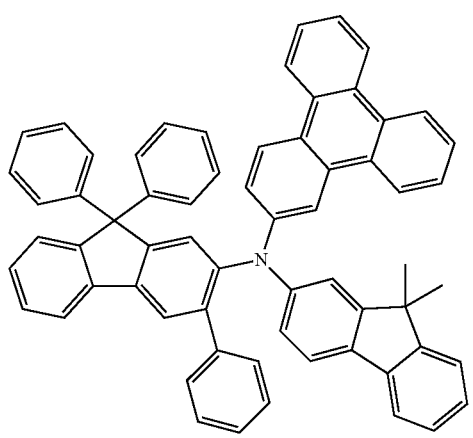
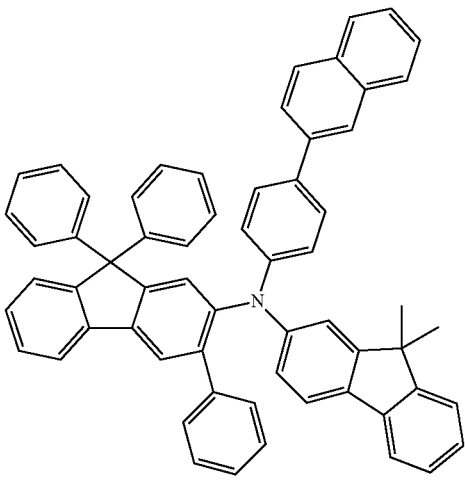

55
-continued
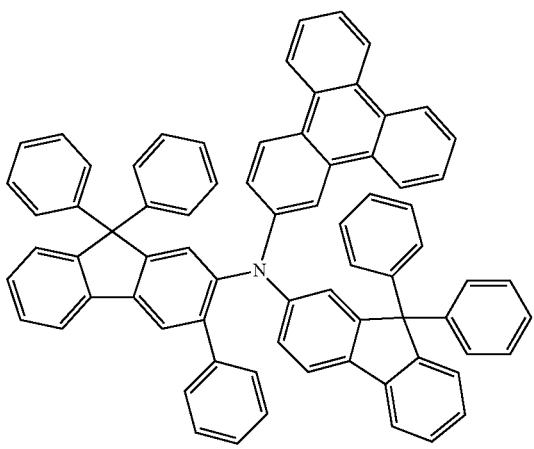
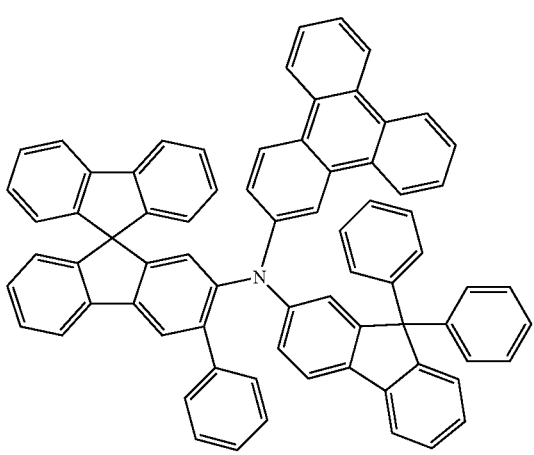
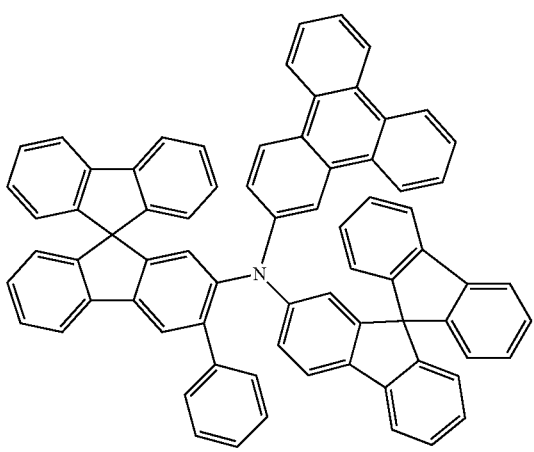
56
-continued
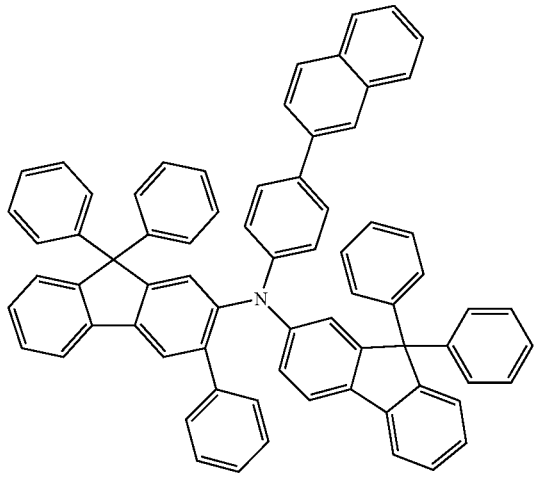
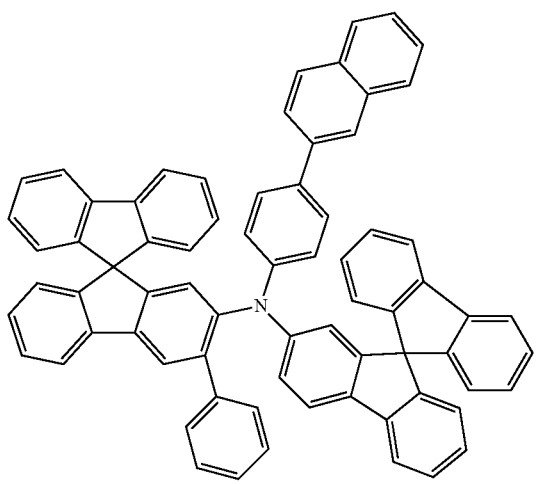

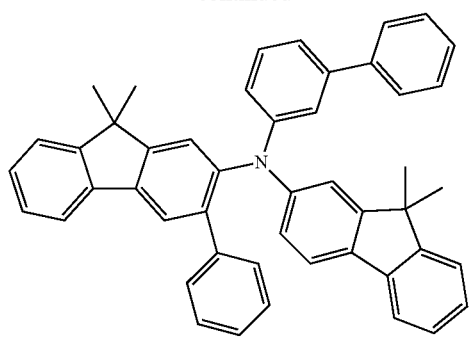
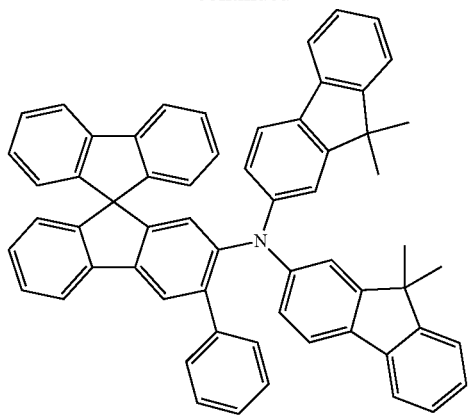
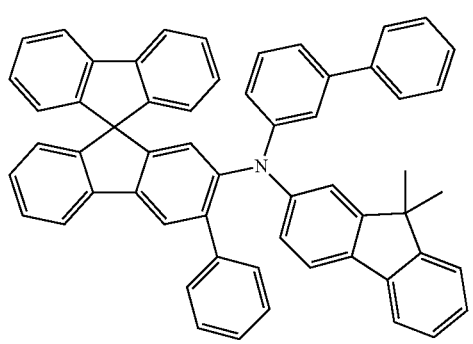
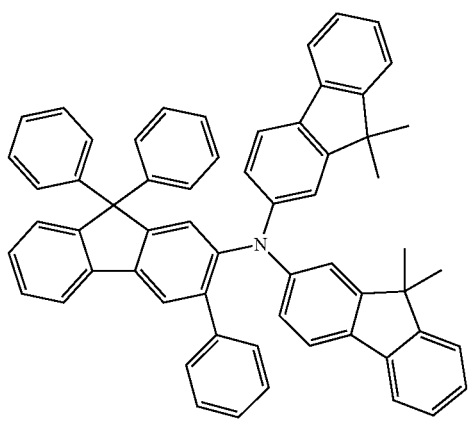
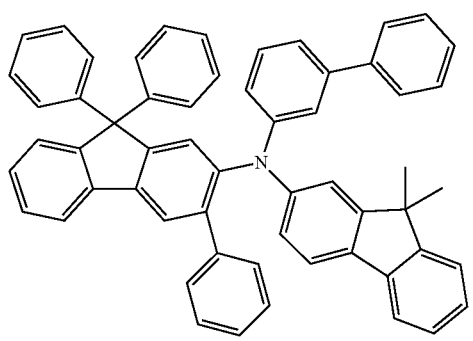
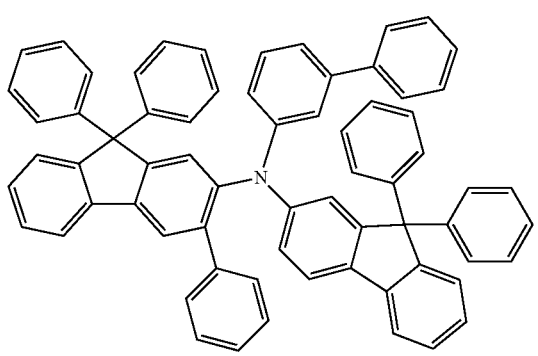
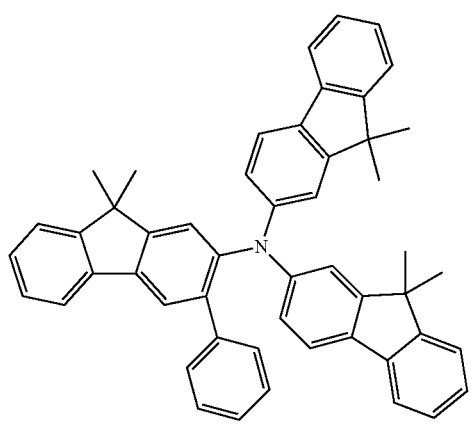
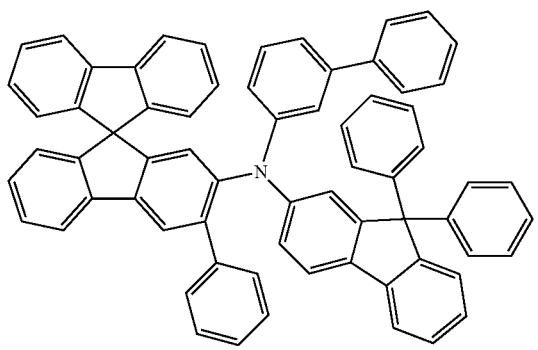

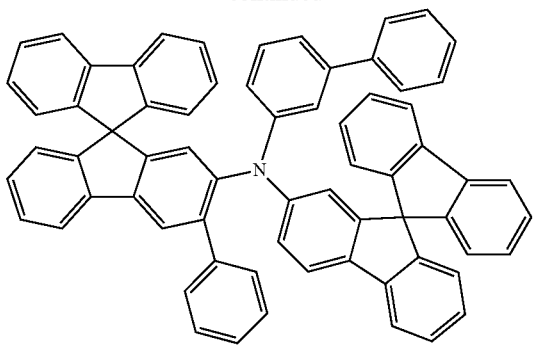
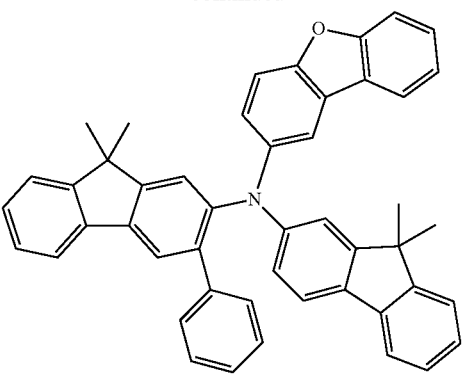
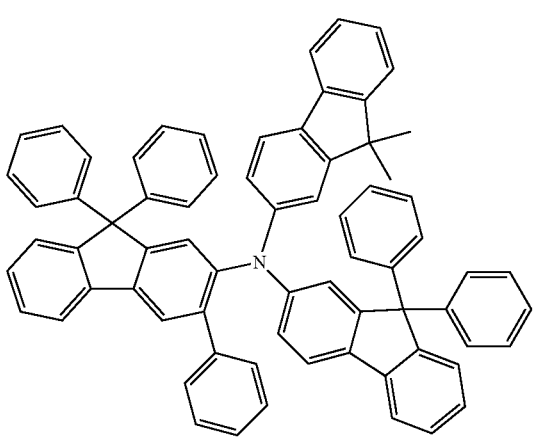
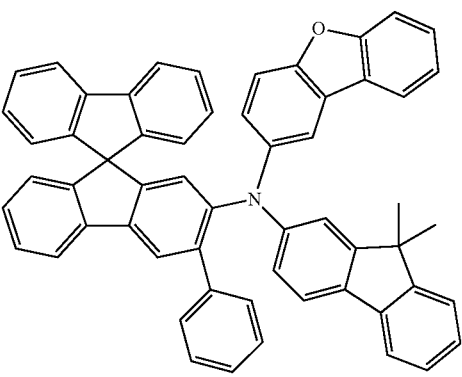
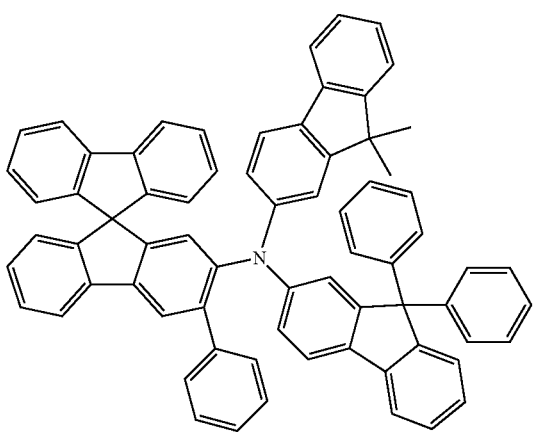
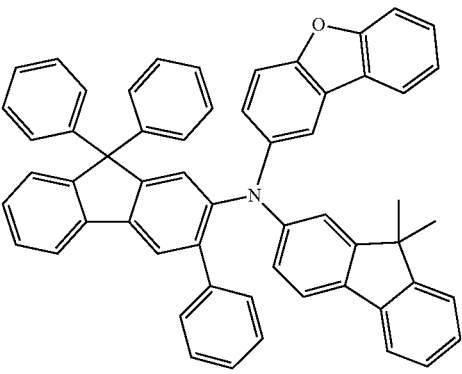
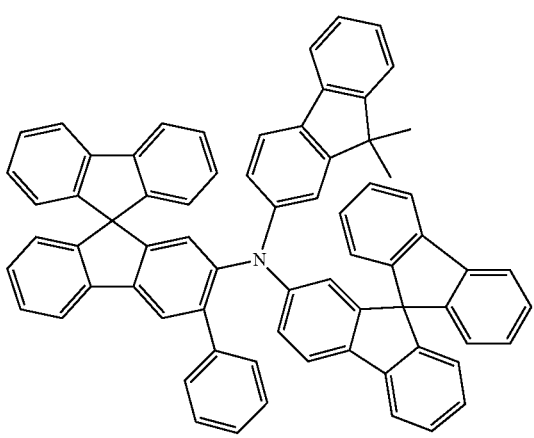
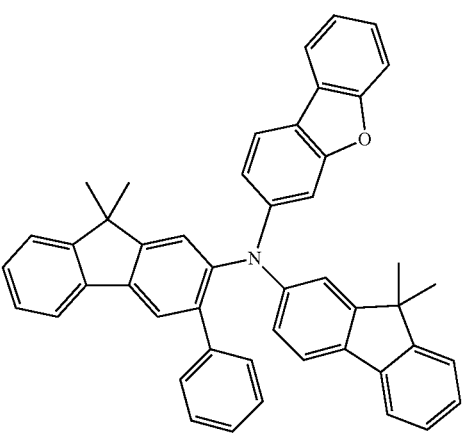

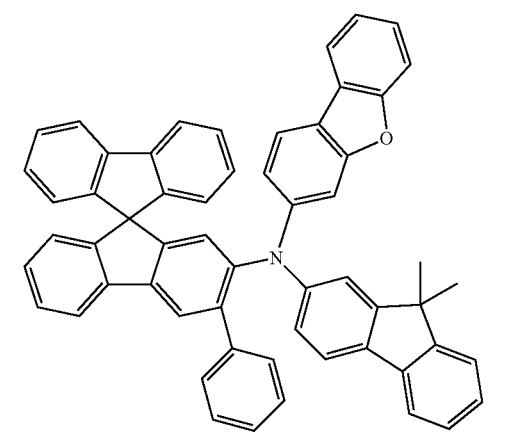
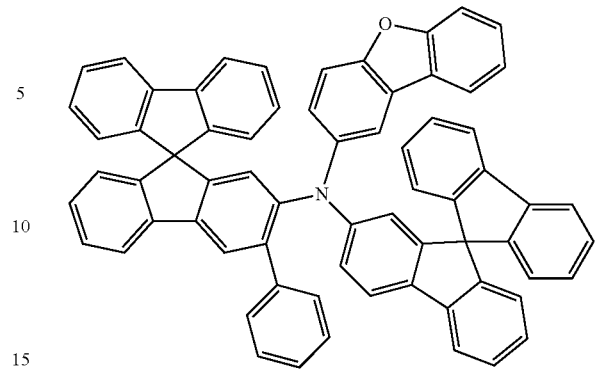
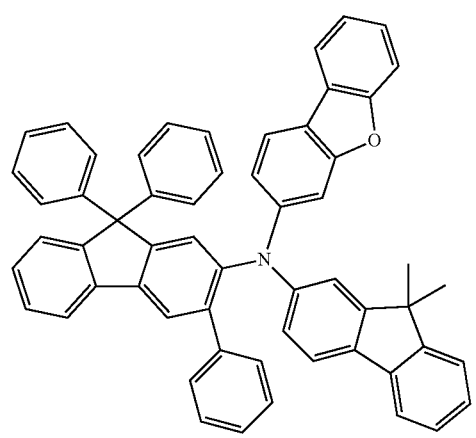
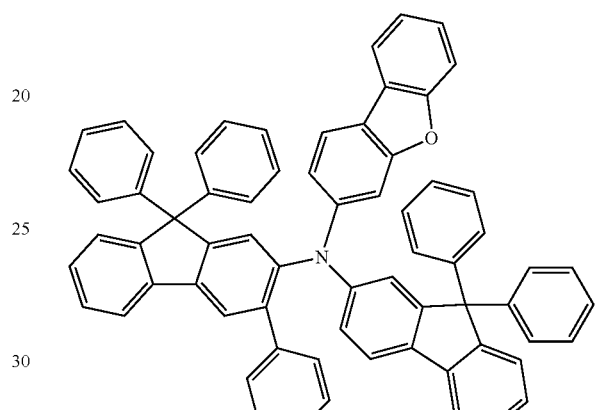
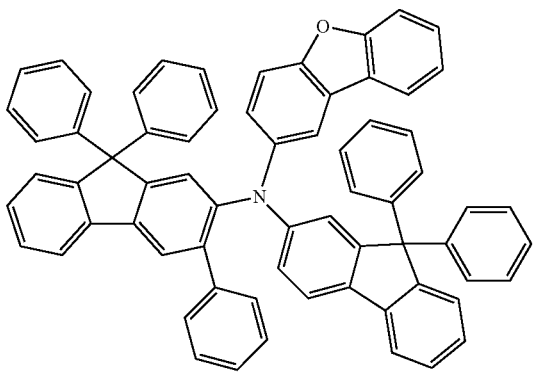
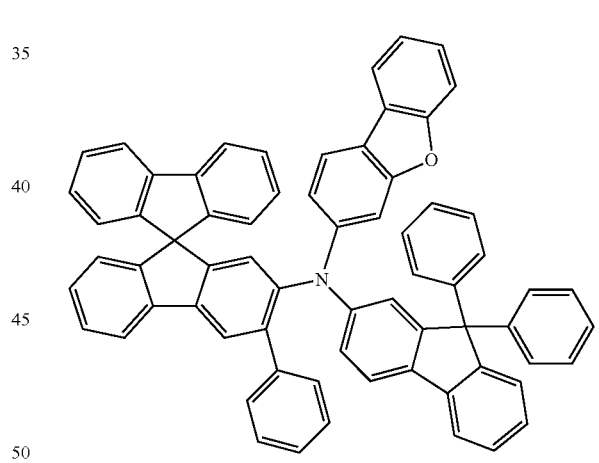
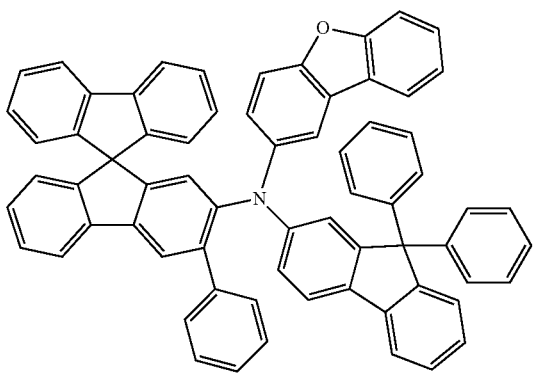
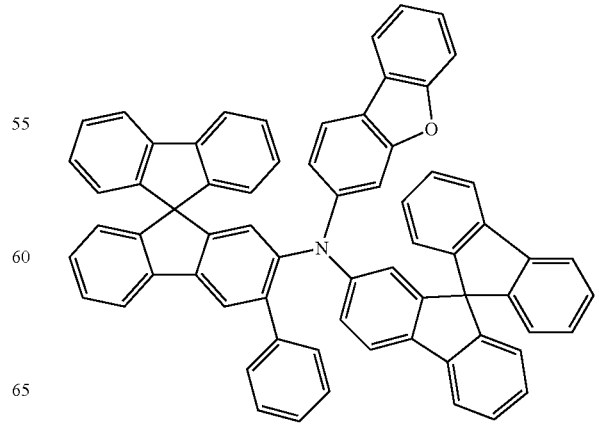

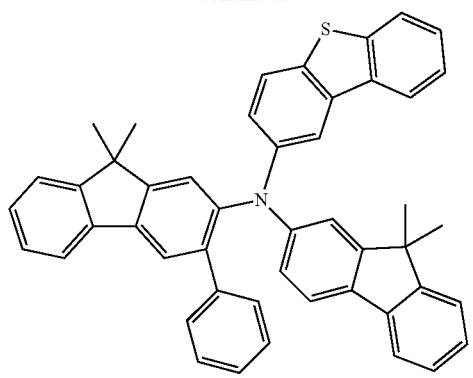
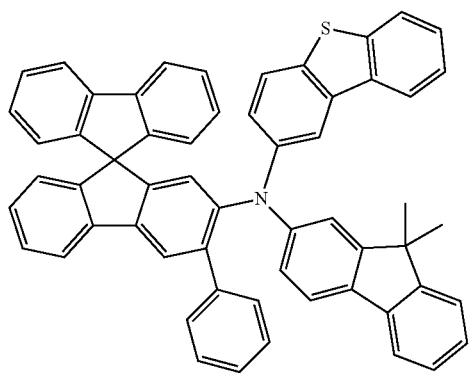
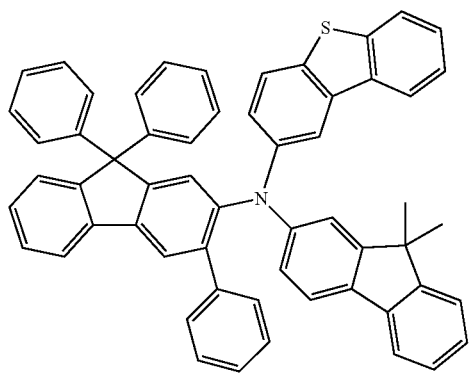
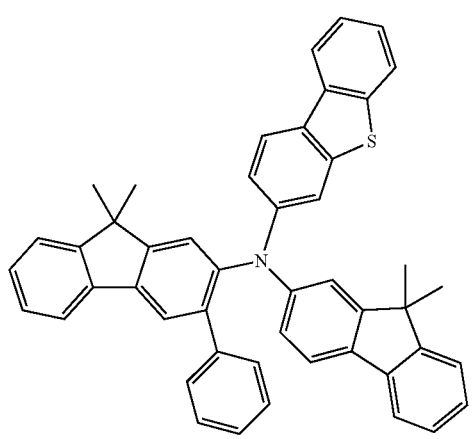
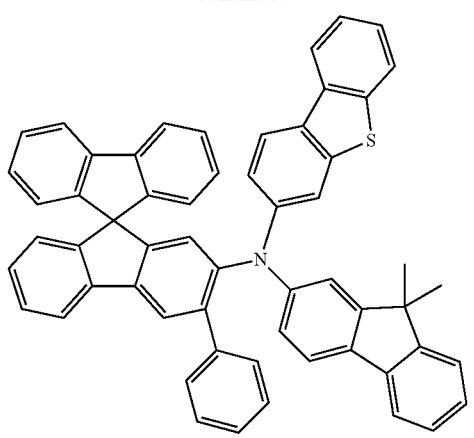
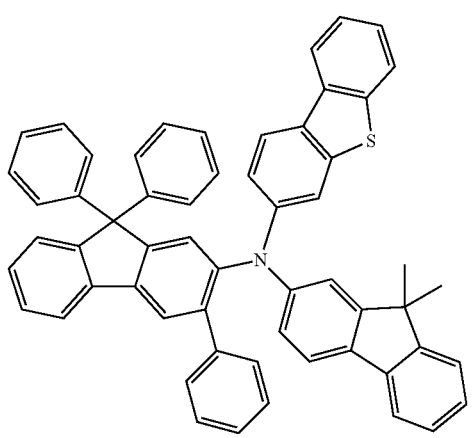
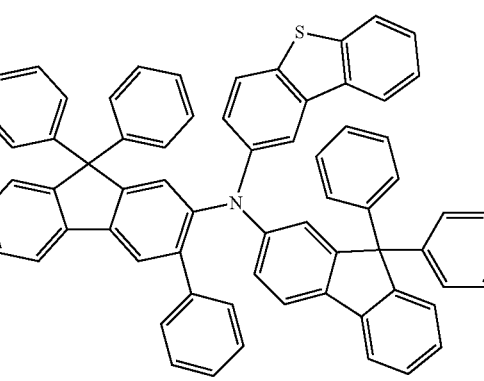
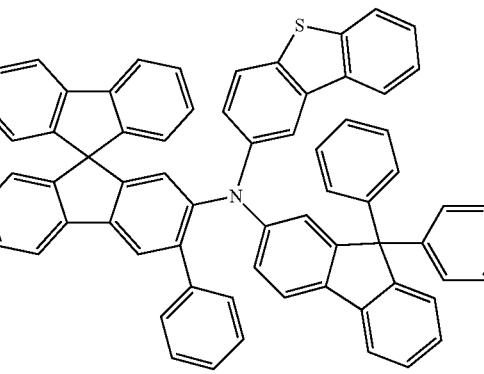

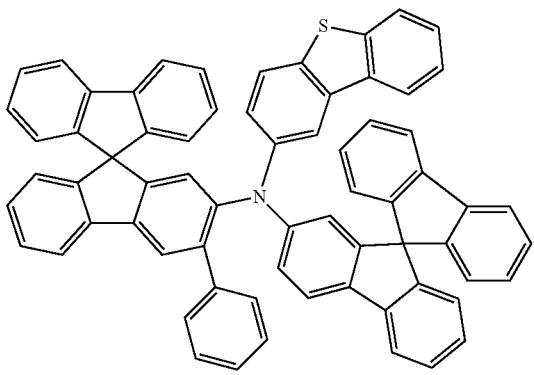
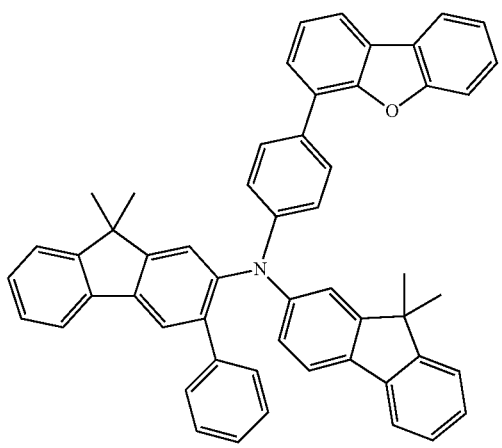
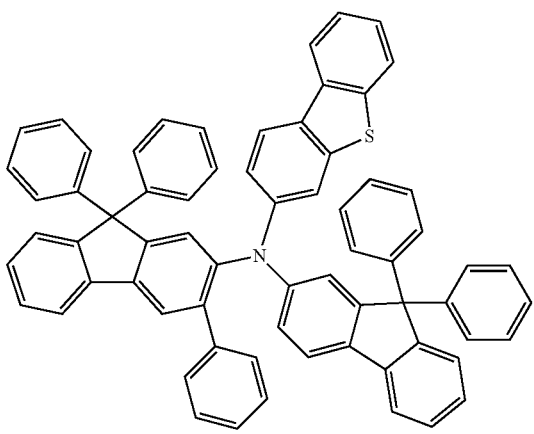
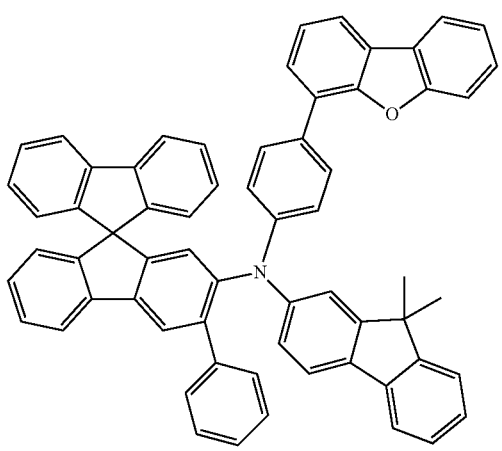
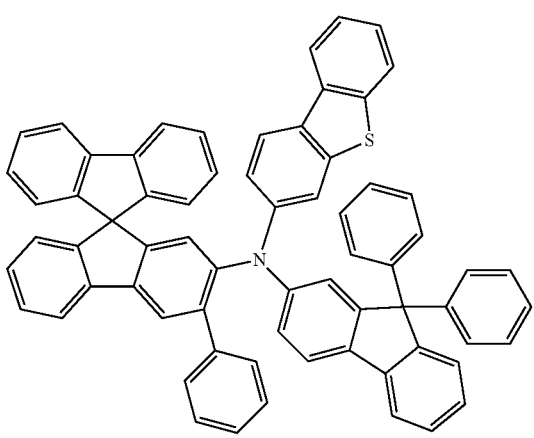
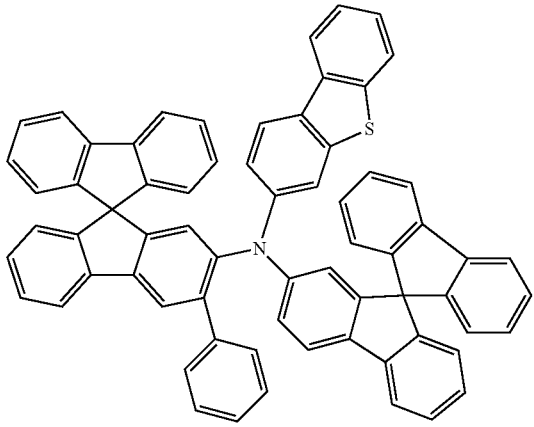
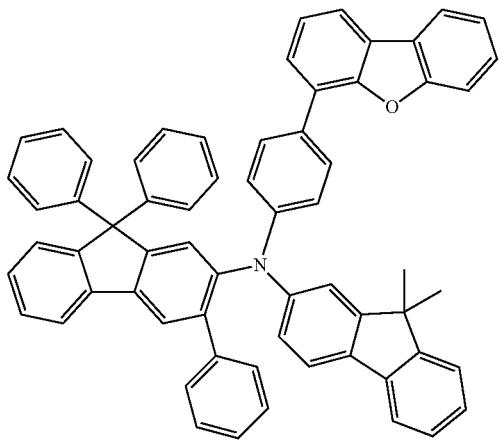

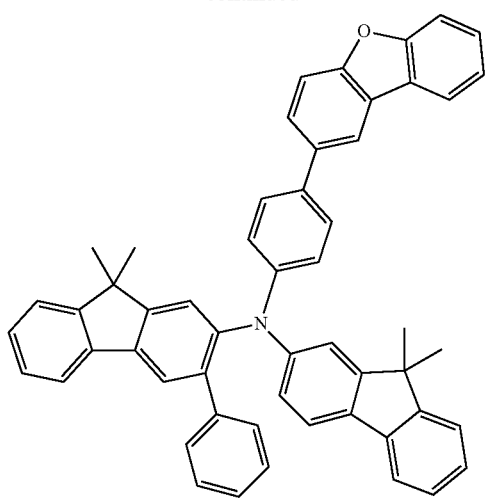
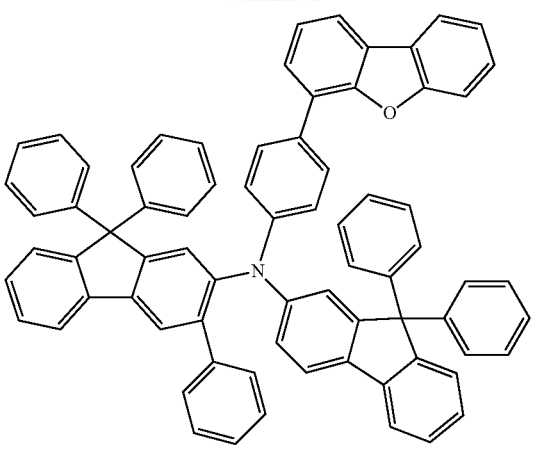
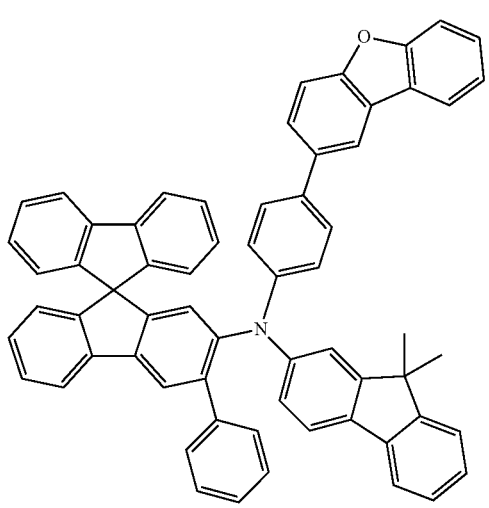
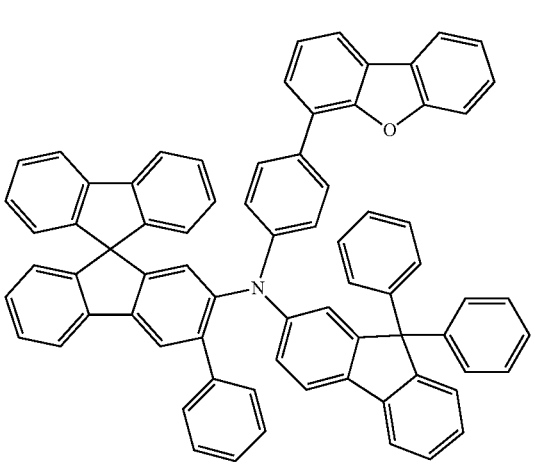
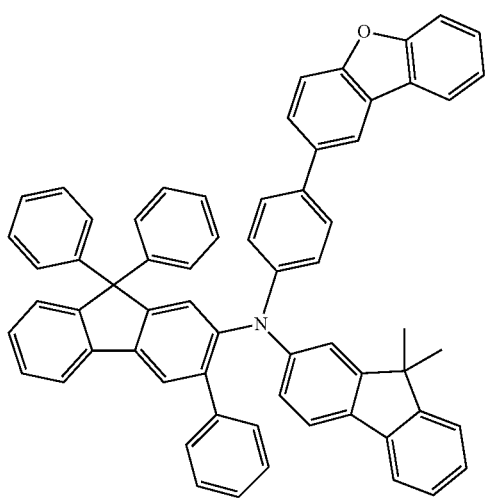
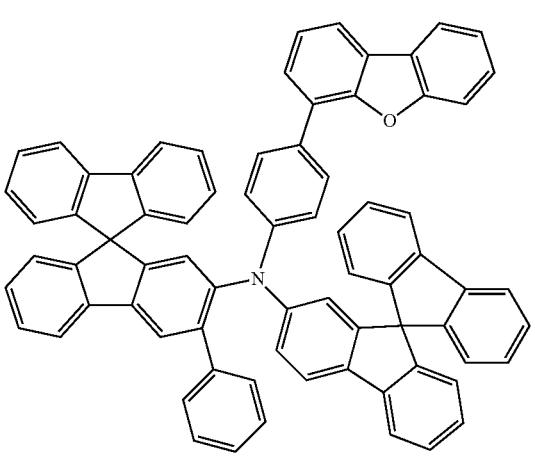

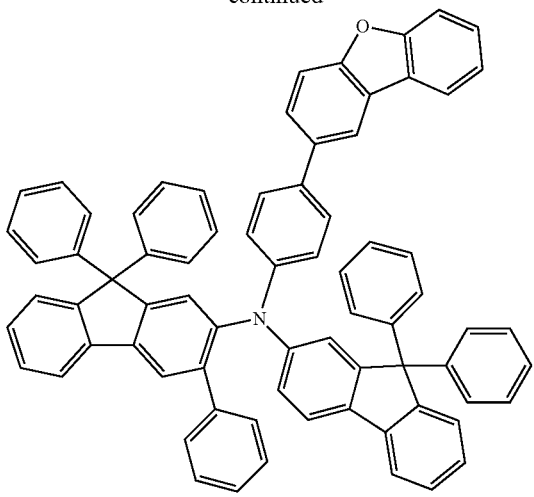
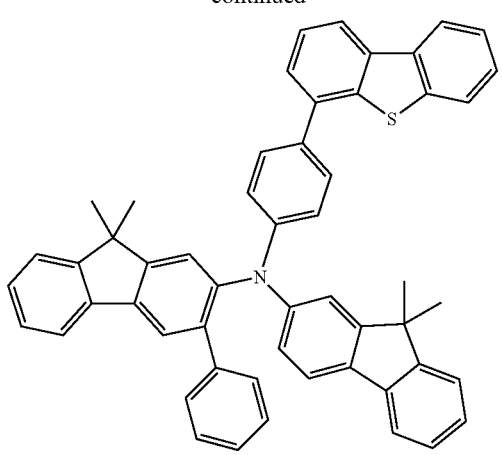
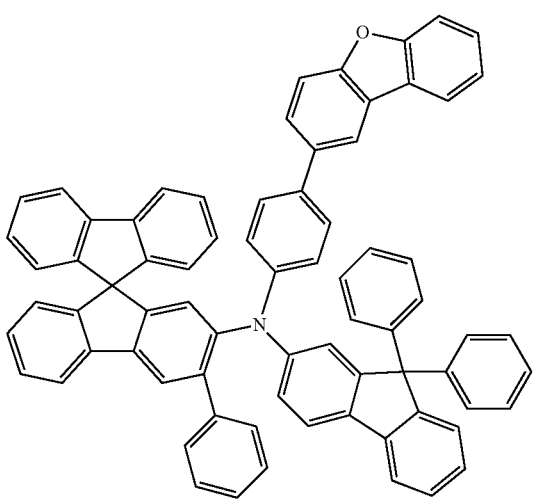
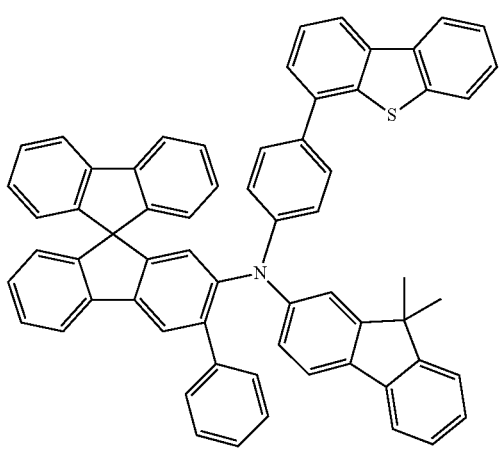
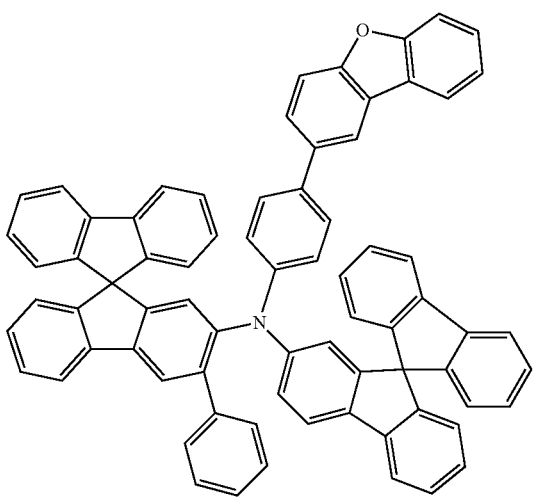
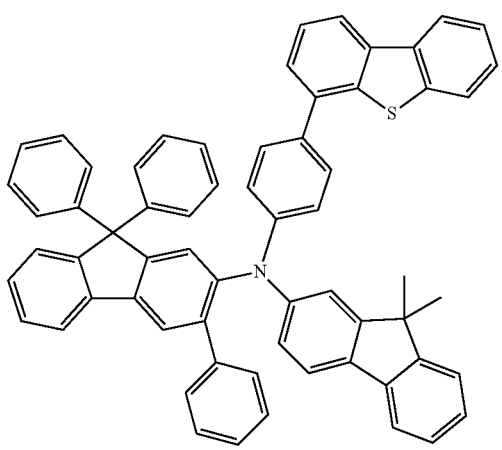

71
-continued
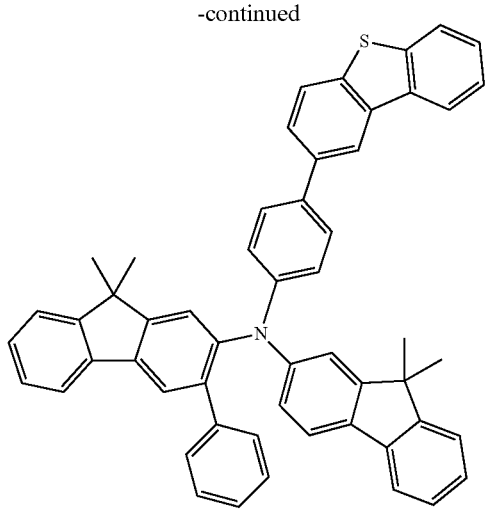
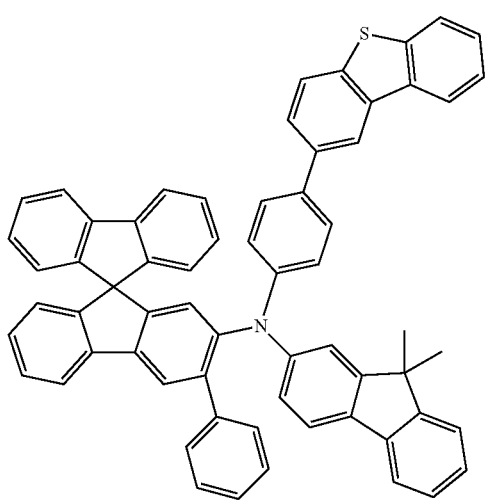
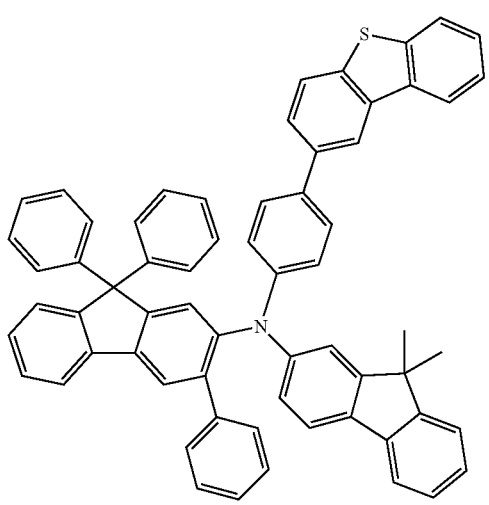
72
-continued
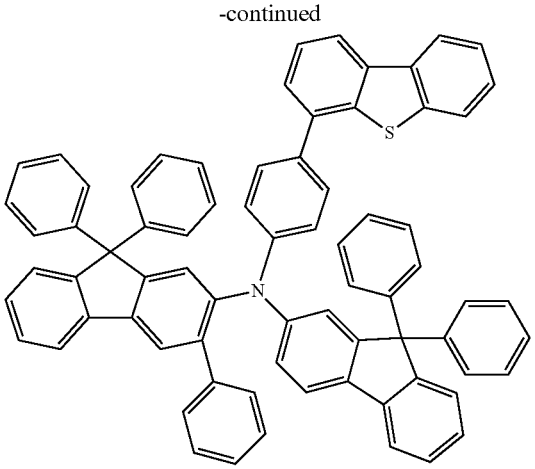
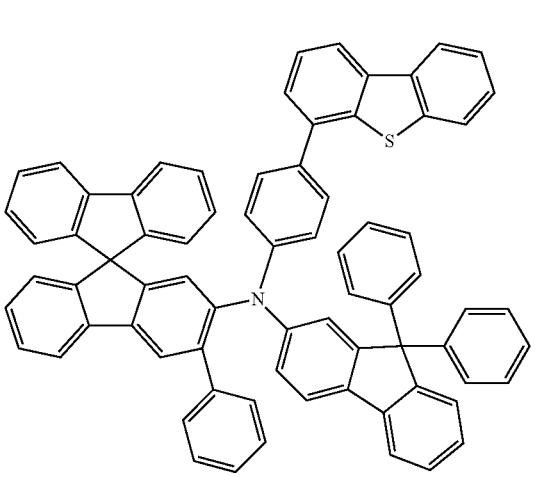
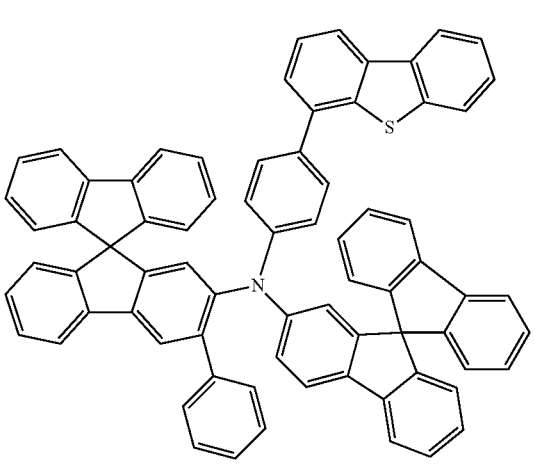

-continued
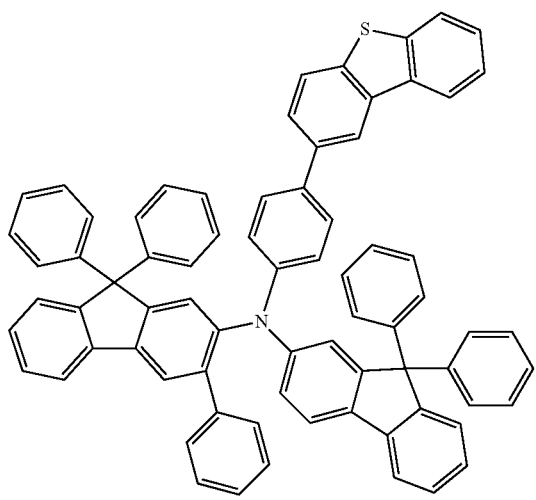
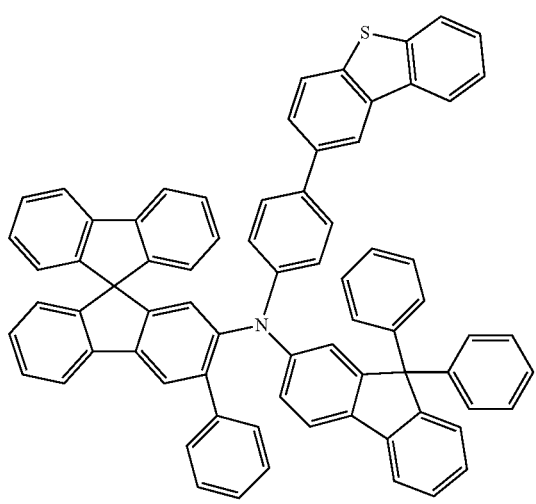
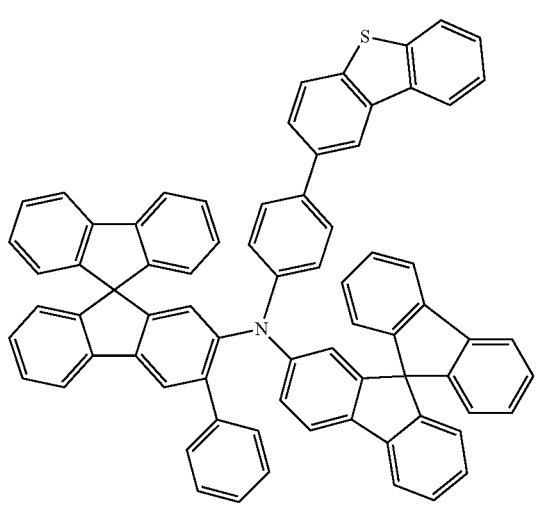
-continued
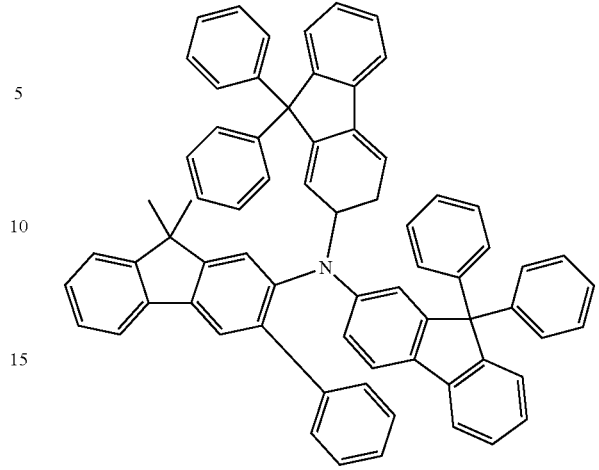
In an exemplary embodiment of the present specification, the compound represented by Chemical Formula 2 is selected from the following structural formulae.
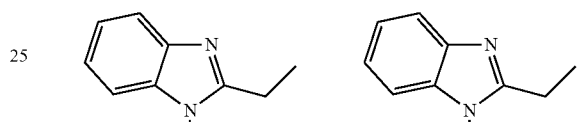
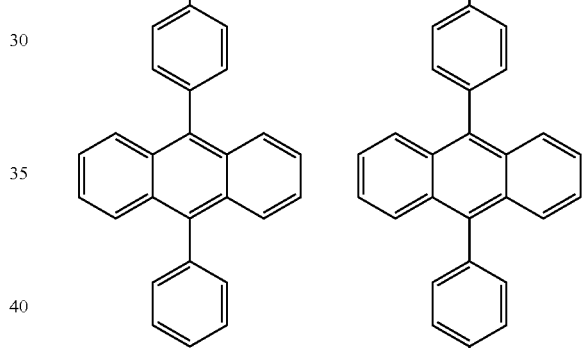
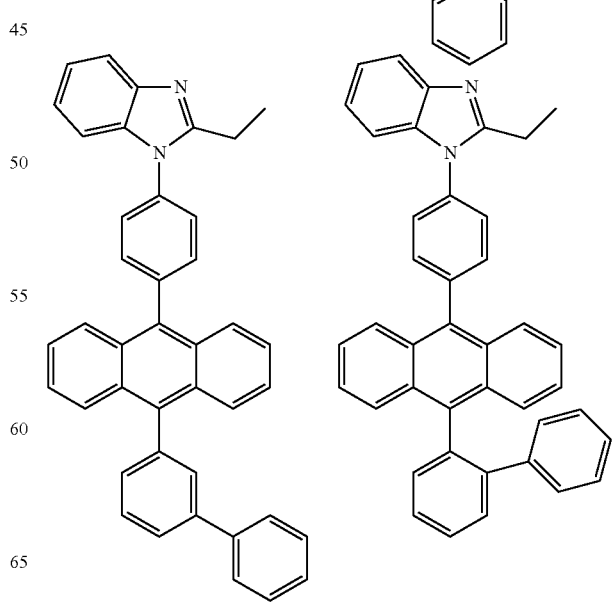

75
-continued
76
-continued
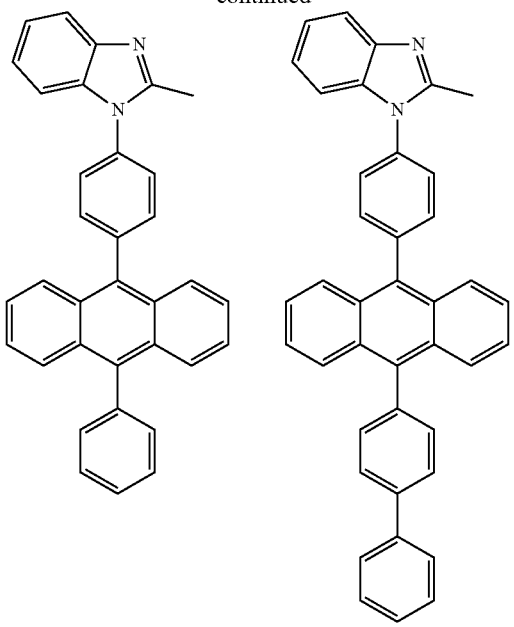
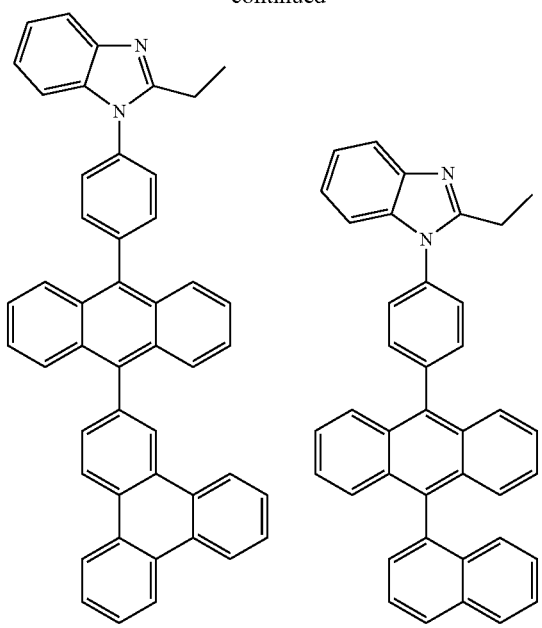
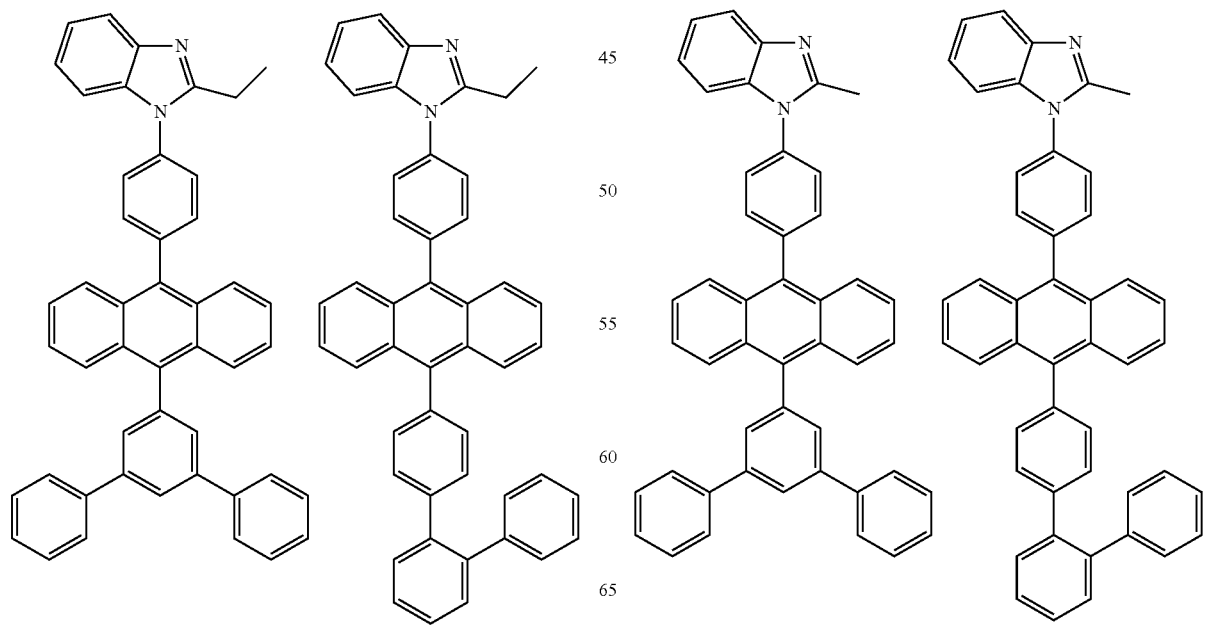

77
-continued
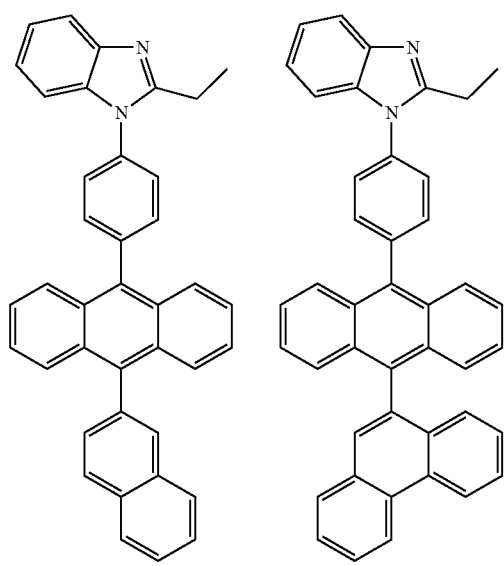
78
-continued
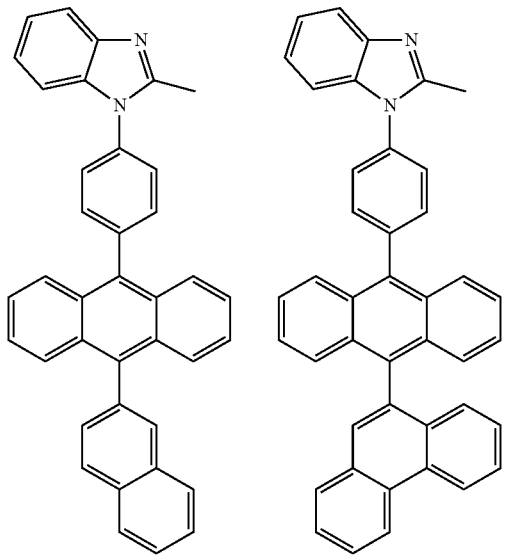
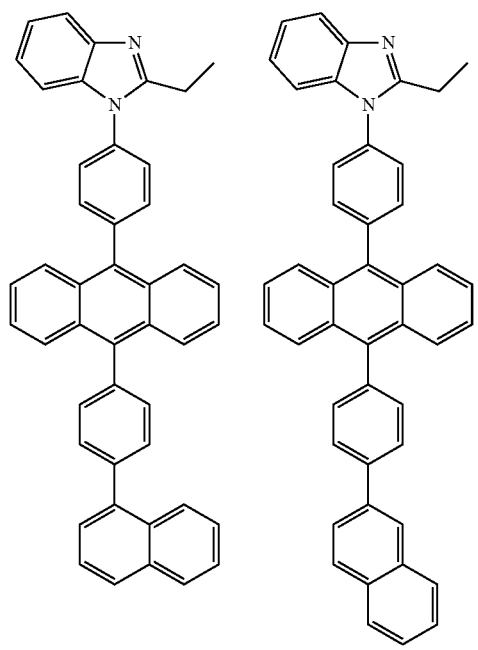
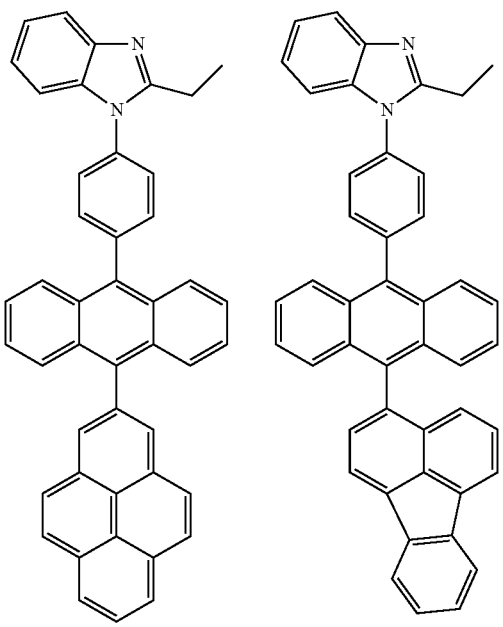

-continued
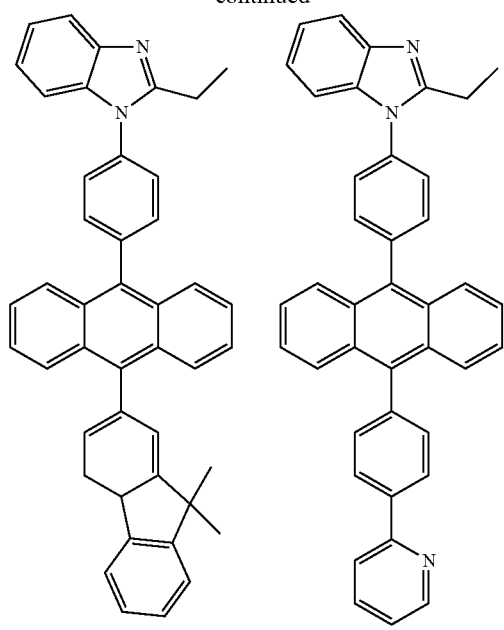
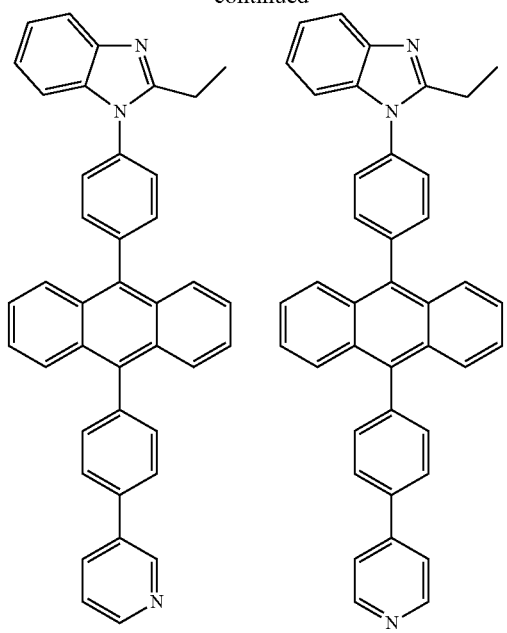
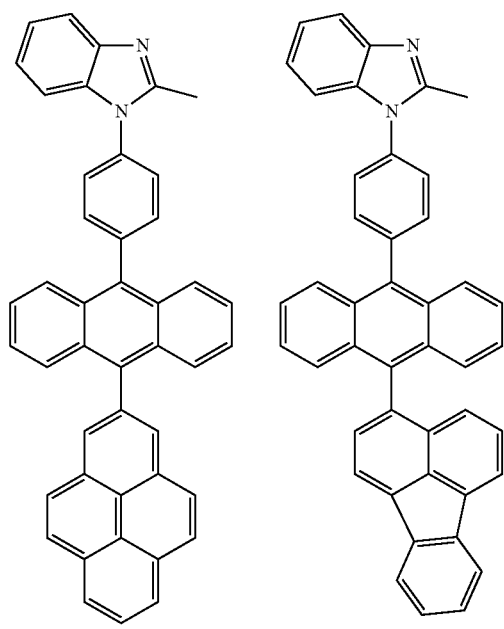
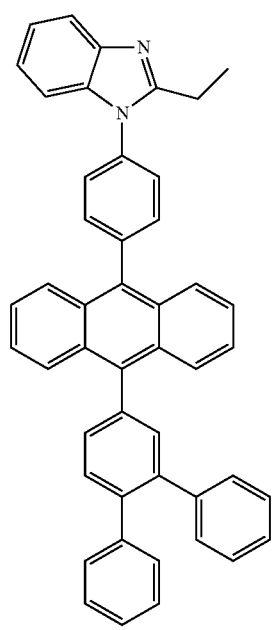

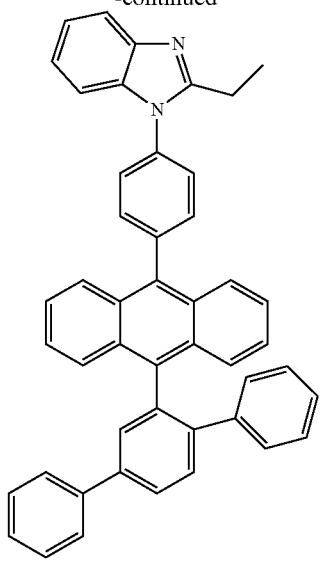
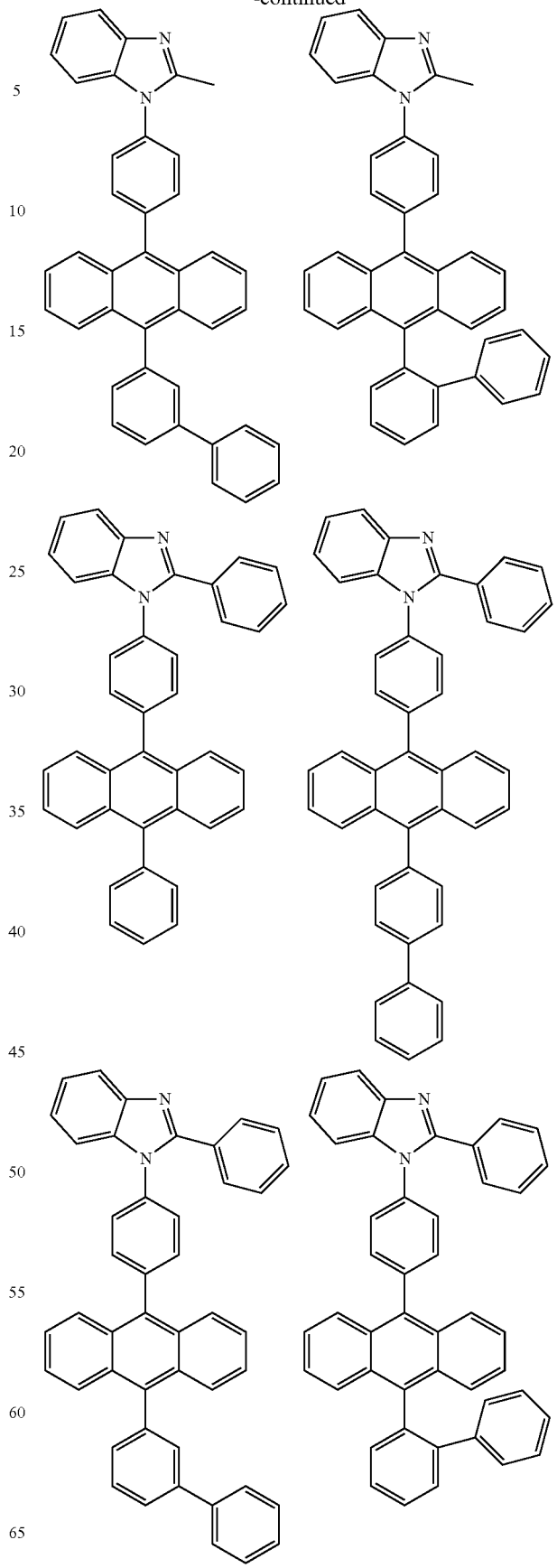
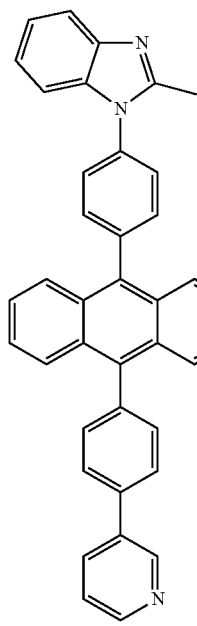
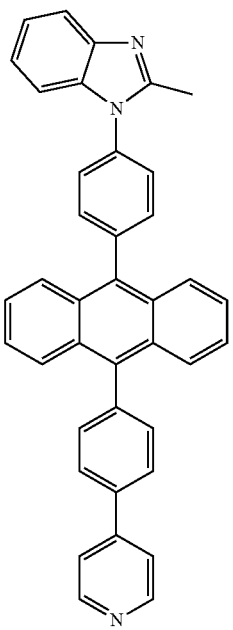

-continued
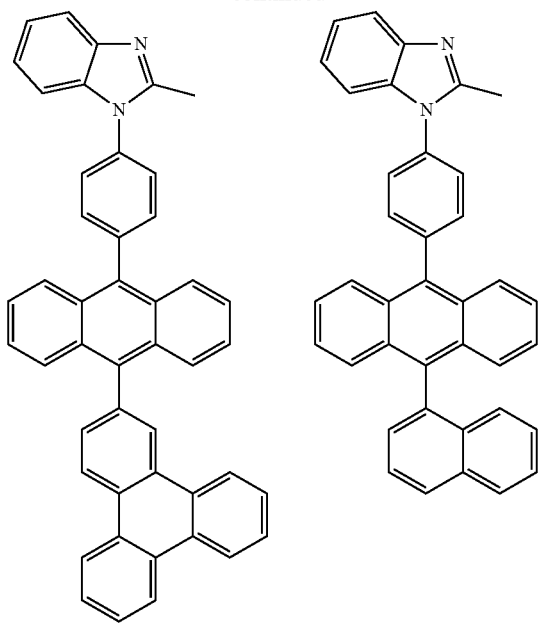
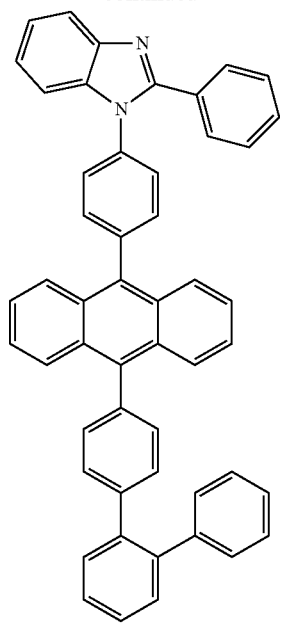
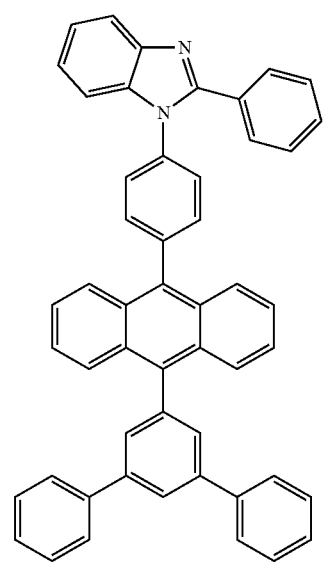
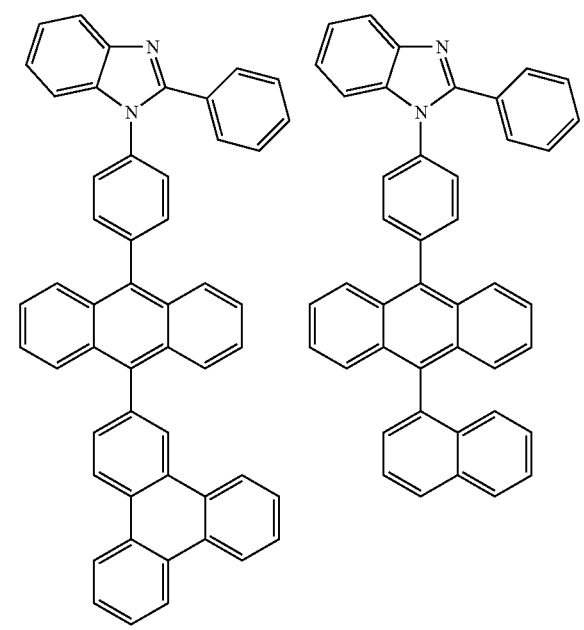

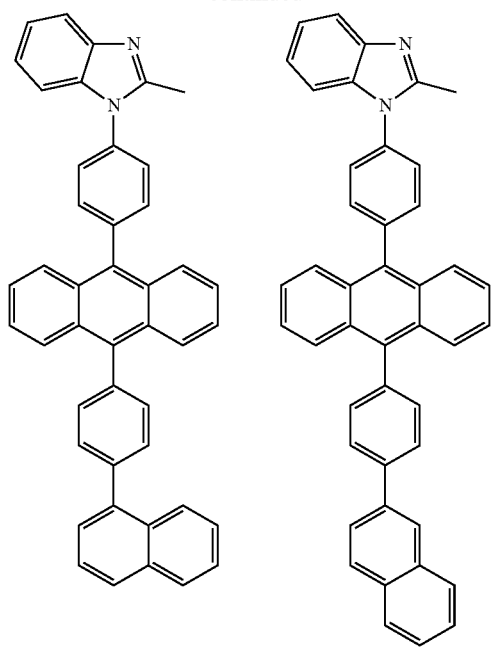
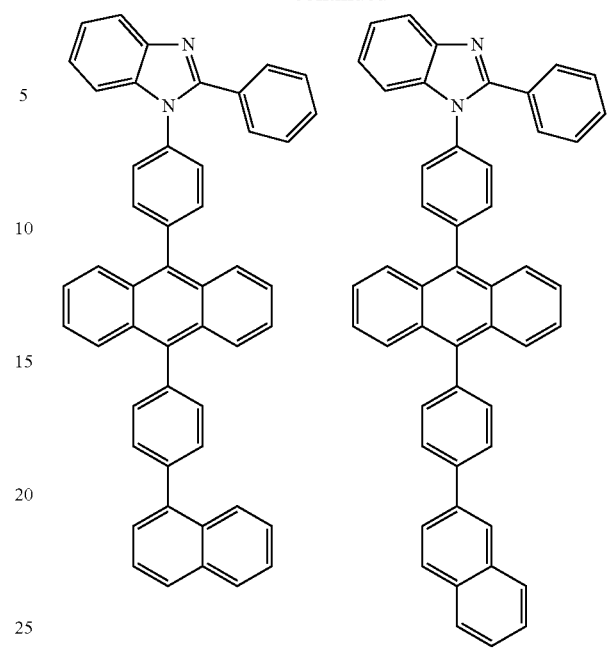
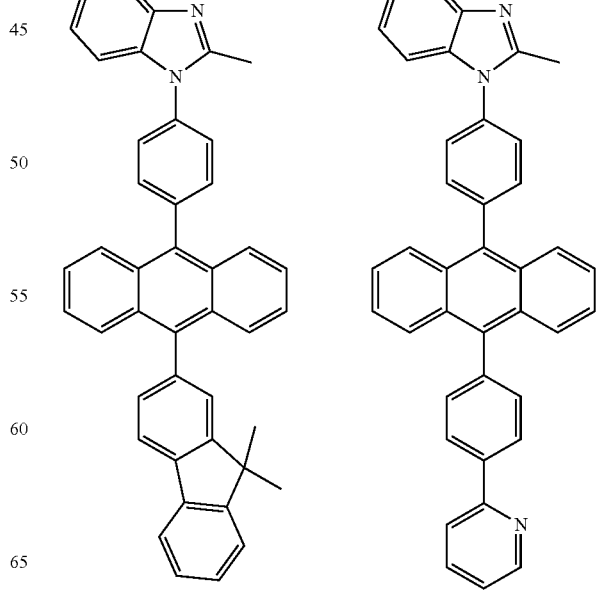

87
-continued
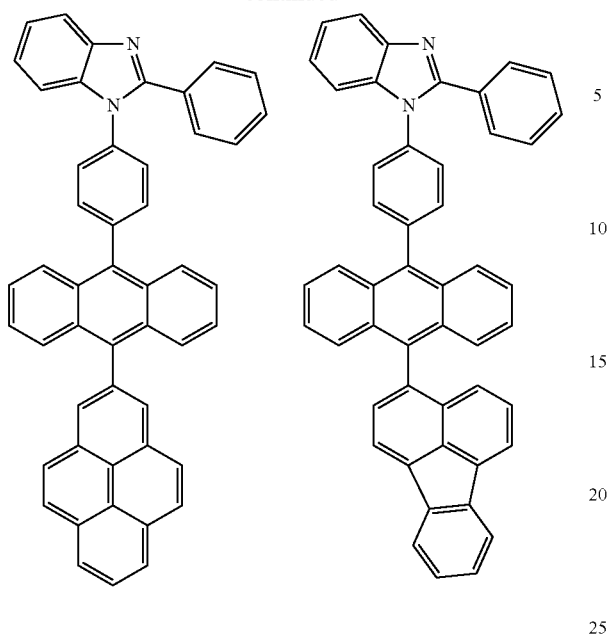
88
-continued
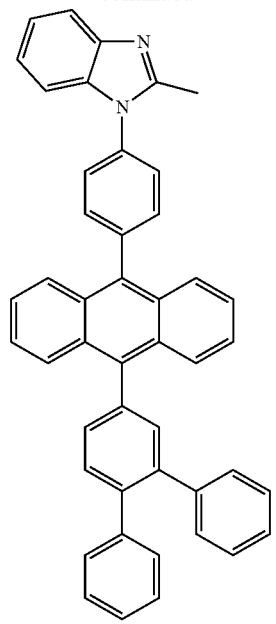
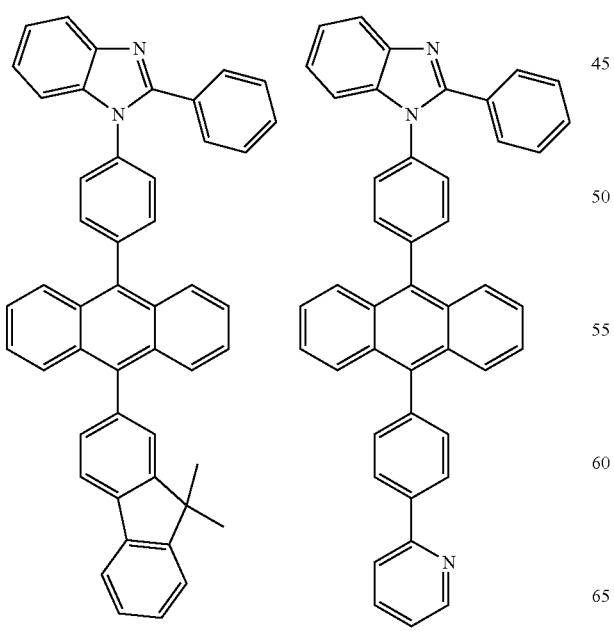
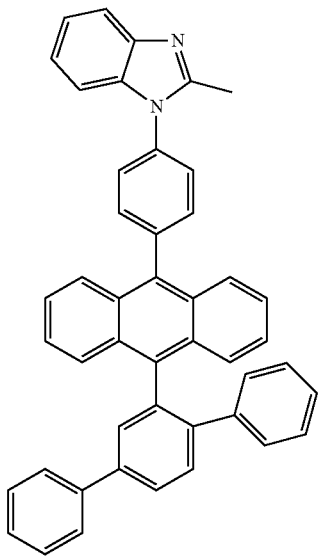

-continued
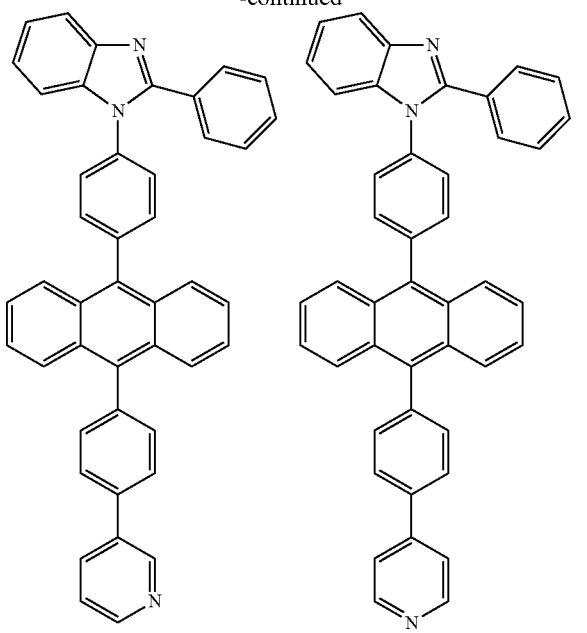
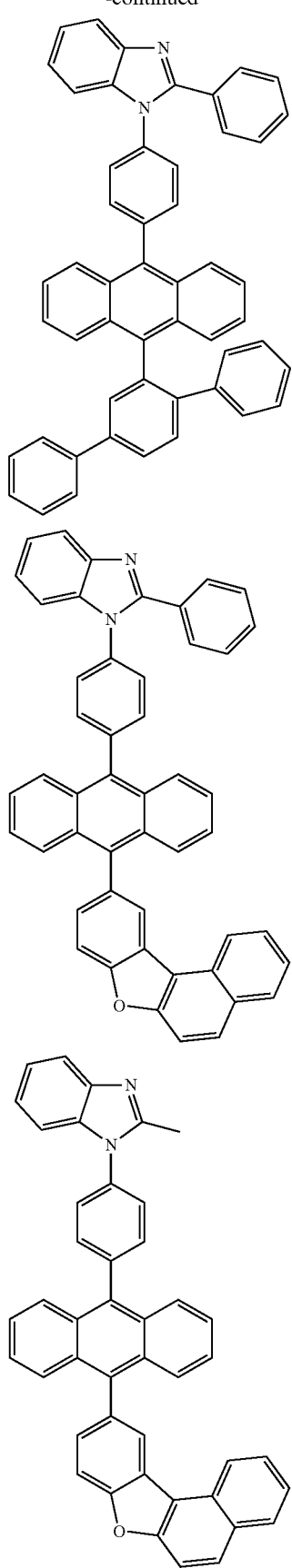

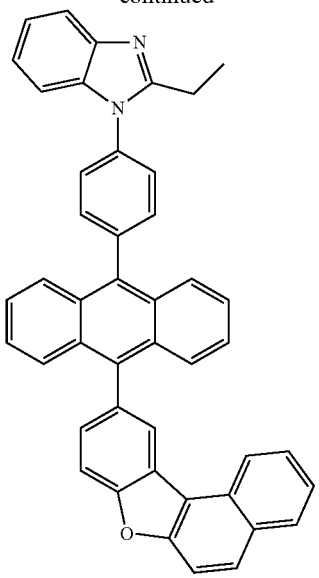
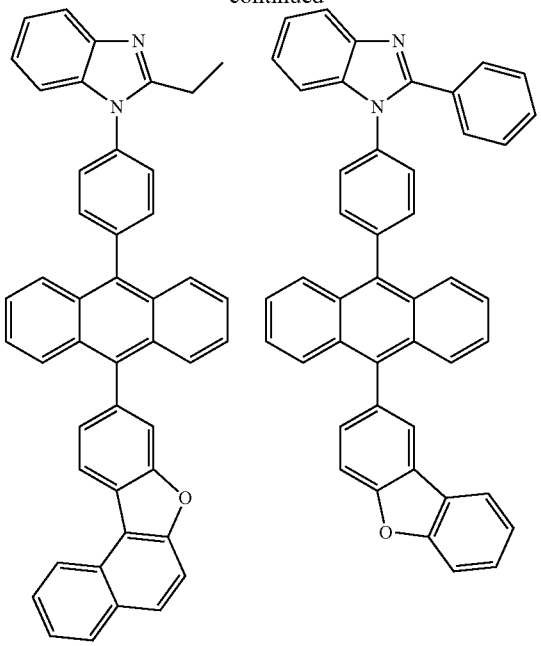
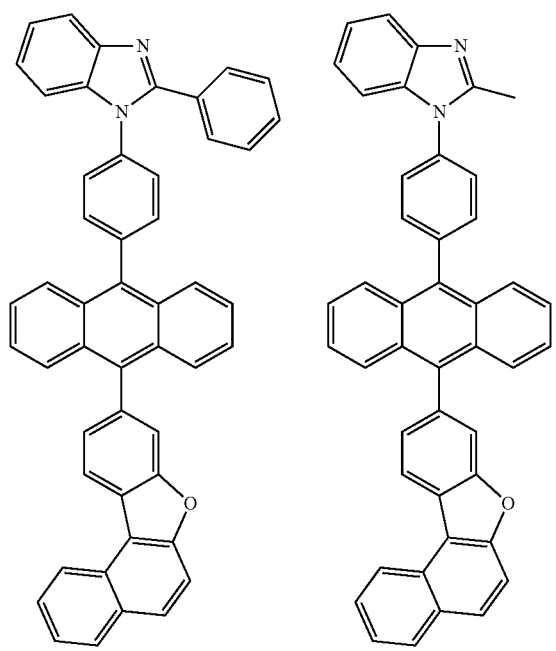
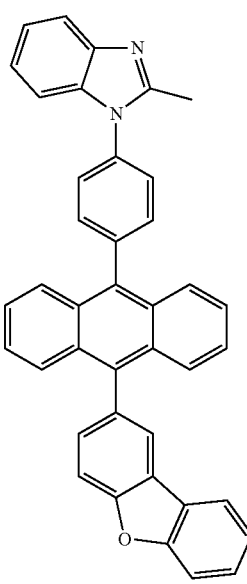
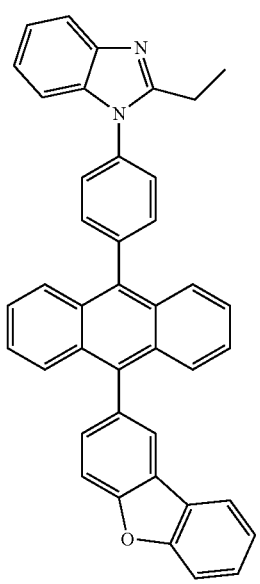

93
-continued
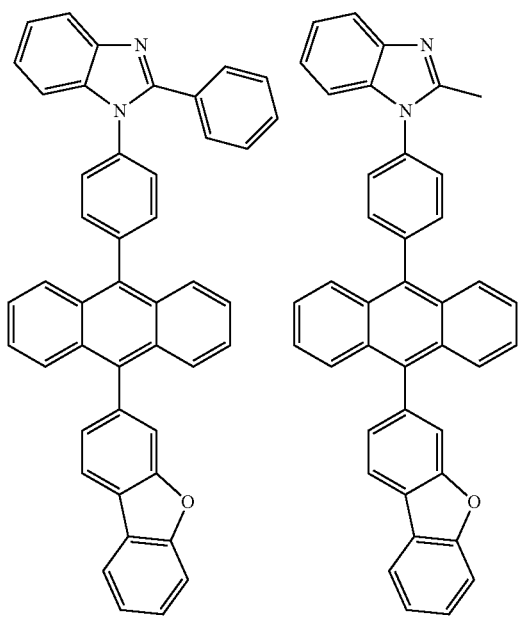
94
-continued
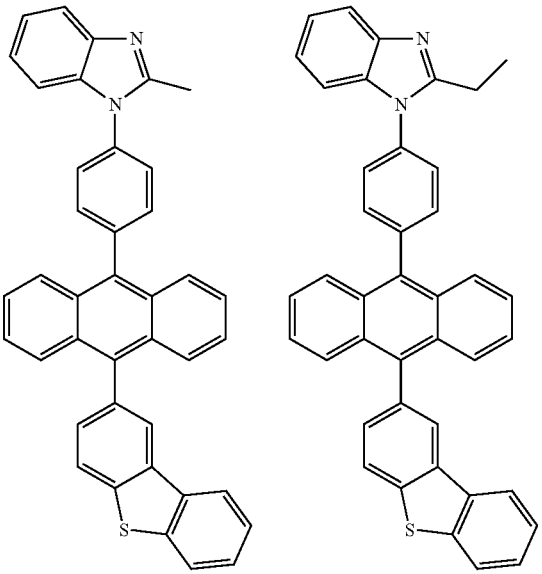
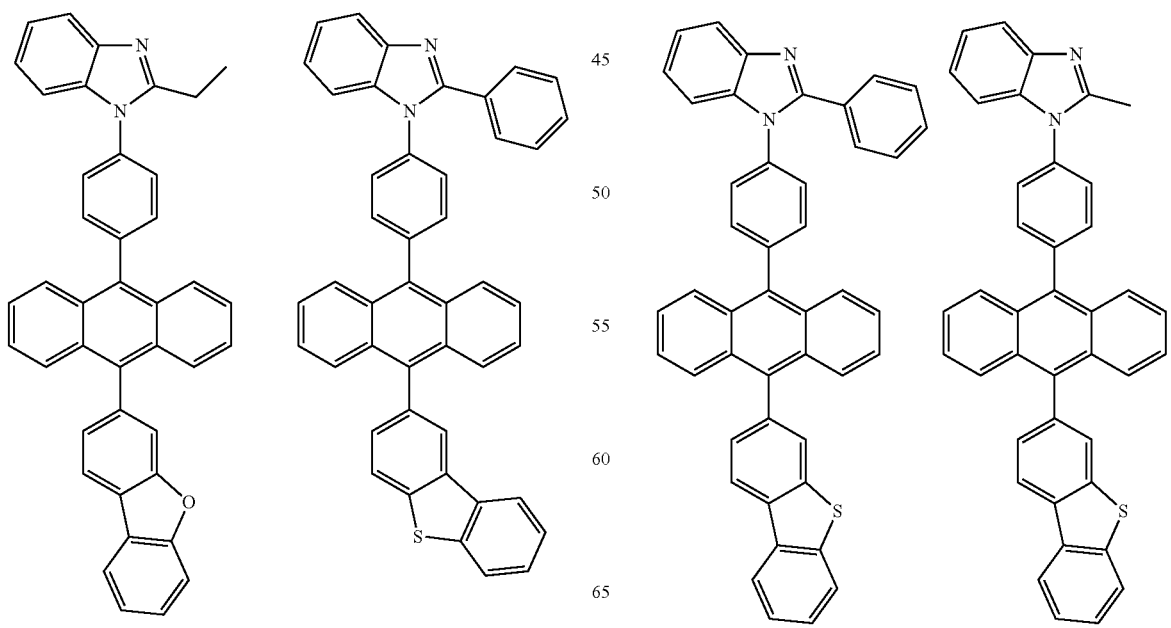

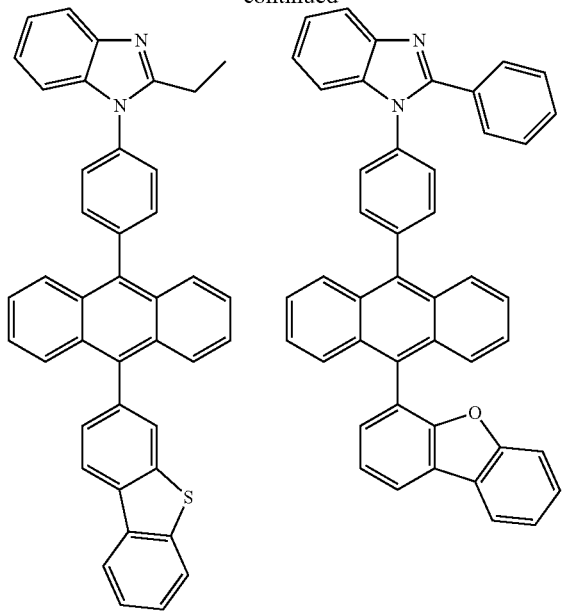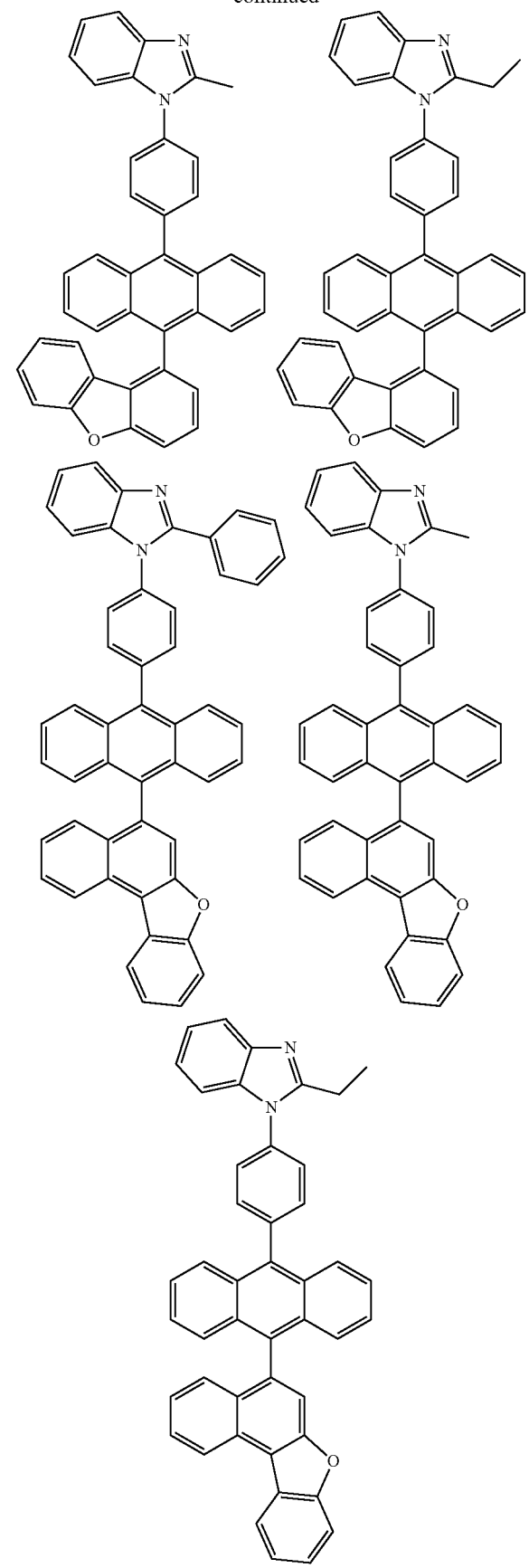

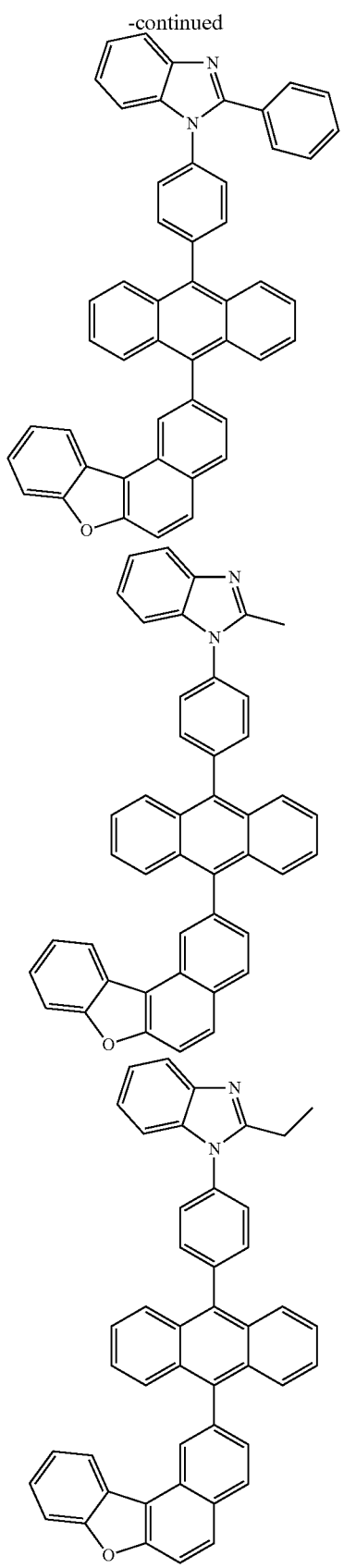

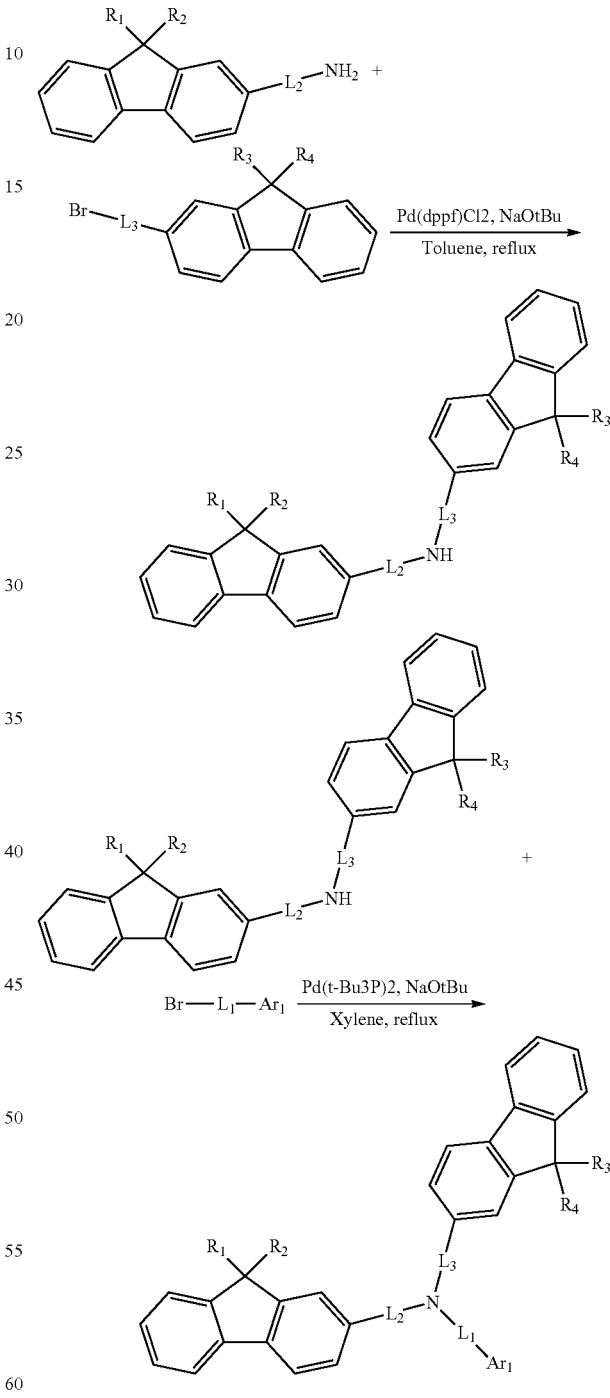

Formula 1. The substituent may be bonded by a method known in the art, and the kind and position of the substituent or the number of substituents may be changed according to the technology known in the art.

For example, a core structure of the compound of Chemical Formula 1 may be prepared as in the following Reaction Formula 1. The substituent may be bonded by a method known in the art, and the kind and position of the substituent or the number of substituents may be changed according to the technology known in the art.

For example, a core structure of the compound of Chemical Formula 2 may be prepared as in the following Reaction Formula 2. The substituent may be bonded by a method known in the art, and the kind and position of the substituent or the number of substituents may be changed according to the technology known in the art.

[Reaction Formula 2]

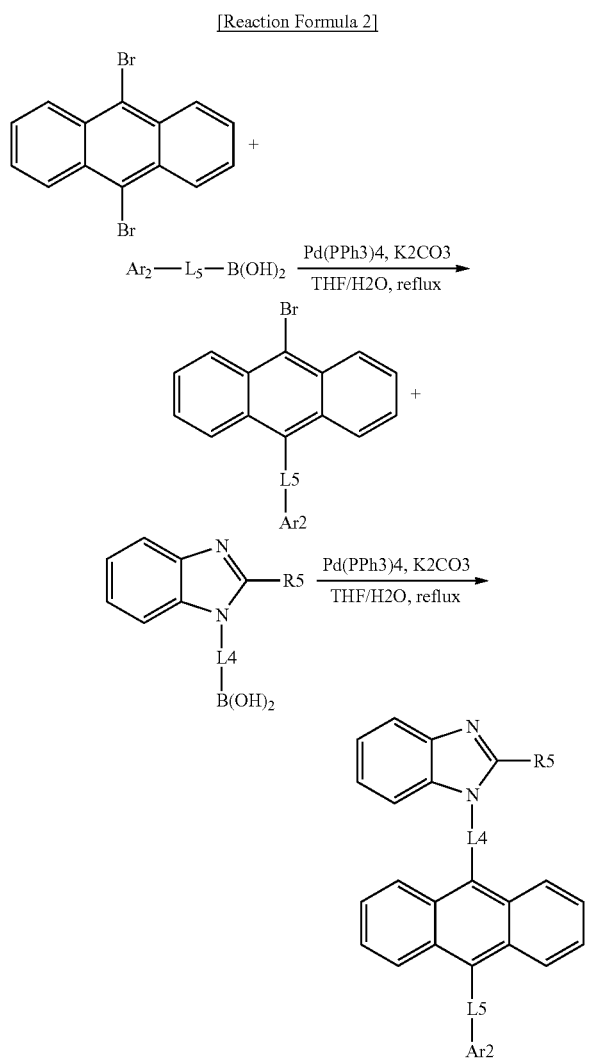

When one member is disposed "on" another member in the present specification, this includes not only a case where the one member is brought into contact with another member, but also a case where still another member is present between the two members.

When one part "includes" one constituent element in the present specification, unless otherwise specifically described, this does not mean that another constituent element is excluded, but means that another constituent element may be further included.

The organic material layer of the organic light emitting device of the present application may also be composed of a single-layered structure, but may be composed of a multi-layered structure in which two or more organic material layers are stacked. For example, as a representative example of the organic light emitting device of the present invention, an organic light emitting device may have a structure including a hole injection layer, a hole transporting layer, a light emitting layer, an electron transporting layer, an electron injection layer, and the like as organic material layers. However, the structure of the organic light emitting device is not limited thereto, and may include a fewer number of organic material layers.

In an exemplary embodiment of the present specification, the first electrode is a positive electrode, and the second electrode is a negative electrode.

In an exemplary embodiment of the present specification, an organic material layer including the compound represented by Chemical Formula 1 is a hole transporting layer.

In an exemplary embodiment of the present specification, an organic material layer including the compound represented by Chemical Formula 1 is an electron blocking layer.

In an exemplary embodiment of the present specification, an organic material layer including the compound represented by Chemical Formula 1 includes a hole transporting layer and an electron blocking layer, and the electron blocking layer includes the compound represented by Chemical Formula 1.

In an exemplary embodiment of the present specification, the electron blocking layer is an organic material layer which is brought into contact with the light emitting layer.

In an exemplary embodiment of the present specification, an organic material layer including the compound represented by Chemical Formula 2 is an electron transporting layer.

In an exemplary embodiment of the present specification, an organic material layer including the compound represented by Chemical Formula 2 includes an electron transporting layer and an electron injection layer, and the electron transporting layer includes the compound represented by Chemical Formula 2.

In an exemplary embodiment of the present application, an organic material layer including the compound represented by Chemical Formula 1 and an organic material layer including the compound represented by Chemical Formula 2 are each an organic material layer having a single layer or two or more layers.

In an exemplary embodiment of the present application, an organic material layer including the compound represented by Chemical Formula 1 is an organic material layer having two or more layers, and as the organic material layer having two or more layers, two or more may be selected from the group consisting of a hole transporting layer, a hole injection layer, a layer which transports and injects holes simultaneously, and an electron blocking layer.

In an exemplary embodiment of the present application, an organic material layer including the compound represented by Chemical Formula 2 is an organic material layer having two or more layers, and as the organic material layer having two or more layers, two or more may be selected from the group consisting of an electron transporting layer, an electron injection layer, a layer which transports and injects electrons simultaneously, and a hole blocking layer.

An exemplary embodiment of the present specification is an organic light emitting device in which one or more layers of the organic material layer include the compound represented by Chemical Formula 1, and include a light emitting layer including a compound of Chemical Formula 3.

[Chemical Formula 3]

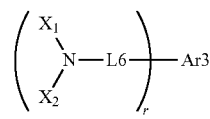

In Chemical Formula 3,

Ar3 is a benzofluorene skeleton, a fluoranthene skeleton, a pyrene skeleton, or a chrysene skeleton, L6 is a single bond, a $C_6$ to $C_{30}$ arylene group, or a $C_5$ to $C_{30}$ divalent heterocyclic group, $X_1$ and $X_2$ are the same as or different from each other, and are each independently selected from the group consisting of a substituted or unsubstituted $C_6$ to $C_{30}$ aryl group, a substituted or unsubstituted $C_5$ to $C_{30}$ heterocyclic group, a substituted or unsubstituted $C_1$ to $C_{30}$ alkyl group, and a substituted or unsubstituted $C_7$ to $C_{30}$ aralkyl group, and $X_1$ and $X_2$ may be bonded to each other to form a saturated or unsaturated ring, r is an integer of 1 or more, and when r is 2 or more, $X_1$'s are the same as or different from each other, and $X_2$'s are the same as or different from each other.

In an exemplary embodiment of the present specification, L6 is a single bond or a $C_6$ to $C_{30}$ aryl group.

In another exemplary embodiment, L6 is a single bond.

In an exemplary embodiment of the present specification, Ar3 is a benzofluorene skeleton, a fluoranthene skeleton or a pyrene skeleton.

In another exemplary embodiment, Ar3 is a pyrene skeleton.

In an exemplary embodiment of the present specification, $X_1$ and $X_2$ are the same as or different from each other, and are each independently a substituted or unsubstituted $C_6$ to $C_{30}$ aryl group, a substituted or unsubstituted $C_5$ to $C_{30}$ heterocyclic group or a substituted or unsubstituted $C_1$ to $C_{30}$ alkyl group.

In another exemplary embodiment, $X_1$ and $X_2$ are the same as or different from each other, and are each independently a substituted or unsubstituted $C_6$ to $C_{30}$ aryl group; or a $C_5$ to $C_{30}$ heterocyclic group.

In still another exemplary embodiment, $X_1$ and $X_2$ are the same as or different from each other, and are each independently a phenyl group unsubstituted or substituted with an alkyl group; or a dibenzofuran group.

In yet another exemplary embodiment, $X_1$ and $X_2$ are the same as or different from each other, and are each independently a phenyl group unsubstituted or substituted with a methyl group; or a dibenzofuran group.

An exemplary embodiment of the present specification is an organic light emitting device in which Ar3 is a pyrene skeleton, L6 is a single bond, and $X_1$ and $X_2$ are the same as or different from each other, and are each independently an aryl group unsubstituted or substituted with an alkyl group; or a $C_5$ to $C_{30}$ heterocyclic group, and r is 2.

Another exemplary embodiment is an organic light emitting device in which Ar3 is a pyrene skeleton, L6 is a single bond, $X_1$ is a phenyl group substituted with a methyl group, $X_2$ is a dibenzofuran group, and r is 2.

In an exemplary embodiment of the present specification, the compound of Chemical Formula 3 may be included as a dopant of a light emitting layer.

An exemplary embodiment of the present specification is an organic light emitting device in which one or more layers of the organic material layer include the compound represented by Chemical Formula 1, and a compound of the following Chemical Formula 4 is included in a light emitting layer of the organic material layer.

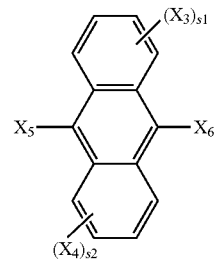

[Chemical Formula 4]

In Chemical Formula 4, $X_5$ is a substituted or unsubstituted 1-naphthyl group, a substituted or unsubstituted 2-naphthyl group, a substituted or unsubstituted 1-anthryl group, a substituted or unsubstituted 2-anthryl group, a substituted or unsubstituted 1-phenanthryl group, a substituted or unsubstituted 2-phenanthryl group, a substituted or unsubstituted 3-phenanthryl group, a substituted or unsubstituted 4-phenanthryl group, a substituted or unsubstituted 9-phenanthryl group, a substituted or unsubstituted 1-naphthacenyl group, a substituted or unsubstituted 2-naphthacenyl group, a substituted or unsubstituted 9-naphthacenyl group, a substituted or unsubstituted 1-pyrenyl group, a substituted or unsubstituted 2-pyrenyl group, a substituted or unsubstituted 4-pyrenyl group, a substituted or unsubstituted 3-methyl-2-naphthyl group, a substituted or unsubstituted 4-methyl-1-naphthyl group or the following structural formula

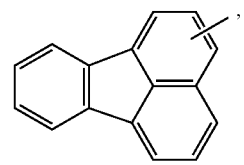

$X_6$ is a group selected from the group consisting of a substituted or unsubstituted phenyl group, a substituted or unsubstituted 1-naphthyl group, a substituted or unsubstituted 2-naphthyl group, a substituted or unsubstituted 1-anthryl group, a substituted or unsubstituted 2-anthryl group, a substituted or unsubstituted 9-anthryl group, a substituted or unsubstituted 1-phenanthryl group, a substituted or unsubstituted 2-phenanthryl group, a substituted or unsubstituted 3-phenanthryl group, a substituted or unsubstituted 4-phenanthryl group, a substituted or unsubstituted 9-phenanthryl group, a substituted or unsubstituted 1-naphthacenyl group, a substituted or unsubstituted 2-naphthacenyl group, a substituted or unsubstituted 9-naphthacenyl group, a substituted or unsubstituted 1-pyrenyl group, a substituted or unsubstituted 2-pyrenyl group, a substituted or unsubstituted 4-pyrenyl group, a substituted or unsubstituted 2-biphenylyl group, a substituted or unsubstituted 3-biphenylyl group, a substituted or unsubstituted 4-biphenylyl group, a substituted or unsubstituted p-terphenyl-4-yl group, a substituted or unsubstituted p-terphenyl-3-yl group, a substituted or unsubstituted p-terphenyl-2-yl group, a substituted or unsubstituted m-terphenyl-4-yl group, a substituted or unsubstituted m-terphenyl-3-yl group, a substituted or unsubstituted m-terphenyl-2-yl group, a substituted or unsubstituted o-tolyl group, a substituted or unsubstituted m-tolyl group, a substituted or unsubstituted p-tolyl group, a substituted or unsubstituted p-t-butylphenyl group, a substituted or unsubstituted p-(2-phenylpropyl)phenyl group, a substituted or unsubstituted 3-methyl-2-naphthyl group, a substituted or unsubstituted 4-methyl-1-naphthyl group, a substituted or unsubstituted 4-methyl-1-anthryl group, a substituted or unsubstituted 4'-methylbiphenylyl group, a substituted or unsubstituted 4"-t-butyl-p-terphenyl-4-yl group, and a substituted or unsubstituted 3-fluoranthenyl group, $X_3$ and $X_4$ are the same as or different from each other, and are each independently a substituted or unsubstituted aryl group having 6 to 50 carbon atoms, a substituted or unsubstituted heteroaryl group having 5 to 50 nuclear atoms, a substituted or unsubstituted alkyl group having 1 to 50 carbon atoms, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 nuclear atoms, a substituted or unsubstituted arylthio group having 5 to 50 nuclear atoms, a substituted or unsubstituted alkoxycarbonyl group having 1 to 50 carbon atoms, a carboxyl group, a halogen atom, a cyano group, a nitro group or a hydroxyl group, and s1 and s2 are each an integer from 0 to 4.

In an exemplary embodiment of the present specification, $X_5$ is a substituted or unsubstituted 1-naphthyl group or 2-naphthyl group.

In another exemplary embodiment, $X_5$ is a substituted or unsubstituted 1-naphthyl group.

In still another exemplary embodiment, $X_5$ is a 1-naphthyl group.

In an exemplary embodiment of the present specification, $X_6$ is a phenyl group, a 1-naphthyl group, or a 2-naphthyl group.

In another exemplary embodiment, $X_6$ is a 2-naphthyl group.

In an exemplary embodiment of the present specification, $X_3$ and $X_4$ are the same as or different from each other, and are each independently a substituted or unsubstituted $C_6$ to $C_{50}$ aryl group; or a substituted or unsubstituted $C_5$ to $C_{50}$ heteroaryl group.

In an exemplary embodiment of the present specification, s1 and s2 are each an integer from 0 to 2.

In another exemplary embodiment, s1 and s2 are 0.

An exemplary embodiment of the present specification is an organic light emitting device in which $X_5$ and $X_6$ are the same as or different from each other, and are each independently a 1-naphthyl group or a 2-naphthyl group, and s1 and s2 are 0.

In an exemplary embodiment of the present specification, the compound of Chemical Formula 4 is selected from the following structural formulae.

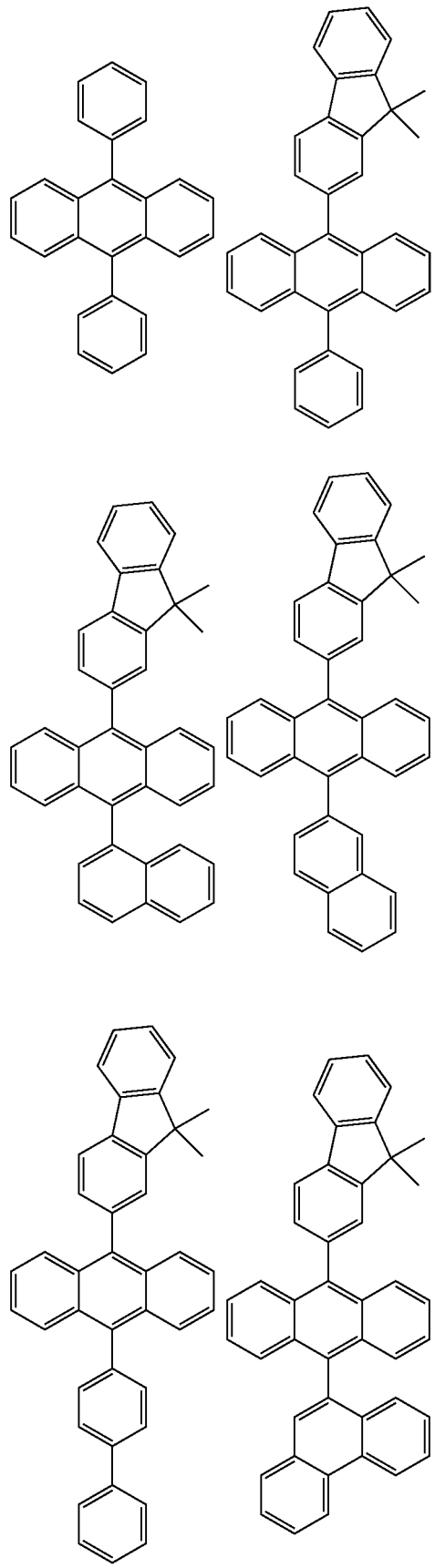

105
-continued
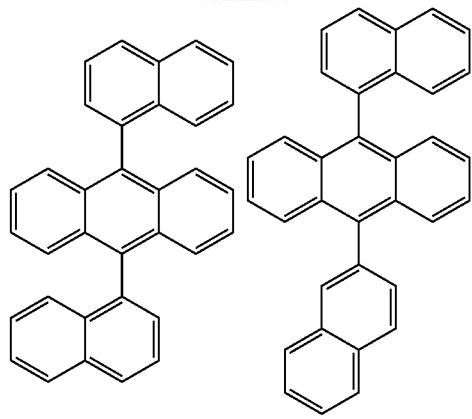
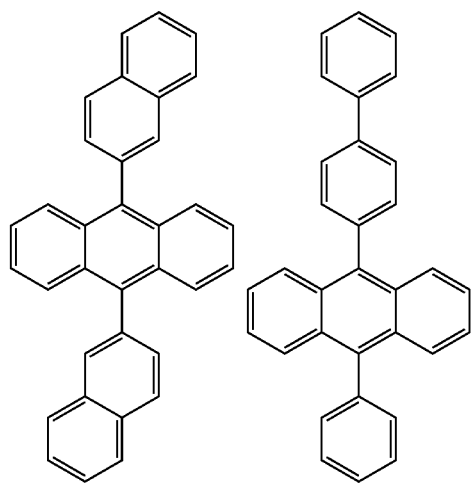
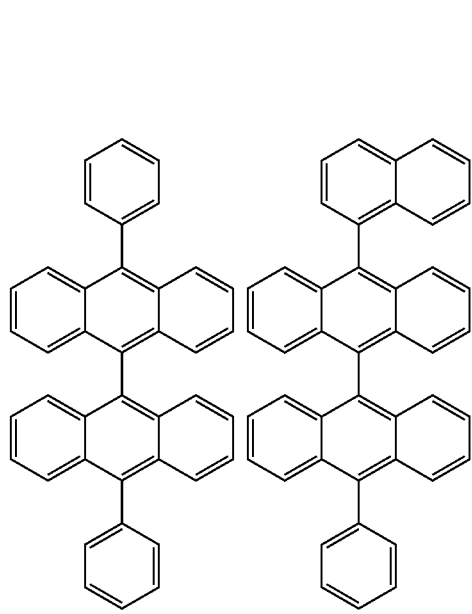
106
-continued
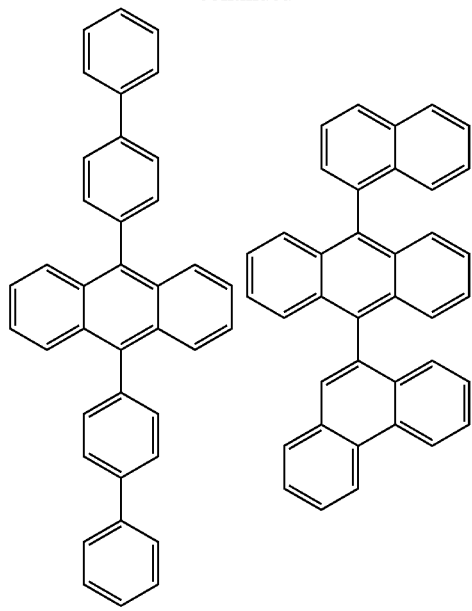
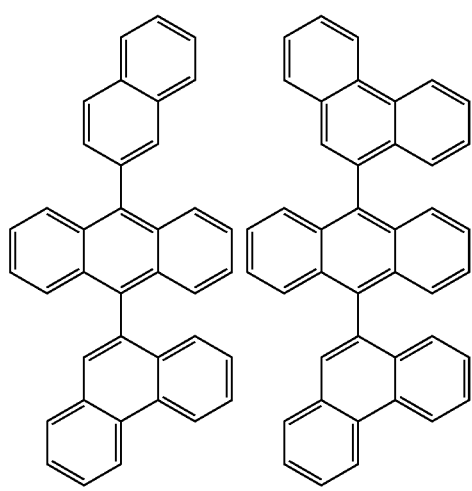
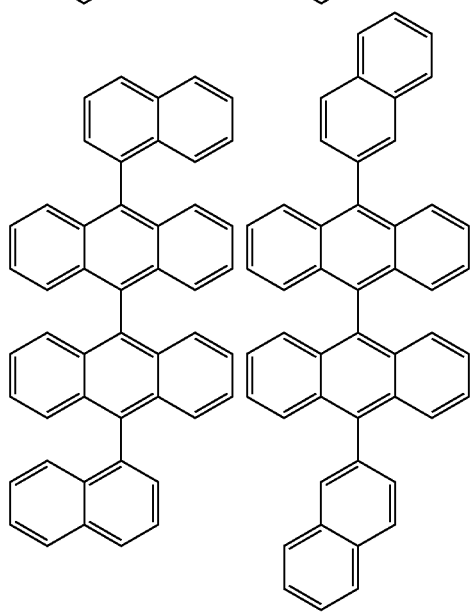

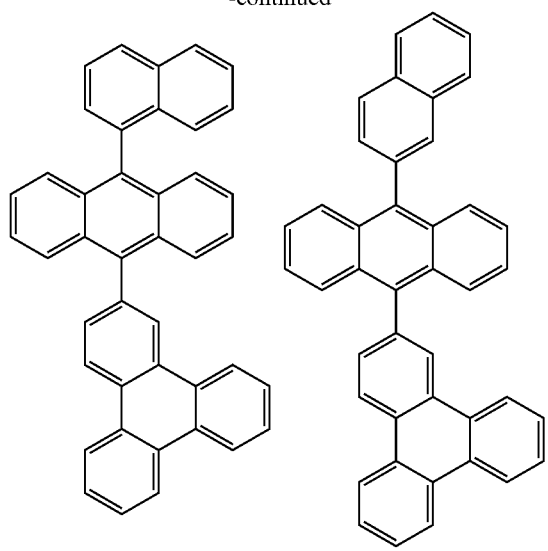
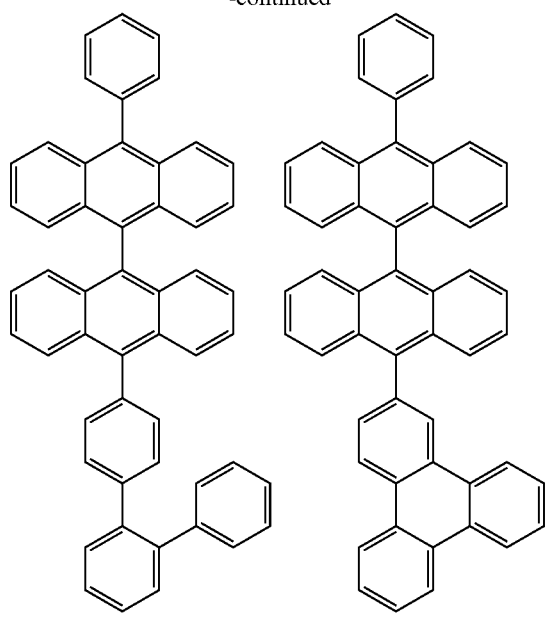
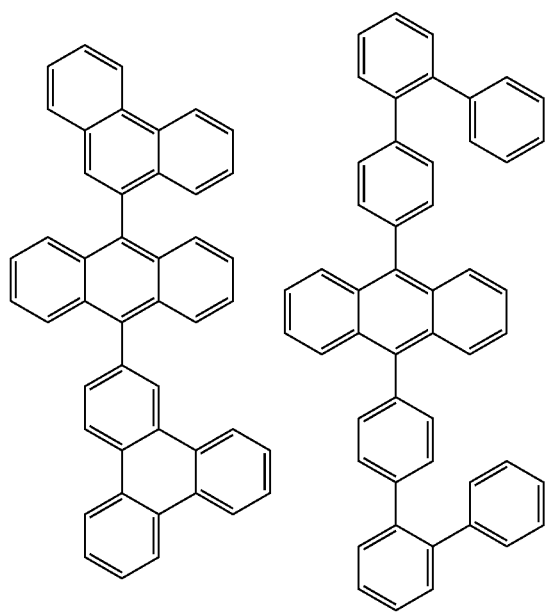
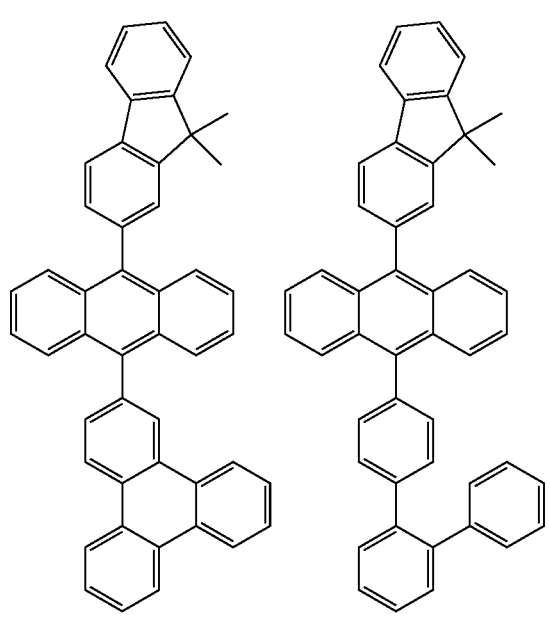

109
-continued
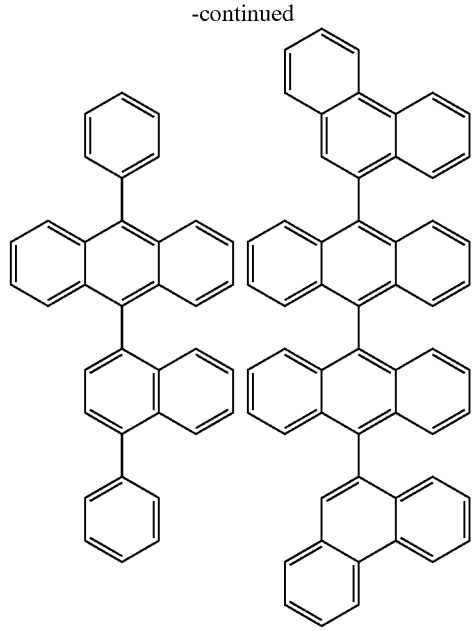
110
-continued
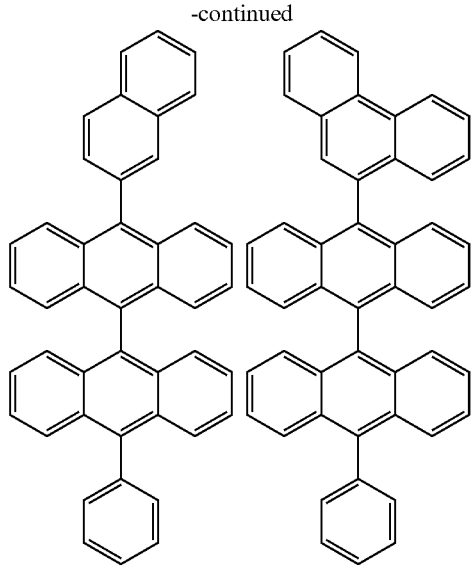
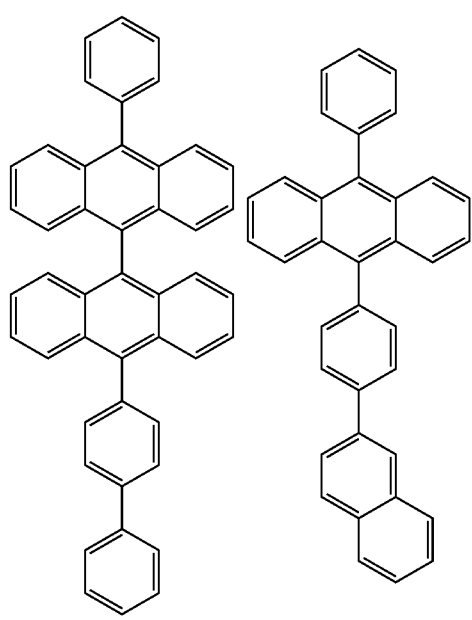
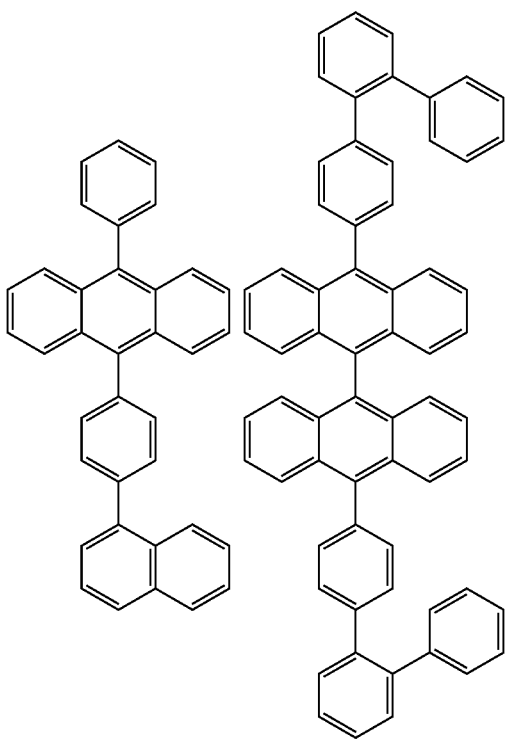

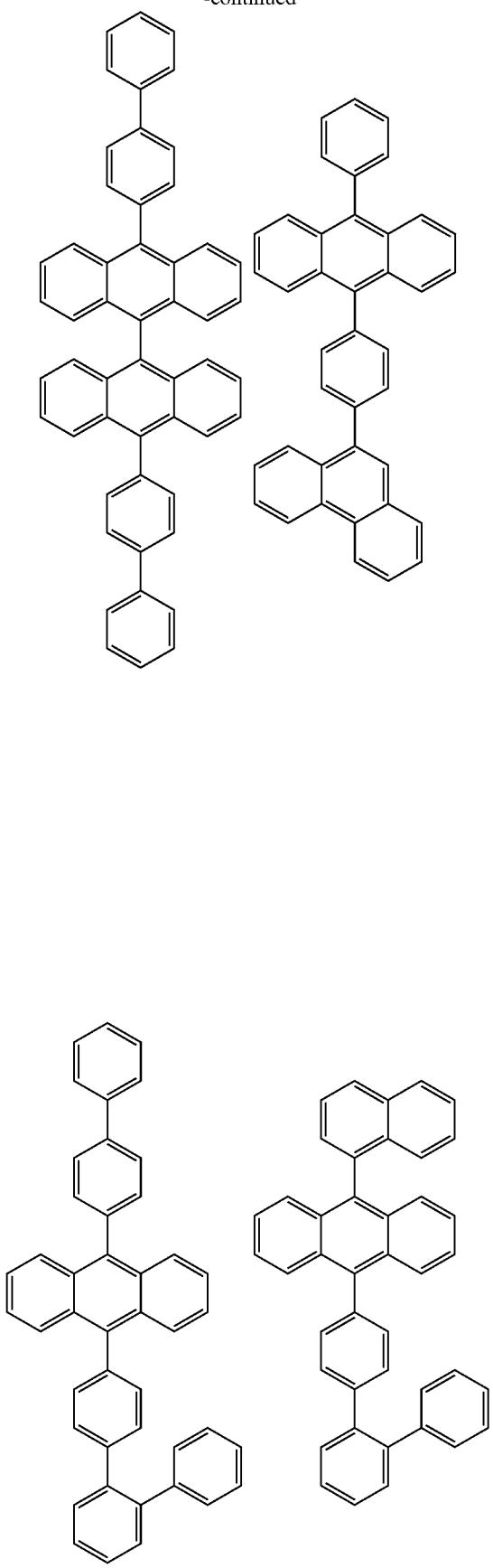

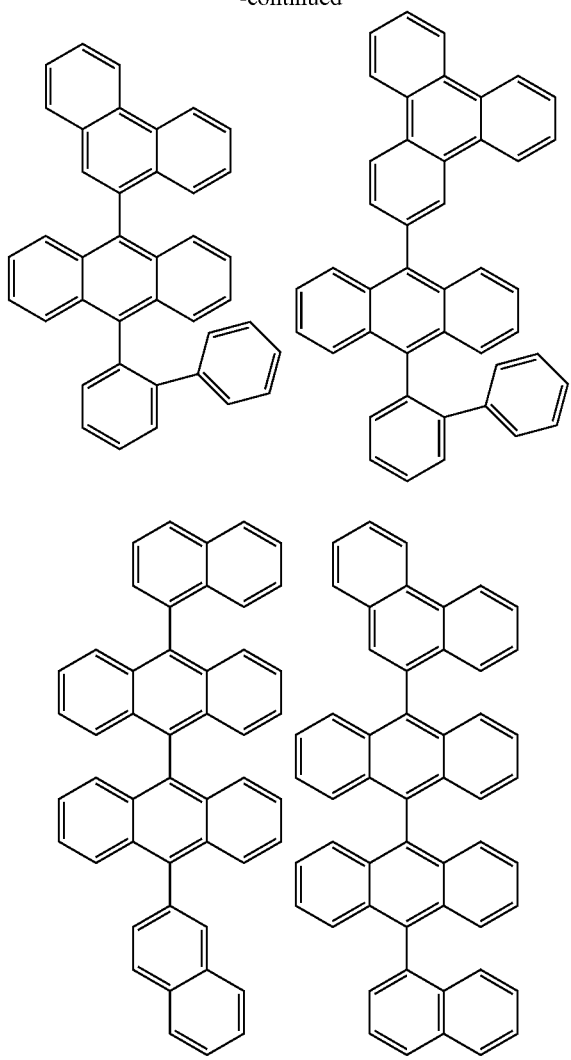
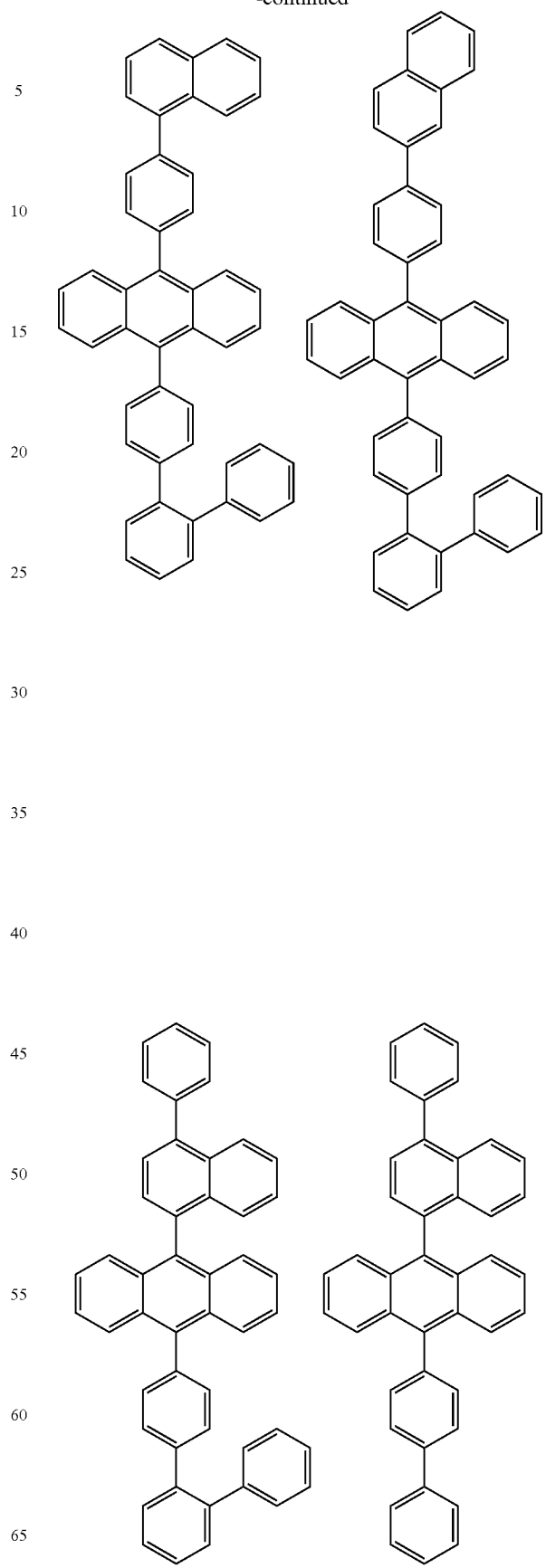

115
-continued
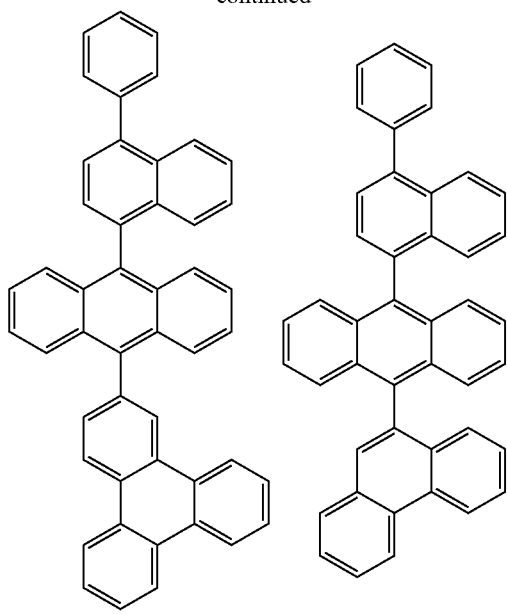
116
-continued
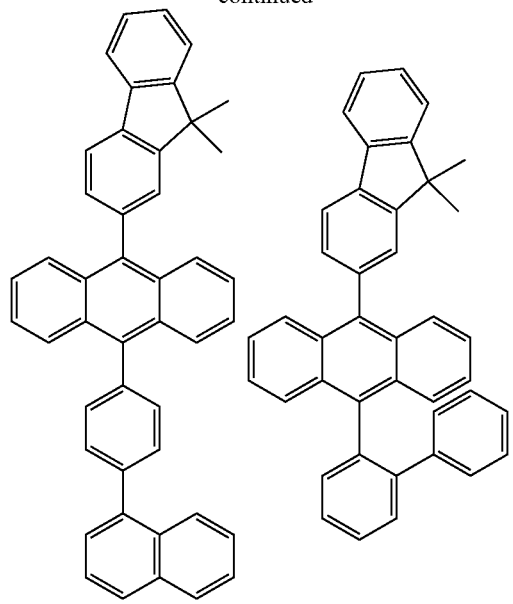
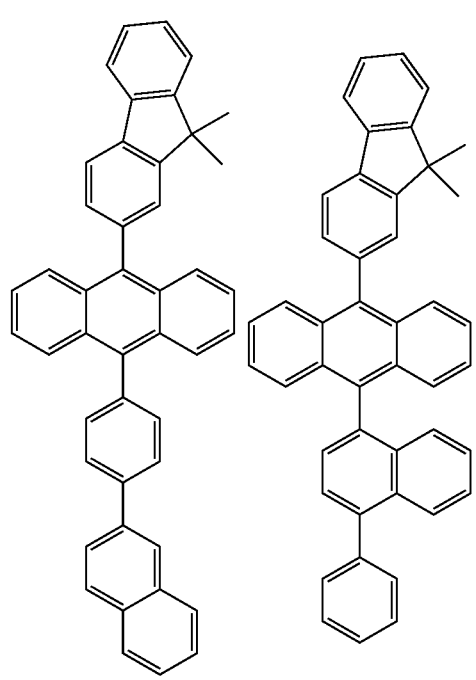
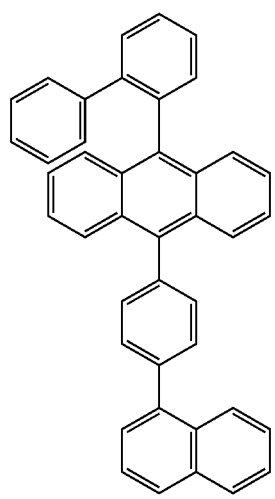

117
-continued
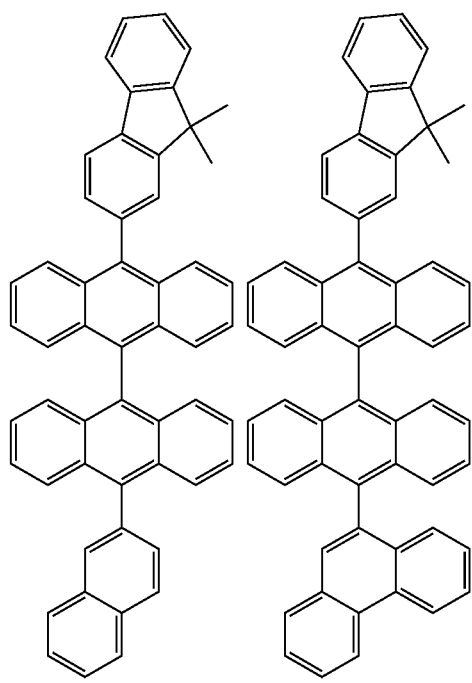
118
-continued
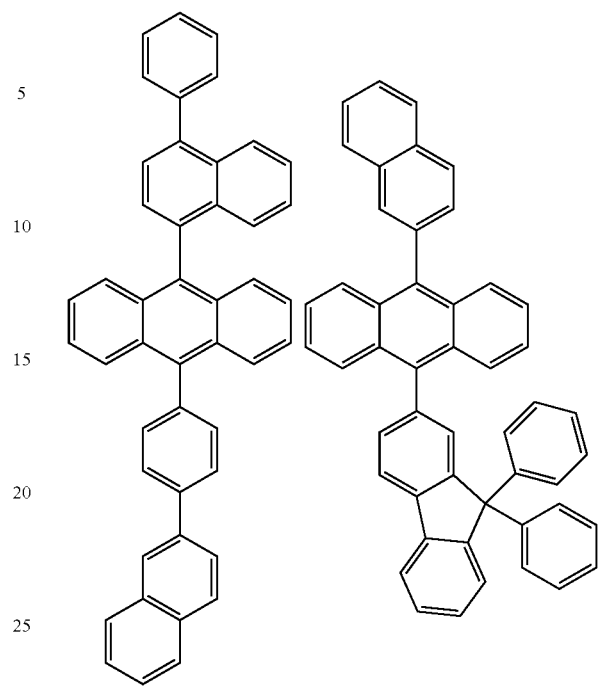
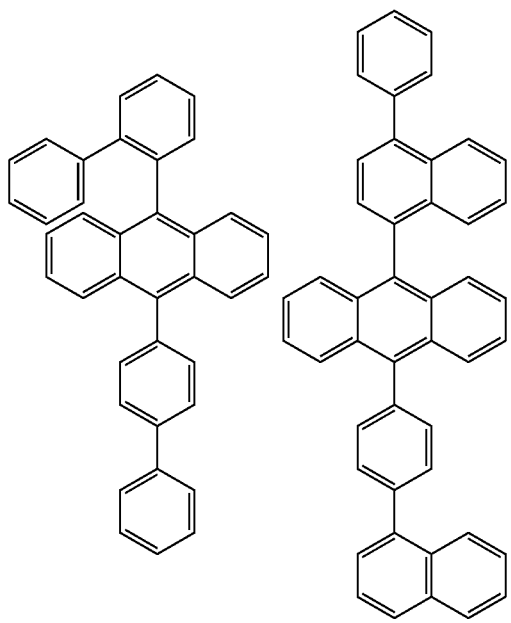
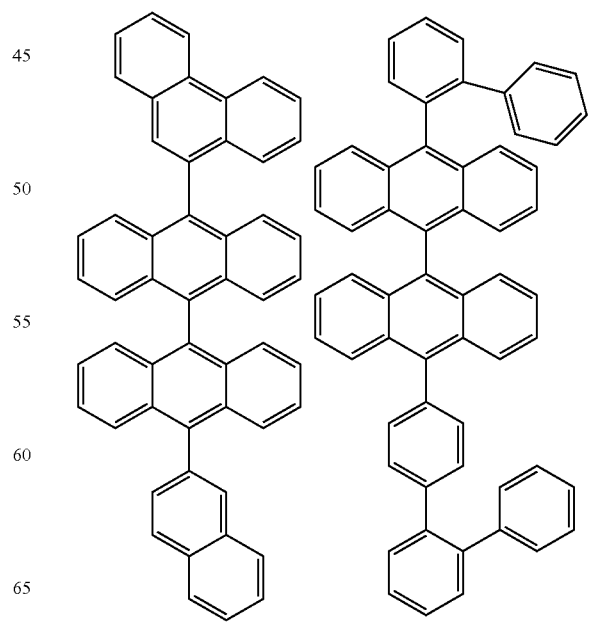

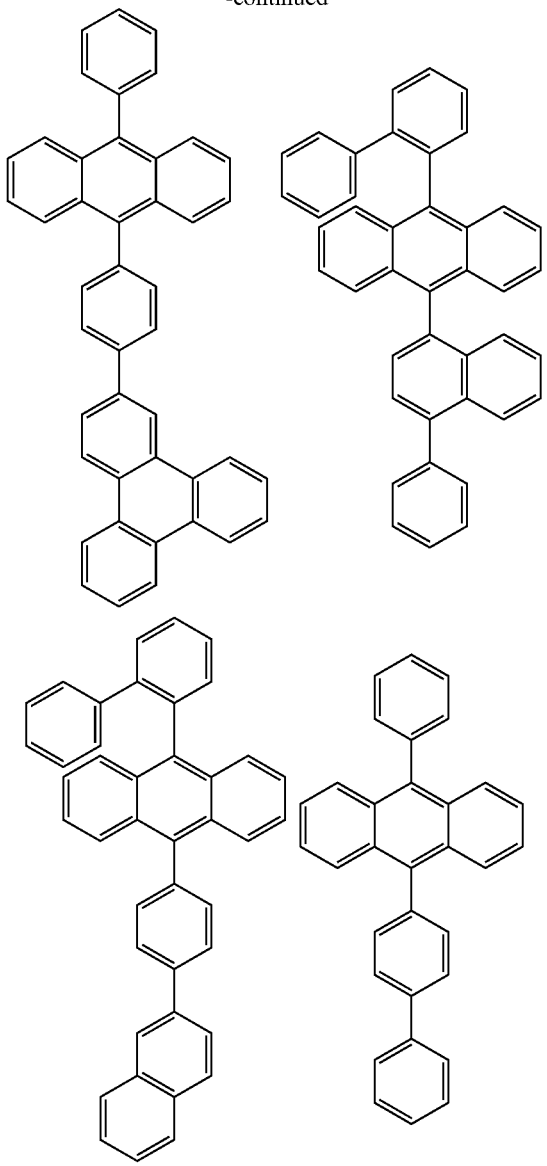

In an exemplary embodiment of the present specification, the compound of Chemical Formula 4 may be included as a host of a light emitting layer.

An exemplary embodiment of the present specification is an organic light emitting device in which one or more layers of the organic material layer includes the compound represented by Chemical Formula 1, and the compound of Chemical Formula 3 and the compound of Chemical Formula 4 are included in a light emitting layer of the organic material layer.

Another exemplary embodiment is an organic light emitting device in which one or more layers of the organic material layer include the compound represented by Chemical Formula 1, Ar3 of Chemical Formula 3 is a pyrene skeleton, L6 is a single bond, $X_1$ and $X_2$ are an aryl group unsubstituted or substituted with an alkyl group; or a heterocyclic group, r is 2, $X_5$ and $X_6$ of Chemical Formula 4 are the same as or different from each other, and are each independently a 1-naphthyl group or a 2-naphthyl group, and s1 and s2 are 0.

In still another exemplary embodiment, the organic light emitting device may be an organic light emitting device having a normal type structure in which a positive electrode, an organic material layer having one or more layers, and a negative electrode are sequentially stacked on a substrate.

In yet another exemplary embodiment, the organic light emitting device may be an organic light emitting device having an inverted type structure in which a negative electrode, an organic material layer having one or more layers, and a positive electrode are sequentially stacked on a substrate.

For example, the structure of the organic light emitting device according to an exemplary embodiment of the present application is exemplified in FIGS. 1 and 2.

FIG. 1 exemplifies a structure of an organic light emitting device in which a substrate 1, a positive electrode 2, a hole injection layer 5, a hole transporting layer 6, a light emitting layer 3, an electron transporting layer 7, and a negative electrode 4 are sequentially stacked. In the structure as described above, the compound represented by Chemical Formula 1 may be included in the hole transporting layer 6, and the compound represented by Chemical Formula 2 may be included in the electron transporting layer 7.

FIG. 2 exemplifies a structure of an organic light emitting device in which the substrate 1, the positive electrode 2, the hole injection layer 5, the hole transporting layer 6, an electron blocking layer 8, the light emitting layer 3, the electron transporting layer 7, and the negative electrode 4 are sequentially stacked. In the structure as described above, the compound represented by Chemical Formula 1 may be included in the electron blocking layer 8, and the compound represented by Chemical Formula 2 may be included in the electron transporting layer 7.

The organic light emitting device of the present application may be manufactured by the materials and methods known in the art, except that two or more layers of the organic material layer each include the compounds of Chemical Formula 1 and Chemical Formula 2 of the present application.

When the organic light emitting device includes a plurality of organic material layers, the organic material layers may be formed of the same material or different materials.

For example, the organic light emitting device of the present application may be manufactured by sequentially stacking a first electrode, an organic material layer, and a second electrode on a substrate. In this case, the organic light emitting device may be manufactured by depositing a metal or a metal oxide having conductivity, or an alloy thereof on a substrate to form a positive electrode, forming an organic material layer including a hole injection layer, a hole transporting layer, a light emitting layer, and an electron transporting layer thereon, and then depositing a material, which may be used as a negative electrode, thereon, by using a physical vapor deposition (PVD) method such as sputtering or e-beam evaporation. In addition to the method as described above, an organic light emitting device may be made by sequentially depositing a negative electrode material, an organic material layer, and a positive electrode material on a substrate.

Further, the compounds of Chemical Formulae 1 and 2 may be formed as an organic material layer by not only a vacuum deposition method, but also a solution application method when an organic light emitting device is manufactured. Here, the solution application method means spin coating, dip coating, doctor blading, inkjet printing, screen printing, a spray method, roll coating, and the like, but is not limited thereto.

As the positive electrode material, materials having a high work function are usually preferred so as to facilitate the injection of holes into an organic material layer. Specific examples of the positive electrode material which may be used in the present invention include: a metal such as vanadium, chromium, copper, zinc, and gold, or an alloy thereof; a metal oxide such as zinc oxide, indium oxide, indium tin oxide (ITO), and indium zinc oxide (IZO); a combination of a metal and an oxide, such as ZnO:Al or $SnO_2$:Sb; a conductive polymer such as poly(3-methylthiophene), poly[3,4-(ethylene-1,2-dioxy)thiophene] (PEDOT), polypyrrole, and polyaniline; and the like, but are not limited thereto.

As the negative electrode material, materials having a low work function are usually preferred so as to facilitate the injection of electrons into an organic material layer. Specific examples of the negative electrode material include: a metal such as magnesium, calcium, sodium, potassium, titanium, indium, yttrium, lithium, gadolinium, aluminum, silver, tin, and lead, or an alloy thereof; a multi-layer structured material, such as LiF/Al or $LiO_2$/Al, and the like, but are not limited thereto.

A hole injection material is preferably a compound which has a capability of transporting holes and thus has an effect of injecting holes at a positive electrode and an excellent effect of injecting holes for a light emitting layer or a light emitting material, prevents excitons produced from the light emitting layer from moving to an electron injection layer or an electron injection material, and is also excellent in the ability to form a thin film. The highest occupied molecular orbital (HOMO) of the hole injection material is preferably a value between the work function of the positive electrode material and the HOMO of the neighboring organic material layer. Specific examples of the hole injection material include metal porphyrin, oligothiophene, arylamine-based organic materials, hexanitrile hexaazatriphenylene-based organic materials, quinacridone-based organic materials, perylene-based organic materials, anthraquinone, polyaniline-based and polythiophene-based conductive polymers, and the like, but are not limited thereto.

The hole transporting layer is a layer which accepts holes from a hole injection layer and transports the holes to a light emitting layer, and a hole transporting material is suitably a material having high hole mobility which may accept holes from a positive electrode or a hole injection layer and transfer the holes to a light emitting layer. Specific examples thereof include arylamine-based organic materials, conductive polymers, block copolymers having both conjugated portions and non-conjugated portions, and the like, but are not limited thereto.

The light emitting material is a material which may emit light in a visible light region by accepting and combining holes and electrons from a hole transporting layer and an electron transporting layer, respectively, and preferably a material having high quantum efficiency for fluorescence or phosphorescence. Specific examples thereof include: 8-hydroxy-quinoline-aluminum complex ($Alq_3$); carbazole-based compounds; dimerized styryl compounds; BAlq; 10-hydroxybenzoquinoline-metal compounds; benzoxazole-based, benzothiazole-based and benzimidazole-based compounds; poly(p-phenylenevinylene) (PPV)-based polymers; spiro compounds; polyfluorene, lubrene, and the like, but are not limited thereto.

The light emitting layer may include a host material and a dopant material. Examples of the host material include a fused aromatic ring derivative, or a hetero ring-containing compound, and the like. Specific examples of the fused aromatic ring derivative include an anthracene derivative, a pyrene derivative, a naphthalene derivative, a pentacene derivative, a phenanthrene compound, a fluoranthene compound, and the like, and specific examples of the hetero ring-containing compound include a compound, a dibenzofuran derivative, a ladder-type furan compound, a pyrimidine derivative, and the like, but the examples are not limited thereto.

The electron transporting layer is a layer which accepts electrons from an electron injection layer and transports the electrons to a light emitting layer, and an electron transporting material is suitably a material having high electron mobility which may proficiently accept electrons from a negative electrode and transfer the electrons to a light emitting layer. Specific examples thereof include: Al complexes of 8-hydroxyquinoline; complexes including $Alq_3$; organic radical compounds; hydroxyflavone-metal complexes, and the like, but are not limited thereto. The electron transporting layer may be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and an electron injection material is preferably a compound which has a capability of transporting electrons, has an effect of injecting electrons from a negative electrode and an excellent effect of injecting electrons into a light emitting layer or a light emitting material, prevents excitons produced from the light emitting layer from moving to a hole injection layer, and is also excellent in the ability to form a thin film. Specific examples thereof include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and a derivative thereof, a metal complex compound, a nitrogen-containing 5-membered ring derivative, and the like, but are not limited thereto. Examples of the metal complex compound include 8-hydroxyquinolinato lithium, bis(8-hydroxyquinolinato) zinc, bis(8-hydroxyquinolinato) copper, bis(8-hydroxyquinolinato) manganese, tris(8-hydroxyquinolinato) aluminum, tris(2-methyl-8-hydroxyquinolinato) aluminum, tris(8-hydroxyquinolinato) gallium, bis(10-hydroxybenzo[h]quinolinato) beryllium, bis(10-hydroxybenzo[h]quinolinato) zinc, bis(2-methyl-8-quinolinato) chlorogallium, bis(2-methyl-8-quinolinato)(o-cresolato) gallium, bis(2-methyl-8-quinolinato)(1-naphtholato) aluminum, bis(2-methyl-8-quinolinato)(2-naphtholato) gallium, and the like, but are not limited thereto.

The hole blocking layer is a layer which blocks holes from reaching a negative electrode, and may be generally formed under the same conditions as those of the hole injection layer. Specific examples thereof include an oxadiazole derivative or a triazole derivative, a phenanthroline derivative, BCP, an aluminum complex, and the like, but are not limited thereto.

The organic light emitting device according to the present specification may be a top emission type, a bottom emission type, or a dual emission type according to the materials to be used.

The manufacture of the organic light emitting device will be specifically described in the following Examples. However, the following Examples are provided for exemplifying the present specification, and the scope of the present specification is not limited thereby.

EXAMPLES

Experimental Example 1

A glass substrate thinly coated with indium tin oxide (ITO) to have a thickness of 1,000 Å was put into distilled water in which a detergent was dissolved, and ultrasonically washed. In this case, a product manufactured by Fischer Co., was used as the detergent, and distilled water twice filtered using a filter manufactured by Millipore Co., was used as the distilled water. After the ITO was washed for 30 minutes, ultrasonic washing was repeated twice using distilled water for 10 minutes. After the washing using distilled water was completed, ultrasonic washing was conducted using a solvent of isopropyl alcohol, acetone, and methanol, and the resultant product was dried and then transported to a plasma washing machine. Furthermore, the substrate was washed by using an oxygen plasma for 5 minutes, and then was transported to a vacuum deposition machine.

Hexanitrile hexaazatriphenylene (HAT) of the following Chemical Formula was thermally vacuum deposited to have a thickness of 500 Å on the thus prepared ITO transparent electrode, thereby forming a hole injection layer.

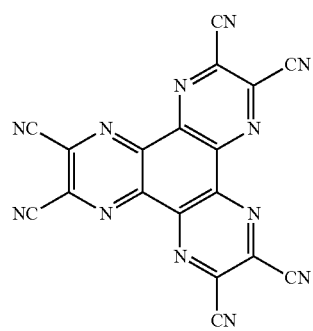

[HAT]

The following compound N4,N4,N4',N4'-tetra([1,1'-biphenyl]-4-yl)-[1,1'-biphenyl]-4,4'-diamine [HT-1] (300 Å) being a material for transporting holes was vacuum deposited on the hole injection layer, thereby forming a hole transporting layer.

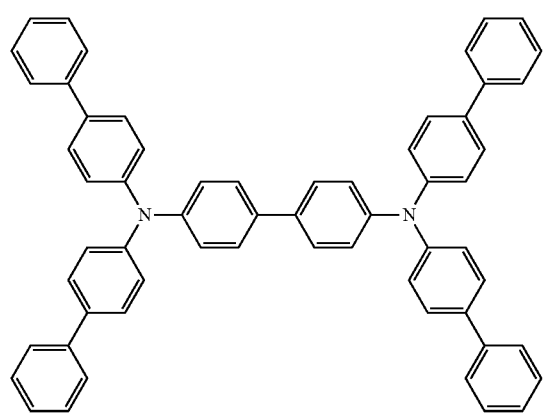

[HT-1]

Subsequently, the following compound N-([1,1'-biphenyl]-4-yl)-N-(4-(11-([1,1'-biphenyl]-4-yl)-11H-benzo[a]carbazol-5-yl)phenyl)-[1,1'-biphenyl]-4-amine [EB-1] (100 Å) was vacuum deposited to have a film thickness of 100 Å on the hole transporting layer, thereby forming an electron blocking layer.

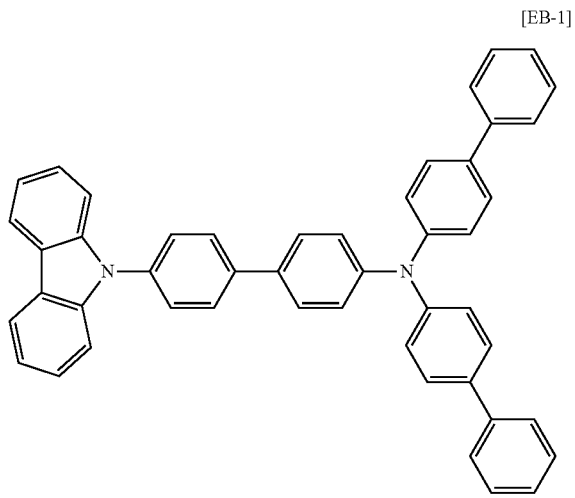 [SMILES: c1ccc(-c2ccc(N(c3ccc(-c4ccccc4)cc3)c3ccc(-c4ccc(-n5c6ccccc6c6ccccc65)cc4)cc3)cc2)cc1]

[EB-1]

Subsequently, the following BH and BD were vacuum deposited at a weight ratio of 25:1 to have a film thickness of 300 Å on the electron blocking layer, thereby forming a light emitting layer.

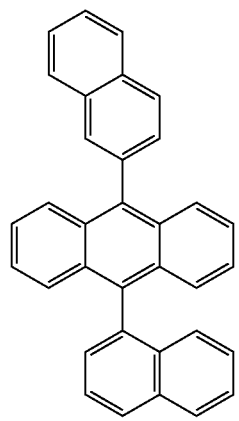

[BH]

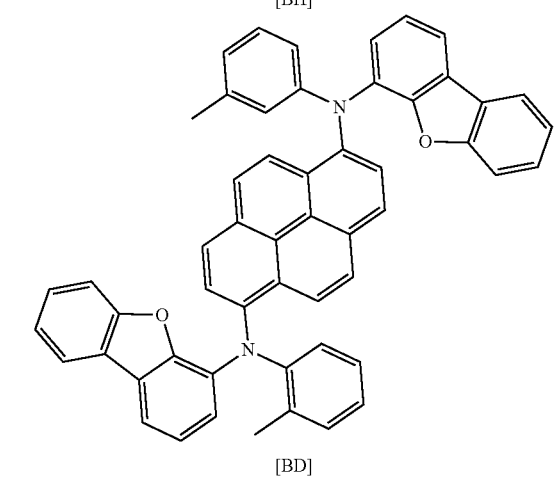

[BD]

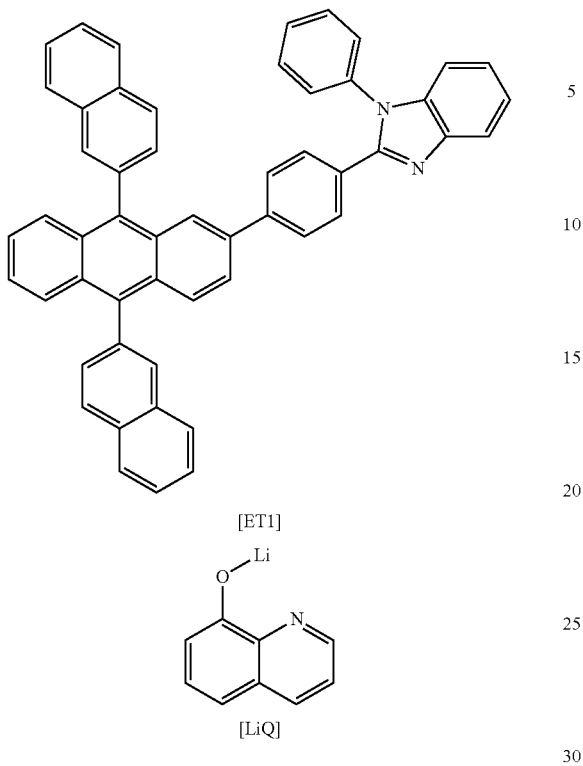

[ET1]

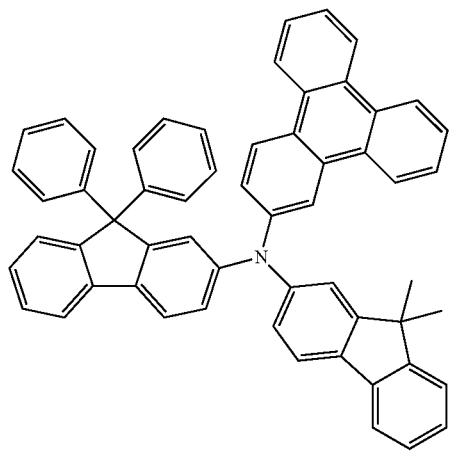

[LiQ]

Compound ET1 and Compound LiQ (lithium quinolate) were vacuum deposited at a weight ratio of 1:1 on the light emitting layer, thereby forming an electron injection and transporting layer having a thickness of 300 Å. Lithium fluoride (LiF) and aluminum were sequentially deposited on the electron injection and transporting layer to have a thickness of 12 Å and 2,000 Å, respectively, thereby forming a negative electrode.

In the aforementioned procedure, the deposition rate of the organic material was maintained at 0.4 to 0.7 Å/sec, the deposition rates of lithium fluoride and aluminum of the negative electrode were maintained at 0.3 Å/sec and at 2 Å/sec, respectively, and the degree of vacuum during the deposition was maintained at $2 \times 10^{-7}$ to $5 \times 10^{-6}$ torr, thereby manufacturing an organic light emitting device.

1-1

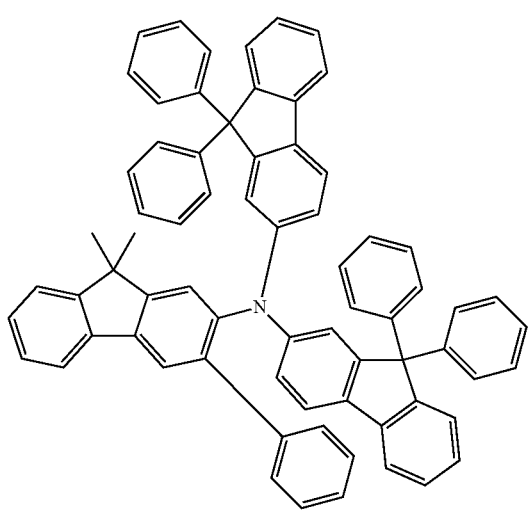

1-2

1-3

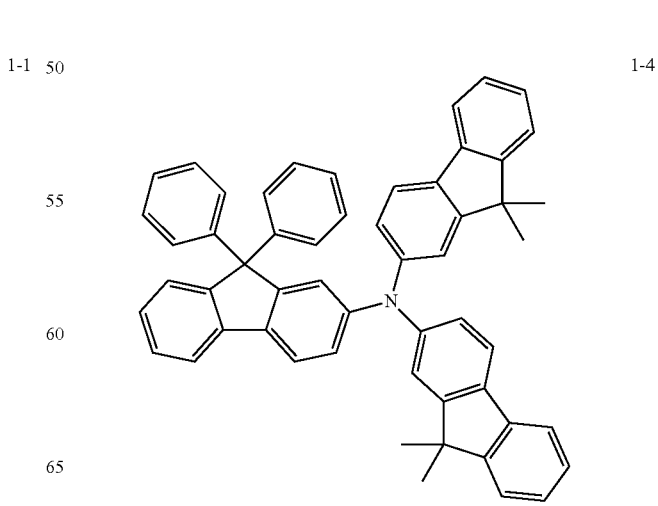

1-4

127
-continued
1-5
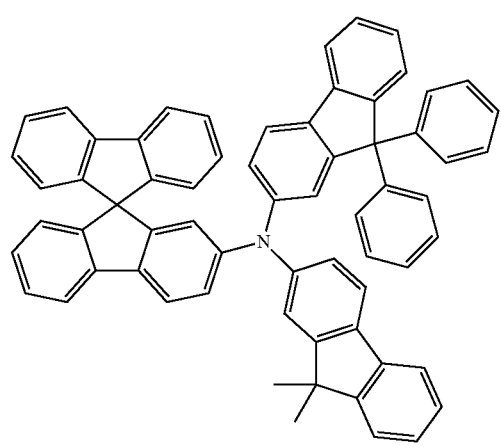
1-6
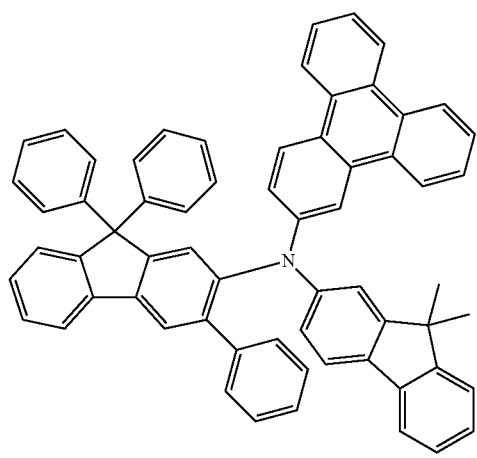
128
-continued
2-2
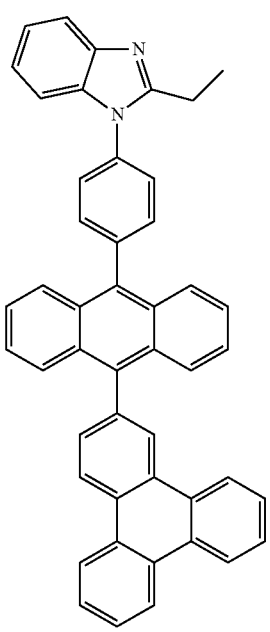
2-1
2-3
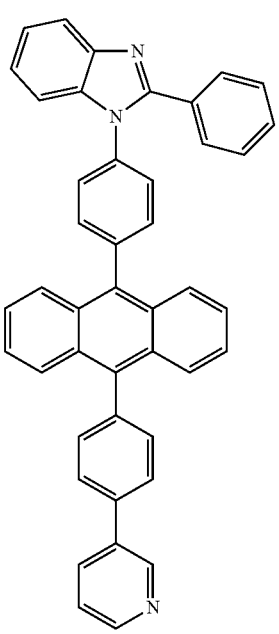

-continued 2-4

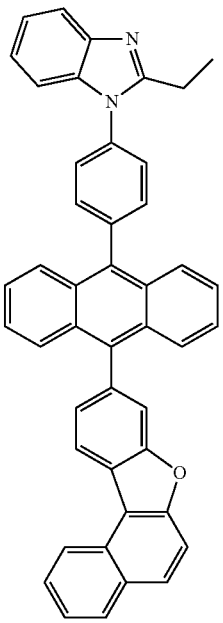

Experimental Example 1-1

An organic light emitting device was manufactured in the same manner as in Experimental Example 1, except that Compound 1-1 was used instead of EB-1 in Experimental Example 1.

Experimental Example 1-2

An organic light emitting device was manufactured in the same manner as in Experimental Example 1, except that Compound 1-2 was used instead of EB-1 in Experimental Example 1.

Experimental Example 1-3

An organic light emitting device was manufactured in the same manner as in Experimental Example 1, except that Compound 1-3 was used instead of Compound EB-1 in Experimental Example 1.

Experimental Example 1-4

An organic light emitting device was manufactured in the same manner as in Experimental Example 1, except that Compound 1-4 was used instead of Compound EB-1 in Experimental Example 1.

Experimental Example 1-5

An organic light emitting device was manufactured in the same manner as in Experimental Example 1, except that Compound 2-1 was used instead of Compound ET-1 in Experimental Example 1.

Experimental Example 1-6

An organic light emitting device was manufactured in the same manner as in Experimental Example 1, except that Compound 2-2 was used instead of Compound ET-1 in Experimental Example 1.

Experimental Example 1-7

An organic light emitting device was manufactured in the same manner as in Experimental Example 1, except that Compound 2-3 was used instead of Compound ET-1 in Experimental Example 1.

Experimental Example 1-8

An organic light emitting device was manufactured in the same manner as in Experimental Example 1, except that Compound 2-4 was used instead of Compound ET-1 in Experimental Example 1.

Experimental Example 1-9

An organic light emitting device was manufactured in the same manner as in Experimental Example 1, except that Compound 1-1 was used instead of Compound EB-1 and Compound 2-1 was used instead of Compound ET-1 in Experimental Example 1.

Experimental Example 1-10

An organic light emitting device was manufactured in the same manner as in Experimental Example 1, except that Compound 1-1 was used instead of Compound EB-1 and Compound 2-2 was used instead of Compound ET-1 in Experimental Example 1.

Experimental Example 1-11

An organic light emitting device was manufactured in the same manner as in Experimental Example 1, except that Compound 1-1 was used instead of Compound EB-1 and Compound 2-3 was used instead of Compound ET-1 in Experimental Example 1.

Experimental Example 1-12

An organic light emitting device was manufactured in the same manner as in Experimental Example 1, except that Compound 1-1 was used instead of Compound EB-1 and Compound 2-4 was used instead of Compound ET-1 in Experimental Example 1.

Experimental Example 1-13

An organic light emitting device was manufactured in the same manner as in Experimental Example 1, except that Compound 1-2 was used instead of Compound EB-1 and Compound 2-1 was used instead of Compound ET-1 in Experimental Example 1.

Experimental Example 1-14

An organic light emitting device was manufactured in the same manner as in Experimental Example 1, except that Compound 1-2 was used instead of Compound EB-1 and Compound 2-2 was used instead of Compound ET-1 in Experimental Example 1.

Experimental Example 1-15

An organic light emitting device was manufactured in the same manner as in Experimental Example 1, except that Compound 1-2 was used instead of Compound EB-1 and Compound 2-3 was used instead of Compound ET-1 in Experimental Example 1.

Experimental Example 1-16

An organic light emitting device was manufactured in the same manner as in Experimental Example 1, except that Compound 1-2 was used instead of Compound EB-1 and Compound 2-4 was used instead of Compound ET-1 in Experimental Example 1.

Experimental Example 1-17

An organic light emitting device was manufactured in the same manner as in Experimental Example 1, except that Compound 1-3 was used instead of Compound EB-1 and Compound 2-1 was used instead of Compound ET-1 in Experimental Example 1.

Experimental Example 1-18

An organic light emitting device was manufactured in the same manner as in Experimental Example 1, except that Compound 1-3 was used instead of Compound EB-1 and Compound 2-2 was used instead of Compound ET-1 in Experimental Example 1.

Experimental Example 1-19

An organic light emitting device was manufactured in the same manner as in Experimental Example 1, except that Compound 1-3 was used instead of Compound EB-1 and Compound 2-3 was used instead of Compound ET-1 in Experimental Example 1.

Experimental Example 1-20

An organic light emitting device was manufactured in the same manner as in Experimental Example 1, except that Compound 1-3 was used instead of Compound EB-1 and Compound 2-4 was used instead of Compound ET-1 in Experimental Example 1.

Experimental Example 1-21

An organic light emitting device was manufactured in the same manner as in Experimental Example 1, except that Compound 1-4 was used instead of Compound EB-1 and Compound 2-1 was used instead of Compound ET-1 in Experimental Example 1.

Experimental Example 1-22

An organic light emitting device was manufactured in the same manner as in Experimental Example 1, except that Compound 1-4 was used instead of Compound EB-1 and Compound 2-2 was used instead of Compound ET-1 in Experimental Example 1.

Experimental Example 1-23

An organic light emitting device was manufactured in the same manner as in Experimental Example 1, except that Compound 1-4 was used instead of Compound EB-1 and Compound 2-3 was used instead of Compound ET-1 in Experimental Example 1.

Experimental Example 1-24

An organic light emitting device was manufactured in the same manner as in Experimental Example 1, except that Compound 1-4 was used instead of Compound EB-1 and Compound 2-4 was used instead of Compound ET-1 in Experimental Example 1.

TABLE 1

| Experimental Example | Electron transporting layer | Electron blocking layer | Voltage | Luminance (V) | T95 (hr) |
| --- | --- | --- | --- | --- | --- |
| 1 | ET-1 | EB-1 | 4.45 | 5.91 | 265 |
| 1-1 | ET-1 | 1-1 | 4.36 | 6.22 | 260 |
| 1-2 | ET-1 | 1-2 | 4.27 | 6.28 | 270 |
| 1-3 | ET-1 | 1-3 | 4.29 | 6.18 | 260 |
| 1-4 | ET-1 | 1-4 | 4.35 | 6.23 | 280 |
| 1-5 | 2-1 | EB-1 | 4.34 | 6.17 | 275 |
| 1-6 | 2-2 | EB-1 | 4.35 | 6.20 | 275 |
| 1-7 | 2-3 | EB-1 | 4.25 | 6.12 | 270 |
| 1-8 | 2-4 | EB-1 | 4.28 | 6.32 | 285 |
| 1-9 | 2-1 | 1-1 | 3.66 | 6.68 | 325 |
| 1-10 | 2-2 | 1-1 | 3.68 | 6.64 | 345 |
| 1-11 | 2-3 | 1-1 | 3.69 | 6.73 | 335 |
| 1-12 | 2-4 | 1-1 | 3.60 | 6.80 | 320 |
| 1-13 | 2-1 | 1-2 | 3.66 | 6.74 | 330 |
| 1-14 | 2-2 | 1-2 | 3.63 | 6.72 | 355 |
| 1-15 | 2-3 | 1-2 | 3.60 | 6.70 | 330 |
| 1-16 | 2-4 | 1-2 | 3.60 | 6.71 | 315 |
| 1-17 | 2-1 | 1-3 | 3.81 | 6.56 | 305 |
| 1-18 | 2-2 | 1-3 | 3.88 | 6.57 | 360 |
| 1-19 | 2-3 | 1-3 | 3.87 | 6.58 | 330 |
| 1-20 | 2-4 | 1-3 | 3.84 | 6.59 | 325 |
| 1-21 | 2-1 | 1-4 | 3.76 | 6.67 | 345 |
| 1-22 | 2-2 | 1-4 | 3.74 | 6.65 | 370 |
| 1-23 | 2-3 | 1-4 | 3.73 | 6.62 | 355 |
| 1-24 | 2-4 | 1-4 | 3.71 | 6.64 | 355 |

When current was applied to the organic light emitting devices manufactured in Experimental Examples 1-1 to 1-24, the results of Table 1 were obtained. In Experimental Examples of the present invention, the blue organic light emitting devices have a structure in which materials widely used are used as the Reference, EB-1 is used as an electron blocking layer, and ET-1 is used as an electron transporting layer.

According to Table 1, Experimental Examples 1-1 to 1-4 and Experimental Examples 1-5 to 1-8 exhibited basic characteristics of a device when Chemical Formula 1 and Chemical Formula 2 were separately used by using the compound of Chemical Formula 1 instead of EB-1 and the compound of Chemical Formula 2 instead of ET-1, respectively.

Experimental Examples 1-9 to 1-24 exhibited characteristics of a device when the compounds of Chemical Formula 1 were used instead of EB-1 and the compounds of Chemical Formula 2 were used instead of ET-1 and thus were both applied to one device. On the whole, a result, in which the light emitting efficiency was increased by 10% or more, the voltage was lowered by 15 to 20%, and the service life was lengthened by 20% or more, was exhibited.

In Experimental Examples 1-9 to 1-12, when Compound 1-1 was used as EB-1 and Compounds of Chemical Formula 2 were used as ET-1, the voltage was the lowest, and in Experimental Examples 1-21 to 1-24, when Compound 1-4 was used as EB-1, the service life was the longest.

Through the results, it can be confirmed that it is possible to improve the driving voltage, light emitting efficiency, and service life characteristics of a blue organic light emitting device which is made by using Chemical Formula 1 (a structure in the form of a monoamine having two fluorene-type substituents) of the present invention as a material (EB-1) for an electron blocking layer and combining the compound of Chemical Formula 2 having a benzimidazole-type substituent at the ninth position of anthracene having excellent ability as an electron injection and excellent thermal stability as a material (ET-1) for an electron transporting layer provided between the negative electrode and the light emitting layer.

Experimental Example 2

An organic light emitting device was manufactured in the same manner as in Experimental Example 1, except that Chemical Formulae 1-1, 1-2, 1-4, and 1-5 were used instead of HT-1 in Experimental Example 1. However, in Combination Experimental Examples 1-9 to 1-24 of Chemical Formula 1 and Chemical Formula 2, Chemical Formulae 1-1, 1-2, 1-4, and 1-5 were used instead of HT-1.

TABLE 2

| Experimental Example | Electron transporting layer | Hole transporting layer | Voltage | Luminance (V) | T95 (hr) |
|---|---|---|---|---|---|
| 2 | ET-1 | HT-1 | 4.15 | 6.02 | 285 |
| 2-1 | ET-1 | 1-1 | 3.82 | 6.33 | 280 |
| 2-2 | ET-1 | 1-2 | 3.95 | 6.42 | 290 |
| 2-3 | ET-1 | 1-4 | 3.84 | 6.31 | 285 |
| 2-4 | ET-1 | 1-5 | 4.08 | 6.45 | 300 |
| 2-5 | 2-1 | HT-1 | 3.92 | 6.47 | 295 |
| 2-6 | 2-2 | HT-1 | 3.88 | 6.46 | 290 |
| 2-7 | 2-3 | HT-1 | 4.03 | 6.44 | 290 |
| 2-8 | 2-4 | HT-1 | 3.95 | 6.38 | 305 |
| 2-9 | 2-1 | 1-1 | 3.56 | 6.79 | 340 |
| 2-10 | 2-2 | 1-1 | 3.58 | 6.77 | 350 |
| 2-11 | 2-3 | 1-1 | 3.59 | 6.86 | 350 |
| 2-12 | 2-4 | 1-1 | 3.50 | 6.97 | 340 |
| 2-13 | 2-1 | 1-2 | 3.56 | 6.85 | 355 |
| 2-14 | 2-2 | 1-2 | 3.53 | 6.84 | 355 |
| 2-15 | 2-3 | 1-2 | 3.50 | 6.86 | 350 |
| 2-16 | 2-4 | 1-2 | 3.52 | 6.87 | 330 |
| 2-17 | 2-1 | 1-4 | 3.71 | 6.63 | 375 |
| 2-18 | 2-2 | 1-4 | 3.78 | 6.61 | 385 |
| 2-19 | 2-3 | 1-4 | 3.77 | 6.60 | 370 |
| 2-20 | 2-4 | 1-4 | 3.74 | 6.69 | 370 |
| 2-21 | 2-1 | 1-5 | 3.66 | 6.75 | 325 |
| 2-22 | 2-2 | 1-5 | 3.64 | 6.71 | 345 |
| 2-23 | 2-3 | 1-5 | 3.63 | 6.73 | 330 |
| 2-24 | 2-4 | 1-5 | 3.61 | 6.70 | 335 |

When current was applied to the organic light emitting devices manufactured in Experimental Examples 2-1 to 2-24, the results of Table 2 were obtained. In Experimental Examples of the present invention, the blue organic light emitting devices have a structure in which materials widely used are used as the Reference, HT-1 is used as a hole transporting layer, and ET-1 is used as an electron transporting layer.

According to Table 2, Experimental Examples 2-1 to 2-4 and Experimental Examples 2-5 to 2-8 exhibited basic characteristics of a device when Chemical Formula 1 and Chemical Formula 2 were separately used by using the compound of Chemical Formula 1 instead of HT-1 and the compound of Chemical Formula 2 instead of ET-1, respectively.

On the whole, a result, in which the light emitting efficiency was increased by 5% or more, the driving voltage was lowered by 8 to 12%, and the service life was lengthened by 30% or more, was exhibited.

In Experimental Examples 2-9 to 2-12, when Compound 1-1 was used as HT-1 and Compounds of Chemical Formula 2 were used as ET-1, the voltage was the lowest, and in Experimental Examples 2-17 to 2-20, when Compound 1-4 was used as HT-1, the service life was the longest.

Through the result, it can be confirmed that it is possible to improve the driving voltage, light emitting efficiency, and service life characteristics of a blue organic light emitting device which is made by using Chemical Formula 1 (a structure in the form of a monoamine having two fluorene-type substituents) of the present invention as a material (HT-1) for a hole transporting layer and combining the compound of Chemical Formula 2 having a benzimidazole-type substituent at the ninth position of anthracene having excellent ability as an electron injection and excellent thermal stability as a material (ET-1) for an electron transporting layer provided between the negative electrode and the light emitting layer.

EXPLANATION OF REFERENCE NUMERALS AND SYMBOLS

1: Substrate
2: Positive electrode
3: Light emitting layer
4: Negative electrode
5: Hole injection layer
6: Hole transporting layer
7: Electron transporting layer
8: Electron blocking layer

The invention claimed is:

1. An organic light emitting device comprising:

a first electrode;

a second electrode disposed to face the first electrode; and a light emitting layer disposed between the first electrode and the second electrode, wherein the organic light emitting device comprises a first organic material layer including a compound represented by the following Chemical Formula 1 between the first electrode and the light emitting layer, and a second organic material layer including a compound represented by the following Chemical Formula 2 between the second electrode and the light emitting layer:

[Chemical Formula 1]

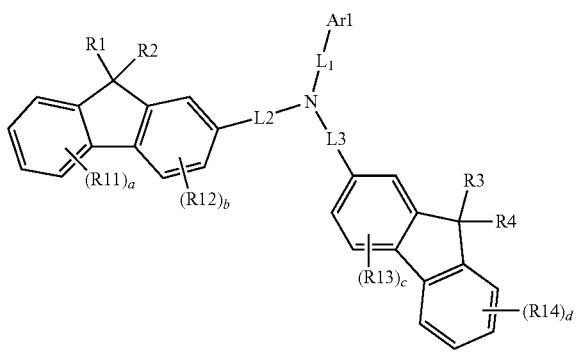

[Chemical Formula 2]

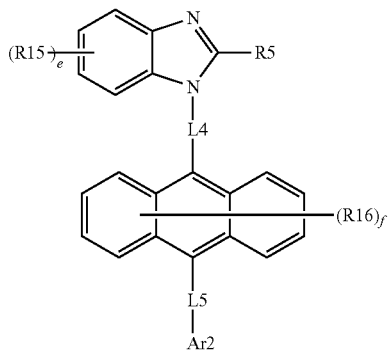

in Chemical Formulae 1 and 2,

Ar1 is a substituted or unsubstituted aryl group having 6 to 30 carbon atoms; or a substituted or unsubstituted heterocyclic group having 2 to 30 carbon atoms, Ar2 is a substituted or unsubstituted carbazole group; a substituted or unsubstituted benzocarbazole group; a substituted or unsubstituted benzonaphthofuran group; a substituted or unsubstituted dibenzofuran group; a substituted or unsubstituted dibenzothiophene group; a substituted or unsubstituted pyridine group; or a substituted or unsubstituted quinoline group, L1 to L4 are the same as or different from each other, and are each independently a direct bond; or a substituted or unsubstituted arylene group having 6 to 30 carbon atoms, L5 is a direct bond; a substituted or unsubstituted phenylene group; a substituted or unsubstituted naphthylene group; a substituted or unsubstituted biphenylylene group; a substituted or unsubstituted terphenylylene group; or a substituted or unsubstituted divalent phenanthrene group, R1 to R5 are the same as or different from each other, and are each independently hydrogen; deuterium; a substituted or unsubstituted alkyl group having 1 to 20 carbon atoms; a substituted or unsubstituted cycloalkyl group having 3 to 30 carbon atoms; or a substituted or unsubstituted aryl group having 6 to 30 carbon atoms, or R1 and R2 or R3 and R4 are optionally bonded to each other to form a ring, R11 to R16 are the same as or different from each other, and are each independently hydrogen; deuterium; a substituted or unsubstituted alkyl group having 1 to 20 carbon atoms; a substituted or unsubstituted cycloalkyl group having 3 to 30 carbon atoms; a substituted or unsubstituted aryl group having 6 to 30 carbon atoms; or a substituted or unsubstituted heterocyclic group having 2 to 30 carbon atoms, and a, d, and e are each an integer from 0 to 4, b and c are each an integer from 0 to 3, f is an integer from 0 to 8, and when a to f are 2 or more, each of R11 to R16 is the same as or different from each other, provided that when R5 is a substituted or unsubstituted alkyl group having 1 to 20 carbon atoms or a substituted or unsubstituted cycloalkyl group having 3 to 30 carbon atoms, and L5 is a bond, then Ar2 is a substituted or unsubstituted benzonaphthofuran group, provided that when Ar2 is a substituted or unsubstituted pyridine group, then L5 is a substituted or unsubstituted phenylene group; a substituted or unsubstituted naphthylene group; a substituted or unsubstituted biphenylylene group; a substituted or unsubstituted terphenylylene group; or a substituted or unsubstituted divalent phenanthrene group.

2. The organic light emitting device of claim 1, wherein Chemical Formula 1 is represented by any one of the following Chemical Formulae 1-1 to 1-6:

[Chemical Formula 1-1]

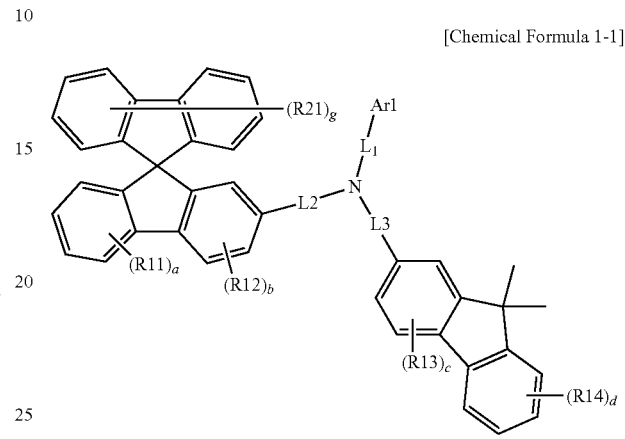

[Chemical Formula 1-2]

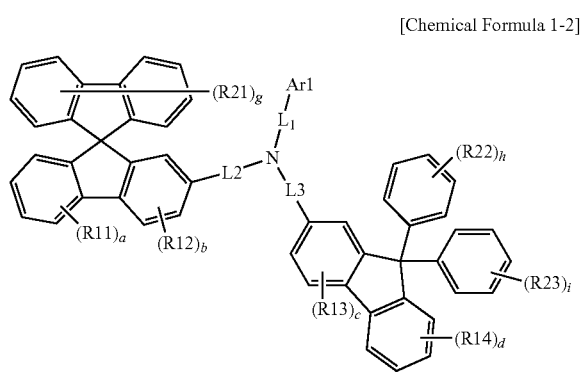

[Chemical Formula 1-3]

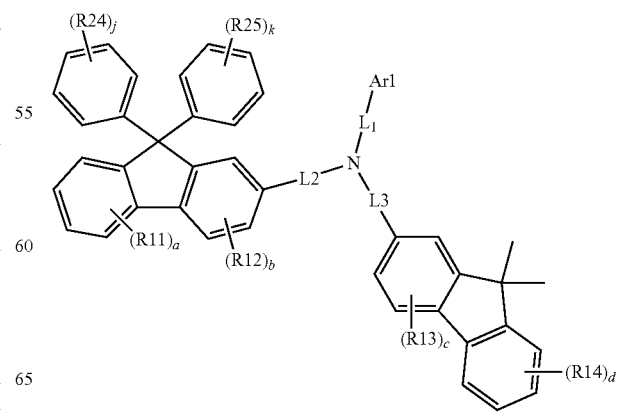

137
-continued

[Chemical Formula 1-4]

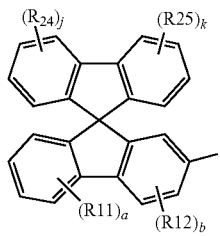

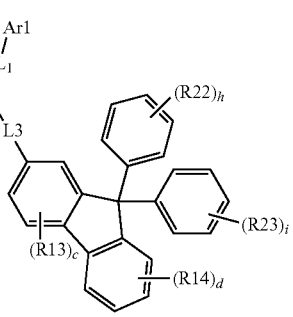

[Chemical Formula 1-5]

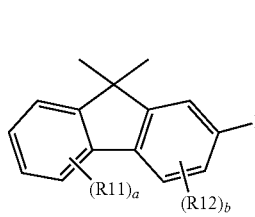

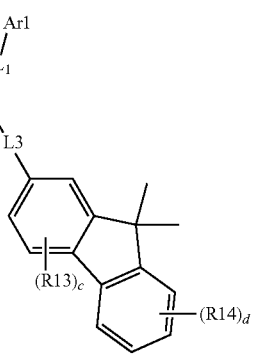

[Chemical Formula 1-6]

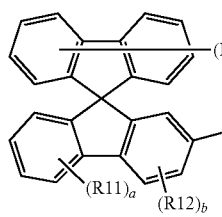

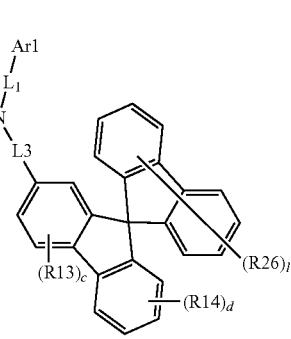

in Chemical Formulae 1-1 to 1-6, the definitions of Ar1, L1 to L3, R11 to R14, and a to d are the same as those in Chemical Formula 1, R21 to R26 are the same as or different from each other, and are each independently hydrogen; deuterium; a substituted or unsubstituted alkyl group having 1 to 20 carbon atoms; a substituted or unsubstituted cycloalkyl group having 3 to 30 carbon atoms; a substituted or unsubstituted aryl group having 6 to 30 carbon atoms; or a substituted or unsubstituted heterocyclic group having 2 to 30 carbon atoms, and g and l are an integer from 0 to 8, h to k are each an integer from 0 to 5, and when g to l are 2 or more, each of R21 to R26 is the same as or different from each other.

3. The organic light emitting device of claim 1, wherein Ar1 is a substituted or unsubstituted phenyl group; a substituted or unsubstituted naphthyl group; a substituted or unsubstituted biphenyl group; a substituted or unsubstituted terphenyl group; a substituted or unsubstituted quarterphenyl group; a substituted or unsubstituted fluorene group; a substituted or unsubstituted phenanthrene group; a substituted or unsubstituted triphenylene group; a substituted or unsubstituted anthracene group; a substituted or unsubstituted fluoranthene group; a substituted or unsubstituted pyrene group; a substituted or unsubstituted carbazole group; a substituted or unsubstituted benzocarbazole group; a substituted or unsubstituted benzonaphthofuran group; a substituted or unsubstituted dibenzofuran group; a substituted or unsubstituted dibenzothiophene group; a substituted or unsubstituted pyridine group; or a substituted or unsubstituted quinoline group.

4. The organic light emitting device of claim 1, wherein L1 to L4 are the same as or different from each other, and are each independently a direct bond; a substituted or unsubstituted phenylene group; a substituted or unsubstituted naphthylene group; a substituted or unsubstituted biphenylylene group; a substituted or unsubstituted terphenylylene group; or a substituted or unsubstituted divalent phenanthrene group.

5. The organic light emitting device of claim 1, wherein the compound represented by Chemical Formula 1 is selected from the following structural formulae:

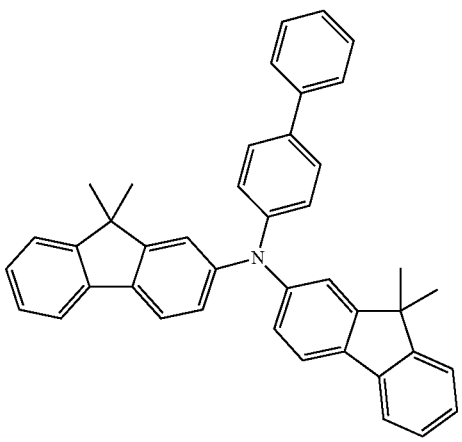

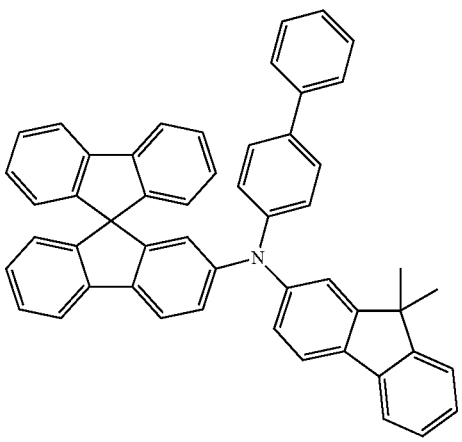

139
-continued
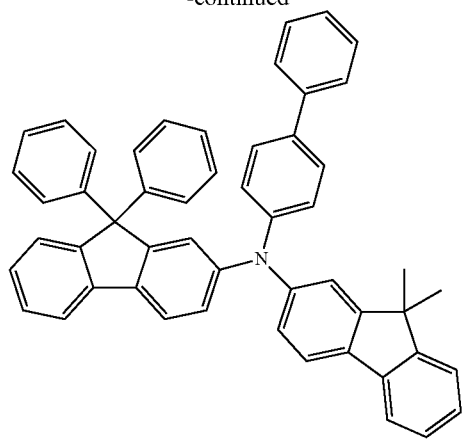
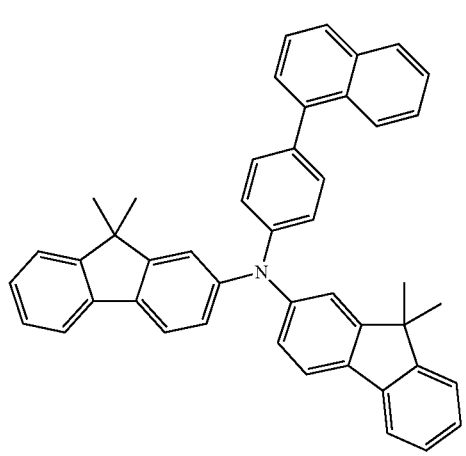
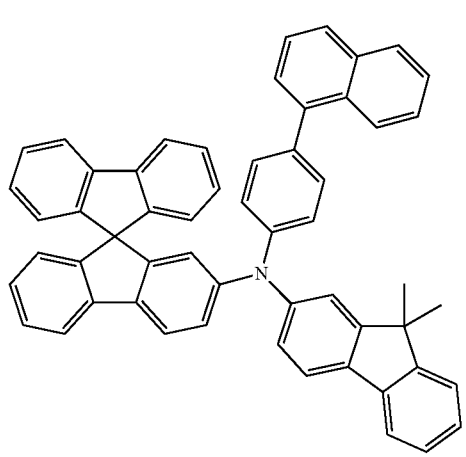
140
-continued
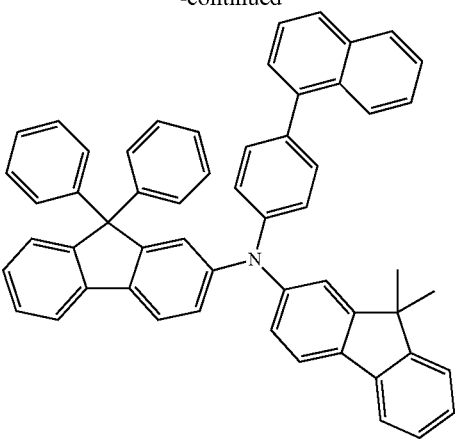
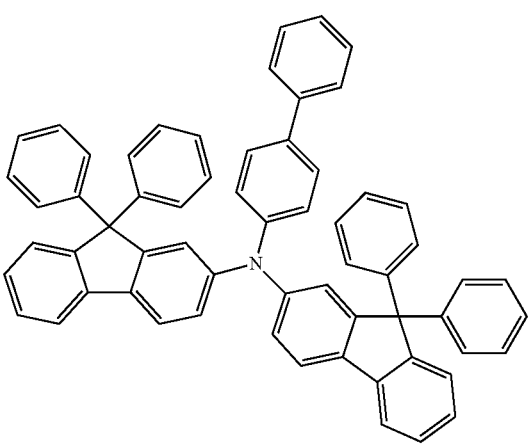
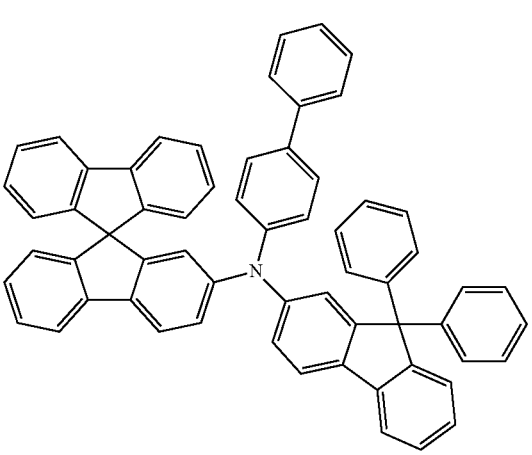

-continued
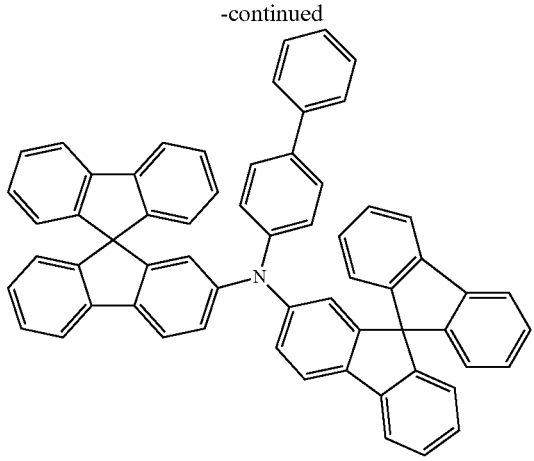
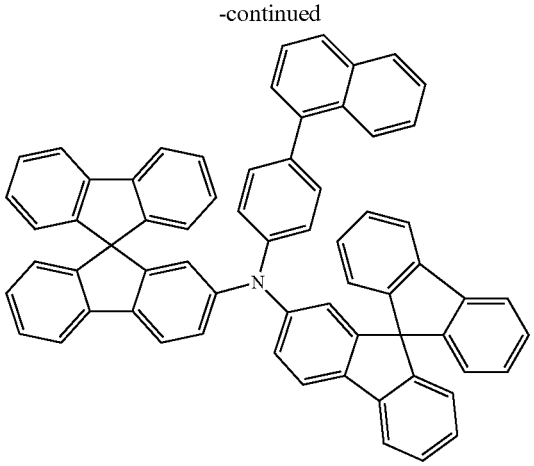
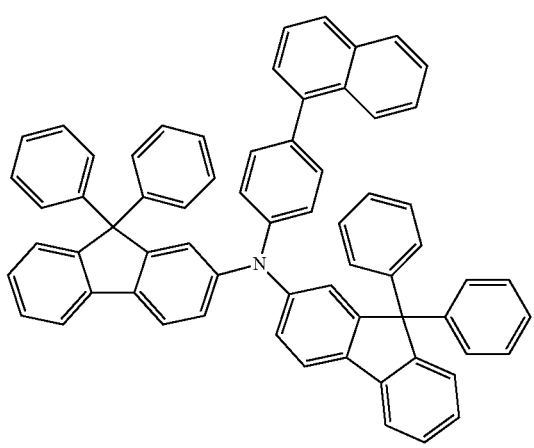
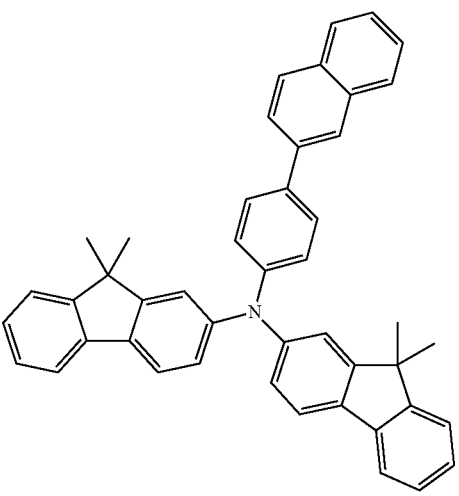
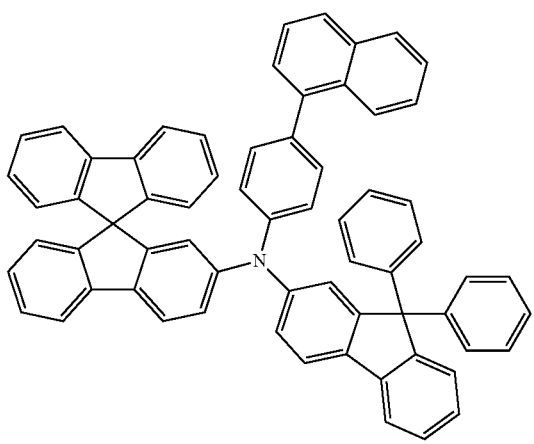
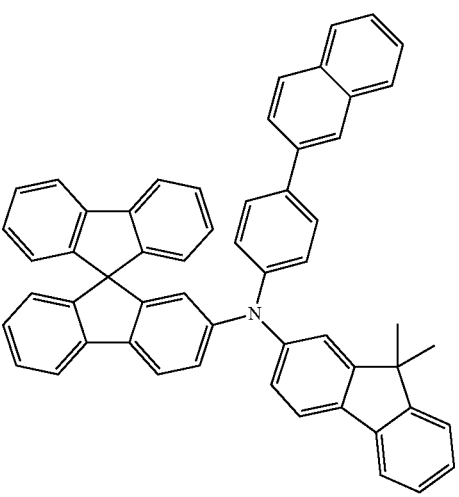

143
-continued
144
-continued
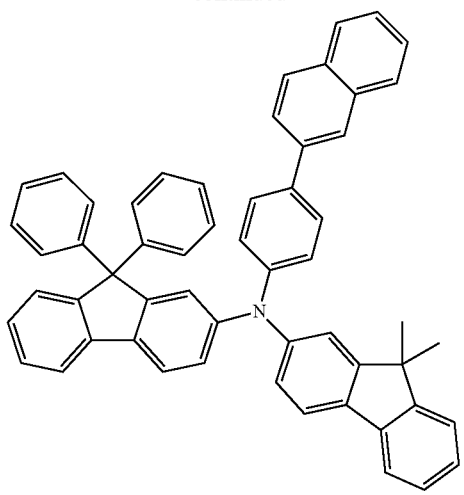
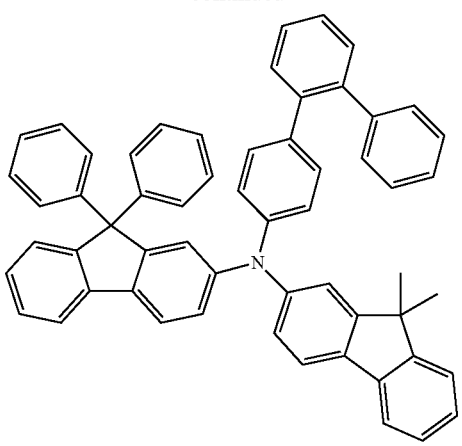
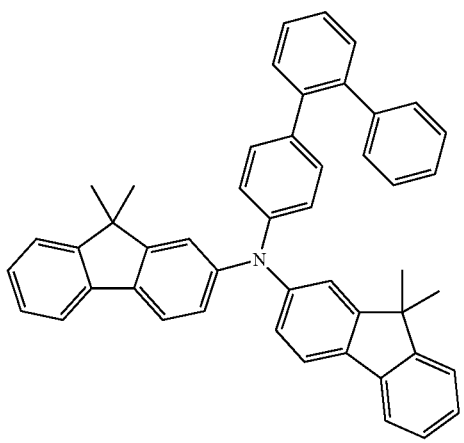
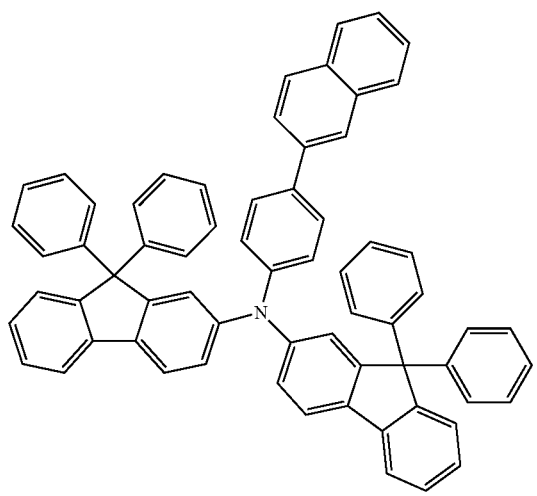
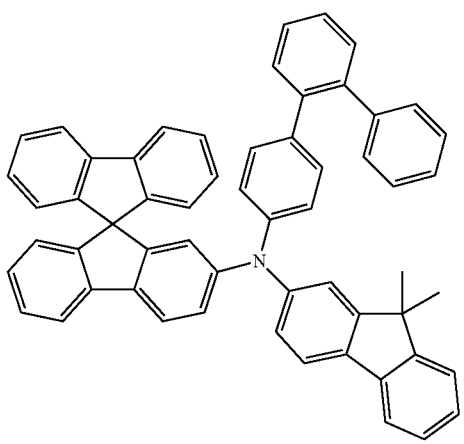
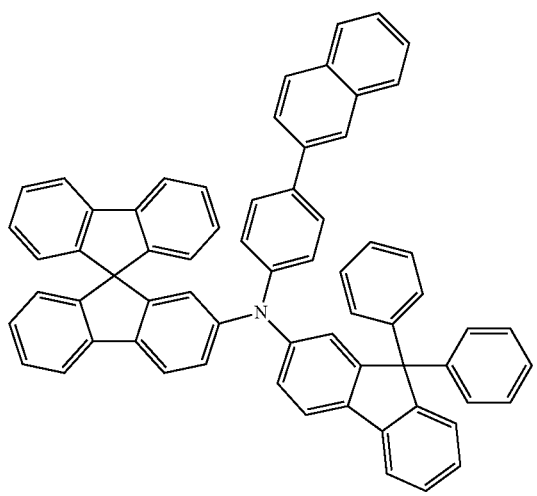

145
-continued
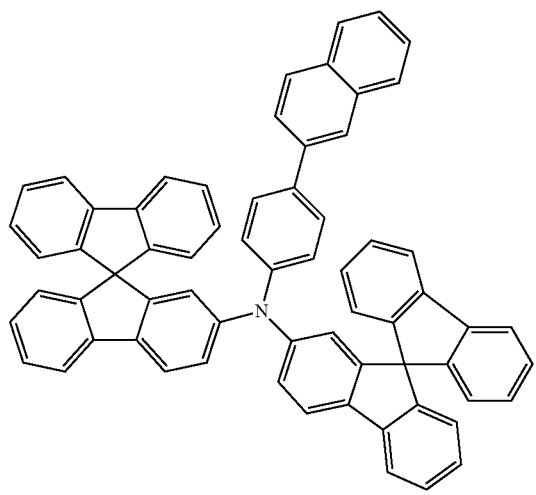
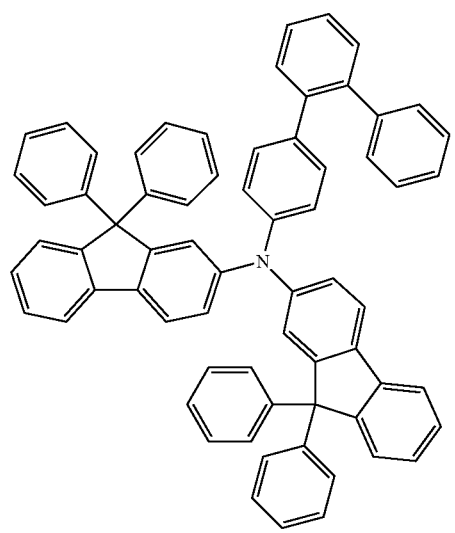
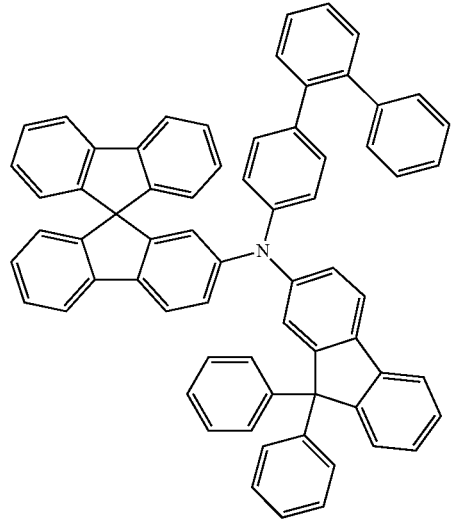
146
-continued
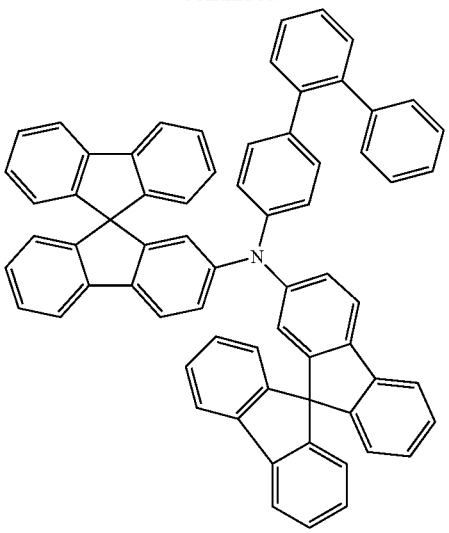
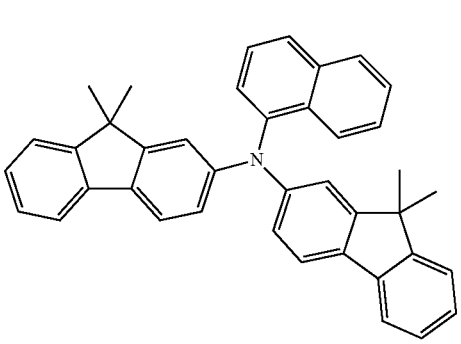
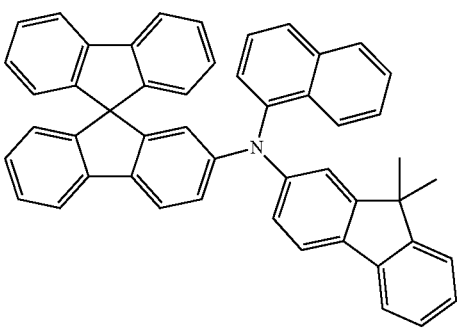
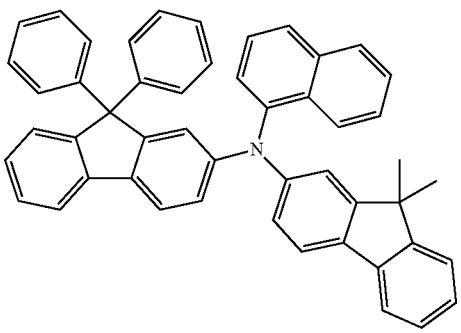

-continued
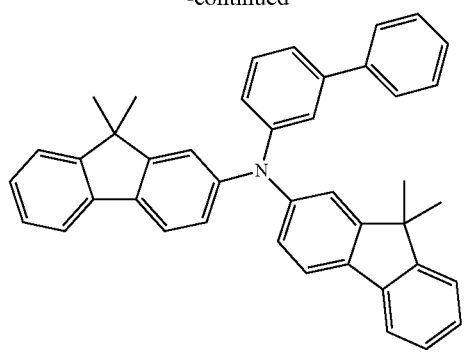
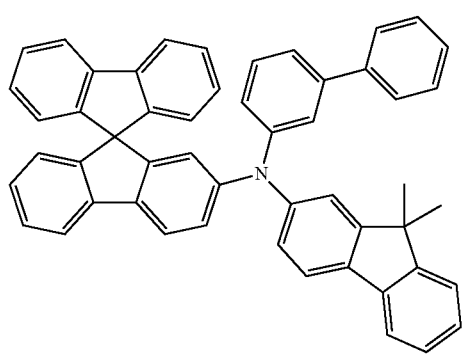
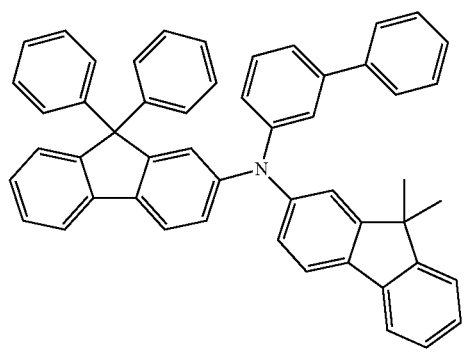
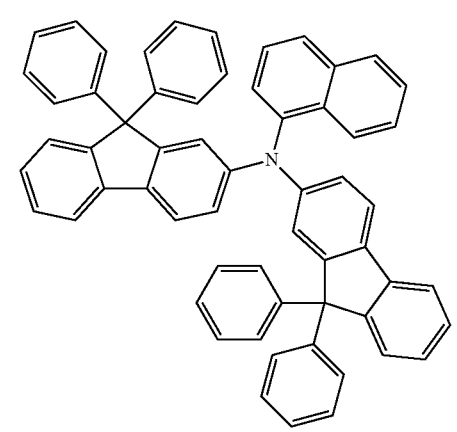
-continued
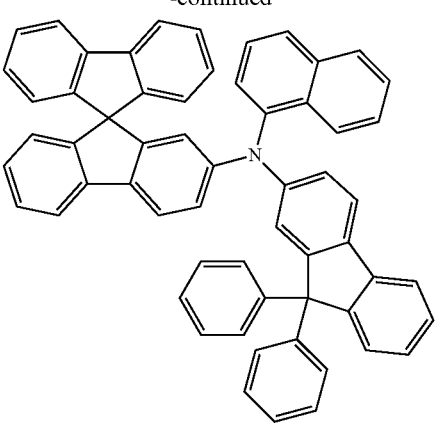
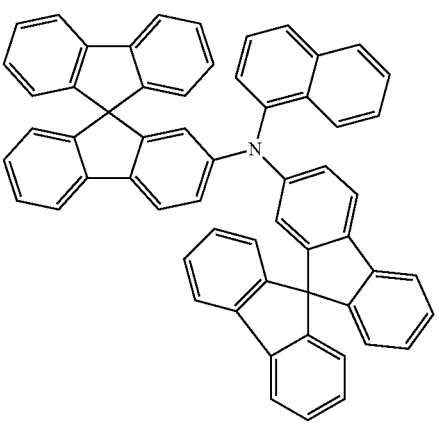
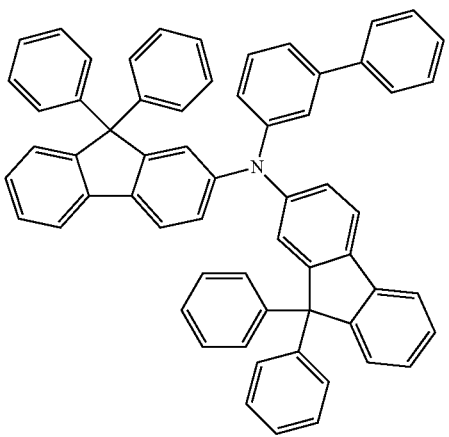
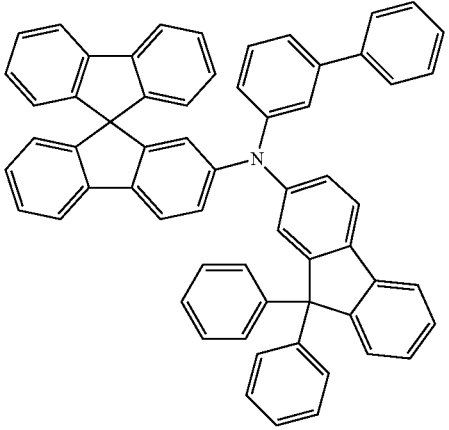

149
-continued
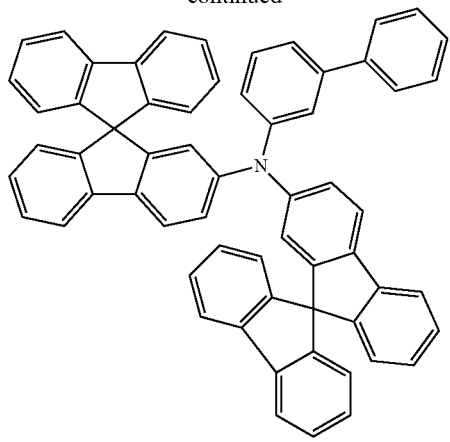
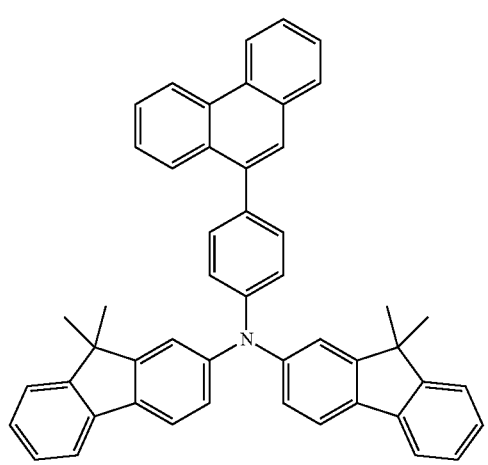
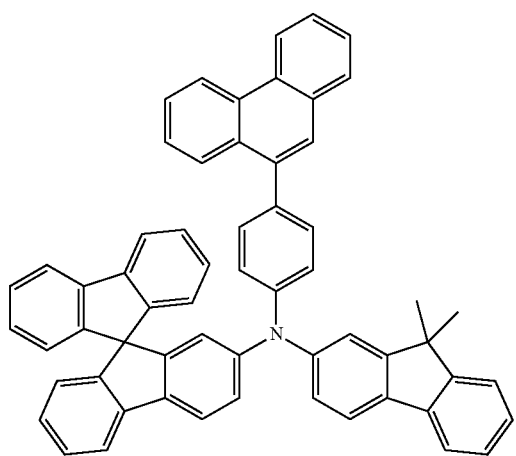
150
-continued
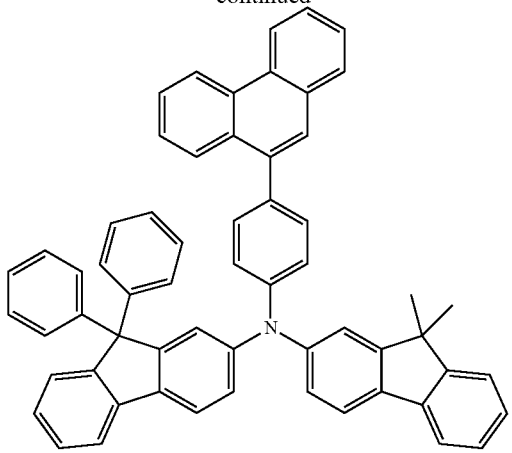
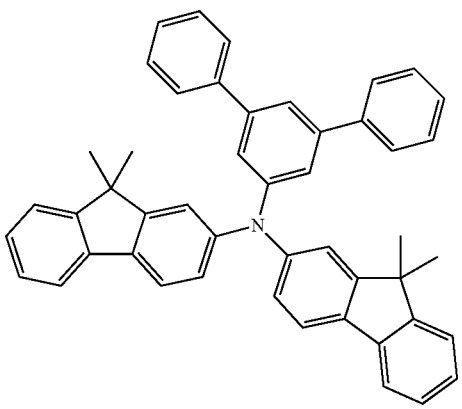
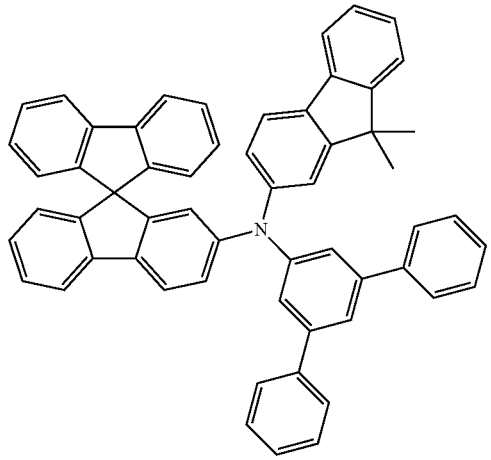

151
-continued
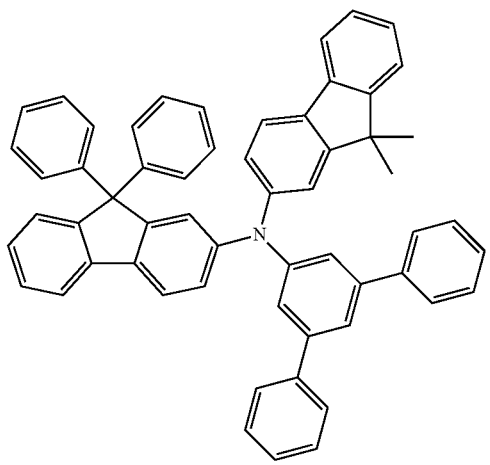
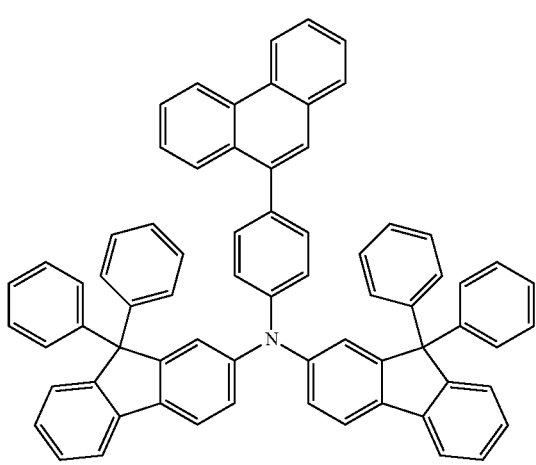
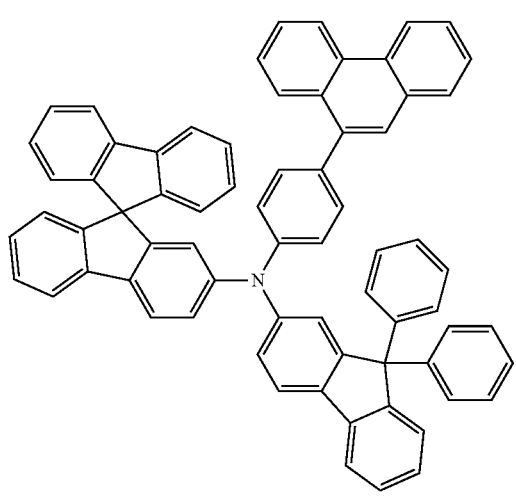
152
-continued
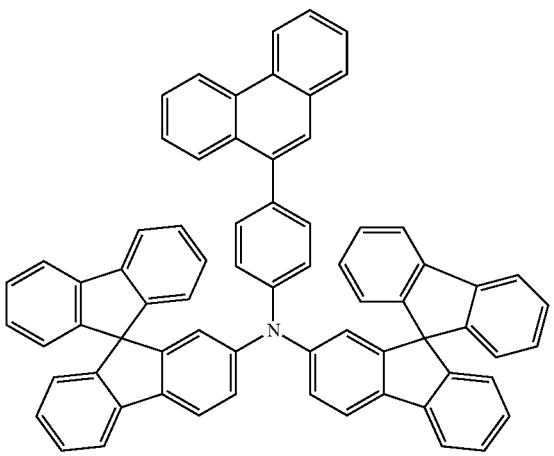
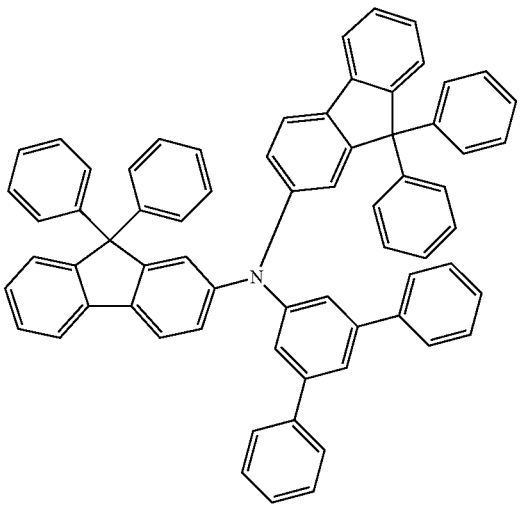
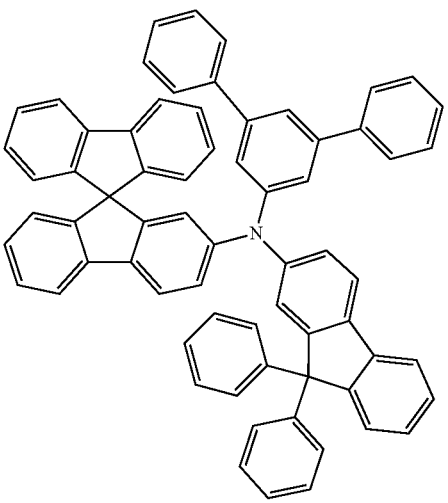

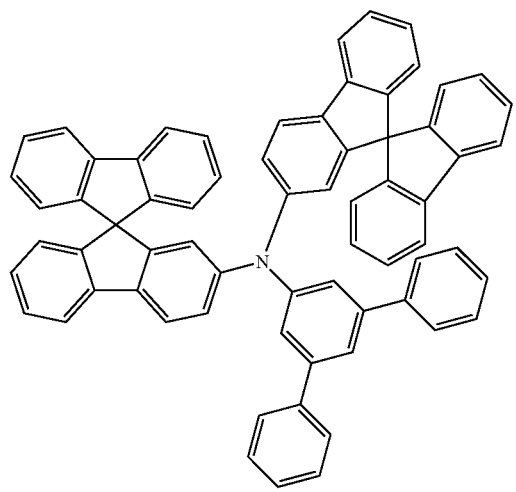
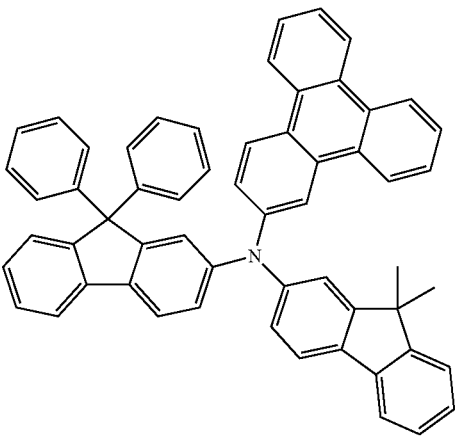
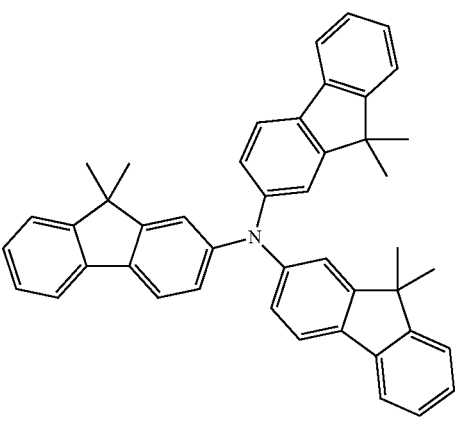
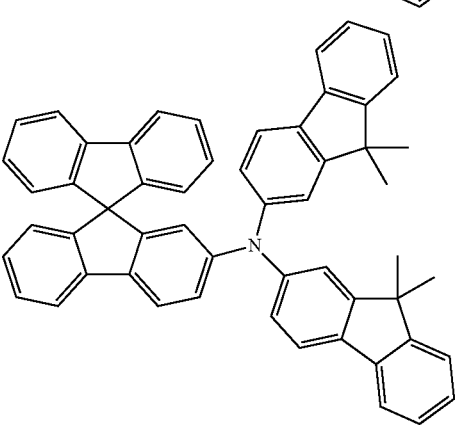
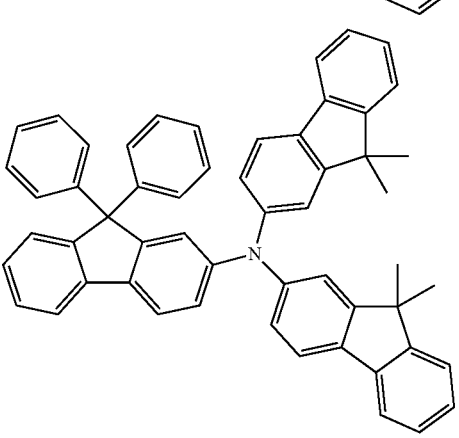

155
-continued
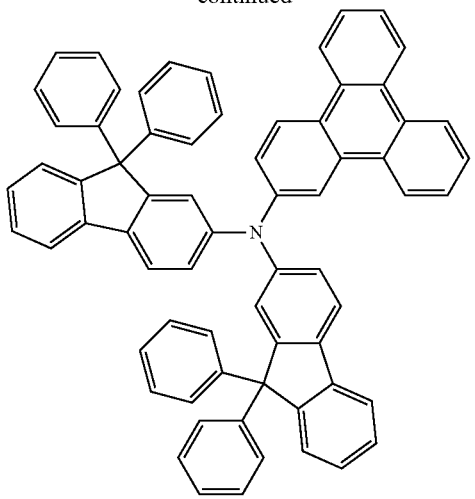
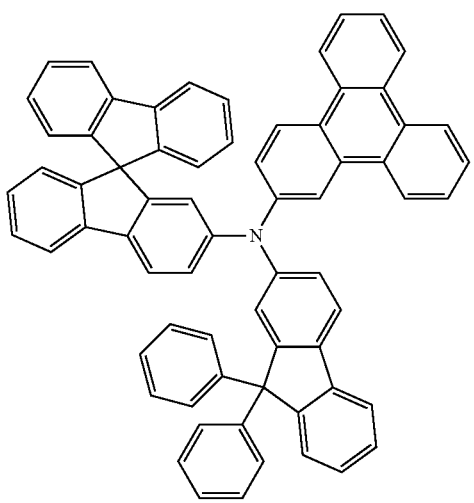
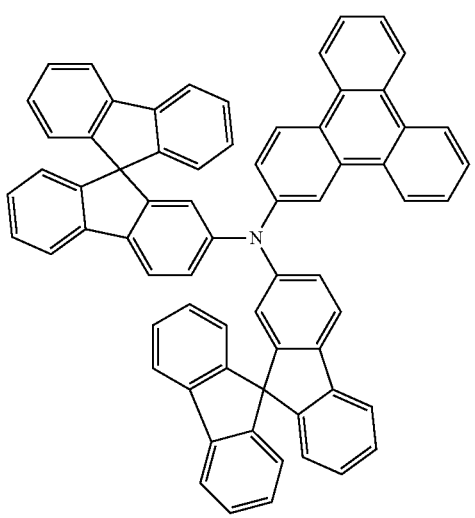
156
-continued
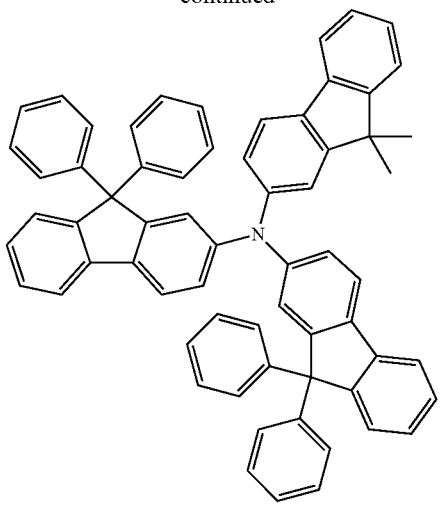
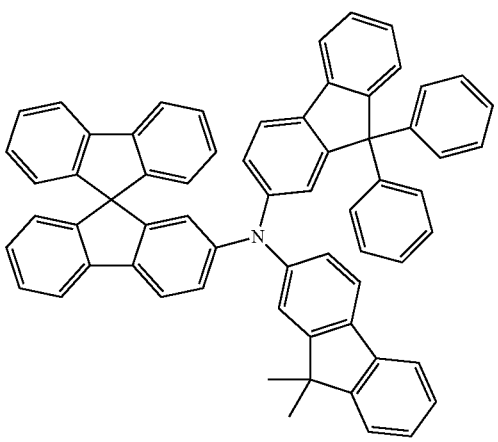
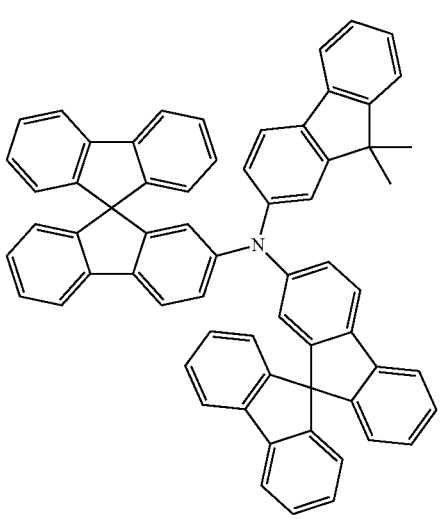

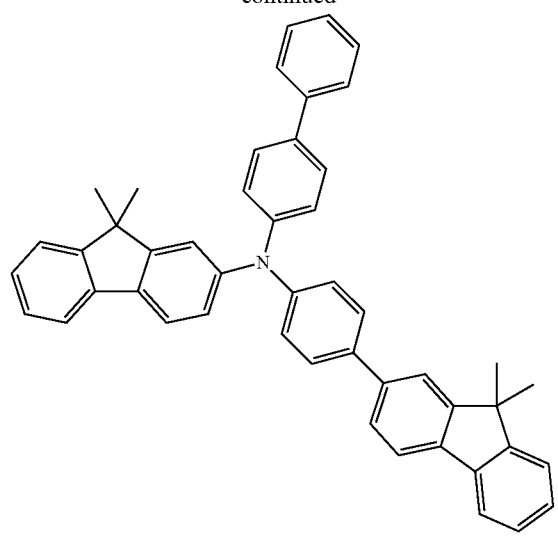
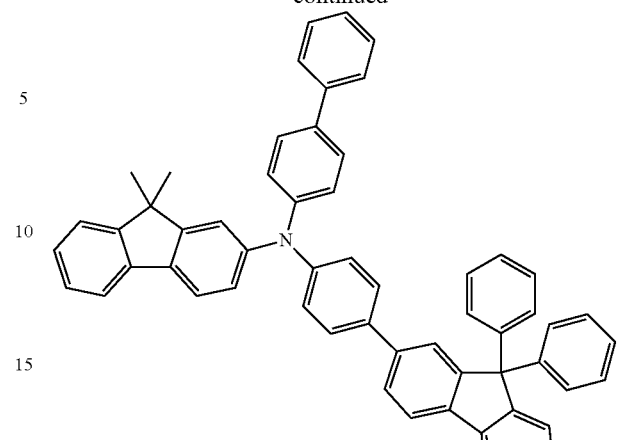
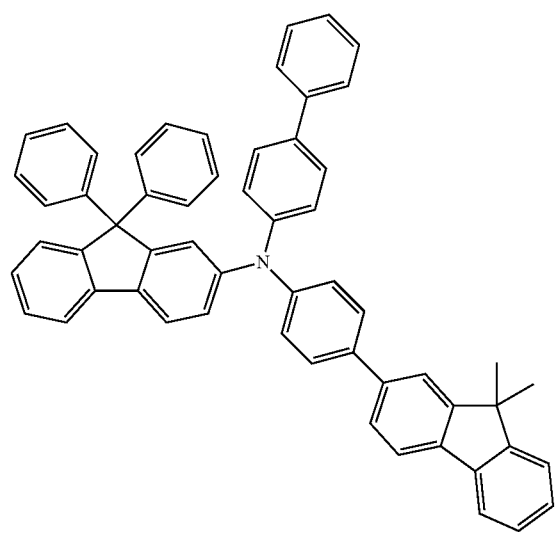
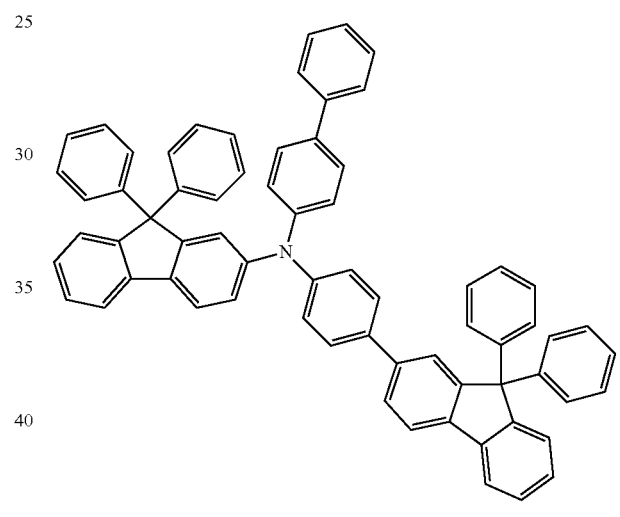
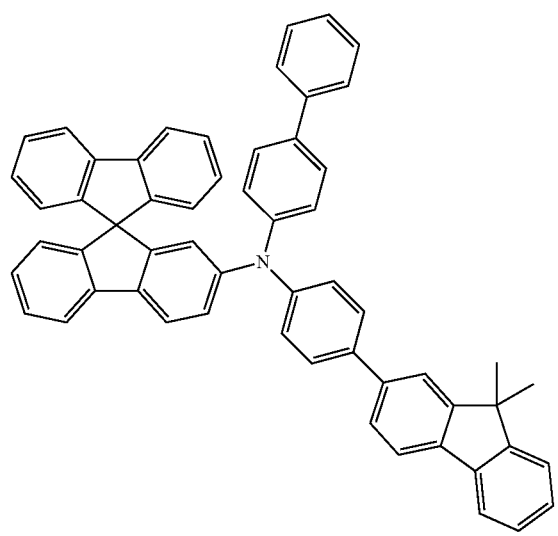
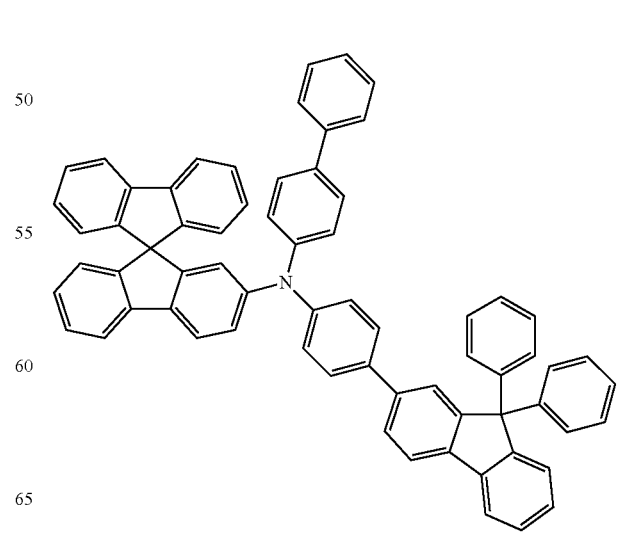

159
-continued
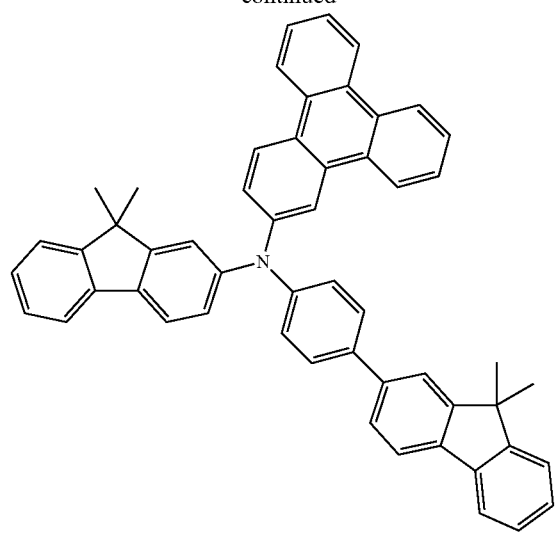
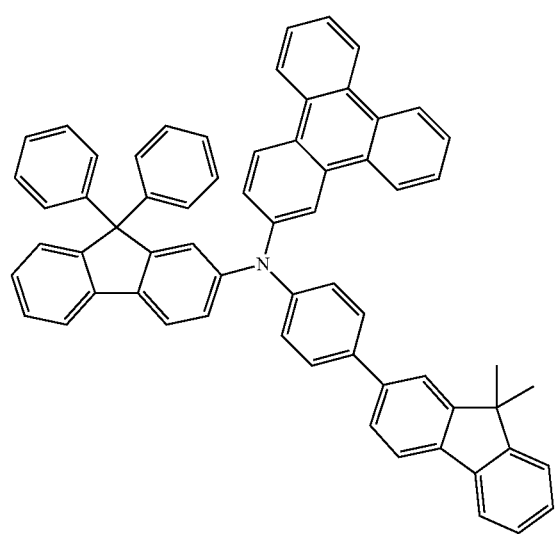
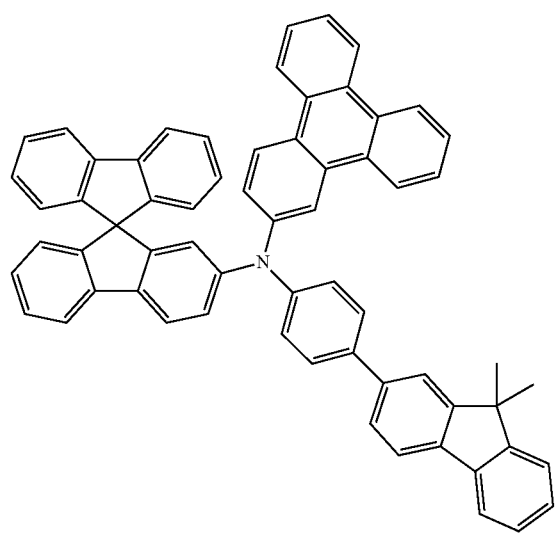
160
-continued
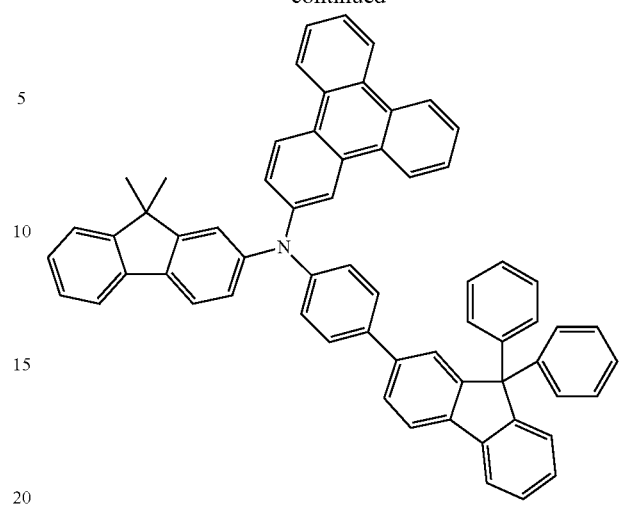
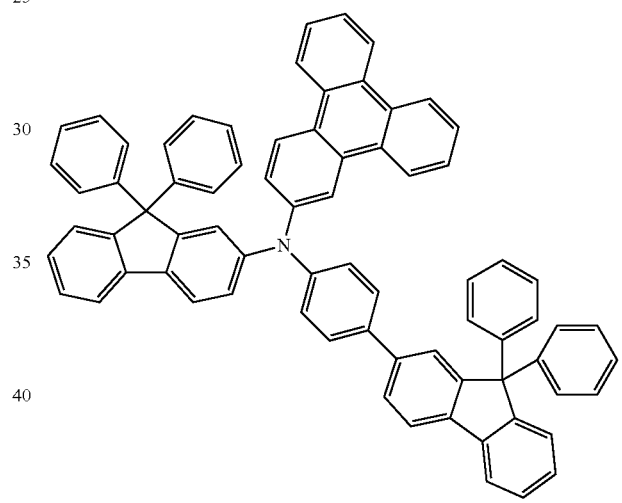
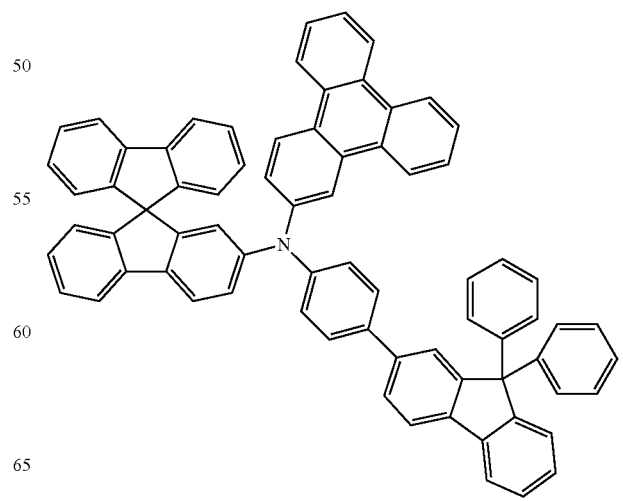

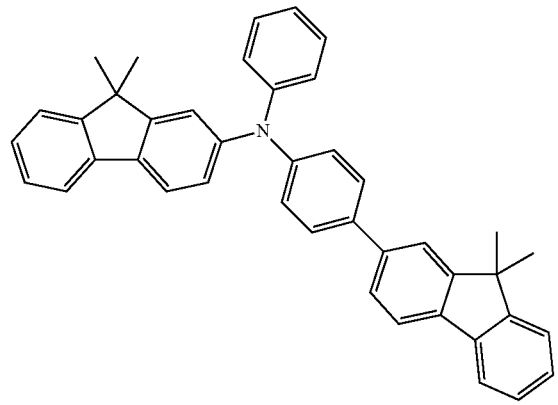
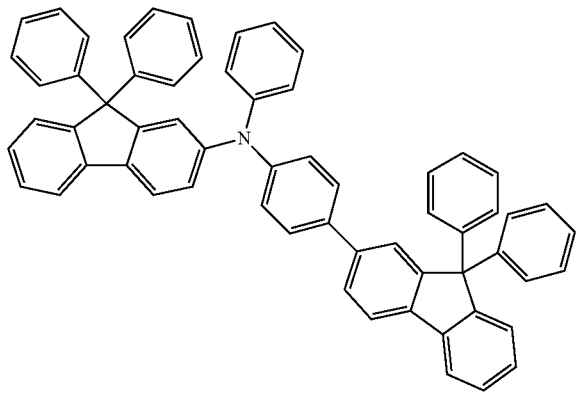
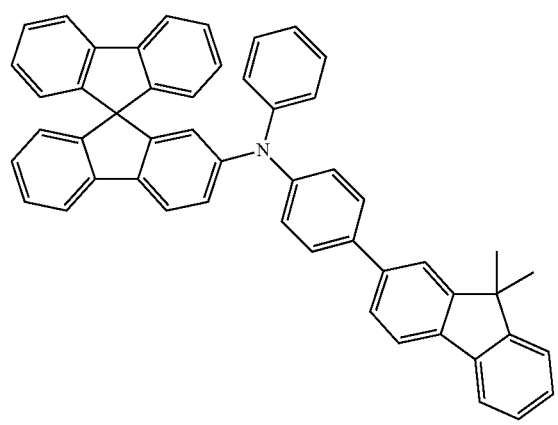
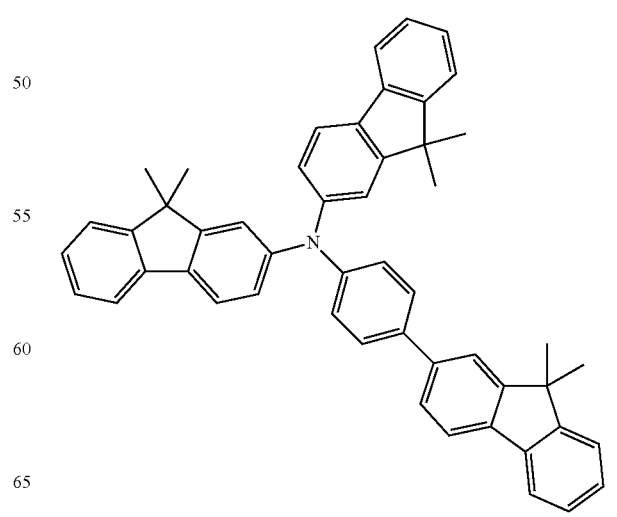

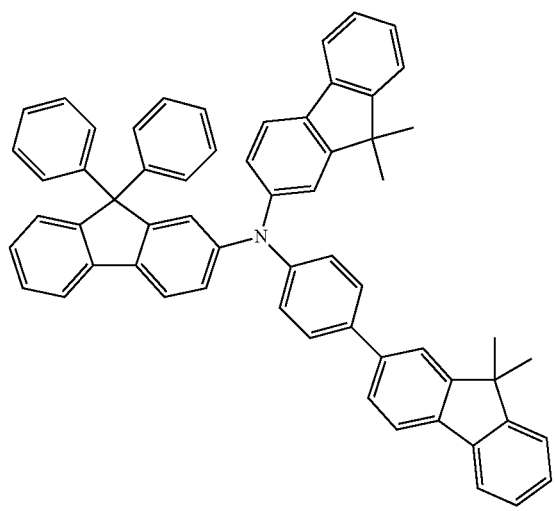
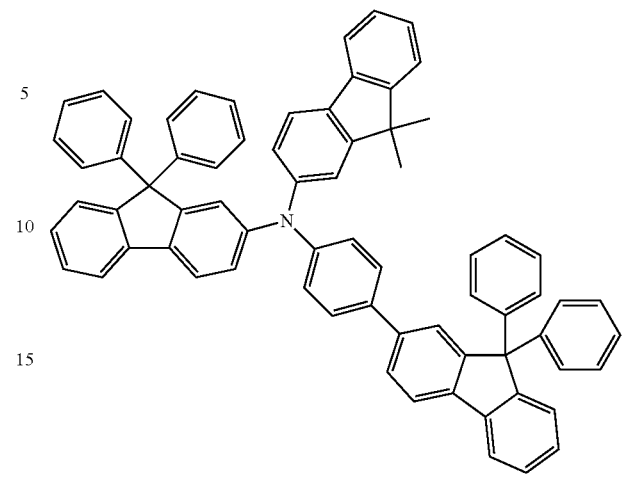
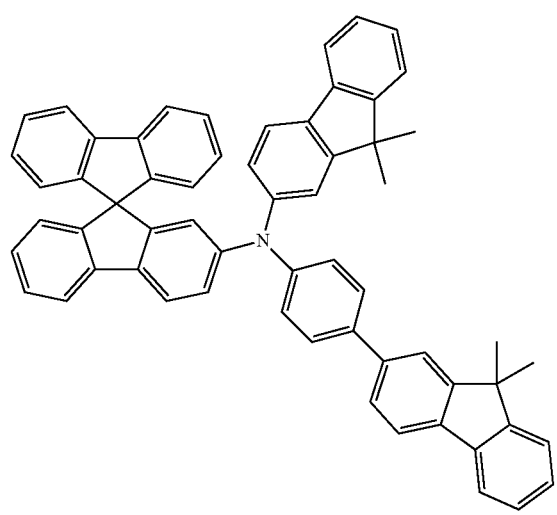
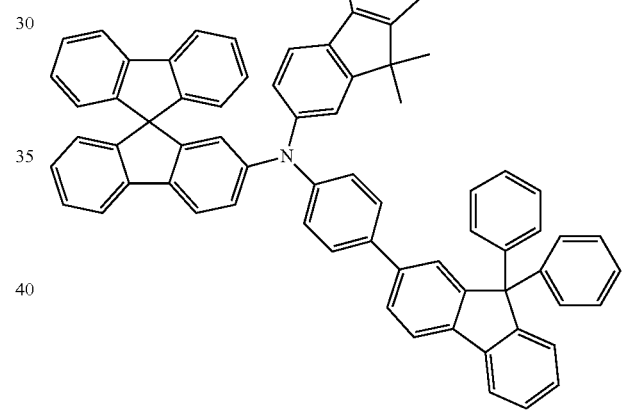
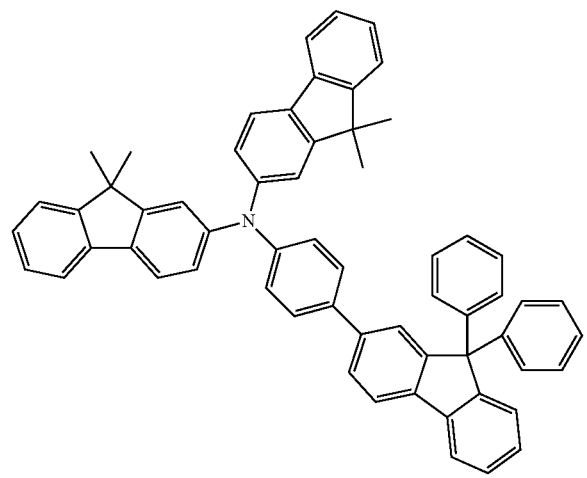
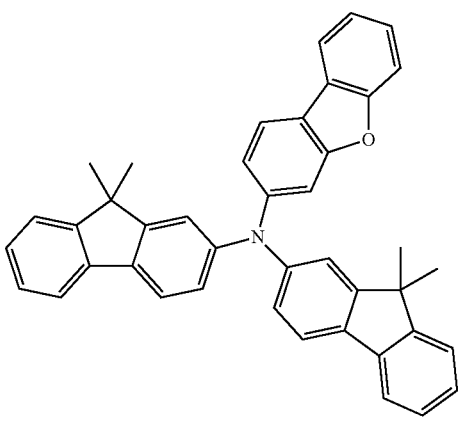

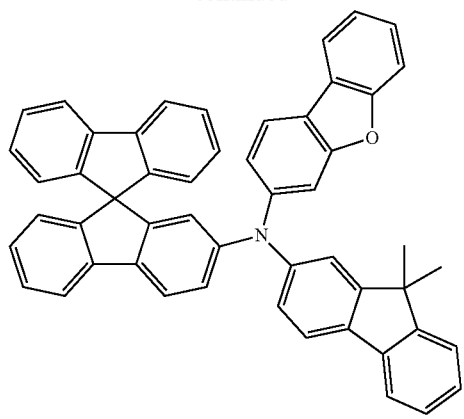
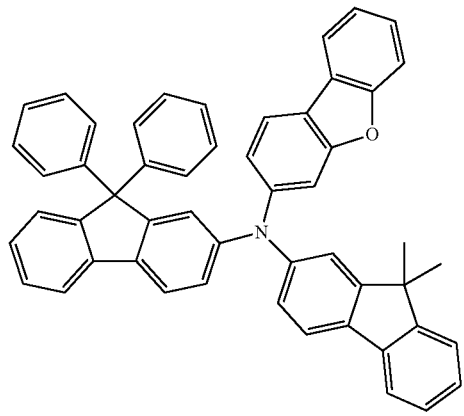
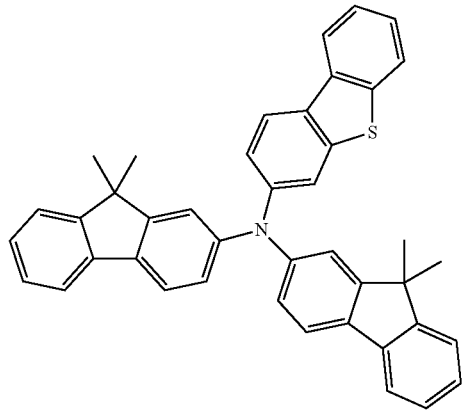
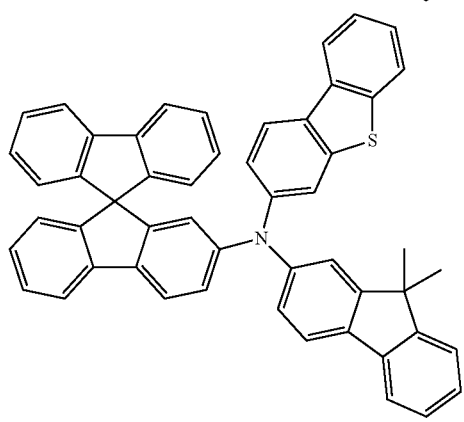
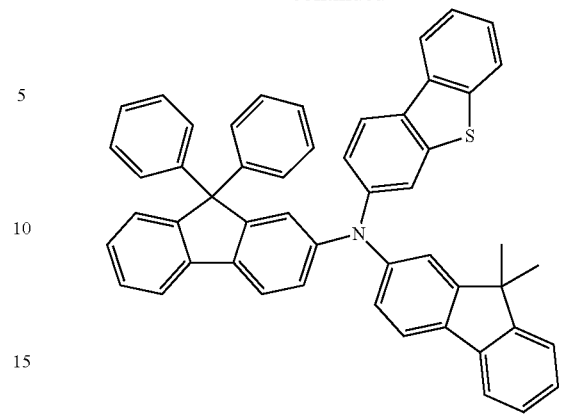
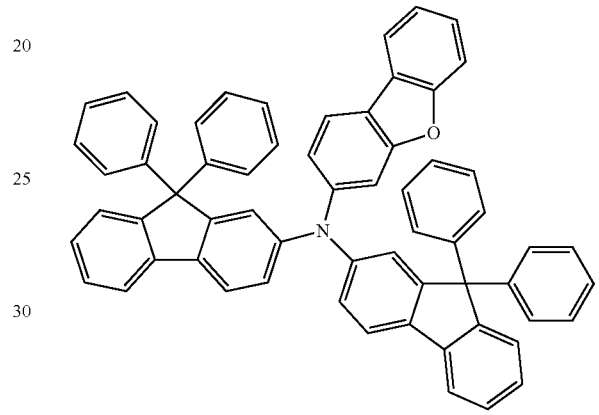
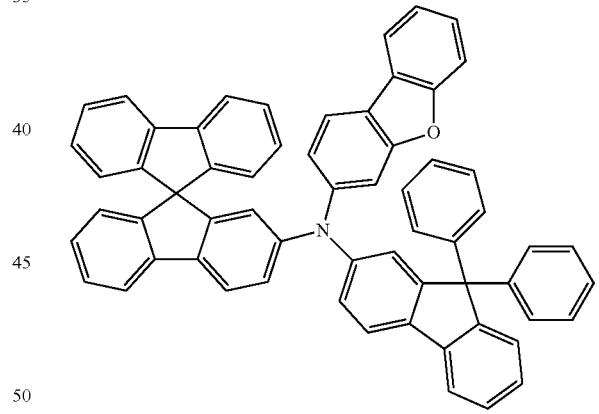
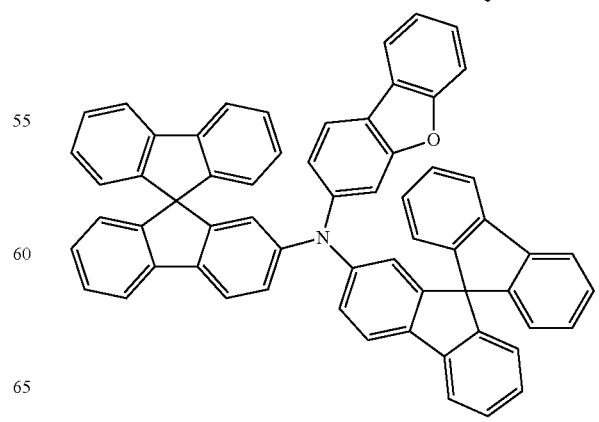

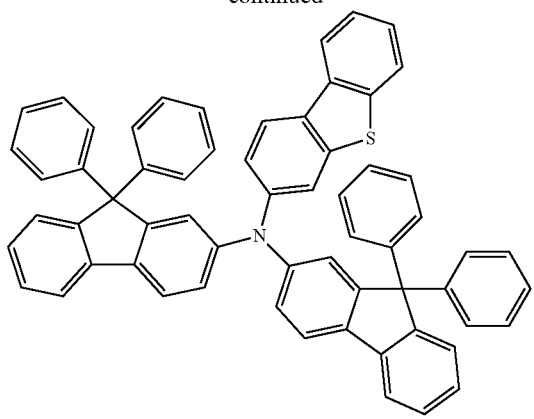
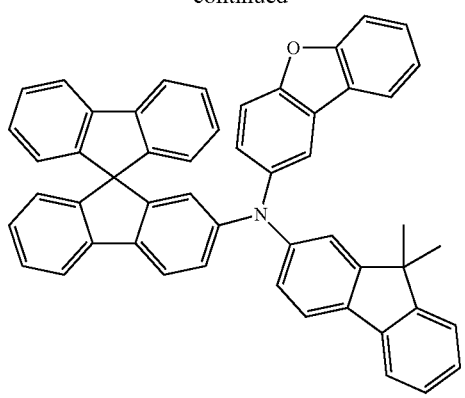
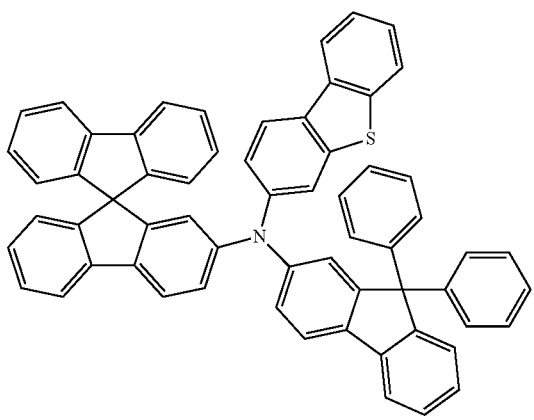
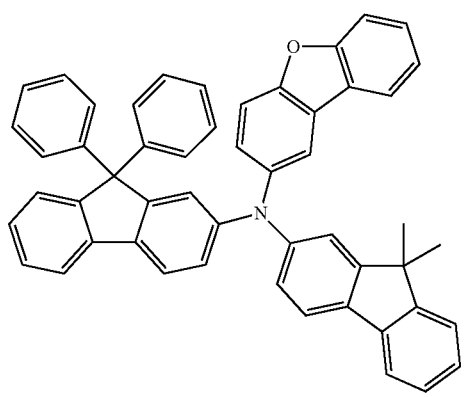
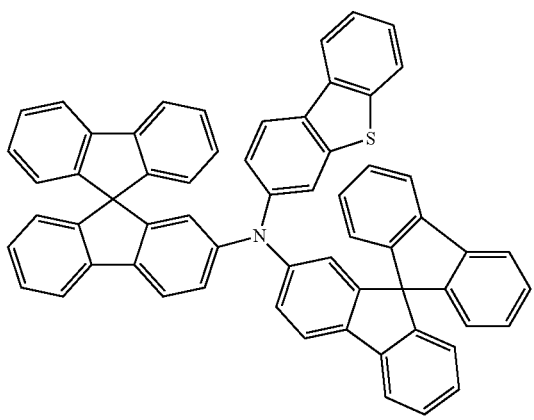
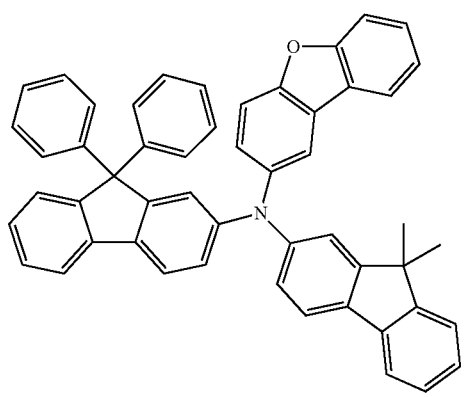
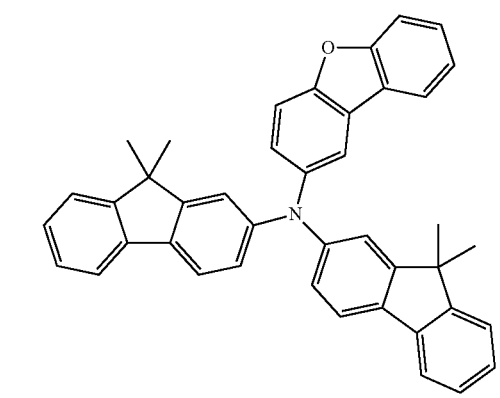
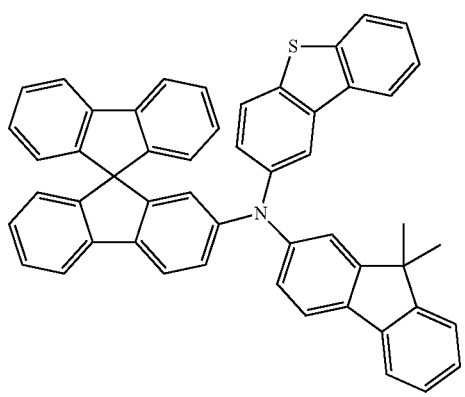

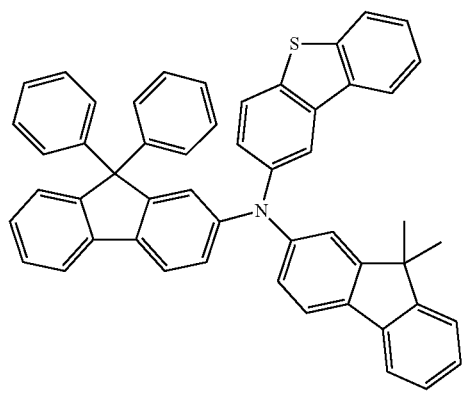
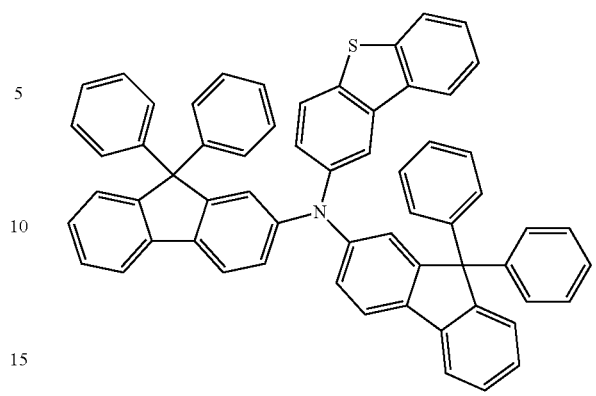
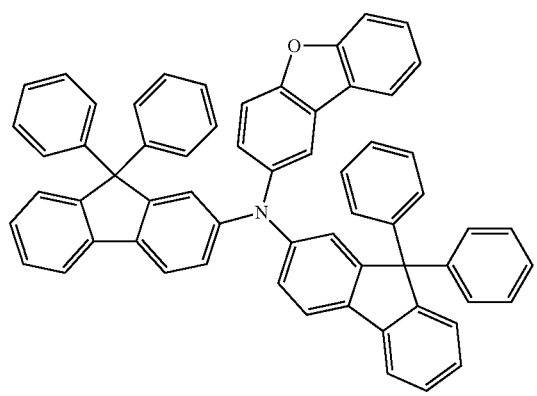
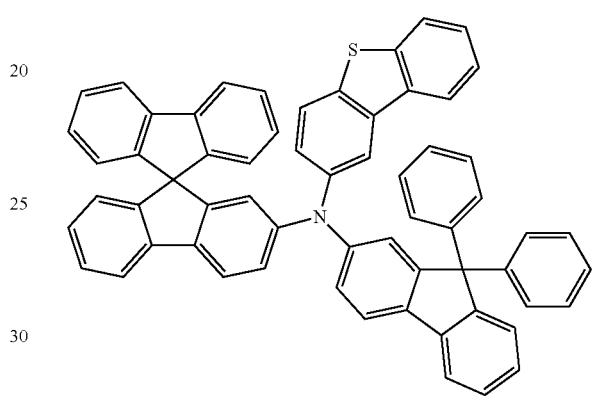
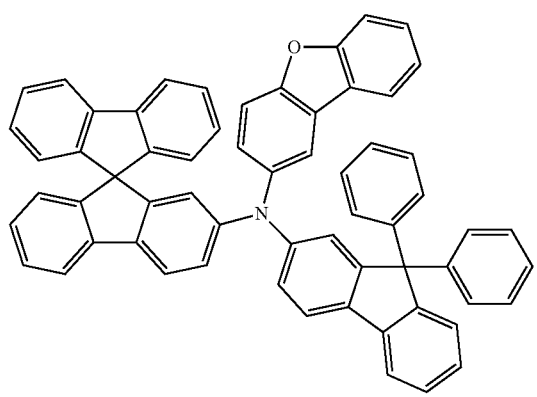
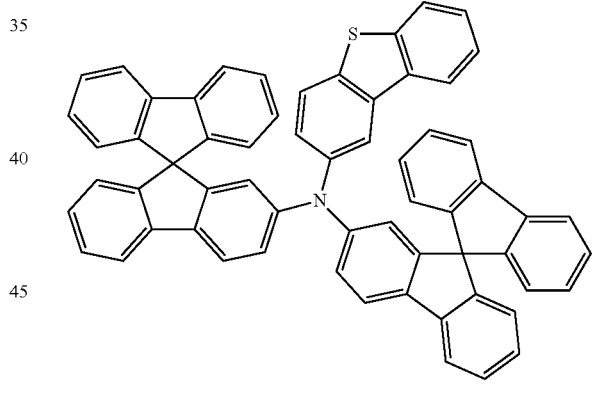
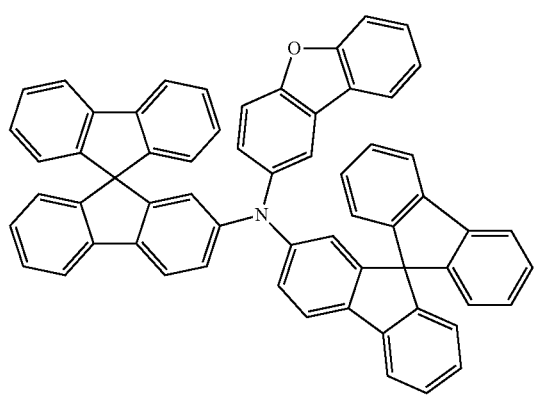
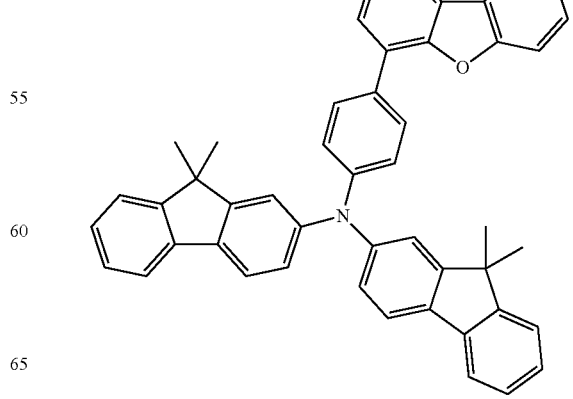

171
-continued
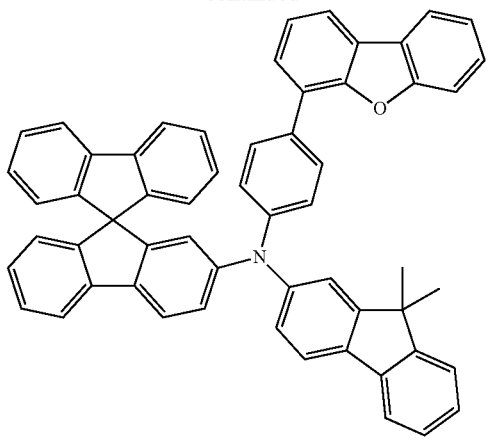
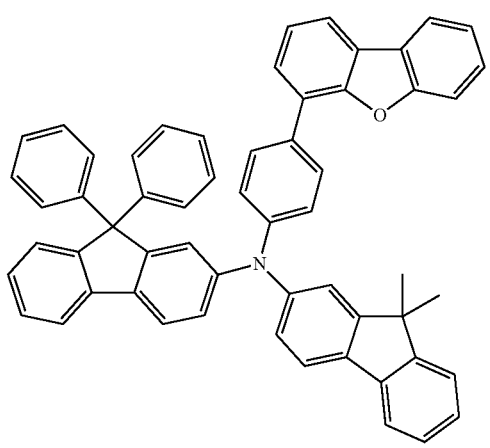
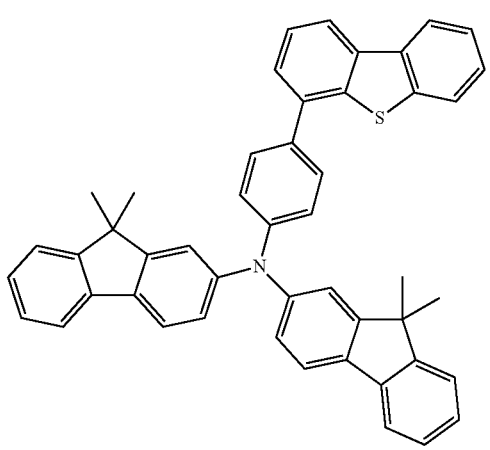
172
-continued
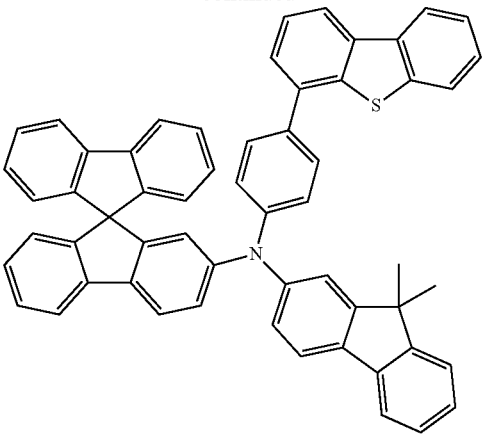
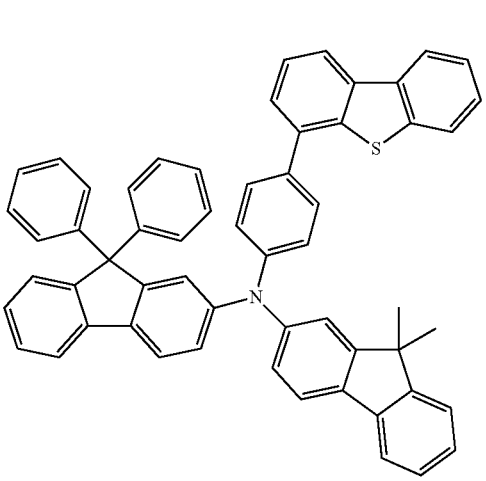
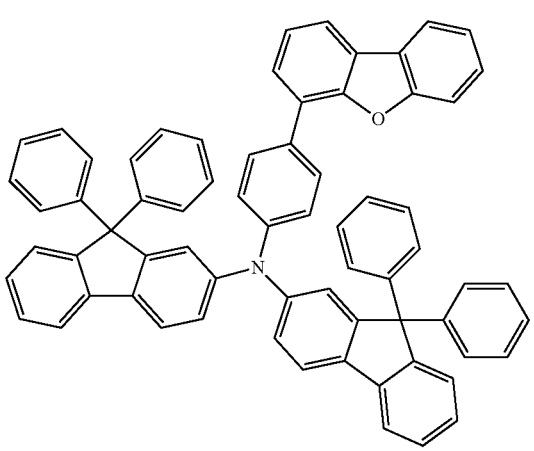

173
-continued
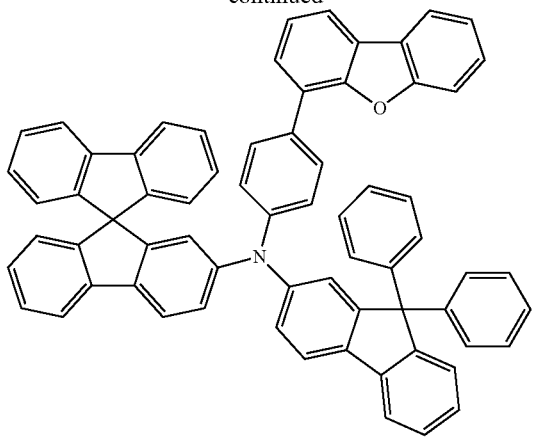
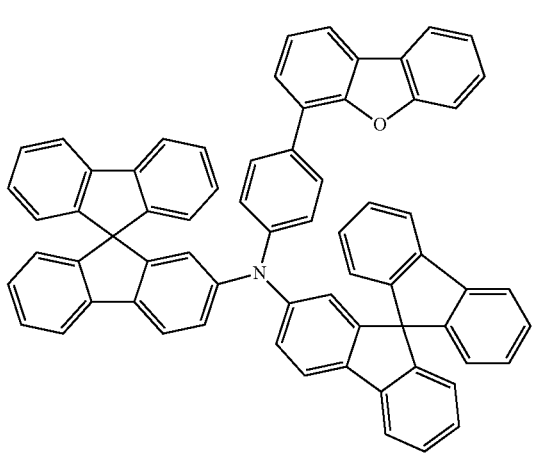
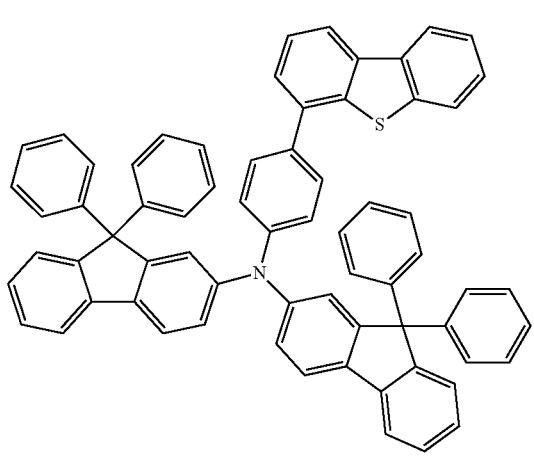
174
-continued
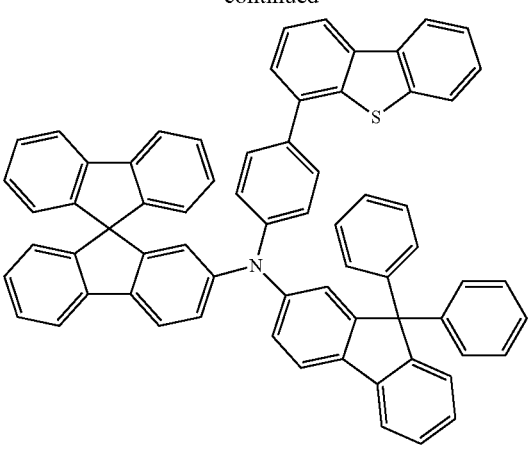
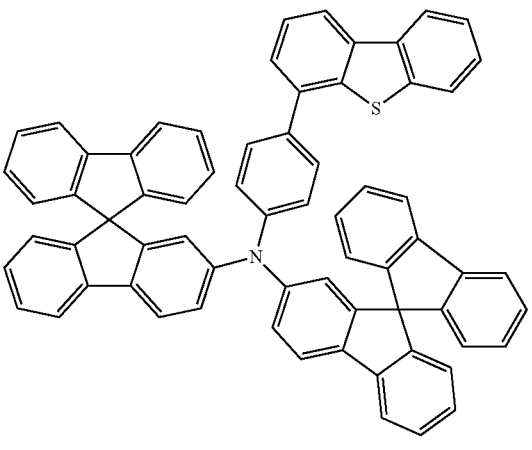
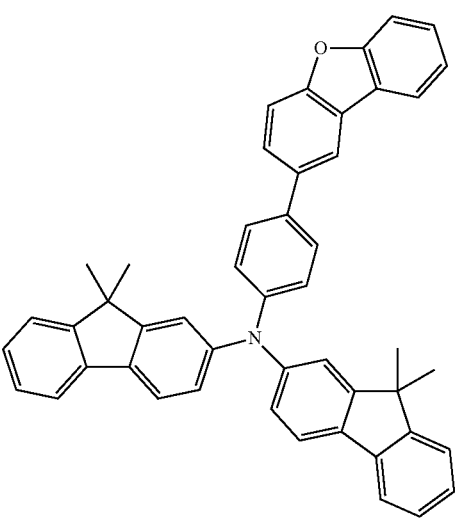

-continued
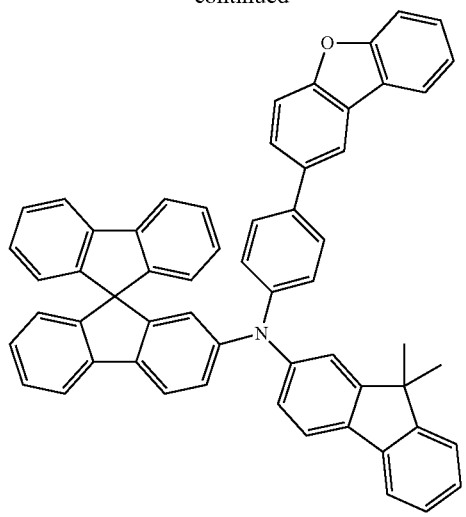
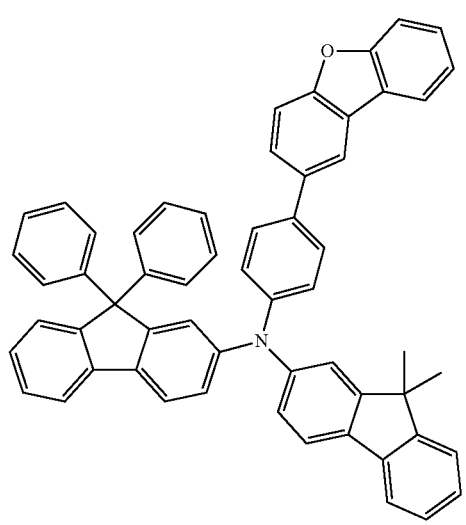
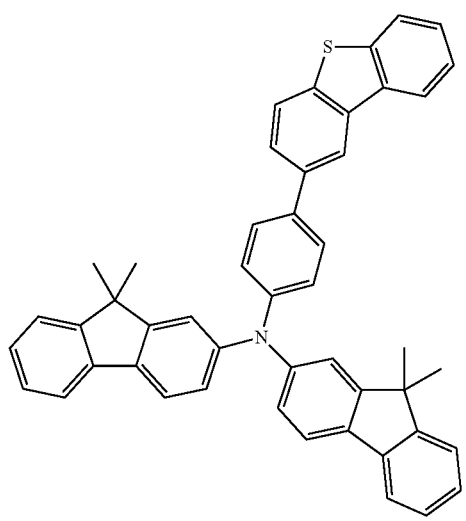
-continued
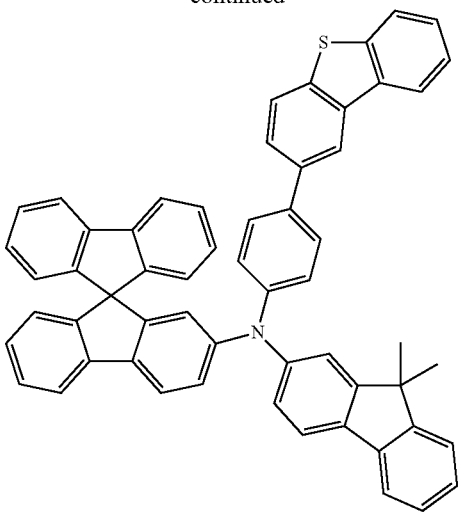
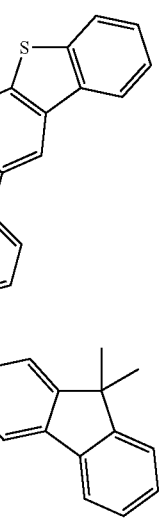
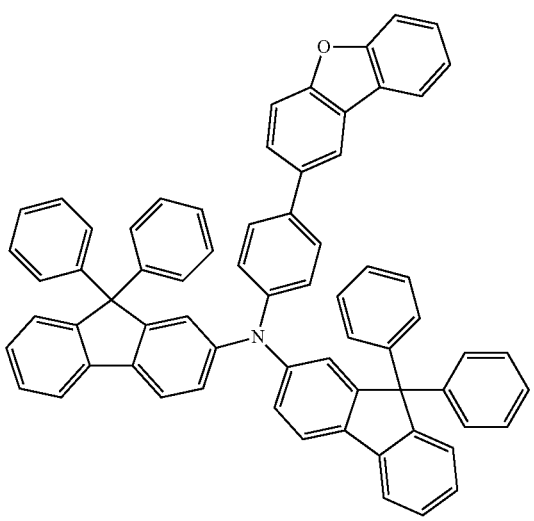

177
-continued
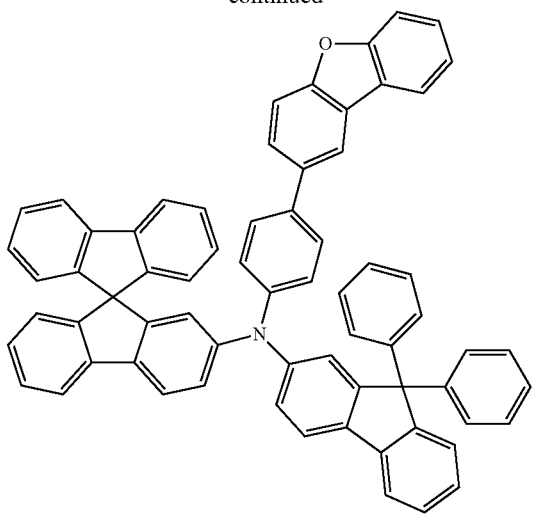
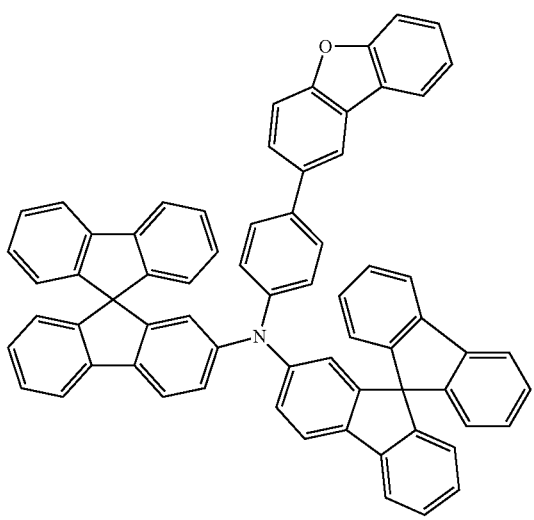
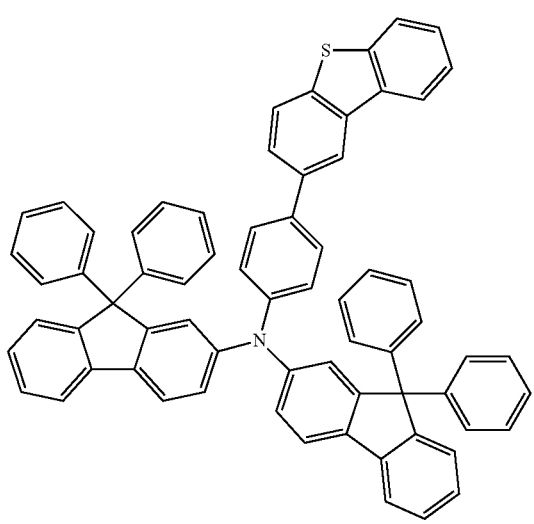
178
-continued
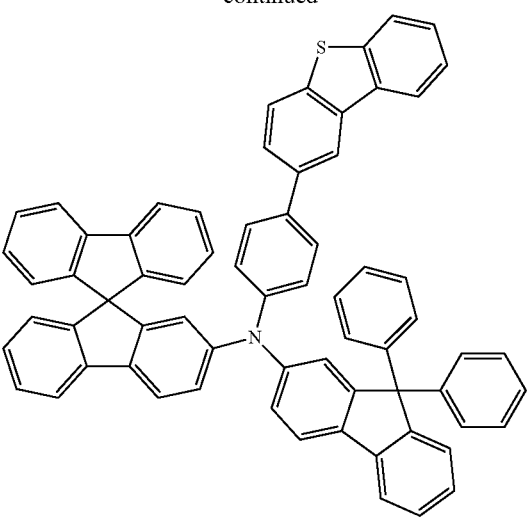
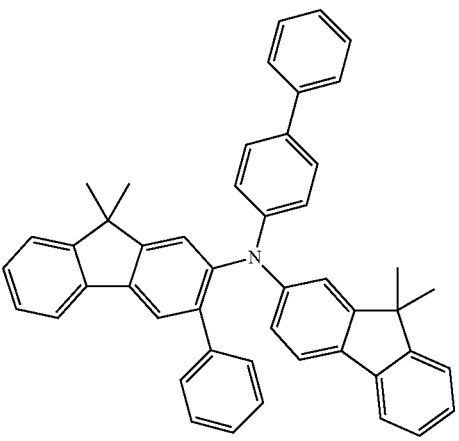

179
-continued
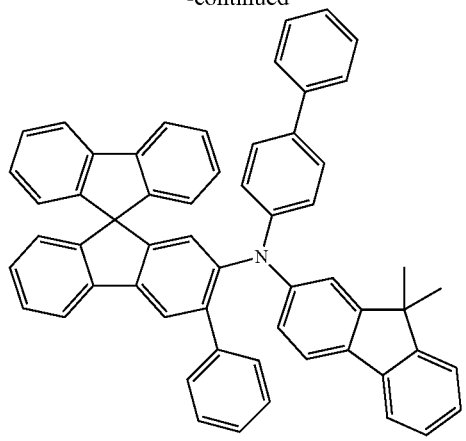
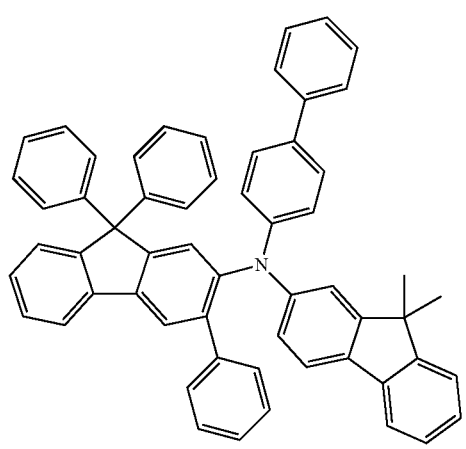
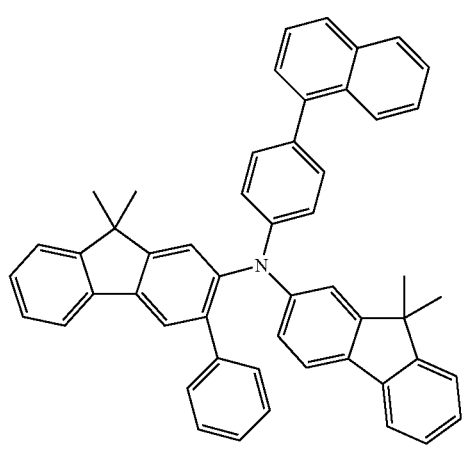
180
-continued
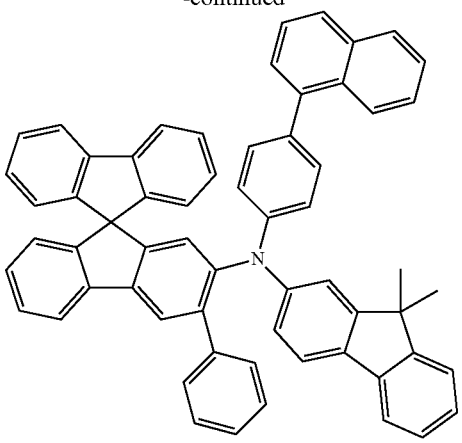
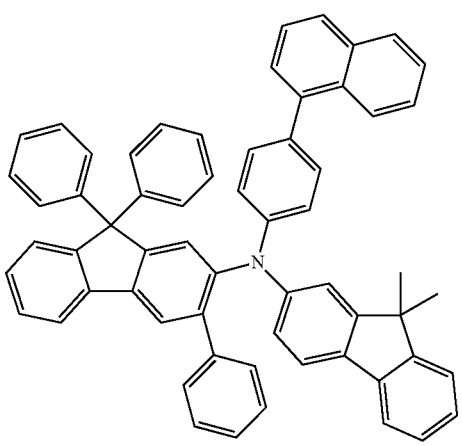
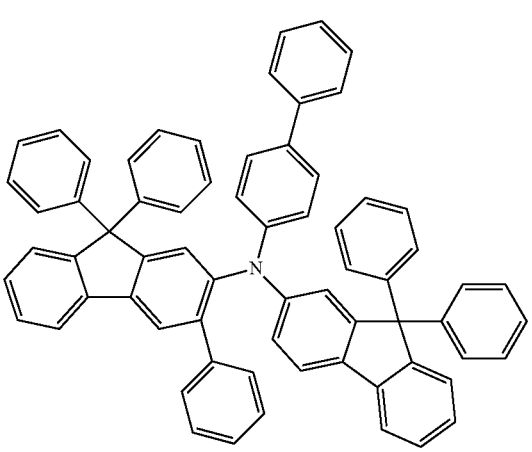

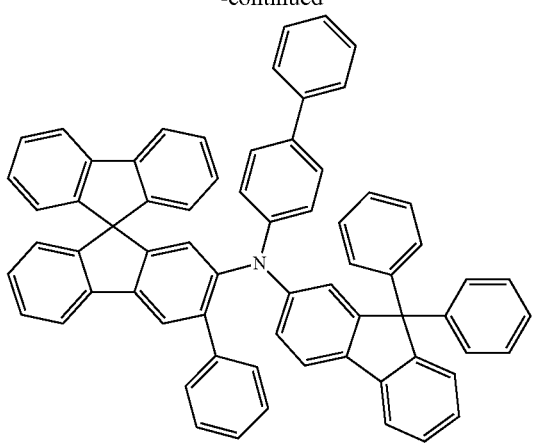
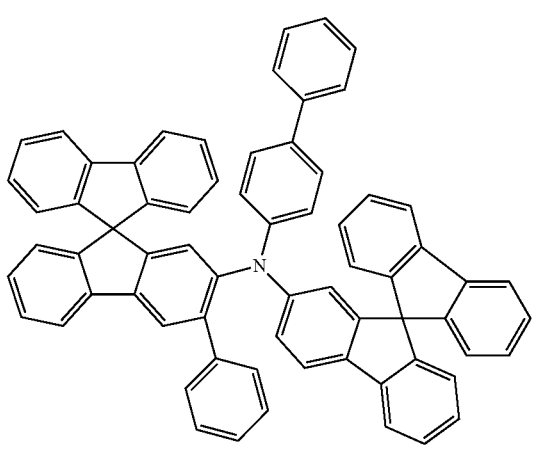
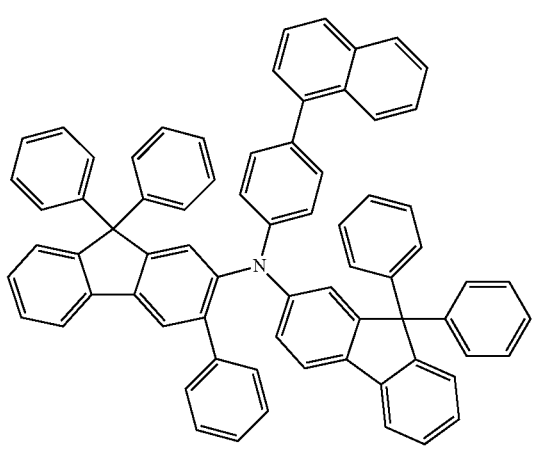
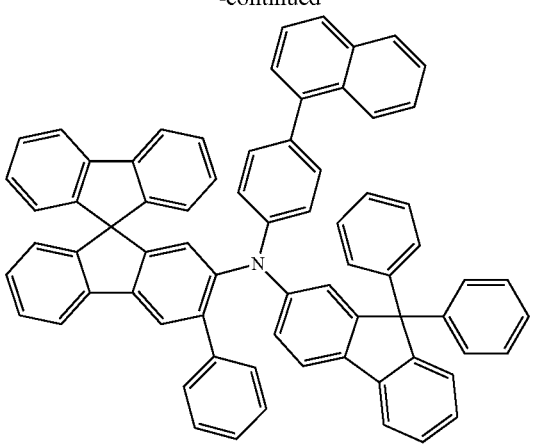
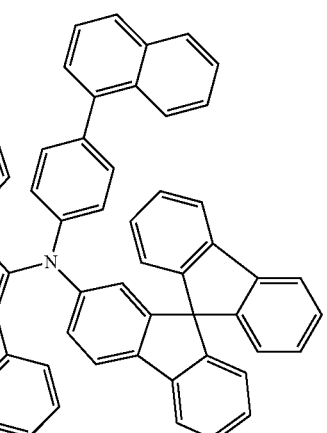
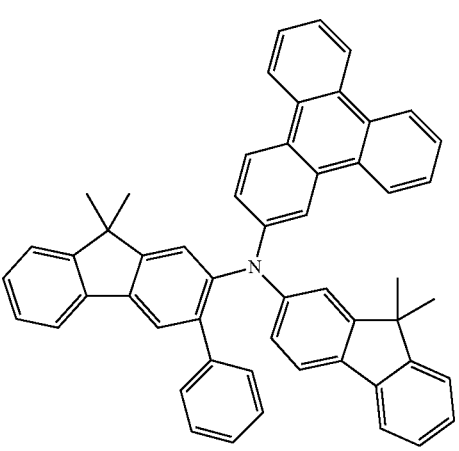

183
-continued
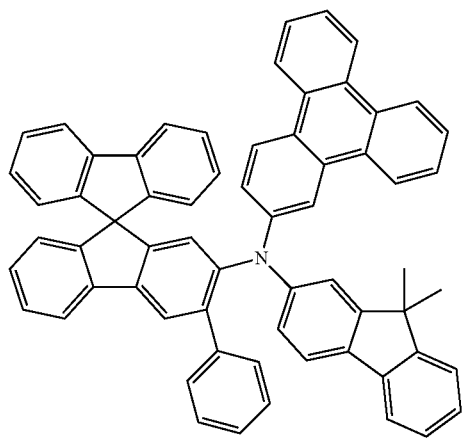
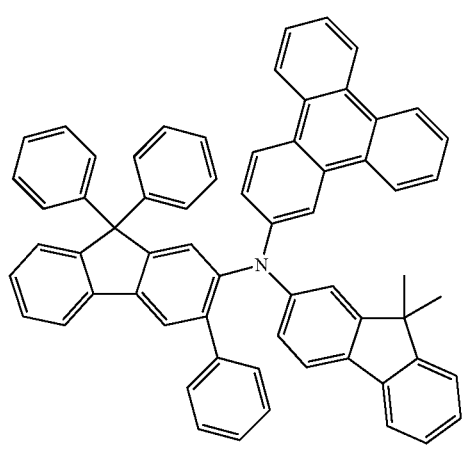
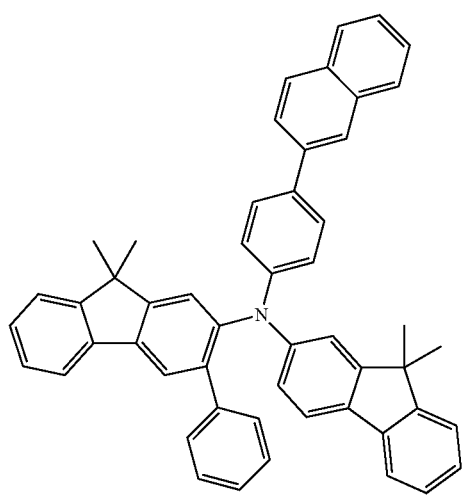
184
-continued
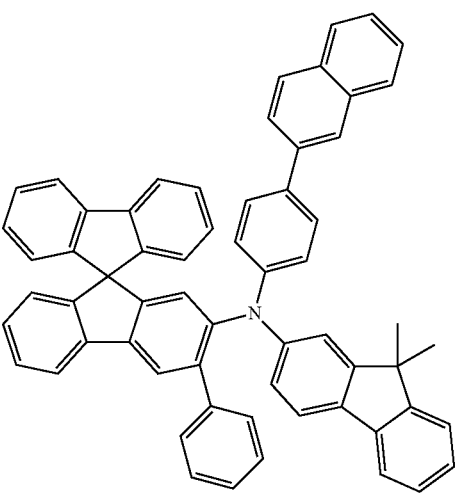
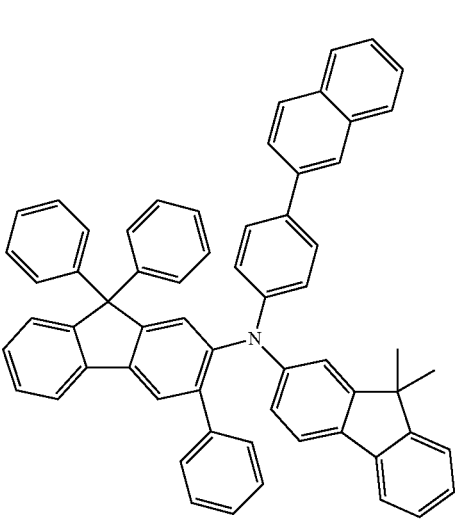
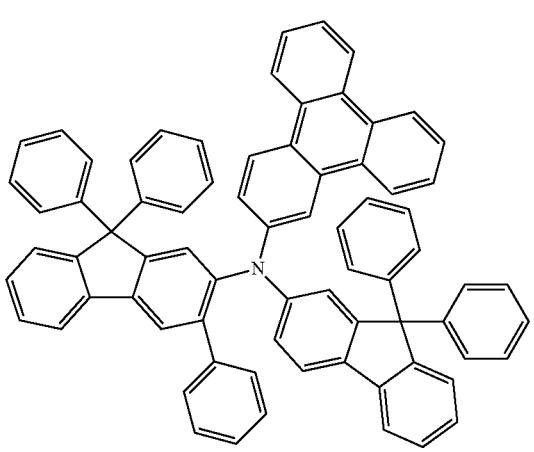

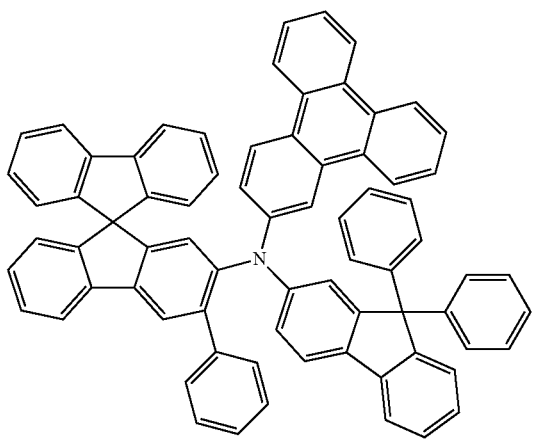
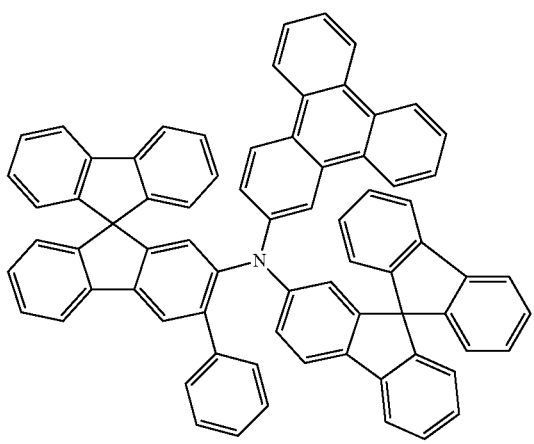
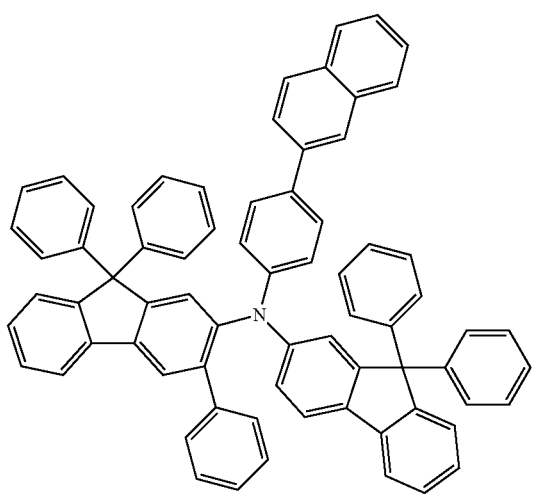
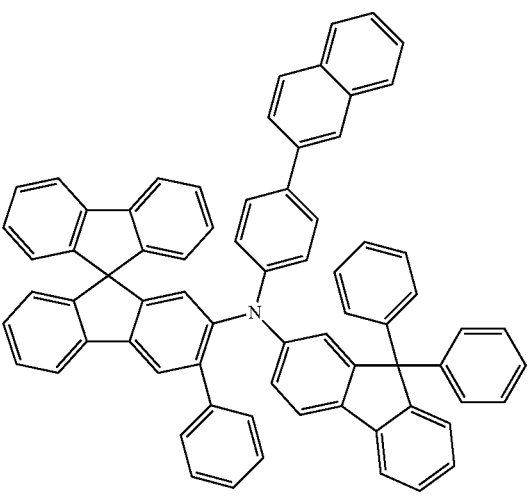
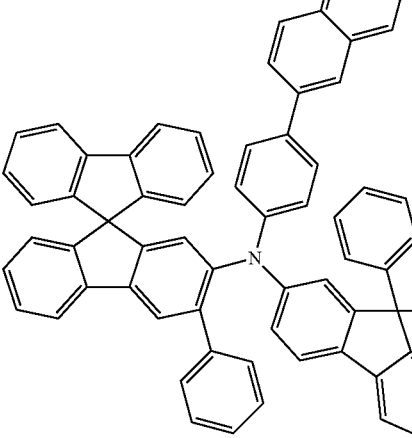
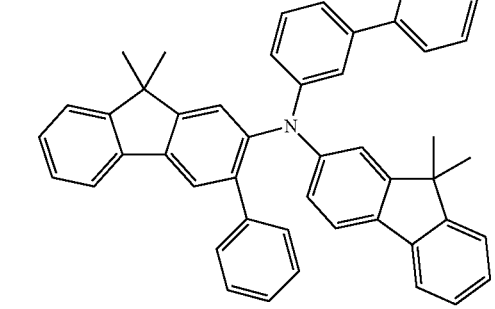
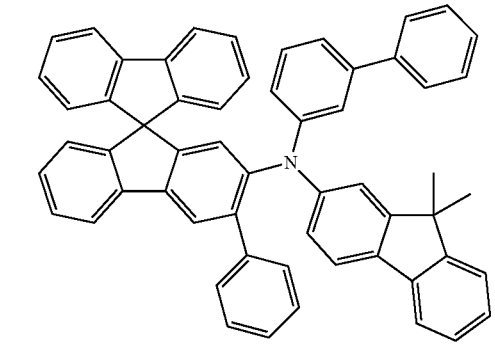

187
-continued
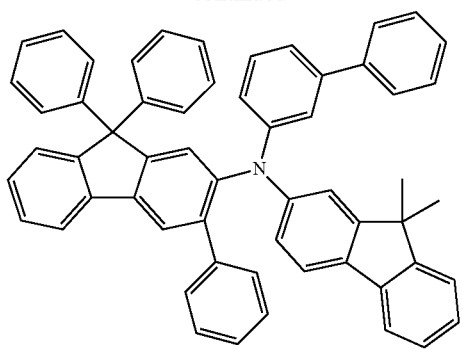
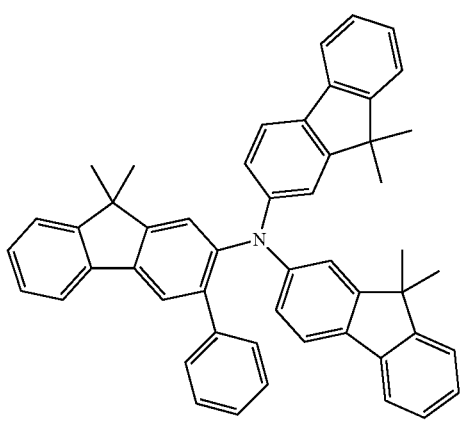
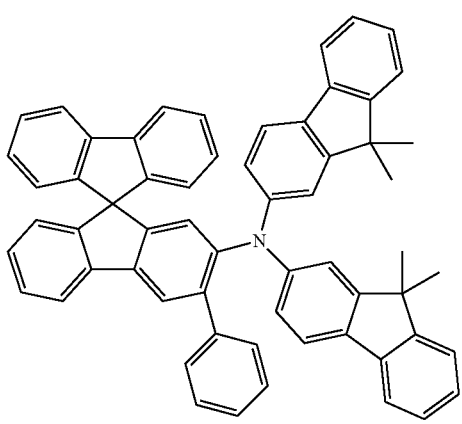
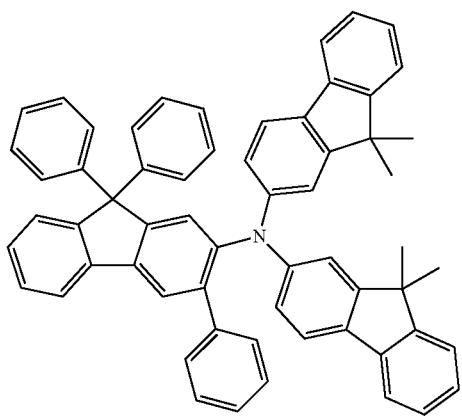
188
-continued
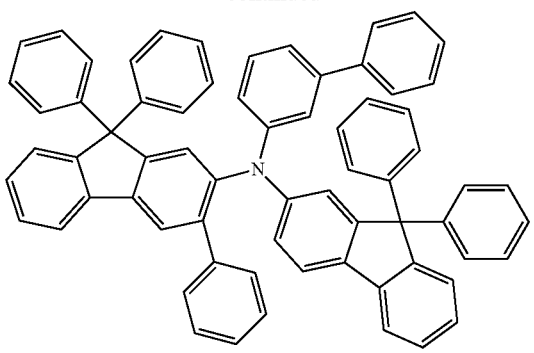
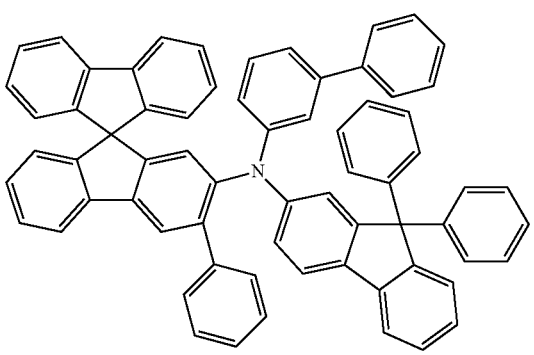
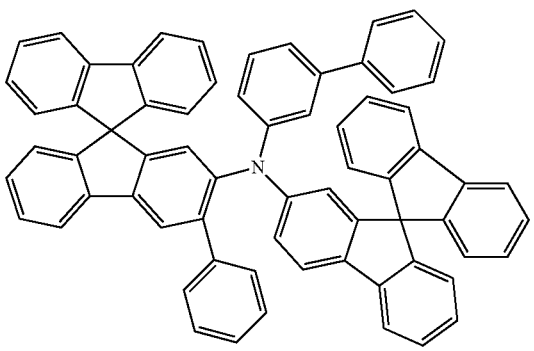
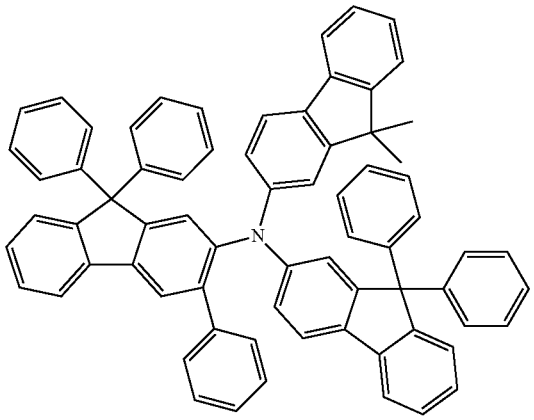

-continued
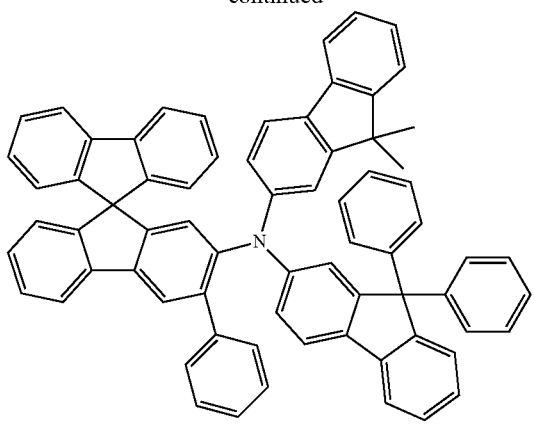
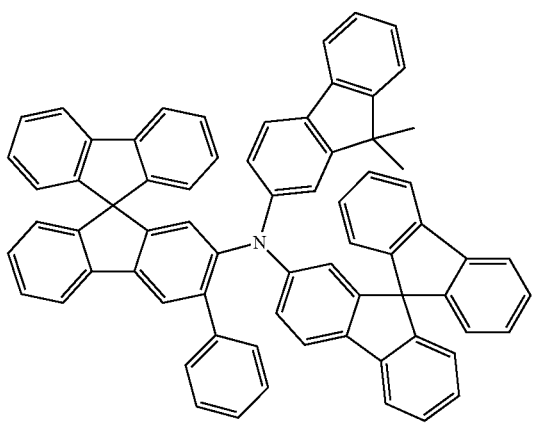
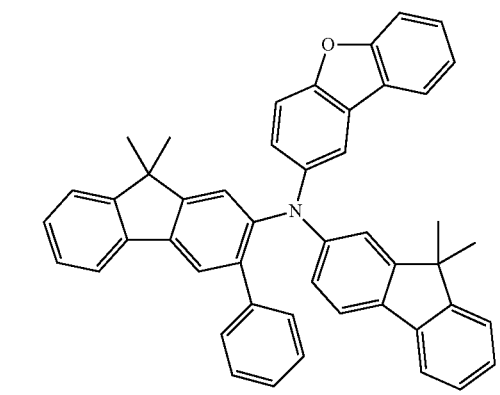
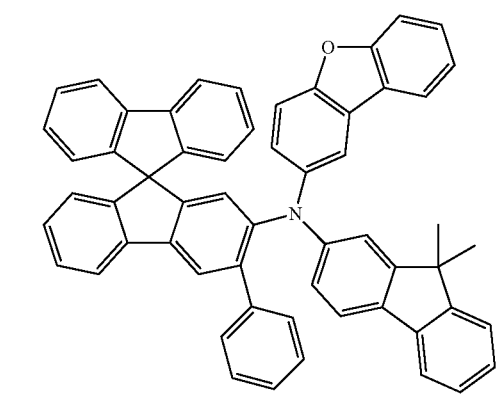
-continued
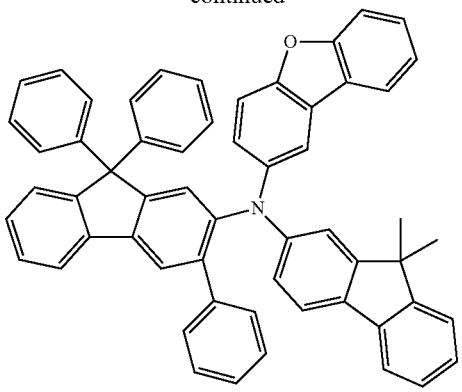
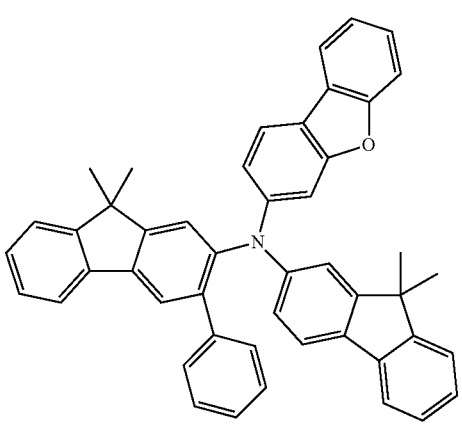
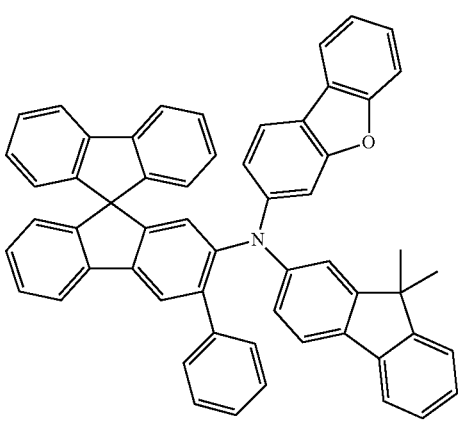
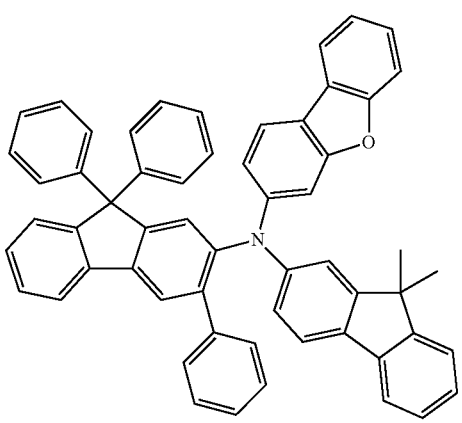

191
-continued
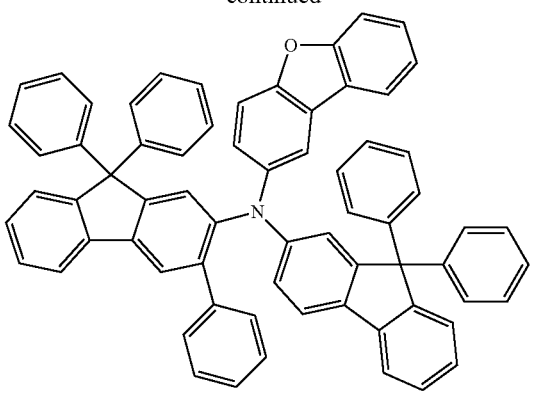
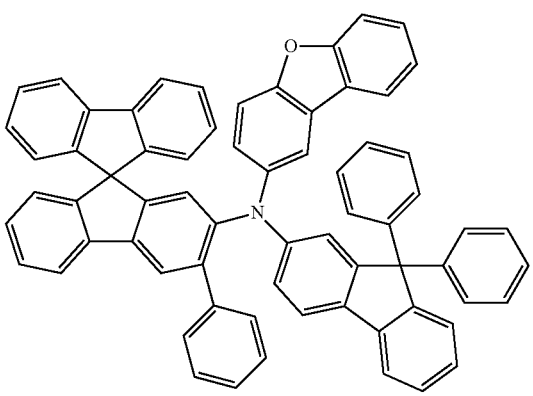
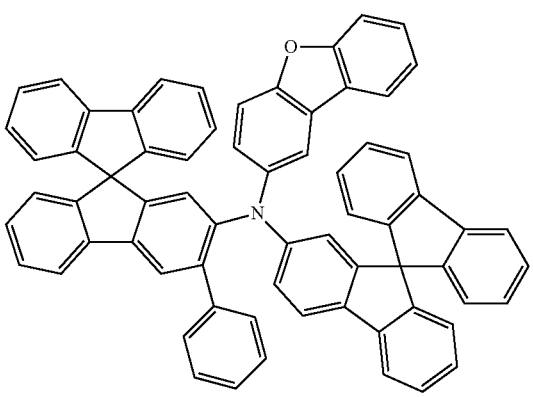
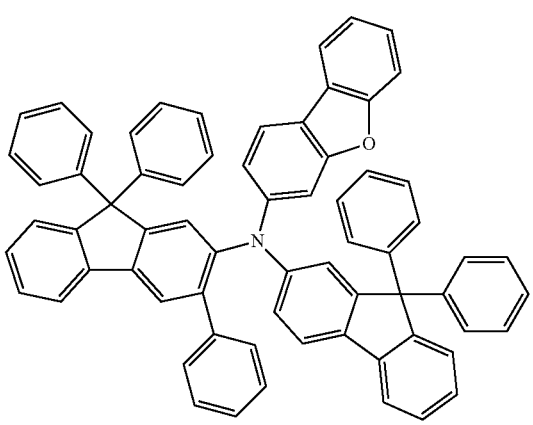
192
-continued
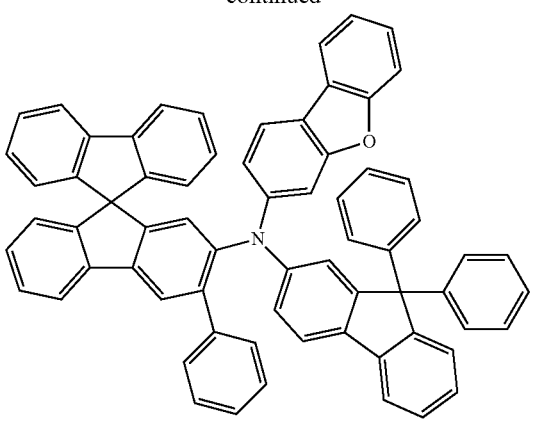
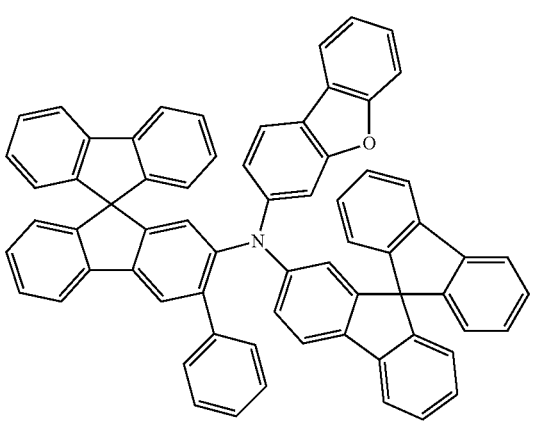
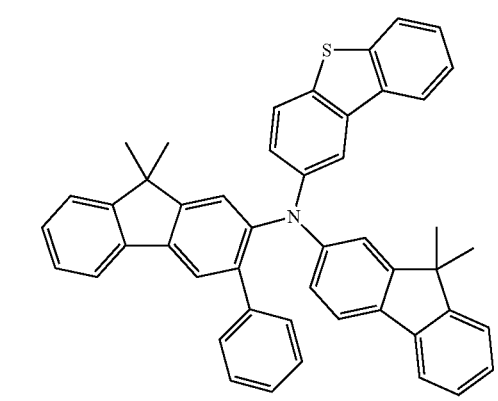
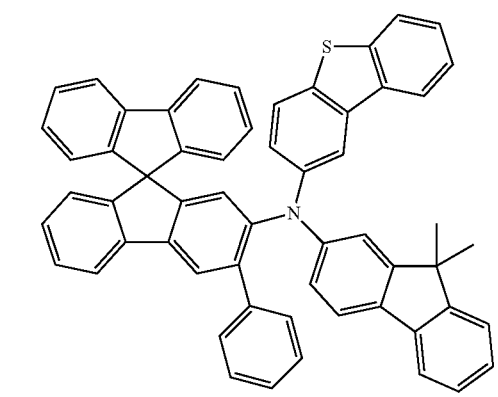

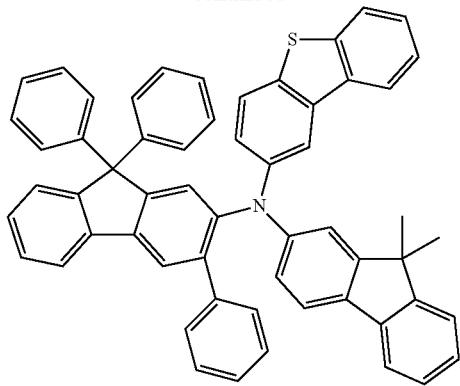
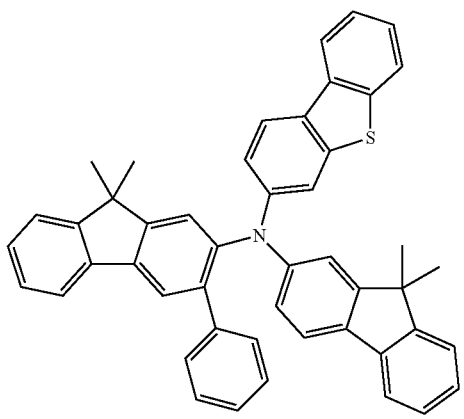
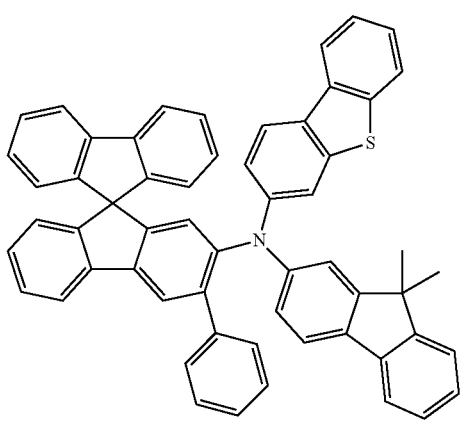
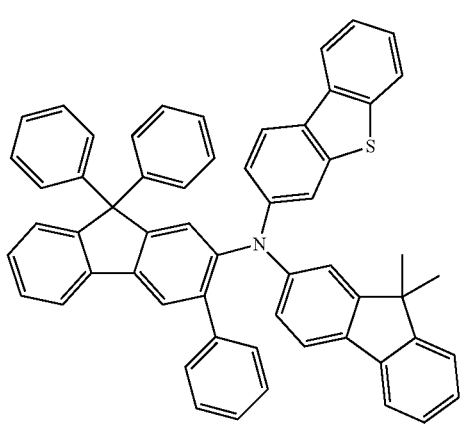
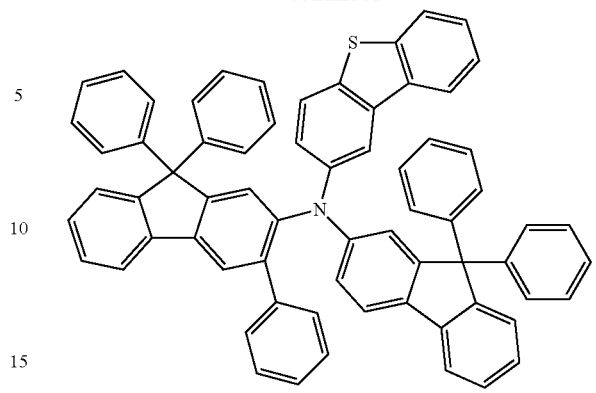
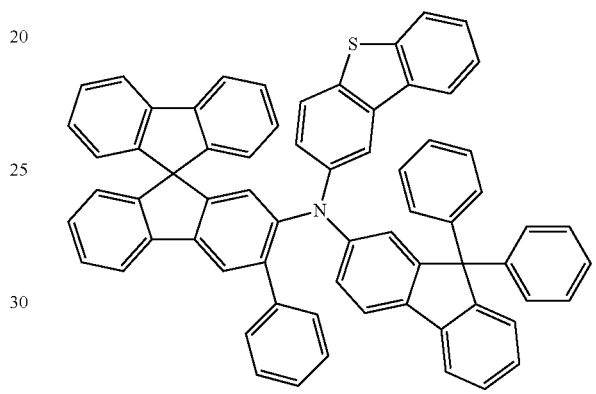
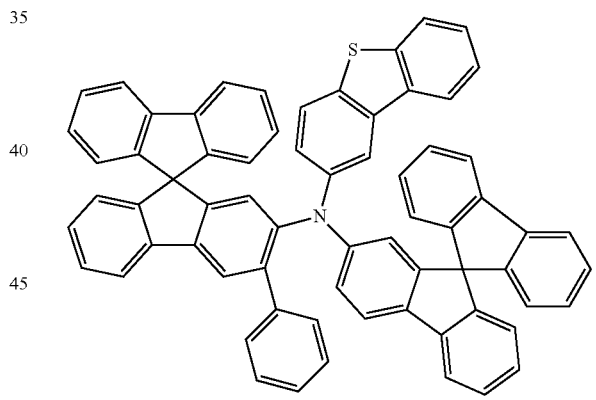
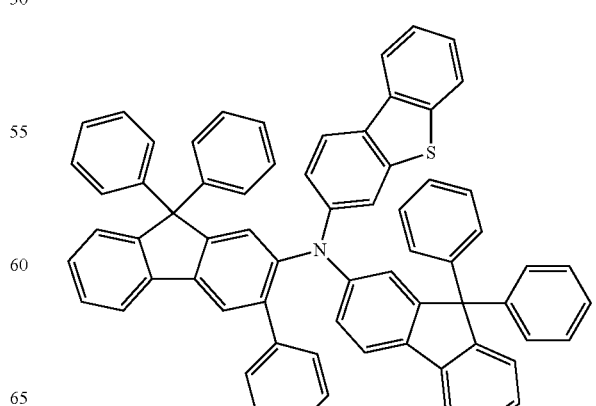

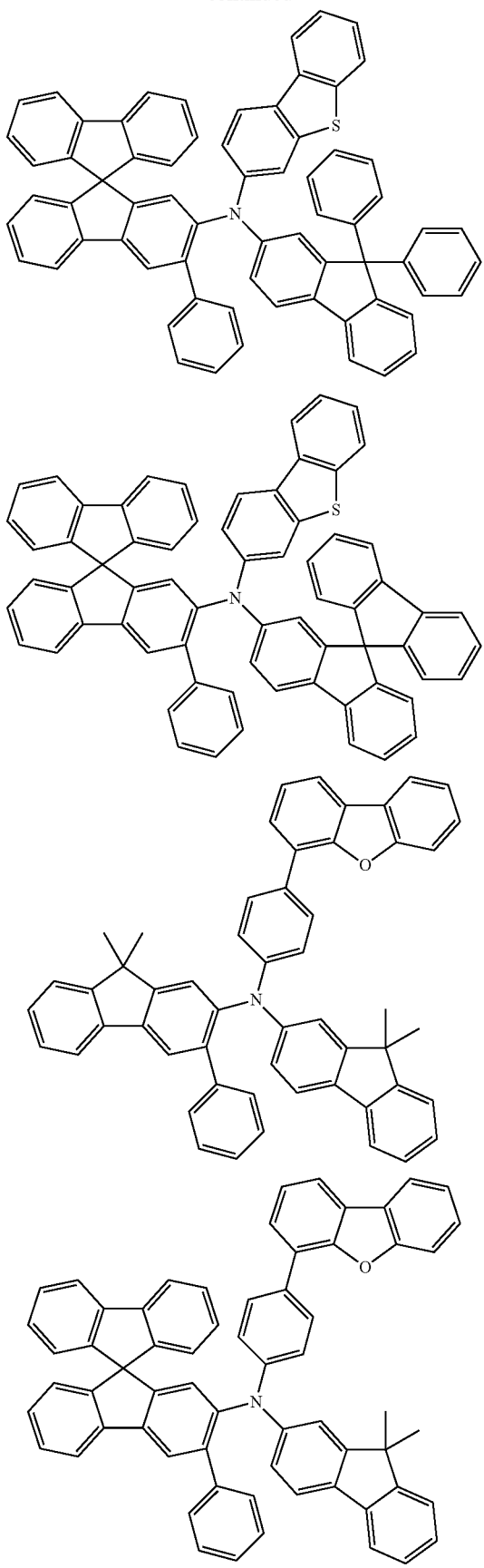
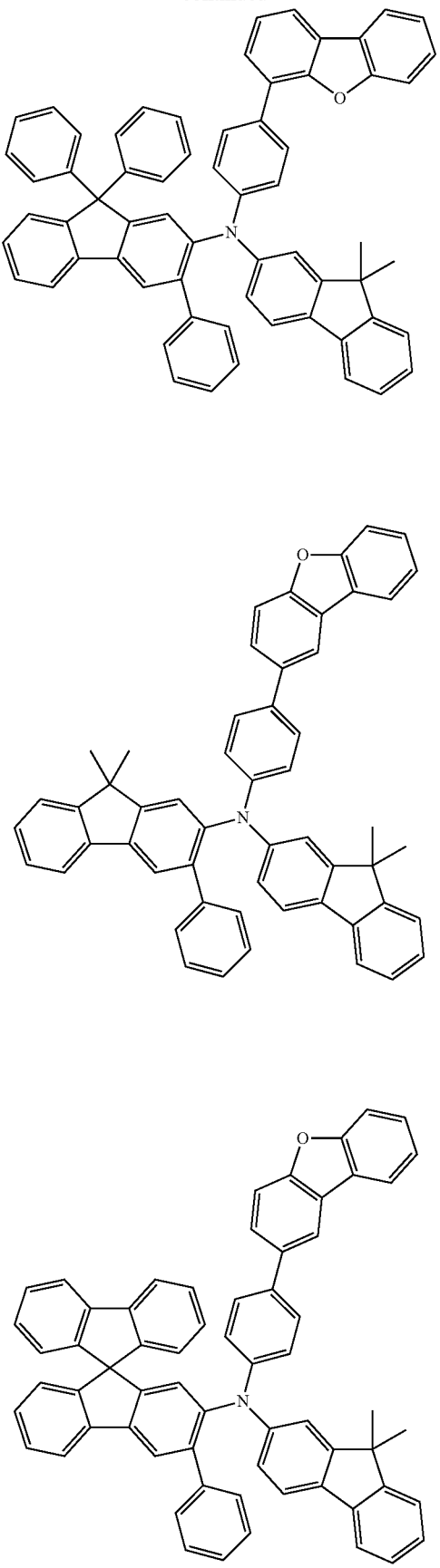

197
-continued
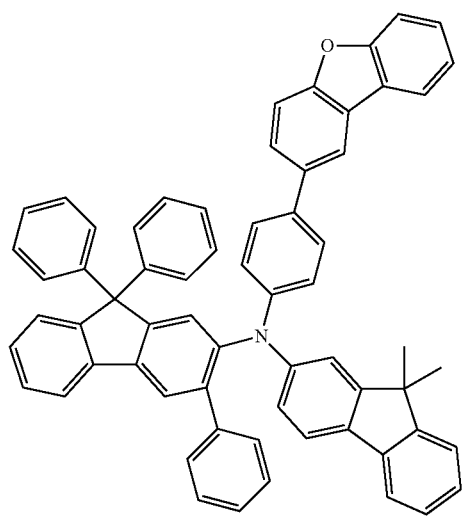
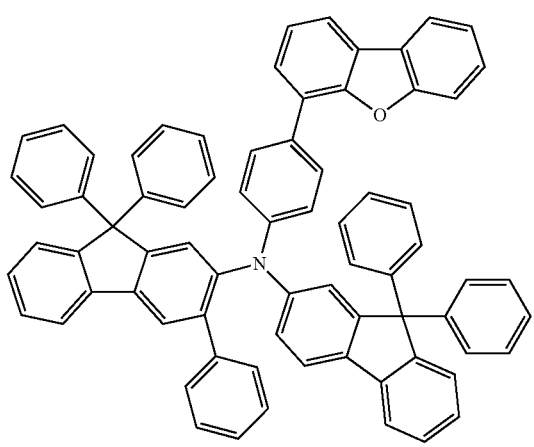
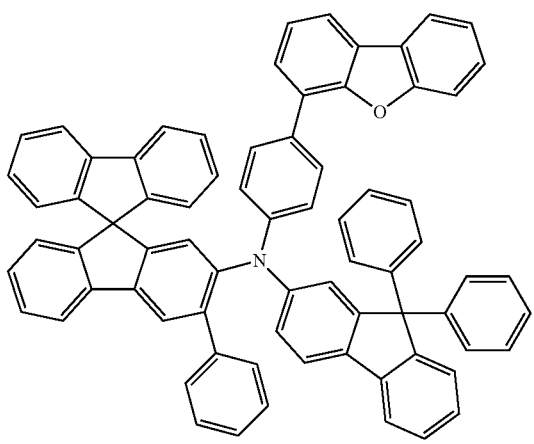
198
-continued
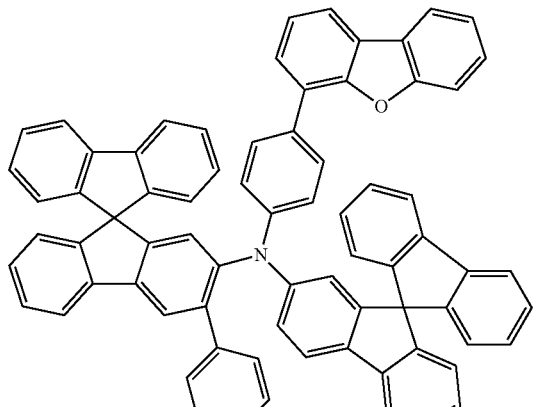
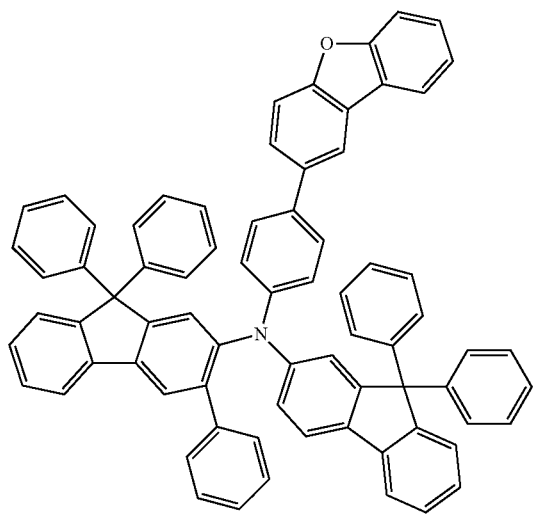
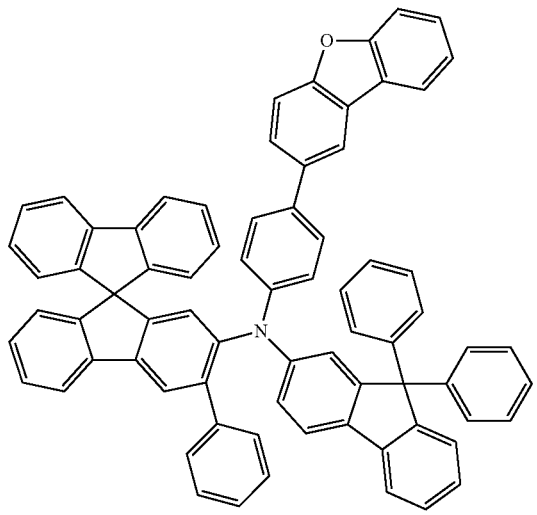

199
-continued
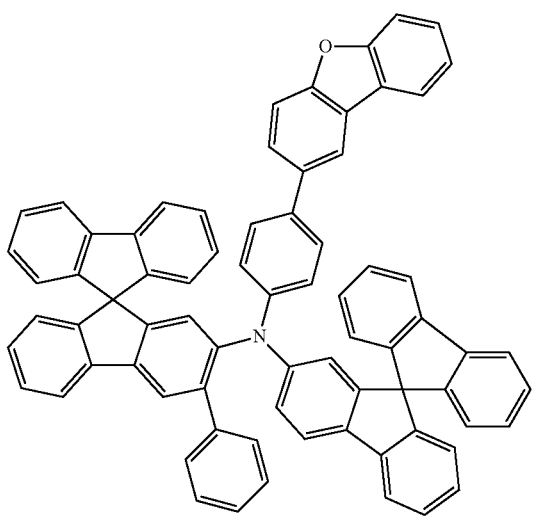
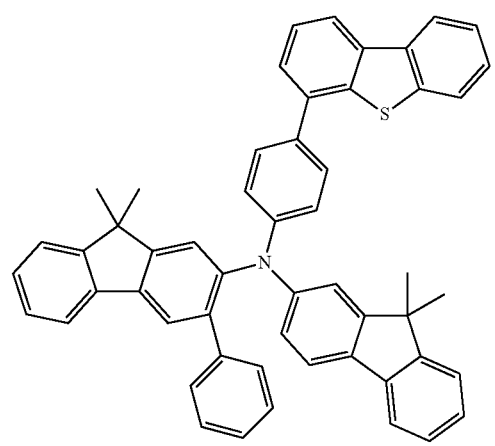
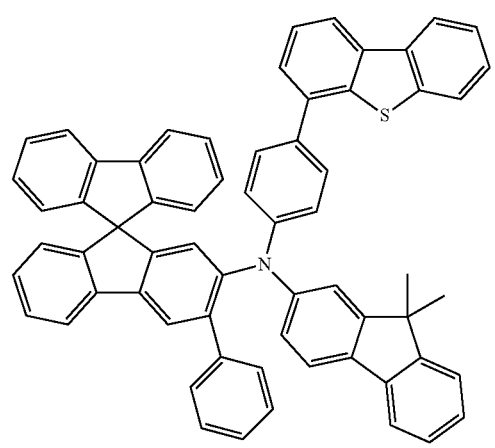
200
-continued
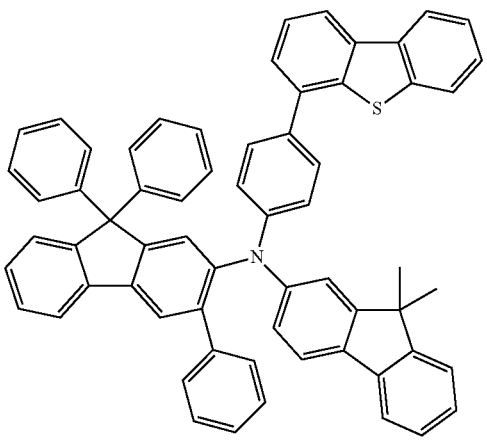
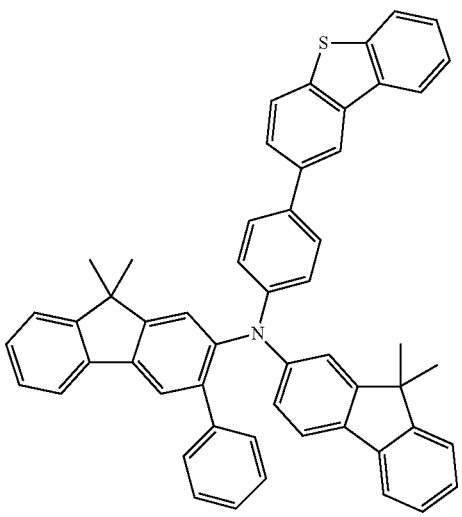
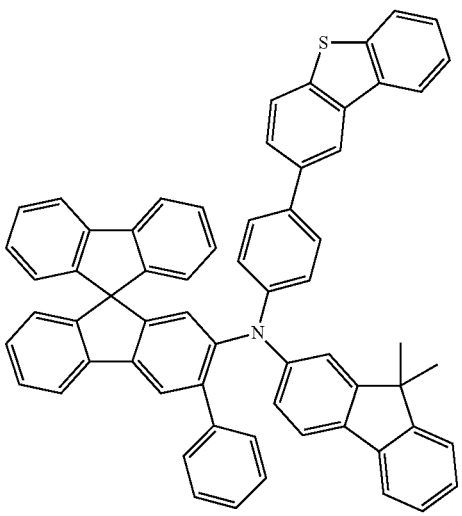

201
-continued
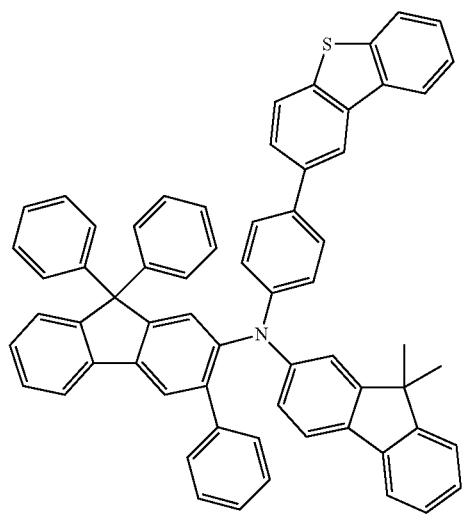
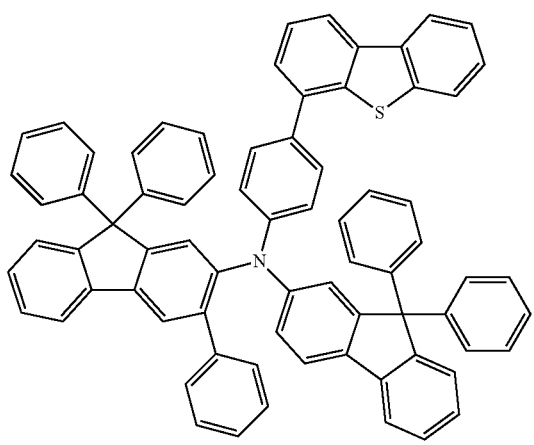
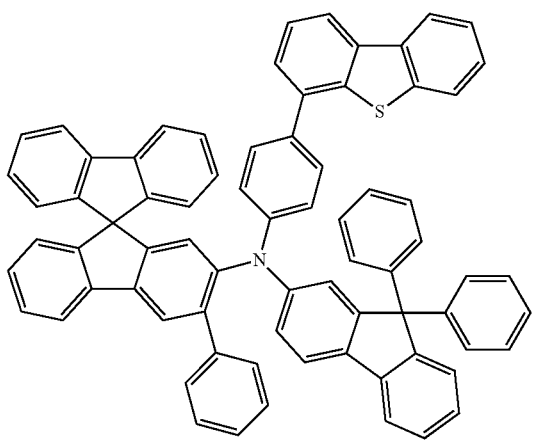
202
-continued
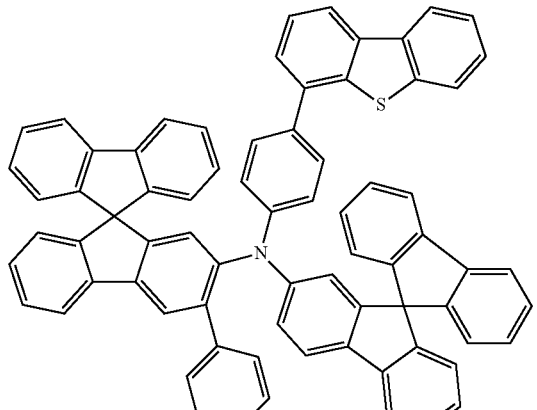
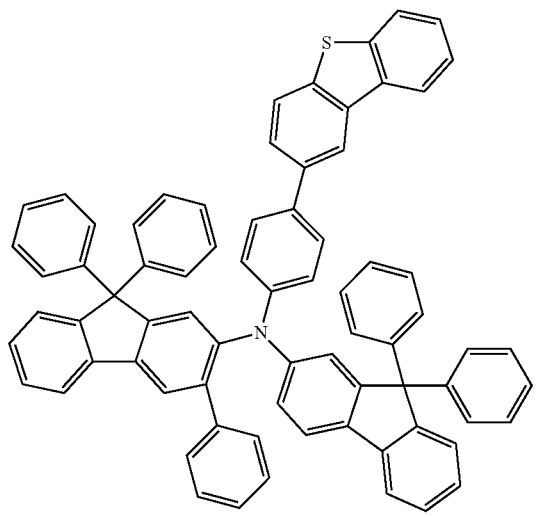
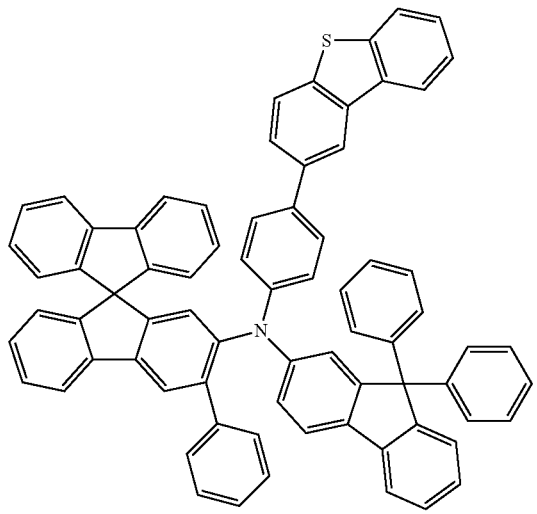

203
-continued
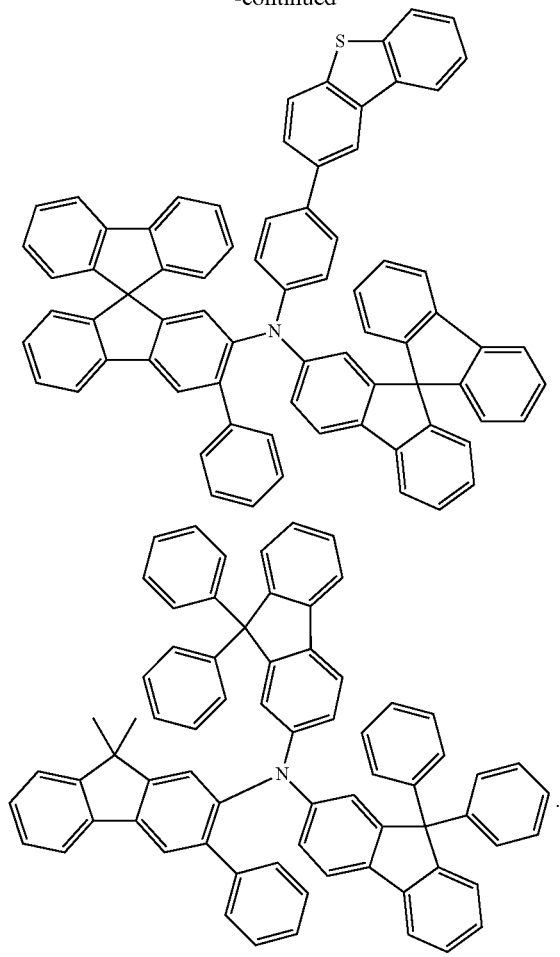
204
-continued
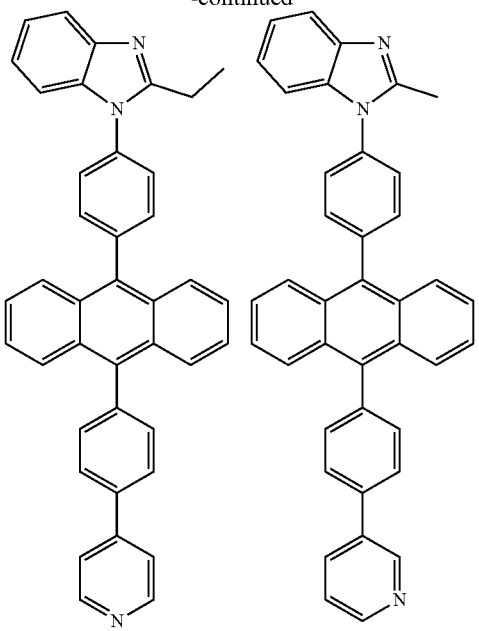
6. The organic light emitting device of claim 1, wherein the compound represented by Chemical Formula 2 is selected from the following structural formulae:
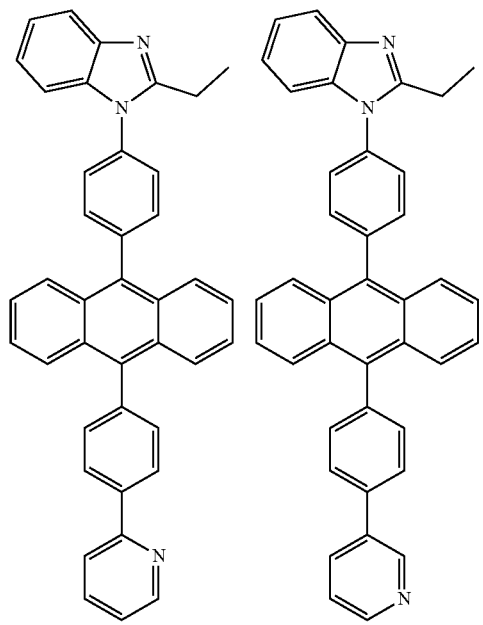
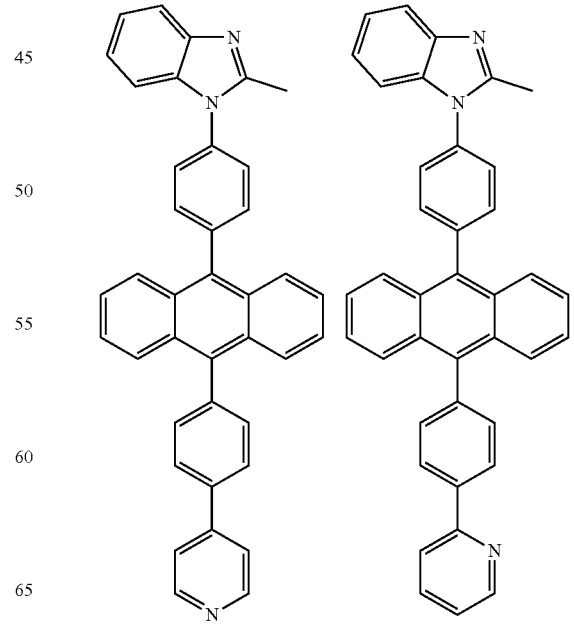

205
-continued
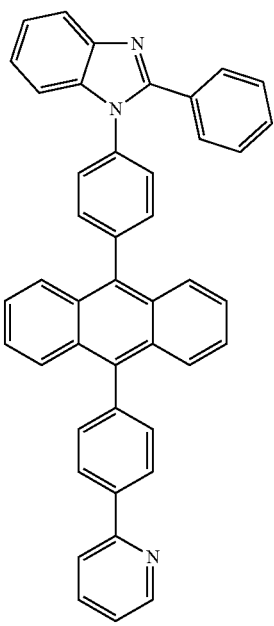
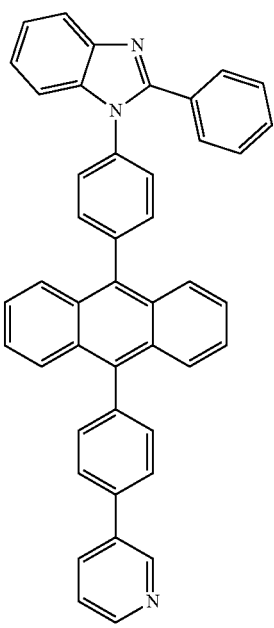
206
-continued
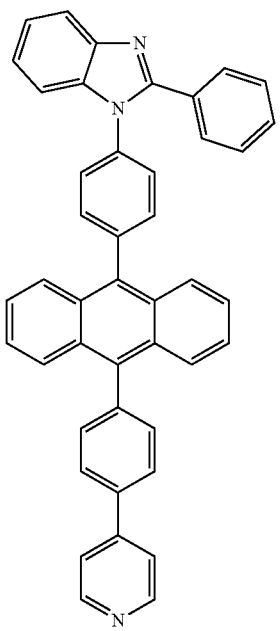
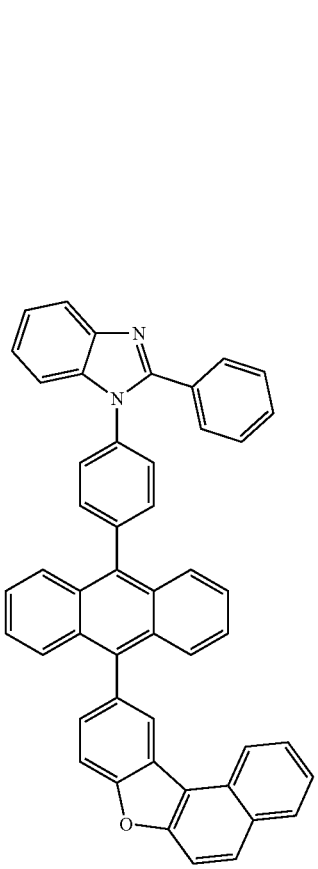

207
-continued
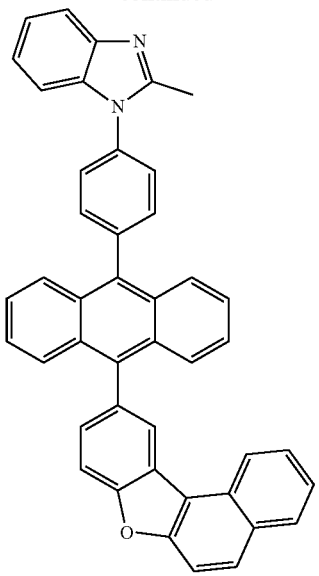
208
-continued
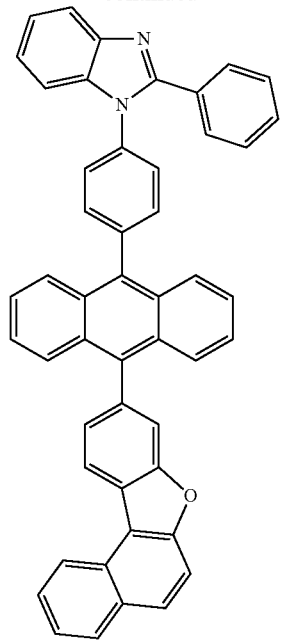
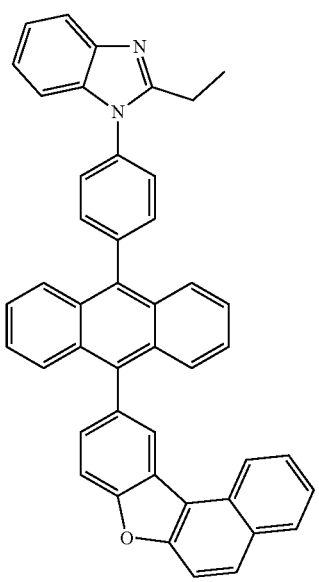
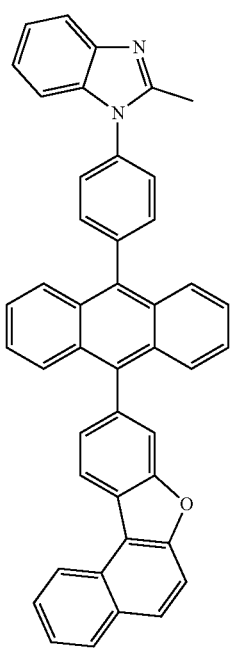

209
-continued
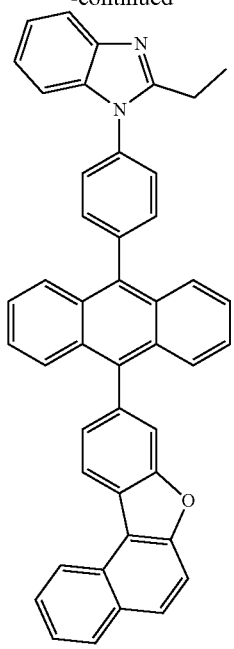
210
-continued
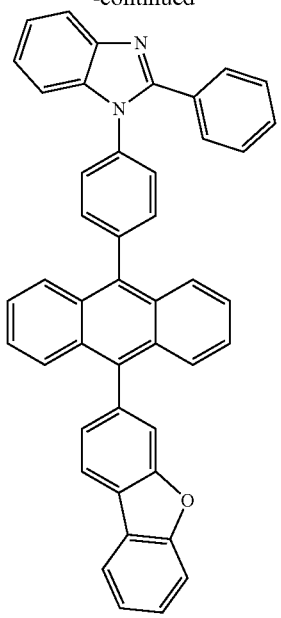
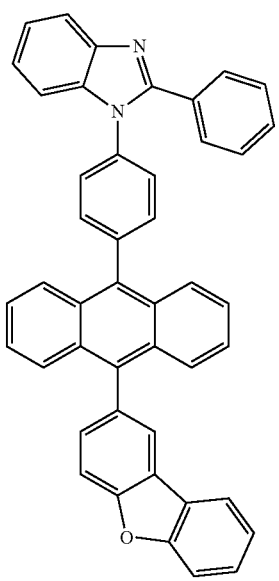
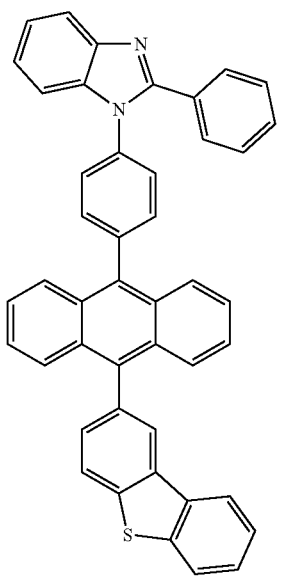

211
-continued
212
-continued
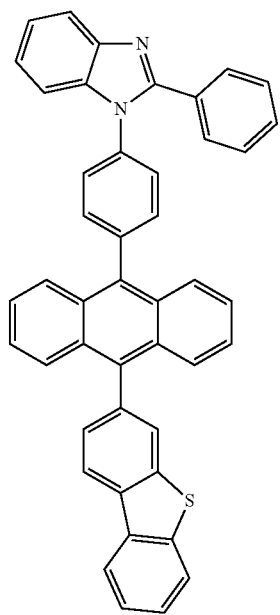
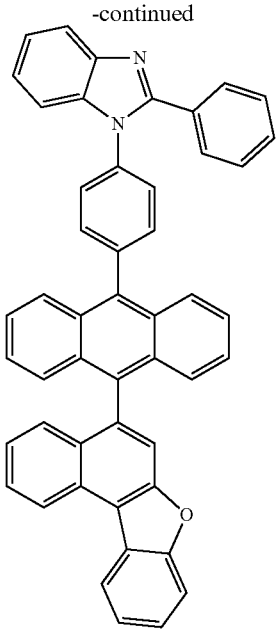

-continued

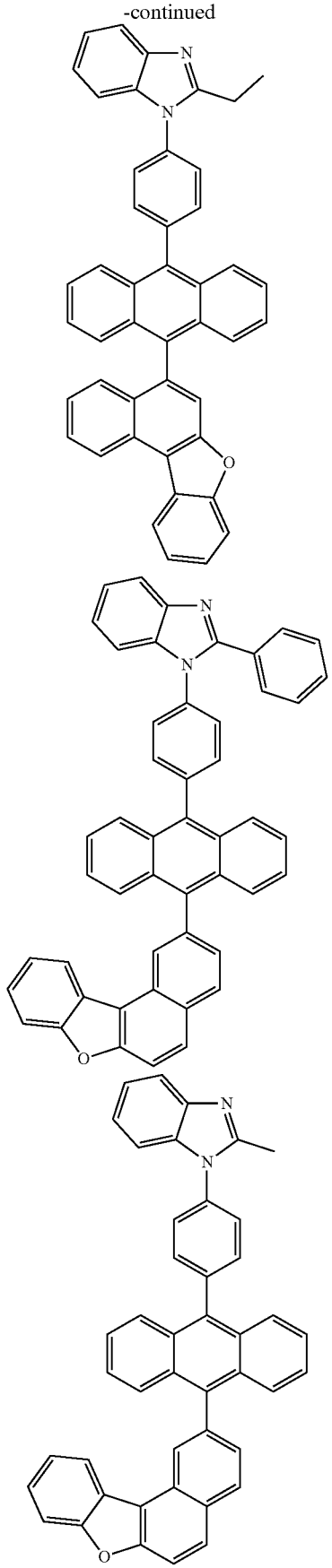

-continued

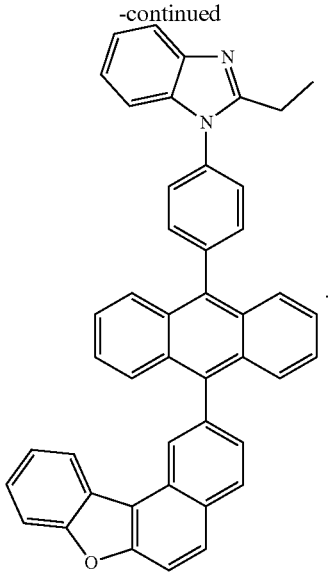

7. The organic light emitting device of claim 1, wherein the first electrode is a positive electrode, and the second electrode is a negative electrode.

8. The organic light emitting device of claim 1, wherein the first organic material layer comprising the compound represented by Chemical Formula 1 is a hole transporting layer.

9. The organic light emitting device of claim 1, wherein the first organic material layer comprising the compound represented by Chemical Formula 1 is an electron blocking layer.

10. The organic light emitting device of claim 1, wherein the second organic material layer comprising the compound represented by Chemical Formula 2 is an electron transporting layer.

11. The organic light emitting device of claim 1, wherein the light emitting layer comprises a compound of the following Chemical Formula 3:

[Chemical Formula 3]

in Chemical Formula 3,

Ar3 is a benzofluorene skeleton, a fluoranthene skeleton, a pyrene skeleton, or a chrysene skeleton, L6 is a single bond, a $C_6$ to $C_{30}$ arylene group, or a $C_5$ to $C_{30}$ divalent heterocyclic group, $X_1$ and $X_2$ are the same as or different from each other, and are each independently selected from the group consisting of a substituted or unsubstituted $C_6$ to $C_{30}$ aryl group, a substituted or unsubstituted $C_5$ to $C_{30}$ heterocyclic group, a substituted or unsubstituted $C_1$ to $C_{30}$ alkyl group, and a substituted or unsubstituted $C_7$ to $C_{30}$ aralkyl group, and $X_1$ and $X_2$ are optionally bonded to each other to form a saturated or unsaturated ring, r is an integer of 1 or more, and when r is 2 or more, each $X_1$ is the same as or different from each other, and each $X_2$ is the same as or different from each other.

12. The organic light emitting device of claim 11, wherein Ar3 is a pyrene skeleton, L6 is a single bond, and $X_1$ and $X_2$ are the same as or different from each other, and are each independently an aryl group unsubstituted or substituted with an alkyl group; or a $C_5$ to $C_{30}$ heterocyclic group, and r is 2.

13. The organic light emitting device of claim 1, wherein the light emitting layer comprises a compound of the following Chemical Formula 4:

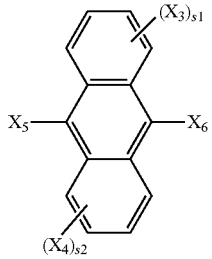

[Chemical Formula 4]

in Chemical Formula 4, $X_5$ is a substituted or unsubstituted 1-naphthyl group, a substituted or unsubstituted 2-naphthyl group, a substituted or unsubstituted 1-anthryl group, a substituted or unsubstituted 2-anthryl group, a substituted or unsubstituted 1-phenanthryl group, a substituted or unsubstituted 2-phenanthryl group, a substituted or unsubstituted 3-phenanthryl group, a substituted or unsubstituted 4-phenanthryl group, a substituted or unsubstituted 9-phenanthryl group, a substituted or unsubstituted 1-naphthacenyl group, a substituted or unsubstituted 2-naphthacenyl group, a substituted or unsubstituted 9-naphthacenyl group, a substituted or unsubstituted 1-pyrenyl group, a substituted or unsubstituted 2-pyrenyl group, a substituted or unsubstituted 4-pyrenyl group, a substituted or unsubstituted 3-methyl-2-naphthyl group, a substituted or unsubstituted 4-methyl-1-naphthyl group or the following structural formula

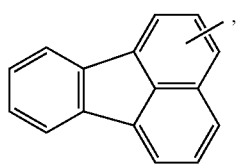

$X_6$ is a group selected from the group consisting of a substituted or unsubstituted phenyl group, a substituted or unsubstituted 1-naphthyl group, a substituted or unsubstituted 2-naphthyl group, a substituted or unsubstituted 1-anthryl group, a substituted or unsubstituted 2-anthryl group, a substituted or unsubstituted 9-anthryl group, a substituted or unsubstituted 1-phenanthryl group, a substituted or unsubstituted 2-phenanthryl group, a substituted or unsubstituted 3-phenanthryl group, a substituted or unsubstituted 4-phenanthryl group, a substituted or unsubstituted 9-phenanthryl group, a substituted or unsubstituted 1-naphthacenyl group, a substituted or unsubstituted 2-naphthacenyl group, a substituted or unsubstituted 9-naphthacenyl group, a substituted or unsubstituted 1-pyrenyl group, a substituted or unsubstituted 2-pyrenyl group, a substituted or unsubstituted 4-pyrenyl group, a substituted or unsubstituted 2-biphenylyl group, a substituted or unsubstituted 3-biphenylyl group, a substituted or unsubstituted 4-biphenylyl group, a substituted or unsubstituted p-terphenyl-4-yl group, a substituted or unsubstituted p-terphenyl-3-yl group, a substituted or unsubstituted p-terphenyl-2-yl group, a substituted or unsubstituted m-terphenyl-4-yl group, a substituted or unsubstituted m-terphenyl-3-yl group, a substituted or unsubstituted m-terphenyl-2-yl group, a substituted or unsubstituted o-tolyl group, a substituted or unsubstituted m-tolyl group, a substituted or unsubstituted p-tolyl group, a substituted or unsubstituted p-t-butylphenyl group, a substituted or unsubstituted p-(2-phenylpropyl)phenyl group, a substituted or unsubstituted 3-methyl-2-naphthyl group, a substituted or unsubstituted 4-methyl-1-naphthyl group, a substituted or unsubstituted 4-methyl-1-anthryl group, a substituted or unsubstituted 4'-methylbiphenylyl group, a substituted or unsubstituted 4"-t-butyl-p-terphenyl-4-yl group, and a substituted or unsubstituted 3-fluoranthenyl group, $X_3$ and $X_4$ are the same as or different from each other, and are each independently a substituted or unsubstituted aryl group having 6 to 50 carbon atoms, a substituted or unsubstituted heteroaryl group having 5 to 50 nuclear atoms, a substituted or unsubstituted alkyl group having 1 to 50 carbon atoms, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 nuclear atoms, a substituted or unsubstituted arylthio group having 5 to 50 nuclear atoms, a substituted or unsubstituted alkoxycarbonyl group having 1 to 50 carbon atoms, a carboxyl group, a halogen atom, a cyano group, a nitro group or a hydroxyl group, and s1 and s2 are each an integer from 0 to 4.

14. The organic light emitting device of claim 13, wherein $X_5$ and $X_6$ are the same as or different from each other, and are each independently a 1-naphthyl group or a 2-naphthyl group, and s1 and s2 are 0.

15. The organic light emitting device of claim 13, wherein the compound of Chemical Formula 4 is selected from the following structural formulae:

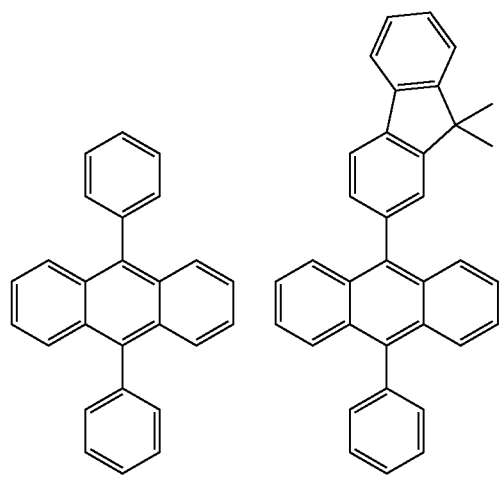

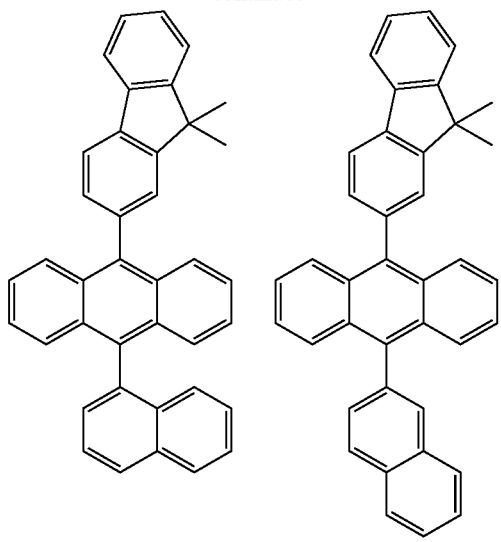
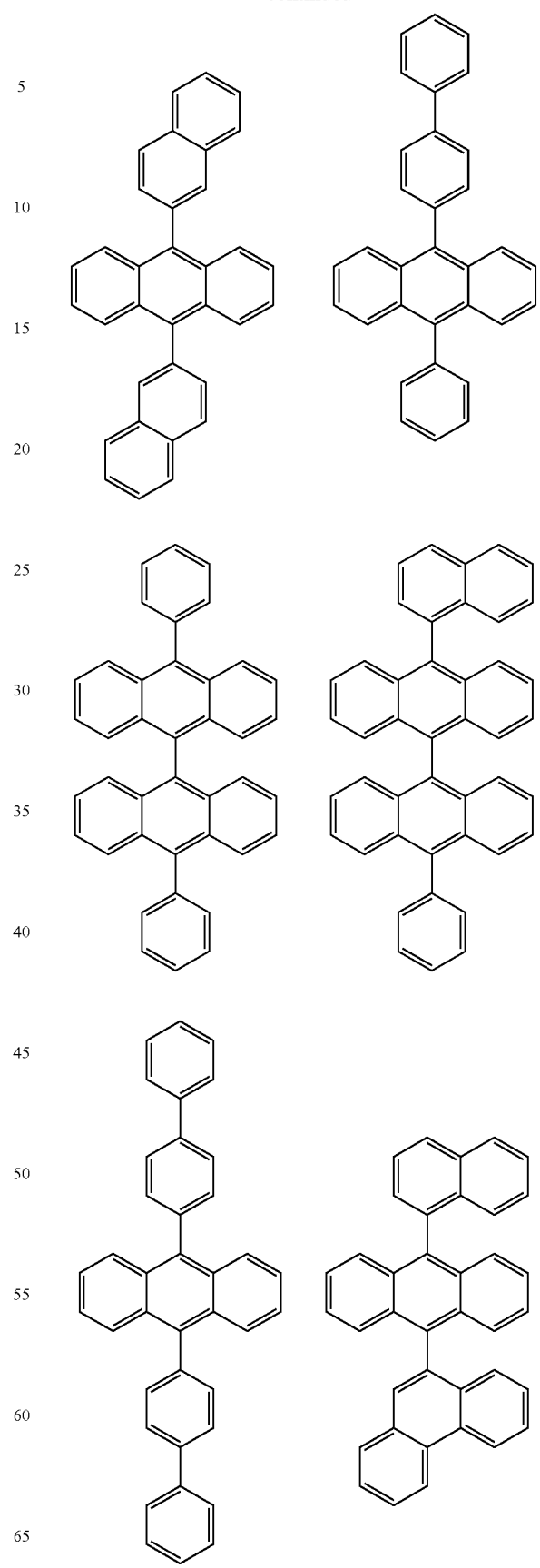

219
-continued
220
-continued
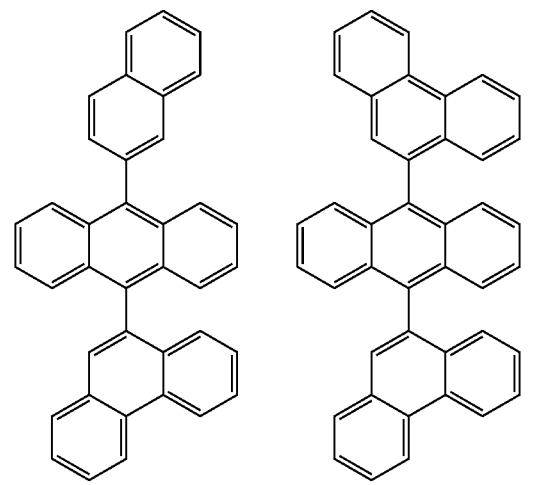
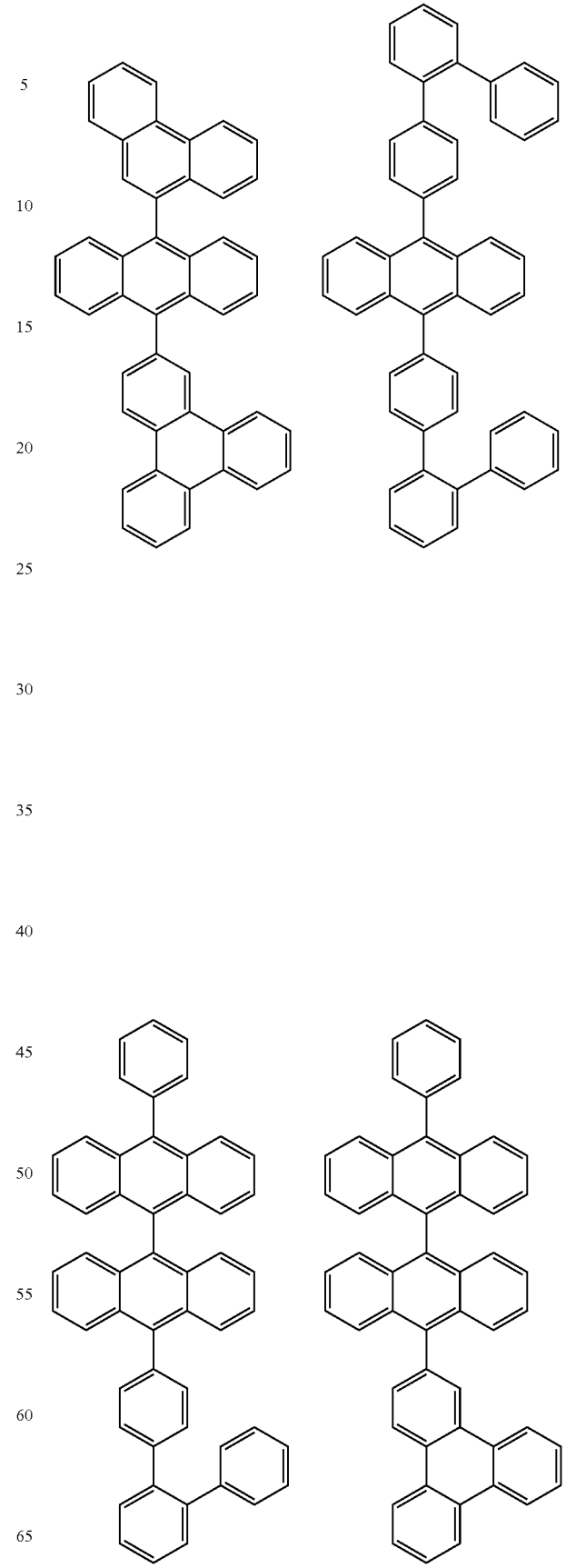

221
-continued
222
-continued
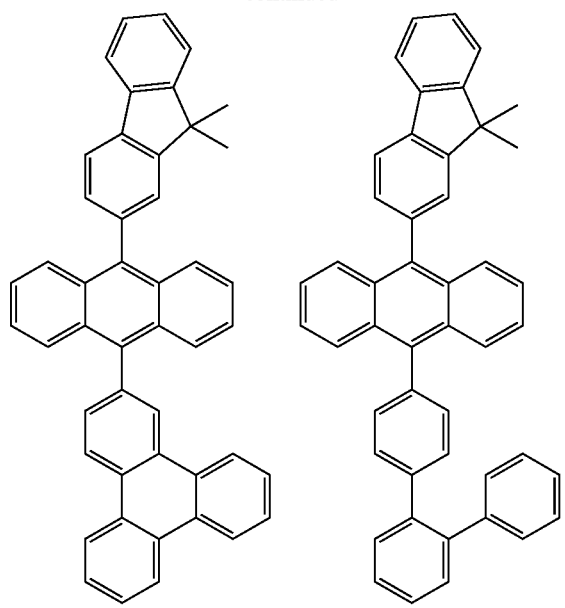
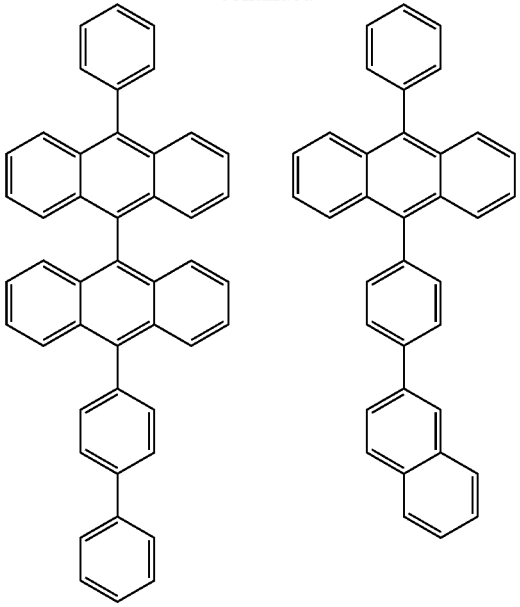
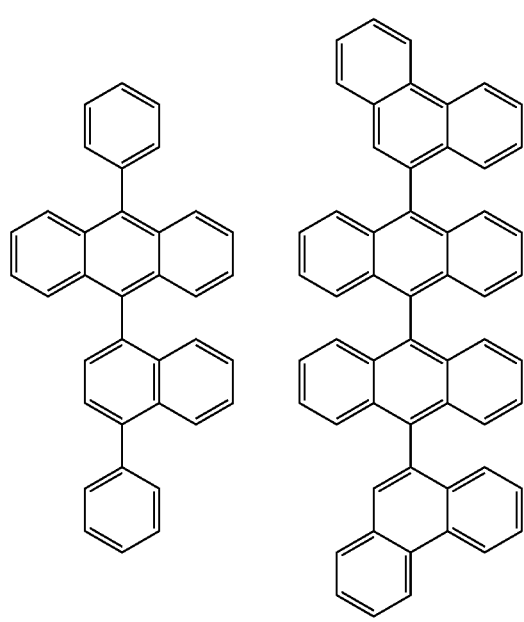
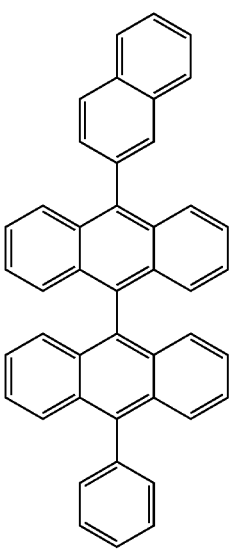

223
-continued
224
-continued
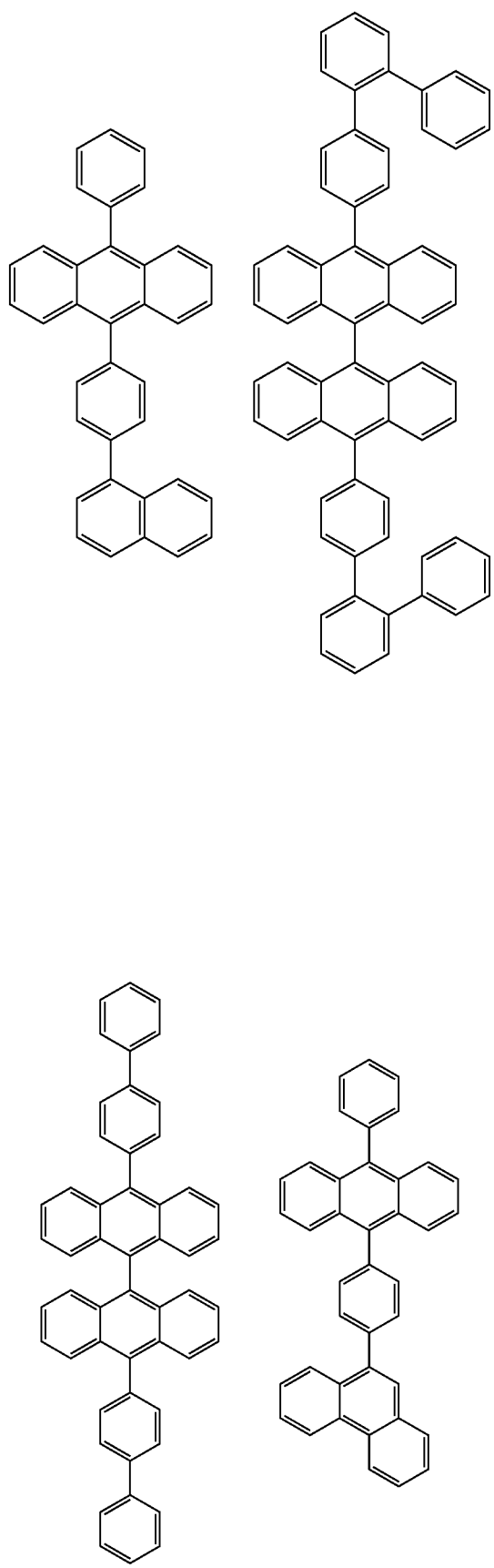
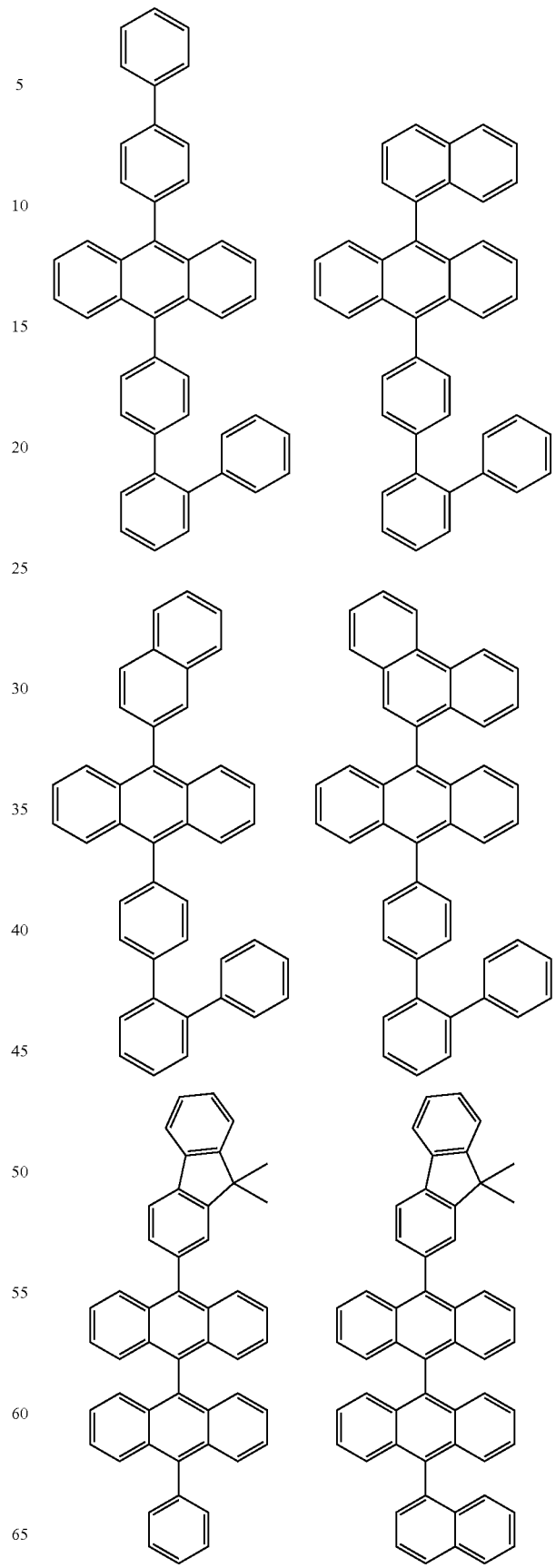

225
-continued
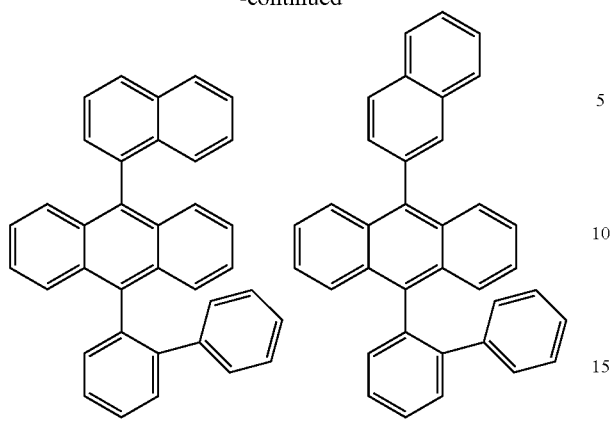
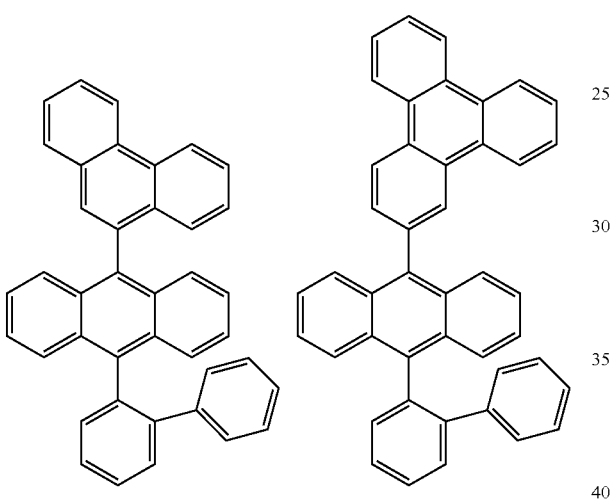
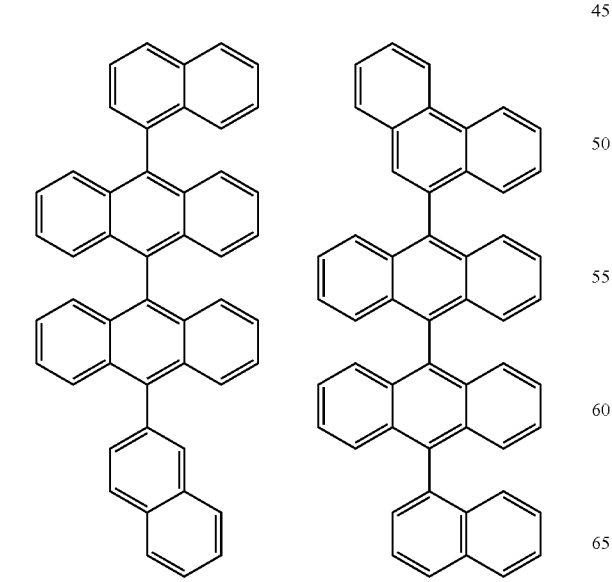
226
-continued
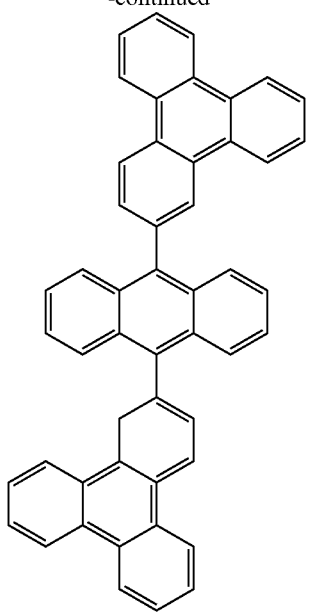
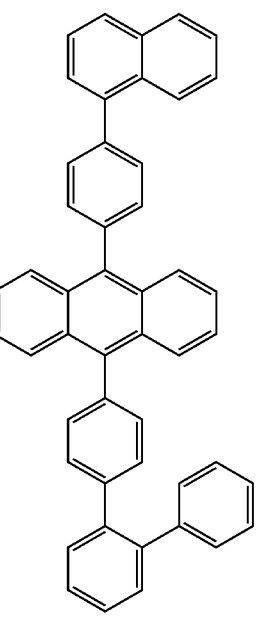

227
-continued
228
-continued
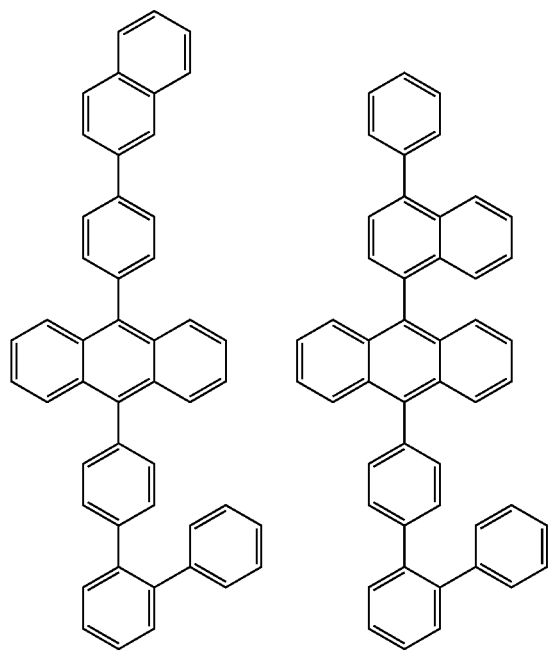
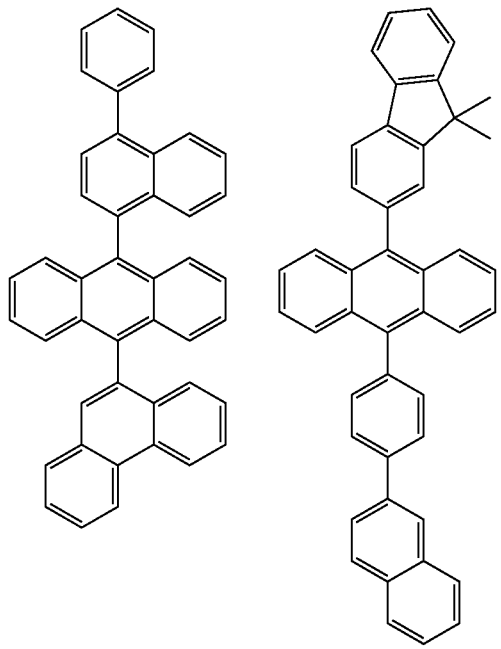
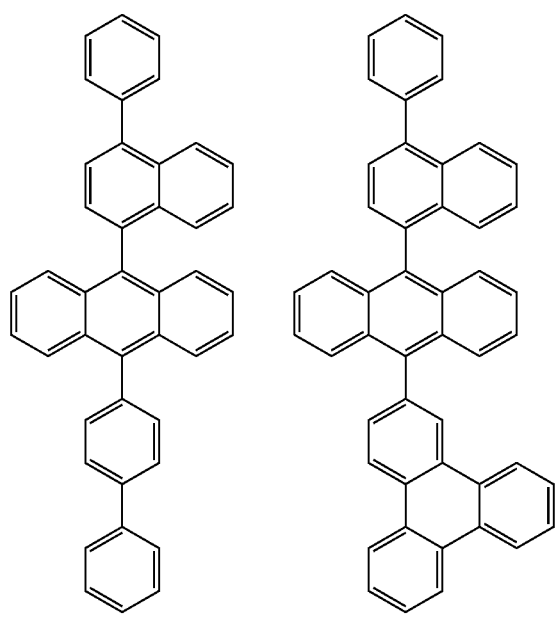
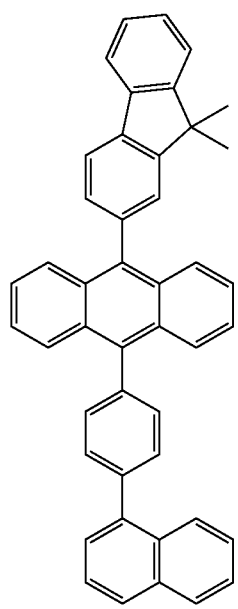

-continued
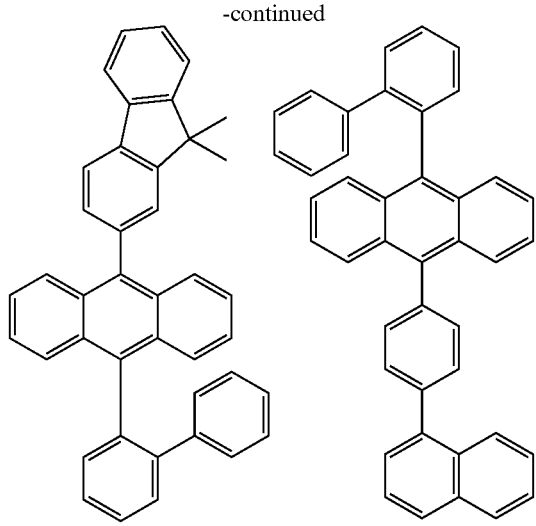
-continued
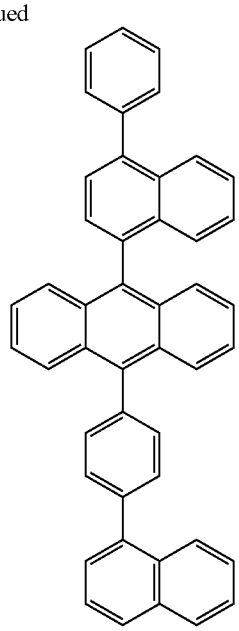
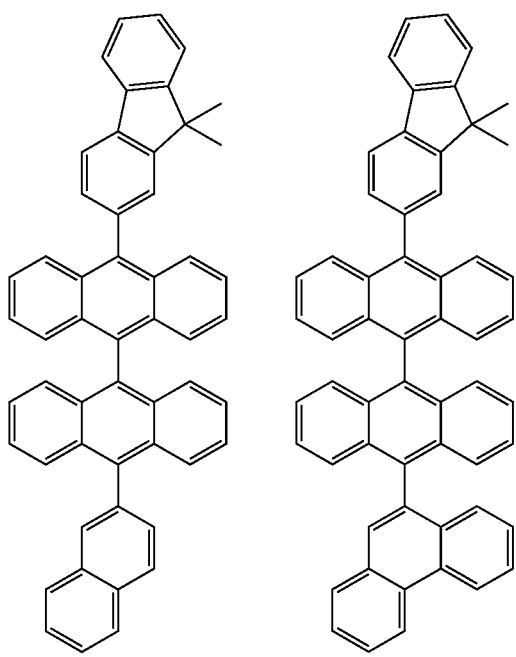
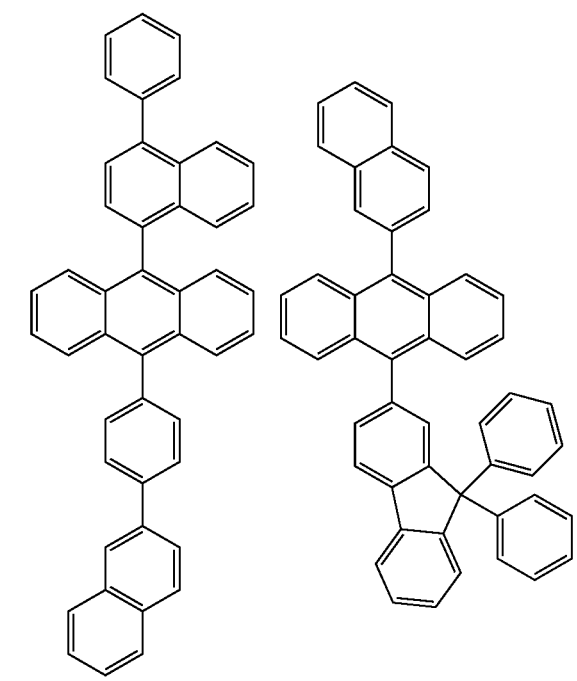

231
-continued

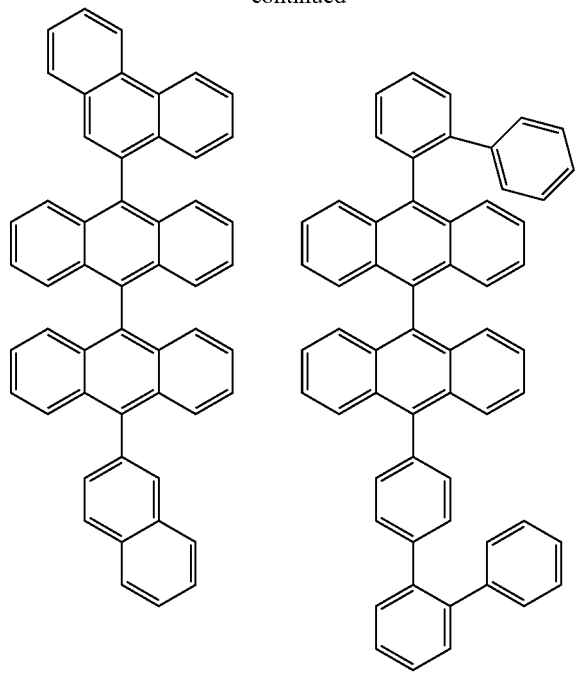

232
-continued

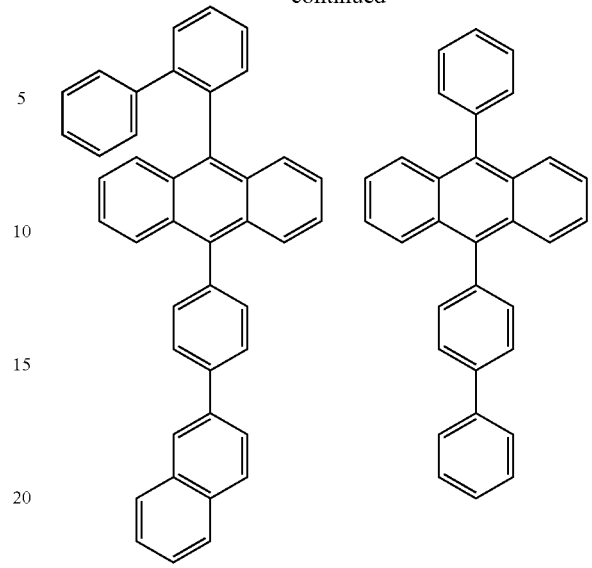

16. The organic light emitting device of claim 11, wherein the light emitting layer further comprises a compound of the following Chemical Formula 4:

[Chemical Formula 4]
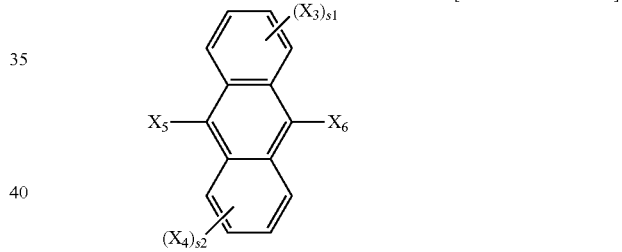

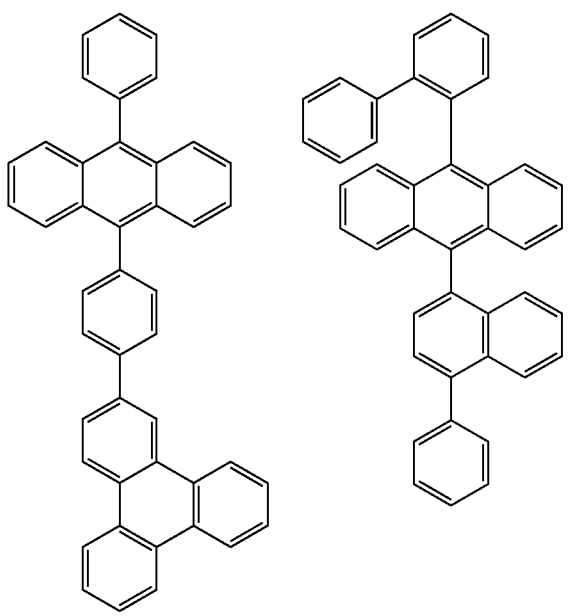

in Chemical Formula 4, $X_5$ is a substituted or unsubstituted 1-naphthyl group, a substituted or unsubstituted 2-naphthyl group, a substituted or unsubstituted 1-anthryl group, a substituted or unsubstituted 2-anthryl group, a substituted or unsubstituted 1-phenanthryl group, a substituted or unsubstituted 2-phenanthryl group, a substituted or unsubstituted 3-phenanthryl group, a substituted or unsubstituted 4-phenanthryl group, a substituted or unsubstituted 9-phenanthryl group, a substituted or unsubstituted 1-naphthacenyl group, a substituted or unsubstituted 2-naphthacenyl group, a substituted or unsubstituted 9-naphthacenyl group, a substituted or unsubstituted 1-pyrenyl group, a substituted or unsubstituted 2-pyrenyl group, a substituted or unsubstituted 4-pyrenyl group, a substituted or unsubstituted 3-methyl-2-naphthyl group, a substituted or unsubstituted 4-methyl-1-naphthyl group or the following structural formula

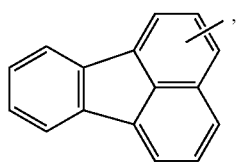

X₆ is a group selected from the group consisting of a substituted or unsubstituted phenyl group, a substituted or unsubstituted 1-naphthyl group, a substituted or unsubstituted 2-naphthyl group, a substituted or unsubstituted 1-anthryl group, a substituted or unsubstituted 2-anthryl group, a substituted or unsubstituted 9-anthryl group, a substituted or unsubstituted 1-phenanthryl group, a substituted or unsubstituted 2-phenanthryl group, a substituted or unsubstituted 3-phenanthryl group, a substituted or unsubstituted 4-phenanthryl group, a substituted or unsubstituted 9-phenanthryl group, a substituted or unsubstituted 1-naphthacenyl group, a substituted or unsubstituted 2-naphthacenyl group, a substituted or unsubstituted 9-naphthacenyl group, a substituted or unsubstituted 1-pyrenyl group, a substituted or unsubstituted 2-pyrenyl group, a substituted or unsubstituted 4-pyrenyl group, a substituted or unsubstituted 2-biphenylyl group, a substituted or unsubstituted 3-biphenylyl group, a substituted or unsubstituted 4-biphenylyl group, a substituted or unsubstituted p-terphenyl-4-yl group, a substituted or unsubstituted p-terphenyl-3-yl group, a substituted or unsubstituted p-terphenyl-2-yl group, a substituted or unsubstituted m-terphenyl-4-yl group, a substituted or unsubstituted m-terphenyl-3-yl group, a substituted or unsubstituted m-terphenyl-2-yl group, a substituted or unsubstituted o-tolyl group, a substituted or unsubstituted m-tolyl group, a substituted or unsubstituted p-tolyl group, a substituted or unsubstituted p-t-butylphenyl group, a substituted or unsubstituted p-(2-phenylpropyl)phenyl group, a substituted or unsubstituted 3-methyl-2-naphthyl group, a substituted or unsubstituted 4-methyl-1-naphthyl group, a substituted or unsubstituted 4-methyl-1-anthryl group, a substituted or unsubstituted 4'-methylbiphenylyl group, a substituted or unsubstituted 4"-t-butyl-p-terphenyl-4-yl group, and a substituted or unsubstituted 3-fluoranthenyl group, $X_3$ and $X_4$ are the same as or different from each other, and are each independently a substituted or unsubstituted aryl group having 6 to 50 carbon atoms, a substituted or unsubstituted heteroaryl group having 5 to 50 nuclear atoms, a substituted or unsubstituted alkyl group having 1 to 50 carbon atoms, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 nuclear atoms, a substituted or unsubstituted arylthio group having 5 to 50 nuclear atoms, a substituted or unsubstituted alkoxycarbonyl group having 1 to 50 carbon atoms, a carboxyl group, a halogen atom, a cyano group, a nitro group or a hydroxyl group, and s1 and s2 are each an integer from 0 to 4.

17. The organic light emitting device of claim 16, wherein Ar3 is a pyrene skeleton, L6 is a single bond, and $X_1$ and $X_2$ are the same as or different from each other, and are each independently an aryl group unsubstituted or substituted with an alkyl group; or a $C_5$ to $C_{30}$ heterocyclic group, and r is 2, and $X_5$ and $X_6$ of Chemical Formula 4 are the same as or different from each other, and are each independently a 1-naphthyl group or a 2-naphthyl group, and s1 and s2 are 0.

18. The organic light emitting device of claim 1, wherein the first organic material layer including the compound represented by Chemical Formula 1 and the second organic material layer including the compound represented by Chemical Formula 2 each independently have a single layer or two or more layers.

19. The organic light emitting device of claim 18, wherein the two or more layers are selected from the group consisting of a hole transporting layer, a hole injection layer, a layer which transports and injects holes simultaneously, and an electron blocking layer.

20. The organic light emitting device of claim 5, wherein the compound represented by Chemical Formula 2 is selected from the following structural formulae:

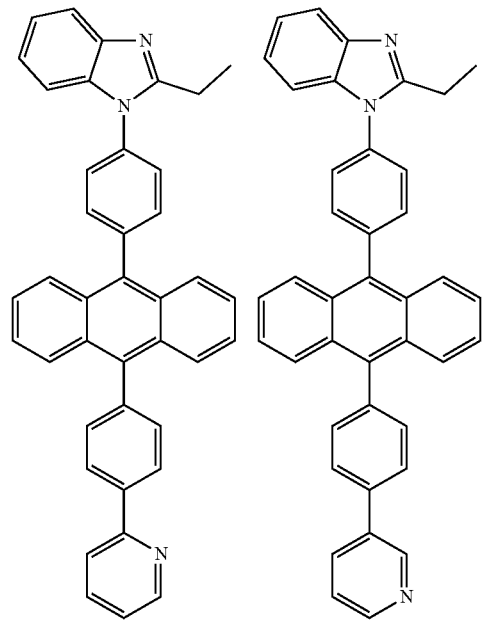

235
-continued
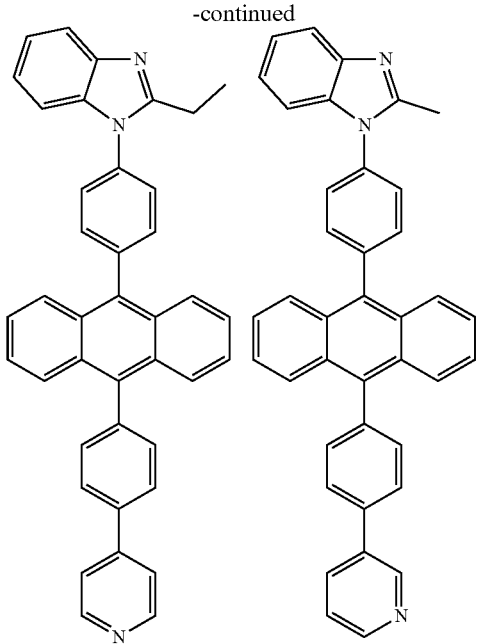
236
-continued
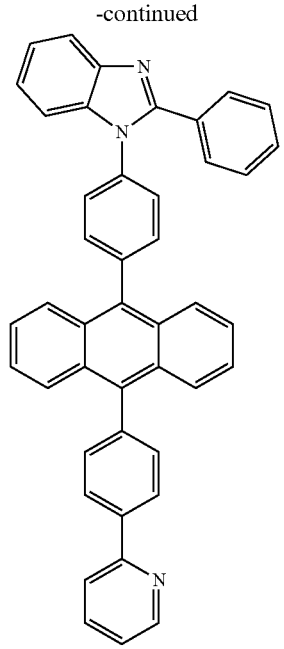
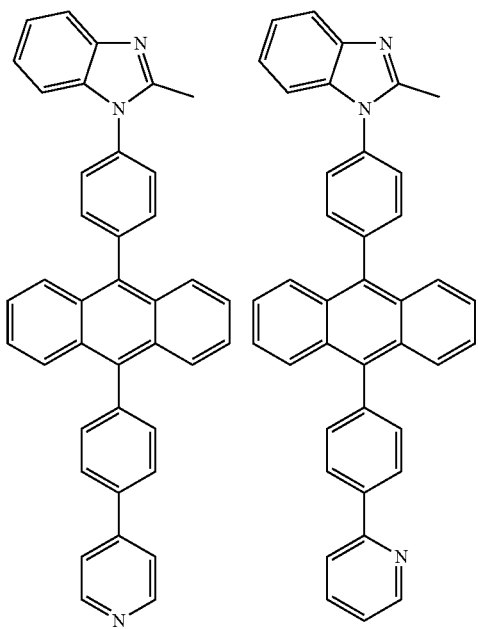
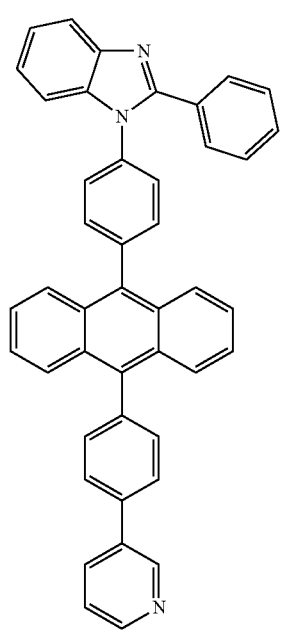

237
-continued
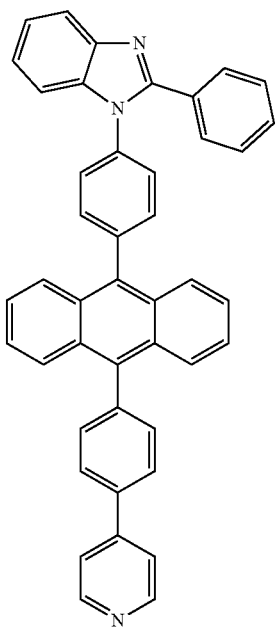
238
-continued
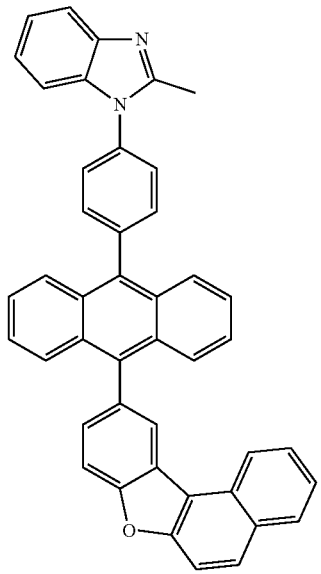
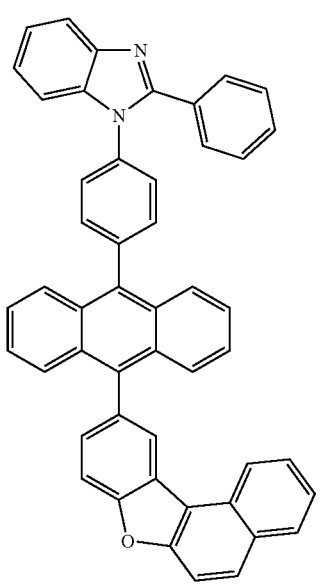
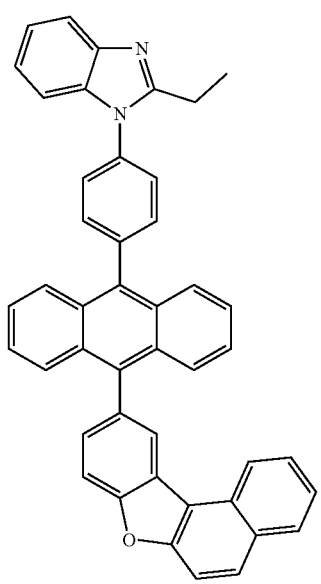

239
-continued
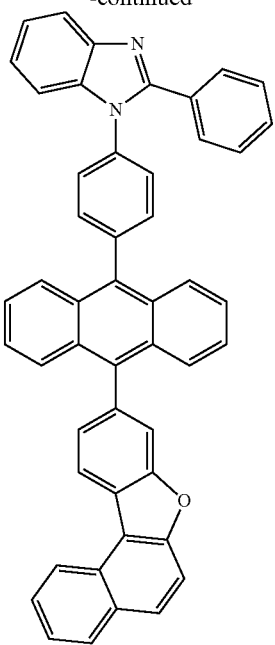
240
-continued
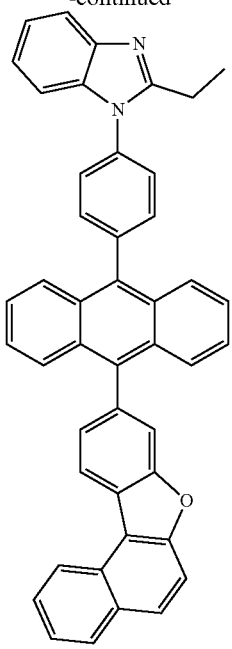
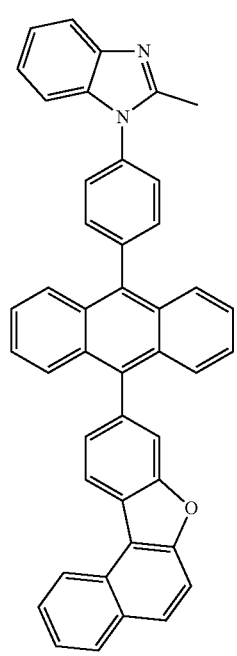
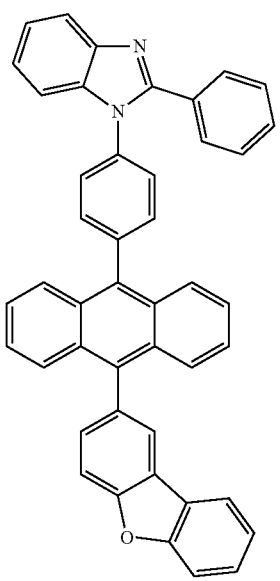

241
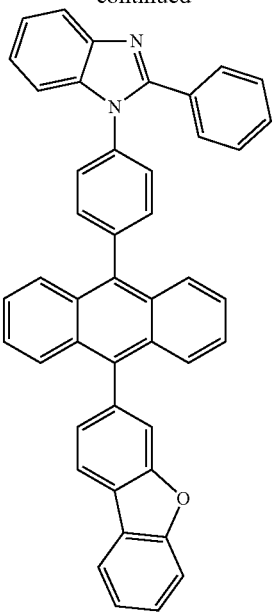
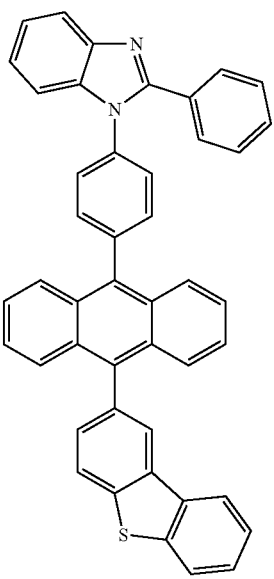
242
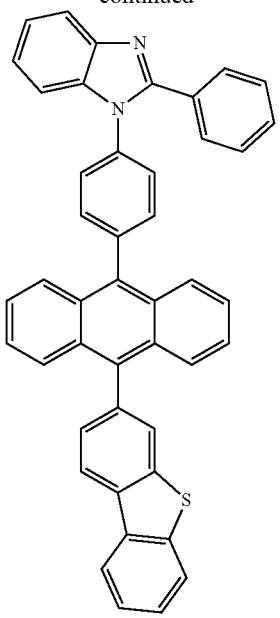
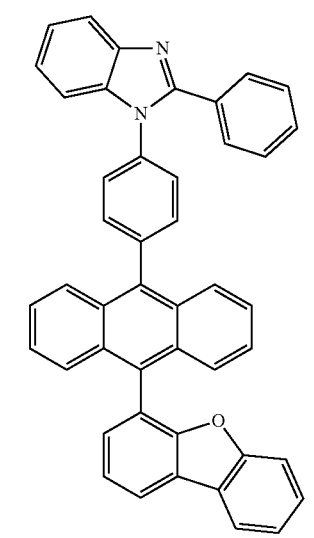
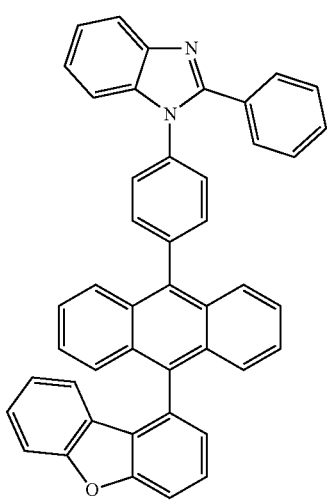

243
-continued
244
-continued
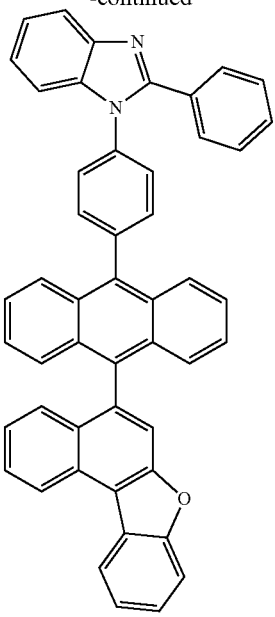
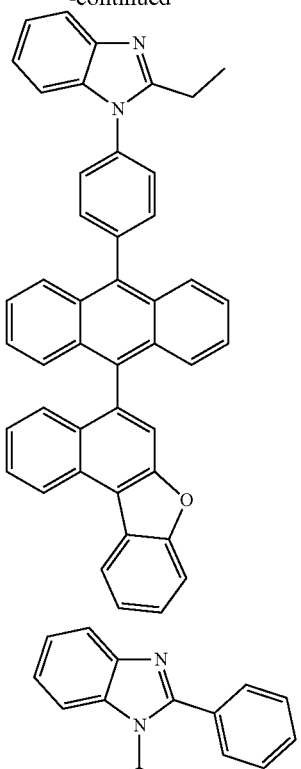
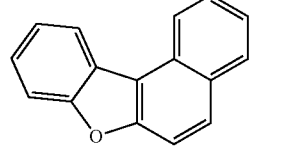

-continued
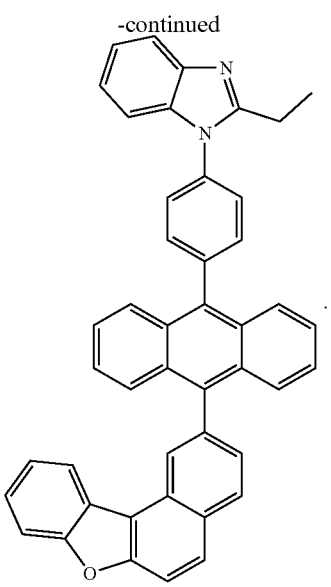
* * * * *